US010414808B2

(12) United States Patent
Eckert et al.

(10) Patent No.: US 10,414,808 B2
(45) Date of Patent: *Sep. 17, 2019

(54) HUWENTOXIN-IV VARIANTS AND METHODS OF USE

(71) Applicant: JANSSEN BIOTECH, INC., Horsham, PA (US)

(72) Inventors: William Eckert, San Diego, CA (US); Mack Flinspach, San Diego, CA (US); Michael Hunter, San Diego, CA (US); Yi Liu, San Diego, CA (US); Robert Neff, San Diego, CA (US); Alan Wickenden, San Diego, CA (US); Alan Gibbs, Spring House, PA (US)

(73) Assignee: JANSSEN BIOTECH, INC., Horsham, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/399,088

(22) PCT Filed: Mar. 15, 2013

(86) PCT No.: PCT/US2013/041572
§ 371 (c)(1),
(2) Date: Nov. 5, 2014

(87) PCT Pub. No.: WO2013/173706
PCT Pub. Date: Nov. 21, 2013

(65) Prior Publication Data

US 2015/0087596 A1 Mar. 26, 2015

Related U.S. Application Data

(63) Continuation-in-part of application No. 13/833,555, filed on Mar. 15, 2013, now Pat. No. 9,102,751.

(60) Provisional application No. 61/648,871, filed on May 18, 2012, provisional application No. 61/702,538, filed on Sep. 18, 2012, provisional application No. 61/781,276, filed on Mar. 14, 2013.

(51) Int. Cl.
*A61K 38/00* (2006.01)
*C07K 14/435* (2006.01)

(52) U.S. Cl.
CPC ........ *C07K 14/43518* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,309,989 | A | 1/1982 | Fahim |
| 4,767,402 | A | 8/1988 | Kost et al. |
| 6,103,495 | A | 8/2000 | Mehta et al. |
| 6,521,427 | B1 | 2/2003 | Evans |
| 6,670,127 | B2 | 12/2003 | Evans |
| 6,881,725 | B2 | 4/2005 | Yerxa et al. |
| 7,998,980 | B2 | 8/2011 | Moran et al. |
| 9,102,751 | B2 * | 8/2015 | Flinspach ........ C07K 14/43518 |
| 9,102,757 | B2 | 8/2015 | Chen et al. |
| 9,624,280 | B2 | 4/2017 | Flinspach et al. |
| 2007/0212685 | A1 | 9/2007 | MacDonald et al. |
| 2011/0065647 | A1 | 3/2011 | Meir et al. |
| 2011/0124711 | A1 | 5/2011 | Sah et al. |
| 2012/0185956 | A1 | 7/2012 | Gingras |
| 2013/0296247 | A1 | 11/2013 | Park et al. |
| 2015/0087596 | A1 | 3/2015 | Eckert et al. |
| 2015/0099705 | A1 | 4/2015 | Flinspach et al. |
| 2016/0257726 | A1 | 9/2016 | Flinspach et al. |
| 2016/0287666 | A1 | 10/2016 | Flinspach et al. |

FOREIGN PATENT DOCUMENTS

| | | | |
|---|---|---|---|
| AU | 2013262630 | A1 | 12/2014 |
| CA | 2873860 | A1 | 11/2013 |
| CN | 101979411 | A | 2/2011 |
| CN | 104768568 | A | 7/2015 |
| CN | 2013825986 | A | 7/2015 |
| EP | 2852397 | A4 | 3/2016 |
| JP | 2015518836 | A | 7/2015 |
| WO | 9853847 | A1 | 12/1998 |
| WO | WO 06/116156 | A2 | 11/2006 |
| WO | WO 07/109324 | A2 | 9/2007 |
| WO | WO 08/088422 | A2 | 7/2008 |
| WO | 2010/028089 | A2 | 3/2010 |
| WO | WO 10/104115 | A1 | 9/2010 |
| WO | WO 12/004664 | A2 | 1/2012 |
| WO | 2013/173706 | A2 | 11/2013 |
| WO | 2014165277 | A2 | 10/2014 |
| WO | 2015/051216 | A1 | 4/2015 |

(Continued)

OTHER PUBLICATIONS

Jiang et al., Molecular diversification based on analysis of expressed sequence tags from the venom glands of the Chinese bird spider Ornithoctonus huwena. Toxicon 51 (2008) 1479-1489.*
Shih et al. (Biophysical Journal, vol. 102, Issue 3, Supplement 1, p324a, Jan. 31, 2012) (Year: 2012).*
Minassian et al. (J Biol Chem. Aug. 2, 2013;288(31):22707-20) (Year: 2013).*
Luo Xuan "A Study of the Interactive Mechanism between Huwentoxin-IV and Sodium Channel", Chinese Master's Theses Full Test Database, Medicine and Health Sciences, No. S1, pp. E079-E241, Dec. 15, 2011.
Yucheng Xiao et aL, "Tarantula Huwentoxin-IV Inhibits Neuronal Sodium channels by Binding to Receptor Site 4 and Trapping the Domain II Voltage Sensor in the Closed Configuration", The Journal of Biological Chemistry, vol. 283, No. 40, pp. 27300-27313, Oct. 3, 2008.

(Continued)

*Primary Examiner* — Sergio Coffa
(74) *Attorney, Agent, or Firm* — Roberts Mlotkowski Safran Cole & Calderon, P.C.

(57) ABSTRACT

The present invention relates to Huwentoxin-IV variants, polynucleotides encoding them, methods of making and using the foregoing, and methods of alleviating pain with peptide inhibitors of Nav1.7.

3 Claims, 47 Drawing Sheets

Specification includes a Sequence Listing.

(56) References Cited

FOREIGN PATENT DOCUMENTS

WO 2016140859 A2 9/2016
WO 2016/161100 A1 10/2016

OTHER PUBLICATIONS

Yucheng Xiao et aL, "Common Molecular Determinants of Tarantula Huwentoxin-IV Inhibition of Na+ Channel Voltage Sensors in Domains II and IV" The Journal of Biological Chemistry, vol. 286, No. 40, pp. 27301-27310, Aug. 5, 2011.
Chinese Search Report of Chinese Application No. 201380025986.1 dated Jan. 19, 2016.
Z. Liu et al., "Isolation and Characterization of Hainantoxin-IV, a Novel Antagonist of Tetrodotoxin-Sensitive Sodium Channels From the Chinese Bird Spider Selenocosmia Hainana", Cellular and Molecular Life Sciences, vol. 60 (5), 2003, pp. 972-978.
European Search Report of European Application No. 13791454.5, dated Jan. 27, 2016.
Dirig et al., "Characterization of variables defining hindpaw withdrawal latency evoked by radiant thermal stimuli", Journal of Neuroscience Methods, No. 76, (1997), pp. 183-191.
Hargreaves et al., "A new and sensitive method for measuring thermal nociception in cutaneous hyperalgesia", Elsevier, (1998), pp. 77-88.
Klint et al., "Spider-venom peptides that target voltage-gated sodium channels: Pharmacological tools and potential therapeutic leads", Toxicon, 60, (2012), pp. 478-491.
Oi et al., "Isolation of specific peptides that home to dorsal root ganglion neurons in mice", Neuroscience Letters, 434, (2008), pp. 266-272.
Sockolosky et al., "Engineering neonatal Fc receptor-mediated recycling and transcytosis in recombinant proteins by short terminal peptide extensions", PNAS, vol. 109, No. 40, (2012), pp. 16095-16100.
Hagman, "Sterilization", Pharmaceutical Manufacturing, Lippincott Williams & Wilkins, Baltimore, MD (2005) Chapters 40, pp. 776-801.
Whitney et al., "Fluorescent peptides highlight peripheral nerves during surgery in mice", nature biotechnology, vol. 29, No. 4, (2011), pp. 352-358.
Dib-Hajj et al., "The NaV1.7 sodium channel: from molecule to man" Nature Reviews Neuroscience, vol. 14, (2013), pp. 49-62.
Park et al., "Studies Examining the Relationship between the Chemical Structure of Protoxin II and Its Activity on Voltage Gated Sodium Channels", Journal of Medicinal Chemistry, 57, (2014), pp. 6623-6631.
Yang et al., "Discovery of a selective NaV1/ inhibitor from centipede venom with analgesic efficacy exceeding morphine in rodent pain models", Proceedings of the National Academy of Sciences (2013), vol. 110, No. 43, pp. 17534-17539.
Smith et al, "Molecular Interactions of the Gating Modifier Toxin, ProTx-II, with Nav1.5: implied existence of a novel toxin binding site coupled to activation", The American Society for Biochemistry and Molecular Biology, Inc. (2007) vol. 282, No. 17, pp. 12687-12697.
Dib-Hajj., "sodium channels in normal and pathological pain" an nu rev neurosci, 2010,vol. 33, pp. 325-347.
Minett, "pain without nociceptors? nav1.7-independent pain mechanisms" cell rep, 2014, vol. 6 No. 2, pp. 301-312.
Revel et al., "Potency optimization of Huwentoxin-IV onhNav1.7: A neurotoxin TTX-S sodium-channel antagonist from the venom of the Chinese bird-eating spiderSelenocosmia huwena", Peptides, Elsevier, Amsterdam, NL, (2013), vol. 44, pp. 40-46, XP028551011.
Genbank:ABY77745.1, "HWTX-IVb precursor [Haplopelma schmidti]", Protein—NCBI (2007).
U.S. Appl. No. 15/090,328, filed Apr. 4, 2016.
International Application No. PCT/US2016/025247 filed Mar. 31, 2016.
International Search Report of International Application No. PCT/US2014/058972 dated Mar. 26, 2015.
International Search Report of International Application No. PCT/US2016/025247 dated Jul. 12, 2016.
Office Action dated Nov. 3, 2015 from U.S. Appl. No. 14/505,592.
Office Action dated Mar. 16, 2016 from U.S. Appl. No. 14/505,592.
Notice of Allowance dated Aug. 9, 2016 from U.S. Appl. No. 14/505,592.
International Search Report and Written Opinion of related International Application No. PCT/US2013/041572 dated Dec. 13, 2013.
International Preliminary Report on Patentability of related International Application No. PCT/US2013/041572 dated Nov. 1, 2014.
International Search Report and Written Opinion of International Application No. PCT/US2016/025247 dated Jul. 12, 2016.
International Search Report and Written Opinion of related International Application No. PCT/US2014/058972 dated Mar. 26, 2015.
International Preliminary Report on Patentability of related International Application No. PCT/US2014/058972 dated Apr. 5, 2016.
International Search Report and Written Opinion of International Application No. PCT/US2016/019549 dated Aug. 30, 2016.
Office Action dated Dec. 24, 2015 from U.S. Appl. No. 14/399,088.
Office Action dated Oct. 7, 2016 from U.S. Appl. No. 14/399,088.
U.S. Appl. No. 61/886,100, filed Oct. 3, 2013.
U.S. Appl. No. 62/127,339, filed Mar. 3, 2015.
U.S. Appl. No. 62,142,069, filed Apr. 2, 2015.
International Search Report dated Dec. 13, 2013 for corresponding Application No. PCT/US2013/041572.
U.S. Appl. No. 61/781,276, filed Mar. 14, 2013.
U.S. Appl. No. 13/833,555, filed Mar. 15, 2013.
U.S. Appl. No. 61,702,538, filed Sep. 18, 2012.
U.S. Appl. No. 61/648,871, filed May 18, 2012.
USSN PCT/US13/41572 filed May 17, 2013.
Ahmad, S., et al., "A Stop Codon Mutation in SCNA9A Causes Lack of Pain Sensation", Human Molecular Genetics, vol. 16, No. 17, p. 2114-2121 (2007).
Berjanskii, M., et al, "Predictor: A Web Server for Predicting Protein Torsion Angle Restraints", Nucleic Acids Research, vol. 34, pp. W63-W69 (2006).
Bodenhausen, G., et al., Natural Abundance Nitrogen-15 NMR by Enhanced Heteronuclear Spectroscopy:, vol. 69, No. 1, Jan. 1980 pp. 185-189.
Bosmans, F., et al., "Four Novel Tarantula Toxins as Selective Modulators of Voltage-Gated Sodium Channel Subtypes", Molecular Pharmacology, vol. 69, pp. 419-429 (2006).
Cannon, S., et al. "Sodium Channels Gone Wild: Resurgent Current From Neuronal and Muscle Channelopathies", Journal of Clinical Investigation, vol. 120, No. 1, pp. 80-83 (2010).
Cheung, M., et al., "Dangle: A Bayesian Inferential Method for Predicting Protein Backbone Dihedral Angles and Secondary Structure", Journal of Magnetic Resonance, vol. 202, pp. 223-233 (2010).
Clare, J., et al., "Voltage-Gated Sodium Channels as Therapeutic Targets", Therapeutic Focus, vol. 15, No. 11, Nov. 2000, pp. 506-520.
Cox, J., et la. "An SCN9A Channelopathy Causes Congenital Inability to Experience Pain", Nature, vol. 444, No. 14, pp. 894-898 (2006).
Cregg, R., et al., "Pain Channelopathies", J. Physiol. vol. 11, pp. 1897-1904 (2010).
Delaglio, F., et al, "NMR Pipe: A Multidimensional Spectral Processing System Based on UNIX Pipes", Journal of Biomolecular NMR, vol. 6, pp. 277-291 (1995).
Estacion, M., et al, "A Sodium Channel Gene SCN9A Polymorphism That Increases Nociceptor Excitability", Annals of Neurology, vol. 66, No. 6, pp. 862-(2009(.
Fertleman, C., et al. "SCN9A Mutations in Paroxysmal Clinical Study Extreme Pain Disorder: Allelic Variants Underlie Distinct Channel Defects and Phenotypes", Neuron, vol. 52, pp. 767-774 (2006).
Goldberg, YP, et al., Loss-Of-Function Mutations in the $Na_v1.7$ Gene Underline Congenital Indifference to Pain in Multiple Human Populations, Clinical Genet, vol. 71, pp. 311-319 (2007).

(56) References Cited

OTHER PUBLICATIONS

Guntert, P., et al., "Torsion Angle Dynamics for NMR structure Calculation with the New Program Dyana", JMB, vol. 273, pp. 283-298 (1997).
Hackel, D., et al., "Transient Opening of the Perineurial Barrier for Analgesic Drug Delivery", PNAS, Jun. 25, 2012, pp. E2018-E2027.
Hubner, C., et al, "Ion Channel Diseases", Human Molecular Genetics, vol. 11, No. 20, pp. 2435-2445 (2002).
Humphrey, W., et al., "VMD: Visual Molecular Dynamics", Journal of Molecular Graphics, vol. 14, pp. 33-38 (1996).
Jeener, J., "Investigation of Exchange Processes by Two-Dimensional NMR Spectroscopy", J. Chem. Phys., vol. 71, No. 11, pp. 4546-4553 (1979).
Kumar, A., et al., "A Two-Dimensional nuclear Overhauser Enhancement (2D NOE) Experiment for the Elucidation of Complete Proton-Proton Cross-Relaxation Networks in Biological Macromolecules", Biochemical and Biophysical Research Communications, vol. 95, No. 1, Jul. 16, 1980, pp. 1-6.
Legroux-Crespel, E., et al. Traitement de l'erythermalgie fajiiale par l'association lidocaine-mexiletine, Ann Dermatol Venereol, vol. 130, pp. 429-433 (2003) (English Abstract).
Liu, Y., "Screening of Peptide-Based Modulators of Voltage-Gated Sodium Channels Using QPatch", Janssen Research & Development, Pharmaceutical Companies, of Johnson & Johnson Powerpoint 2012.
Mackerell, A., et al., "Extending the Treatment of Backbone Energetics in Protein Force Fields Limitations of Gas-Phase Quantum Mechanics in Reproducing Protein Conformational Distributions in Molecular Dynamics Simulations", J. Computer Chemistry, vol. 25, pp. 1400-1415 (2004).
Middleton, R., et al., "Two Tarantula Peptides Inhibit Activation of Multiple Sodium Channels", Biochemistry, vol. 41, pp. 14734-14747 (2002).
Minassian, N., et al., "Analysis of the Structural and Molecular Basis of Voltage-Sensitive Sodium Channel Inhibition by the spider Toxin, Huwentoxin-IV (μ-TRTX-Hh2a)", The Journal of Biological Chemistry, online Jun. 12, 2013.
Minassian, N., et al., "Functional Studies of the Interaction Between Huwentoxin-IV and the Voltage-Gated Sodium Chanel $NA_v1.7$", Johnson & Johnson Pharmaceutical Research & Development, San Diego, CA Poster.
Minett, M., et al., "Distinct Nav1.7-Dependent Pain Sensations Require Different Assets of Sensory and Sympathetic Neurons", Nature Communications.
Muroi, Y., et al., "Selective Silencing of $Na_v$ 1.7 Decreases Excitability and Conduction in Vagal Sensory Neurons", J. Physiology, vol. 589, No. 23 (2011) pp. 5663-5676.
Muroi, Y., et al., "Selective Inhibition of Vagal Afferent Nerve Pathways Regulating Cough Using $Na_v$ 1.7 shRNA Silencing in Guinea Pig Nodose Ganglia", Am. J. Physiol Regul Integr Comp Physiol, vol. 304, pp. R1017-R1023 (2013).
Nassar, M., et al, Nociceptor-Specific Gene Deletion Reveals a Major Role for $Na_v1.7$ (PN1) in Acute and Inflammatory Pain, PNAS, vol. 101, No. 34, pp. 12706-12711 (2004).
Peng, K., et la., "Function and Solution Structure of Huwentoxin-IV, a Potent Neuronal Tetrodotoxin (TTX)-sensitive Sodium Channel Antagonist form Chinese Bird Spider *Selenocosmia huwena",* The Journal of Biological Chemistry, vol. 277, No. 49, pp. 47564-47564 (2002).
Phillips, J., et al, "Scalable Molecular Dynamics with NAMD", J. Comput. Chem, vol. 26, pp. 1781-1802 (2005).
Reimann, F., et al., "Pain Perception is Altered by a M Nucleotide Polymproophism in SCNA9A", PNAS, vol. 107, No. 11, pp. 5148-5153 (2010).
Revell, J., et al., "Potency Optimization of Huwentoxin-IV onh$Na_v1$.7: A Neurotoxin TTX-S Sodium-Channel Antagonist from the Venom of the Chinese Bird-Eating Spider *Selenocosmia huwena",* Peptides, vol. 44, pp. 40-46 (2013).
Schmalhofer, W., et al., "ProTx-11, A Selective Inhibitor of $Na_v1.7$ Sodium Channels, Blocks Action Potential Propagation in Nociceptors", Molecular Pharmacology, vol. 74, No. 5, p. 1476-1484 (2008).
Shih, A., et al., "Functional Studies of the Interaction Between Huwentoxin-IV and the Voltage-Gated Sodium Channel, $Na_v1.7$", Janssen Research & Development, Pharmaceutical Companies of Johnson & Johnson.
Spassov, V., et al., "Introducing an Implicit Membrane in Generalized Born/Solvent Accessibility Continuum Solvent Models", J. Phys. Chem., vol. 106, pp. 8726-8738 (2003).
Tfelt-Hansen, J., et al., "Inherited Cardiac Diseases Caused by Mutations in the Nav1.5 Sodium Channel", J. Cardiovascular Electrophysiol., vol. 21, pp. 107-115 (2010).
Vargas-Alarcon, G., et al., "A SCN9A Gene-Encoded Dorsal Root Ganglia Sodium Channel Polymorphism Associated with Severe Fibromyalgia", Musculoskeletal Disorders, vol. 13 p. 23 (2012).
Xiao, Y., et al., "Tarantla Huwentoxin-IV Inhibits Neuronal Sodium Channels by Binding to Receptor Site 4 and Trapping the Domain II Voltage Sensor in the Closed Configuration", Journal of Biological Chemistry, vol. 283, No. 40, pp. 27300-27313 (2008).
Xiao,Y., et al., "Common Molecular Determinants of Tarantla Huwentoxin-IV Inhibition of $Na^+$ Channel Voltage Sensors in Domains I and IV", Journal of Biological Chemistry, vol. 286, No. 31, pp. 27301-27310 (and Supplement).
Yang, Y., et al., "Mutations in SCN9A, Encoding a Sodium Channel Alpha Subunit, in Patients with Primary Erythermalgia", J. Med Genet, vol. 41, p. 171-174 (2004).
Yogeeswari, P., et la, "Ion Channels as Important Targets for Antiepileptic Drug Design", Current Drug Targets, vol. 5, pp. 589-602 (2004).
Zhang, M., et al., "Structure/Function Characterization of μ-Conotoxin KIIIA, an Analgesic, Nearly Irreversible Blocker of Mammalian Neuronal Sodium Channels", Journal of Biological Chemistry, vol. 282, No. 42, pp. 30699-30706 (2007).
Examination report No. 1 issued in Australian Patent Application No. 2014329454 dated Jan. 4, 2018.
International Preliminary Report on Patentability; PCT/2013/041572; dated Nov. 18, 2014.
International Preliminary Report on Patentability; PCT/US2016/025247; dated Apr. 4, 2017.
International Preliminary Report on Patentability; PCT/US2016/019549; dated Sep. 5, 2017.
Deng Mei-chun, Life Science Research, vol. 17, No. 2 (Apr. 2013) pp. 111-115 (Abstract Only).
Chen, Zai-ran et al., Synthesis, folding and bioactivity analysis of K27A-HWTX-IV: a mutant of the TTX-sensitive sodium channel inhibitor, Hu wentoxin-IV, Hunan Shifan Daxue Ziran Kexue Xuebao, 2003, 26(3), pp. 67-72. (English Abstract).
Minassian, N. A. et al., "Functional studies of the interaction between Huwentoxin-IV and the voltage-gated sodium channel Nav1.7" Neuroscience 2011; Presentation Abstract.
Gingras et al., Global Nav1.7 KO mice recapitulate phenotype of congenital indifference to pain reported in humans; American Pain Society Meeting Abstract 2013.
Spassov et al., "Introducing and Implicit Membrane in Generalized Born/Solvent Accessibility Continuum Solvent Models", J. Phys. Chem, 2002, vol. 106, pp. 8726-8738.
Wang F. et al., Expression and characterization of Huwentoxin-XI(HWTX-XI) and its mutants., Chin. J. Biotech., 27(2) (2011), pp. 262-268. (English Abstract).
Xiao Y. et al., The Tarantula Toxins ProTx-II and Huwentoxin-IV Differentially Interact with Human Nav1.7 Voltage Sensors to Inhibit Channel Activation and Inactivation., Mol Pharmacol., 78(6)(2010), pp. 1124-1134.
Remington's Pharmaceutical Sciences, 15th Edition. Edited under the direction of Arthur Osol and John E. Hoover. Mack Publishing Co., Easton, PA 18042, 1975.
Bax, A. et al: MLEV-17 based two-dimensional homonuclear magnetization transfer spectroscopy. Journal of Magnetic Resonance, vol. 65, (1985) pp. 355-360.
Cavanagh et al., Protein NMR Spectroscopy: Principles and Practice, 2nd Edition, 1995 Academic Press. (Description Only).

(56) References Cited

OTHER PUBLICATIONS

Communication pursuant to Article 94(3) EPC issued in corresponding EP Application No. 14 790 422.4-1410 dated May 4, 2017.
Patent Examination Report No. 1 issued in corresponding Australian Patent Application No. 2013262630 dated Nov. 2, 2016.
English translation of First Office Action issued in corresponding Chinese Patent Application No. 201380025986.1 dated Jan. 27, 2016.
English translation of Second Office Action issued in corresponding Chinese Patent Application No. 201380025986.1 dated Sep. 26, 2016.
Communication pursuant to Article 94(3) EPC issued in corresponding EP Application No. 13 791 454.5-1402 dated Jul. 11, 2017.
English translation of Notice of Reasons for Rejection issued in corresponding Japanese Patent Application No. 2015-512885 dated Mar. 2, 2017.
Communication pursuant to Article 94(3) EPC, issued in European Patent Application No. 14 790 422.1-1410 dated Nov. 16, 2017.
English translation of Japanese Office Action issued in Japanese Application No. 2015-512885 dated Dec. 12, 2017.
Notice of Allowance issued in U.S. Appl. No. 13/833,555, dated Feb. 27, 2015.
Office Action issued in U.S. Appl. No. 15/090,328, dated Jun. 23, 2017.
Office Action issued in U.S. Appl. No. 15/090,328, dated Oct. 13, 2017.
Office Action issued in U.S. Appl. No. 15/583,793 dated Dec. 14, 2017.
Office Action issued in U.S. Appl. No. 13/833,555 dated Sep. 23, 2011.
Office Action issued in U.S. Appl. No. 13/833,555 dated Jan. 8, 2014.
Office Action issued in U.S. Appl. No. 13/833,555 dated Jul. 17, 2014.
Office Action issued in U.S. Appl. No. 13/833,555 dated Nov. 3, 2014.
Notice of Allowance dated Dec. 23 2016, issued in corresponding U.S. Appl. No. 14/505,592.
Corresponding International Application PCT/US2016/019549 filed Feb. 25, 2016.
Corresponding U.S. Appl. No. 15/060,158, filed Mar. 3, 2016.
Corresponding U.S. Appl. No. 15/489,714, filed Apr. 17, 2017.
Office Action issued in U.S. Appl. No. 15/090,328 dated Jun. 6, 2018.
Office Action issued in U.S. Appl. No. 15/583,793 dated May 18, 2018.
Examination Report issued by the Government of Pakistan Intellectual Property Organization The Patent Office in Patent Application No. 129/2016 dated Apr. 25, 2018.
Notice of Reexamination issued in Chinese Patent Application No. 201380025986.1 dated May 8, 2018.
Invitation pursuant to Rule 137(4) EPC and Article 94(3) EPC issued in European Application No. 14790422.1-1120 dated May 17, 2018.
Communication pursuant to Article 94(3) EPC issued in European Application No. 13791454.5-1120 dated May 17, 2018.
M. Flinspach et al., "Insensitivity to pain induced by a potent selective closed-state Nav1.7 inhibitor", Scientific Reports, Jan. 3, 2017, pp. 1-16, vol. 7.
Justin K. Murray et al., "Engineering Potent and Selective Analogues of GpTx-1, a Tarantula Venom Peptide Antagonist of the Nav1.7 Sodium Channel", Journal of Medicinal Chemistry, 2015, pp. 2299-2314, vol. 58, American Chemical Society, ACS Publications.
Extended European Search Report issued in European Patent Application No. 16759288.0 dated Jul. 20, 2018.
Communication pursuant to Rules 70(2) and 70a(2) EPC issued in European Patent Application No. 16759288.0 dated Aug. 7, 2018.
English Translation of Notice of Reasons for Rejection issued in Japanese Patent Application No. 2016-519872, dated Aug. 28, 2018.
Office Action issued in U.S. Appl. No. 15/090,328 dated Sep. 11, 2018.
Communication pursuant to Article 94(3) EPC issued in European Application No. 14 790 422.1-1120 dated Sep. 10, 2018; 6 pages.
Examination report No. 2 issued in Australian Application No. 2014329454 dated Sep. 17, 2018; 2 pages.
English translation of Reexamination Decision No. 162864 issued by the Patent Reexamination Board of National Intellectual Property Administration, P.R. China in Chinese Application No. 201380025986.1 dated Oct. 23, 2018; 25 pages.
English translation of Decision of Rejection issued in Japanese Application No. 2015-512885 dated Oct. 30, 2018; 16 pages.
Examination Report issued by the Government of Pakistan Intellectual Property Organization the Patent Office in Patent Application No. 189/2016 dated Nov. 9, 2018; 2 pages.
Extended European Search Report issued in European Application No. 16774187.5 dated Nov. 15, 2018.
Communication pursuant to Rules 70(2) and 70a(2) EPC issued in European Application No. 16774187.5 dated Dec. 4, 2018.
Notice of Allowance issued in U.S. Appl. No. 15/090,328 dated Dec. 26, 2018.
Office Action issued in U.S. Appl. No. 15/583,793 dated Jan. 4, 2019.
Office Action issued in corresponding European Application No. 14790422.1 dated Feb. 21, 2019, 5 pages.
Chinese Office Action issued in Application No. 201480066344.0 dated Mar. 29, 2019, with English Translation, 19 pages.
U.S. Non-Final Office Action issued in U.S. Appl. No. 15/090,328 dated Mar. 5, 2019, 9 pages.
Japanese Office Action issued in Application No. 2016-519872 dated Apr. 2, 2019, 6 pages.
English translation of Examination Report issued by the Patent Office of the Cooperation Council for the Arab States of the Gulf in Application No. GC 2016-30933 dated Jan. 10, 2019.

* cited by examiner

| | | | Substitution | | | | | | | | | | | | Substitution | | | | | | | Residue substitutions in variants with $IC_{50}$ ≤300 nM* |
|---|---|---|---|---|---|---|---|---|---|---|---|---|---|---|---|---|---|---|---|---|---|---|
| | | | Basic | | | Acidic | | Aromatic | | | Uncharged Polar | | | | Nonpolar | | | | | | | |
| | | | K | R | H | D | E | Y | F | W | N | Q | S | T | G | A | V | L | I | P | M | |
| Reference huwentoxin-IV residue | | G | | | | | | | | | | | | | | | | | | | | |
| | | P | | | | | | | | | | | | | | | | | | | | |
| | 1 | E | 0.06 | 0.05 | 0.07 | 0.16 | | 0.16 | 0.14 | | 0.07 | 0.09 | 0.11 | 0.12 | 0.08 | | >0.07 | 0.11 | 0.07 | 0.05 | | KRHDYFNQSTGLIPE |
| | 2 | C | | | | | | | | | | | | | | | | | | | | C |
| | 3 | L | | 0.27 | | 1.07 | 3.13 | | 0.16 | 0.15 | 0.11 | | 0.07 | 1.72 | | 0.54 | 0.74 | | | 1.88 | | RFWNSL |
| | 4 | E | | 0.02 | 0.05 | 0.07 | | 0.06 | | | 0.03 | 0.02 | | | | | | 0.08 | 0.20 | 0.11 | | RHDYNQLIPE |
| | 5 | I | | >0.36 | 5.35 | | >0.82 | 0.04 | | 0.43 | 16.80 | | | 4.26 | | 0.40 | 0.16 | | | 4.40 | | YVI |
| | 6 | F | | | >7.38 | >8.74 | | | | | >11.28 | | >0.56 | >0.75 | | 3.38 | 3.48 | 0.57 | | | 1.10 | F |
| | 7 | K | | 0.07 | | | 0.76 | | | 0.06 | 0.44 | 0.30 | 0.14 | 0.86 | | | | | | | | RWQSK |
| | 8 | A | | 0.02 | | | 0.06 | 0.11 | 0.18 | 0.37 | | | 1.24 | | | | 0.26 | | | | | REYFVA |
| | 9 | C | | | | | | | | | | | | | | | | | | | | C |
| | 10 | N | 0.27 | 0.11 | | 0.50 | 0.26 | 0.22 | 0.22 | 0.34 | | 0.68 | 0.20 | | | | 0.14 | | | | | KREYFSVN |
| | 11 | P | 3.57 | 0.49 | | | 7.83 | | 0.62 | 0.42 | | 1.27 | 0.39 | | | | 0.23 | | | | | PV |
| | 12 | S | | 0.13 | 0.35 | | 0.46 | | 0.24 | 2.64 | | 0.26 | | | | | 0.16 | | | | | RFQVS |
| | 13 | N | 0.36 | 0.68 | 0.18 | 0.10 | 0.31 | 0.11 | | 0.07 | | 0.06 | 0.26 | 0.10 | 0.19 | 0.03 | 0.23 | 0.28 | 0.14 | 0.26 | | HDYWQSTGAVLIPN |
| | 14 | D | 1.13 | 10.30 | 1.13 | | 1.41 | >1.27 | | 0.30 | | 0.91 | 0.36 | | 0.72 | 0.78 | 1.23 | 1.01 | >1.23 | 0.28 | | DWP |
| | 15 | Q | 0.24 | 0.04 | 0.36 | 0.18 | 0.23 | 0.07 | | 0.11 | 0.02 | | 0.37 | 0.08 | | 0.10 | 0.75 | 0.26 | | 0.35 | | KRDEYWNTALQ |
| | 16 | C | | | | | | | | | | | | | | | | | | | | C |
| | 17 | C | | | | | | | | | | | | | | | | | | | | C |

FIG. 1A

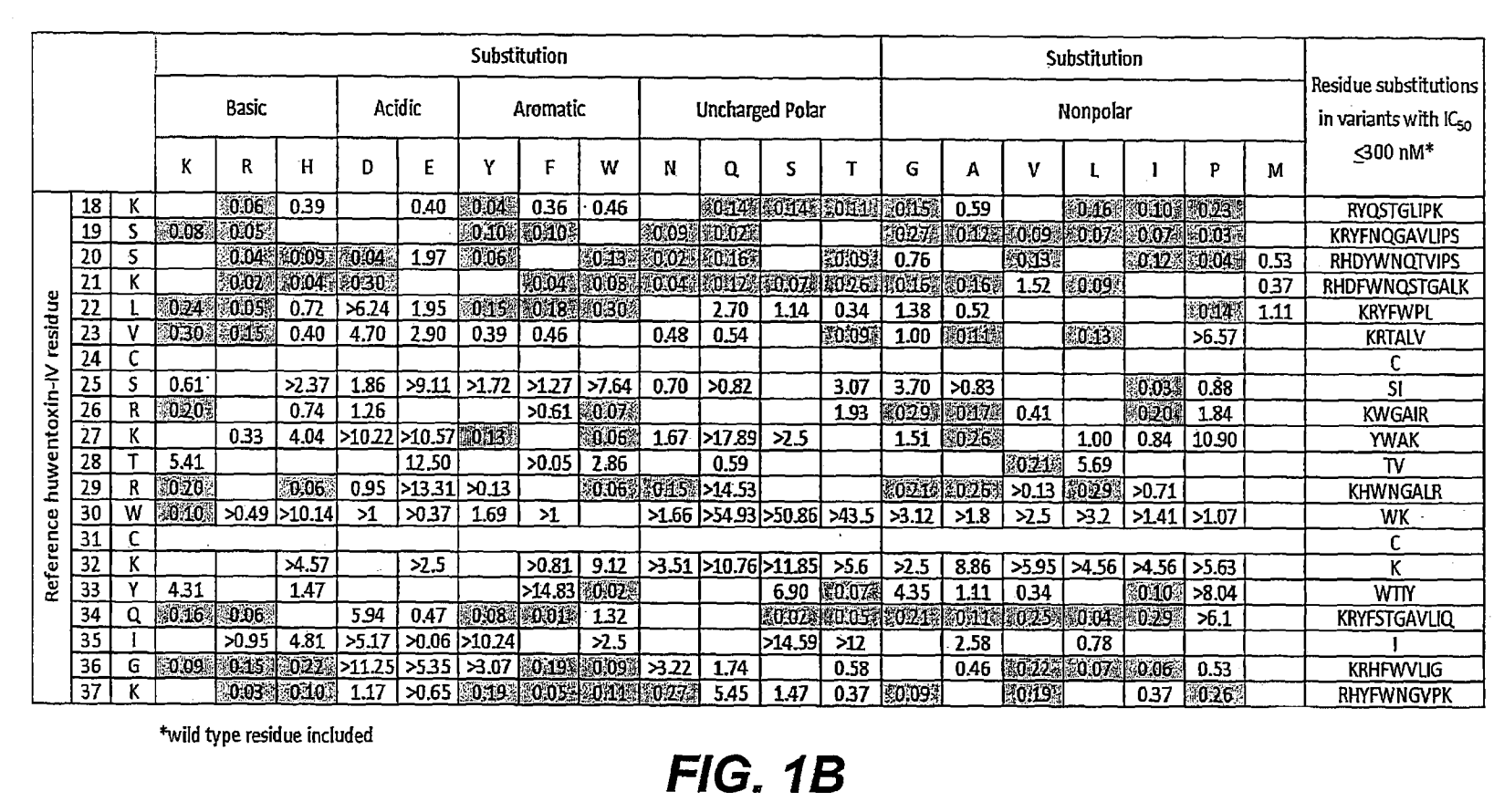

| Reference huwentoxin-IV residue | | Substitution | | | | | | | | | | | | Substitution | | | | | | | Residue substitutions in variants with $IC_{50}$ ≤300 nM* |
|---|---|---|---|---|---|---|---|---|---|---|---|---|---|---|---|---|---|---|---|---|---|
| | | Basic | | | Acidic | | Aromatic | | | Uncharged Polar | | | | Nonpolar | | | | | | | |
| | | K | R | H | D | E | Y | F | W | N | Q | S | T | G | A | V | L | I | P | M | |
| 18 | K | | 0.06 | 0.39 | | 0.40 | 0.04 | 0.36 | 0.46 | | 0.14 | 0.14 | 0.11 | 0.15 | 0.59 | | 0.16 | 0.10 | 0.23 | | RYQSTGLIPK |
| 19 | S | 0.08 | 0.05 | | | | 0.10 | 0.10 | | 0.09 | 0.02 | | | 0.27 | 0.12 | 0.09 | 0.07 | 0.07 | 0.03 | | KRYFNQGAVLIPS |
| 20 | S | | 0.04 | 0.09 | 0.04 | 1.97 | 0.06 | | 0.13 | 0.02 | 0.16 | | 0.09 | 0.76 | | 0.13 | | 0.12 | 0.04 | 0.53 | RHDYWNQTVIPS |
| 21 | K | | 0.02 | 0.04 | 0.30 | | | 0.04 | 0.08 | 0.04 | 0.12 | 0.07 | 0.26 | 0.16 | 0.16 | 1.52 | 0.09 | | | 0.37 | RHDFWNQSTGALK |
| 22 | L | 0.24 | 0.05 | 0.72 | >6.24 | 1.95 | 0.15 | 0.18 | 0.30 | | 2.70 | 1.14 | 0.34 | 1.38 | 0.52 | | | | 0.14 | 1.11 | KRYFWPL |
| 23 | V | 0.30 | 0.15 | 0.40 | 4.70 | 2.90 | 0.39 | 0.46 | | 0.48 | 0.54 | | 0.09 | 1.00 | 0.11 | | 0.13 | | >6.57 | | KRTALV |
| 24 | C | | | | | | | | | | | | | | | | | | | | C |
| 25 | S | 0.61 | | >2.37 | 1.86 | >9.11 | >1.72 | >1.27 | >7.64 | 0.70 | >0.82 | | 3.07 | 3.70 | >0.83 | | | 0.03 | 0.88 | | SI |
| 26 | R | 0.20 | | 0.74 | 1.26 | | | >0.61 | 0.07 | | | | 1.93 | 0.29 | 0.17 | 0.41 | | 0.20 | 1.84 | | KWGAIR |
| 27 | K | | 0.33 | 4.04 | >10.22 | >10.57 | 0.13 | | 0.06 | 1.67 | >17.89 | >2.5 | | 1.51 | 0.26 | | 1.00 | 0.84 | 10.90 | | YWAK |
| 28 | T | 5.41 | | | | 12.50 | | >0.05 | 2.86 | | 0.59 | | | | | 0.21 | 5.69 | | | | TV |
| 29 | R | 0.20 | | 0.06 | 0.95 | >13.31 | >0.13 | | 0.06 | 0.15 | >14.53 | | | 0.21 | 0.26 | >0.13 | 0.29 | >0.71 | | | KHWNGALR |
| 30 | W | 0.10 | >0.49 | >10.14 | >1 | >0.37 | 1.69 | >1 | | >1.66 | >54.93 | >50.86 | >43.5 | >3.12 | >1.8 | >2.5 | >3.2 | >1.41 | >1.07 | | WK |
| 31 | C | | | | | | | | | | | | | | | | | | | | C |
| 32 | K | | | >4.57 | | >2.5 | | >0.81 | 9.12 | >3.51 | >10.76 | >11.85 | >5.6 | >2.5 | 8.86 | >5.95 | >4.56 | >4.56 | >5.63 | | K |
| 33 | Y | 4.31 | | 1.47 | | | | >14.83 | 0.02 | | | 6.90 | 0.07 | 4.35 | 1.11 | 0.34 | | 0.10 | >8.04 | | WTIY |
| 34 | Q | 0.16 | 0.06 | | 5.94 | 0.47 | 0.08 | 0.01 | 1.32 | | | 0.02 | 0.05 | 0.21 | 0.11 | 0.25 | 0.04 | 0.29 | >6.1 | | KRYFSTGAVLIQ |
| 35 | I | | >0.95 | 4.81 | >5.17 | >0.06 | >10.24 | | >2.5 | | | >14.59 | >12 | | 2.58 | | 0.78 | | | | I |
| 36 | G | 0.09 | 0.15 | 0.22 | >11.25 | >5.35 | >3.07 | 0.19 | 0.09 | >3.22 | 1.74 | | 0.58 | | 0.46 | 0.22 | 0.07 | 0.06 | 0.53 | | KRHFWVLIG |
| 37 | K | | 0.03 | 0.10 | 1.17 | >0.65 | 0.19 | 0.05 | 0.11 | 0.27 | 5.45 | 1.47 | 0.37 | 0.09 | | 0.19 | | 0.37 | 0.26 | | RHYFWNGVPK |

*wild type residue included

FIG. 1B

| Reference huwentoxin-IV residue | | Substitution | | | | | | | | | | | | | | | | | | |
|---|---|---|---|---|---|---|---|---|---|---|---|---|---|---|---|---|---|---|---|---|
| | | Basic | | | Acidic | | Aromatic | | | Uncharged Polar | | | | Nonpolar | | | | | | |
| | | K | R | H | D | E | Y | F | W | N | Q | S | T | G | A | V | L | I | P | M |
| | G | | | | | | | | | | | | | | | | | | | |
| | P | | | | | | | | | | | | | | | | | | | |
| 1 | E | 0.02 | 0.02 | 0.03 | 0.22 | | 0.07 | 0.07 | | 0.09 | 0.03 | 0.05 | 0.06 | 0.02 | | >0.03 | 0.03 | 0.03 | 0.03 | |
| 2 | C | | | | | | | | | | | | | | | | | | | |
| 3 | L | | 0.11 | | 1.60 | 2.90 | | 0.29 | 0.16 | 0.07 | | 0.18 | 0.48 | | 0.66 | 0.41 | | | 0.56 | |
| 4 | E | | 0.02 | 0.06 | 0.12 | | 0.04 | | | 0.03 | 0.02 | | | | | | 0.11 | 0.19 | 0.15 | |
| 5 | I | | >0.36 | 2.90 | | >0.82 | 0.07 | | 0.22 | 8.50 | | | 2.46 | | 0.28 | 0.12 | | | 1.17 | |
| 6 | F | | | 2.20 | >8.74 | | | | | >11.28 | | >0.56 | >0.75 | | 3.40 | >3.61 | 2.23 | | | 6.68 |
| 7 | K | | 0.03 | | | 0.67 | | | 0.08 | 0.23 | >0.27 | 0.09 | 0.19 | | | | | | | |
| 8 | A | | 0.01 | | | 0.14 | 0.05 | 0.14 | 0.31 | | | 0.48 | | | | 0.25 | | | | |
| 9 | C | | | | | | | | | | | | | | | | | | | |
| 10 | N | 0.24 | 0.09 | | 0.84 | 0.28 | 0.10 | 0.26 | 0.29 | | 0.40 | 0.17 | | | | 0.16 | | | | |
| 11 | P | 1.65 | >0.43 | | | 9.64 | | 0.44 | 0.34 | | 0.84 | 0.63 | | | | 0.33 | | | | |
| 12 | S | | 0.17 | 0.32 | | 0.97 | | 0.30 | 0.16 | | 0.07 | | | | | 0.15 | | | | |
| 13 | N | 0.57 | 0.17 | 0.77 | 0.43 | 0.77 | 0.23 | | 0.37 | | 0.49 | >0.98 | 0.19 | 3.74 | 0.07 | 0.98 | 1.33 | 0.95 | >0.85 | |
| 14 | D | 3.09 | 11.10 | 5.45 | | 6.86 | >1.27 | | 1.43 | | 7.57 | >1.46 | | >5.18 | 0.35 | 2.99 | >2.5 | >1.23 | 2.71 | |
| 15 | Q | 0.30 | 0.05 | 0.51 | 1.08 | 2.16 | 0.20 | | 0.79 | 0.06 | | 1.42 | 0.21 | | 0.35 | 4.91 | 1.39 | | 4.63 | |
| 16 | C | | | | | | | | | | | | | | | | | | | |
| 17 | C | | | | | | | | | | | | | | | | | | | |

FIG. 2A

| Reference huwentoxin-IV residue | | Substitution | | | | | | | | | | | | | | | | | | |
|---|---|---|---|---|---|---|---|---|---|---|---|---|---|---|---|---|---|---|---|---|
| | | Basic | | | Acidic | | Aromatic | | | Uncharged Polar | | | | Nonpolar | | | | | | |
| | | K | R | H | D | E | Y | F | W | N | Q | S | T | G | A | V | L | I | P | M |
| 18 | K | | 0.08 | 0.76 | | 0.91 | 0.08 | 3.46 | 2.38 | | 0.79 | 0.46 | 0.23 | 0.63 | 0.19 | | 0.72 | 0.32 | 2.40 | |
| 19 | S | 0.36 | 0.05 | | | | 0.20 | 0.31 | | 0.19 | 0.46 | | | 0.33 | 0.19 | 0.15 | 0.19 | 0.14 | 0.09 | |
| 20 | S | | 0.04 | 0.23 | 0.07 | 1.62 | 0.10 | | 0.87 | 0.07 | 0.59 | | 0.19 | 0.64 | | 0.73 | | 0.21 | 0.13 | 0.44 |
| 21 | K | | 0.04 | 0.12 | 0.71 | | | 0.13 | 0.65 | 0.06 | 0.50 | 0.10 | 0.44 | 0.03 | 0.37 | 1.97 | 0.20 | | | 0.35 |
| 22 | L | 1.08 | 0.10 | 2.39 | >6.23 | >7.35 | 0.18 | 0.43 | 2.31 | | >2.09 | 4.82 | 0.74 | 5.93 | >4.08 | | | | 0.25 | 1.41 |
| 23 | V | 1.05 | 0.23 | 1.03 | 6.30 | 6.12 | 0.57 | 1.38 | | 1.44 | 1.33 | | 0.31 | 2.13 | >1.51 | | 0.24 | | >6.57 | |
| 24 | C | | | | | | | | | | | | | | | | | | | |
| 25 | S | 2.58 | | >2.37 | 2.83 | >9.1 | >1.72 | >1.27 | >7.64 | 2.97 | >0.82 | | 5.01 | 2.46 | >0.83 | | | 0.12 | 0.03 | |
| 26 | R | 1.88 | | >6.3 | >5.81 | | | >0.61 | 0.40 | | | | >20.73 | 3.62 | >1.78 | >3.19 | | 1.05 | >3.66 | |
| 27 | K | | 0.04 | >20.3 | >10.22 | >10.57 | 0.10 | | >0.92 | 0.10 | >17.89 | >13.37 | | 0.32 | >2.95 | | 0.25 | >3.86 | >6.79 | |
| 28 | T | >6.64 | | | | 7.71 | | >0.05 | 1.08 | | 1.10 | | | | | 0.43 | >4.53 | | | |
| 29 | R | 0.35 | | 0.37 | >9.59 | >13.31 | >0.13 | | 0.41 | >2.59 | >14.53 | | | 1.59 | 1.03 | >0.13 | >0.9 | >0.71 | | |
| 30 | W | >2.95 | >0.49 | >10.14 | >1 | >0.37 | 36.60 | >1 | | >1.66 | >54.93 | >50.86 | >43.5 | >3.12 | >1.8 | >0.5 | >3.2 | >1.41 | >1.07 | |
| 31 | C | | | | | | | | | | | | | | | | | | | |
| 32 | K | | | >4.57 | | >1.94 | | >0.81 | >7.67 | >3.5 | >10.76 | >11.85 | >5.6 | >3.6 | >7.3 | >5.95 | >4.56 | >4.56 | >5.62 | |
| 33 | Y | 3.26 | | 2.29 | | | | >14.83 | 0.26 | | | 14.40 | 0.70 | 6.79 | 3.26 | 0.98 | | 0.30 | >8.03 | |
| 34 | Q | 0.17 | 0.08 | | 3.49 | >0.85 | 0.15 | >0.06 | 6.87 | | | 0.08 | 0.17 | 1.20 | 0.57 | 0.56 | 0.05 | 0.20 | >6.09 | |
| 35 | I | | >0.95 | >4.91 | >5.17 | >0.06 | >10.24 | | >7.67 | | | >14.59 | >12 | | 3.45 | | 0.82 | | | |
| 36 | G | 0.53 | 0.58 | 0.47 | >11.24 | >5.35 | 1.41 | >0.55 | 0.16 | >3.21 | 10.40 | | >2.85 | | 1.05 | >0.87 | 0.53 | 1.42 | 0.44 | |
| 37 | K | | 0.28 | 0.31 | 0.20 | >0.65 | 0.82 | 0.13 | 0.23 | 0.97 | >17.65 | 10.30 | 2.02 | 0.12 | | 0.63 | | 0.50 | 2.00 | |

FIG. 2B

| Reference huwentoxin-IV residues | | Substitution: Basic | | | Acidic | | Aromatic | | | Uncharged Polar | | | | Nonpolar | | | | | | | Residue substitutions in variants with increased selectivity | Residue substitutions in variants with increased potency and selectivity |
|---|---|---|---|---|---|---|---|---|---|---|---|---|---|---|---|---|---|---|---|---|---|---|
| | | K | R | H | D | E | Y | F | W | N | Q | S | T | G | A | V | L | I | P | M | | |
| | G | | | | | | | | | | | | | | | | | | | | | |
| | P | | | | | | | | | | | | | | | | | | | | | |
| 1 | E | 0.25 | 0.38 | 0.44 | 1.35 | | 0.41 | 0.54 | | 1.30 | 0.37 | 0.47 | 0.50 | 0.29 | | inact | 0.27 | 0.43 | 0.72 | | | |
| 2 | C | | | | | | | | | | | | | | | | | | | | | |
| 3 | L | | 0.43 | | 1.50 | 0.93 | | 1.83 | 1.09 | 0.64 | | 2.63 | 0.28 | | 1.22 | 0.55 | | | 0.30 | | | |
| 4 | E | | 0.91 | 1.28 | 1.60 | | 0.59 | | | 1.10 | 1.20 | | | | | | 1.28 | 0.92 | 1.37 | | | |
| 5 | I | | inact | 0.54 | | inact | 1.66 | | 0.52 | 0.51 | | | 0.58 | | 0.71 | 0.72 | | | 0.27 | | | |
| 6 | F | | | inact | inact | | | | | inact | | inact | inact | | 1.01 | ≥1,037 | 3.94 | | | 6.07 | VM | |
| 7 | K | | 0.51 | | | 0.88 | | | 1.36 | 0.52 | ≥0.891 | 0.61 | 0.22 | | | | | | | | Q | Q |
| 8 | A | | 0.47 | | | 2.33 | 0.50 | 0.79 | 0.84 | | | 0.39 | | | | 0.93 | | | | | | |
| 9 | C | | | | | | | | | | | | | | | | | | | | | |
| 10 | N | 0.89 | 0.84 | | 1.68 | 1.05 | 0.48 | 1.22 | 0.84 | | 0.59 | 0.84 | | | | 1.14 | | | | | | |
| 11 | P | 0.46 | ≥0.872 | | | 1.23 | | 0.71 | 0.82 | | 0.66 | 1.61 | | | | 1.44 | | | | | R | |
| 12 | S | | 1.38 | 0.92 | | 2.12 | | 1.22 | 0.06 | | 0.29 | | | | | 0.93 | | | | | | |
| 13 | N | 1.60 | 0.26 | 4.36 | 4.18 | 2.46 | 2.03 | | 5.15 | | 7.67 | ≥3,740 | 1.88 | 1979 | 2.93 | 4.24 | 4.84 | 6.70 | ≥3,219 | | WQSGIP | WQSGIP |
| 14 | D | 2.73 | 1.08 | 4.82 | | 4.88 | inact | | 4.81 | | 8.36 | ≥4,101 | | ≥7,154 | 0.45 | 2.42 | ≥2,475 | inact | 9.72 | | KQSGLP | P |
| 15 | Q | 1.22 | 1.22 | 1.43 | 6.17 | 9.60 | 2.71 | | 7.44 | 3.44 | | 3.84 | 2.46 | | 3.67 | 6.58 | 531 | | 13.23 | | DEWVLP | DEWL |
| 16 | C | | | | | | | | | | | | | | | | | | | | | |
| 17 | C | | | | | | | | | | | | | | | | | | | | | |

FIG. 3A

| Reference huwentoxin-IV residue | | Substitution | | | | | | | | | | | | | | | | | | | Residue substitutions in variants with increased selectivity | Residue substitutions in variants with increased potency and selectivity |
|---|---|---|---|---|---|---|---|---|---|---|---|---|---|---|---|---|---|---|---|---|---|---|
| | | Basic | | | Acidic | | Aromatic | | | Uncharged Polar | | | | Nonpolar | | | | | | | | |
| | | K | R | H | D | E | Y | F | W | N | Q | S | T | G | A | V | L | I | P | M | | |
| 18 | K | | 1.39 | 1.95 | | 2.31 | 1.81 | 9.56 | 5.21 | | 5.58 | 3.34 | 2.11 | 4.14 | 0.31 | | 4.65 | 3.24 | 10.61 | | FWQP | Q |
| 19 | S | 4.71 | 1.05 | | | | 2.06 | 3.03 | | 2.08 | 18.39 | | | 1.22 | 1.58 | 1.70 | 2.89 | 2.17 | 3.09 | | Q | Q |
| 20 | S | | 1.09 | 2.40 | 1.97 | 0.82 | 1.81 | | 6.81 | 2.81 | 3.67 | | 2.10 | 0.84 | | 5.60 | | 1.76 | 3.31 | 0.83 | WV | WV |
| 21 | K | | 2.00 | 3.01 | 2.38 | | | 3.33 | 8.52 | 1.39 | 4.28 | 1.53 | 1.71 | 0.19 | 2.31 | 1.30 | 2.15 | | | 0.96 | W | W |
| 22 | L | 4.50 | 2.06 | 3.33 | inact | >3.769 | 1.20 | 2.35 | 7.75 | | >0.774 | 4.23 | 2.18 | 4.30 | >7.846 | | | | 1.76 | 1.27 | EWQA | W |
| 23 | V | 3.49 | 1.52 | 2.61 | 1.34 | 2.11 | 1.47 | 2.99 | | 2.98 | 2.48 | | 3.57 | 2.13 | >13.24 | | 1.79 | | inact | | A | A |
| 24 | C | | | | | | | | | | | | | | | | | | | | C | |
| 25 | S | 4.23 | | inact | 1.52 | inact | inact | inact | inact | 4.24 | inact | | 1.63 | 0.66 | inact | | | 4.55 | 0.03 | | | |
| 26 | R | 9.53 | | >8.467 | >4.611 | | | inact | 5.64 | | | | >10.74 | 12.64 | >10.78 | >7.857 | | 5.20 | >1.989 | | KHDWTGAVIP | KWGAI |
| 27 | K | | 0.13 | >5.024 | inact | inact | 0.77 | | >14.74 | 0.06 | inact | inact | | 0.21 | >11.56 | | 0.25 | >4.587 | >0.622 | | HWAIP | WA |
| 28 | T | >1.227 | | | | 0.62 | | inact | 0.38 | | 1.87 | | | | | 2.06 | >0.796 | | | | KL | |
| 29 | R | 1.81 | | 5.75 | >10.14 | inact | inact | | 6.87 | >17.03 | inact | | | 7.67 | 3.99 | inact | >3.125 | inact | | | HDWNGL | HWNGL |
| 30 | W | >28.64 | inact | inact | inact | inact | 21.66 | inact | | inact | inact | inact | inact | inact | inact | inact | inact | inact | inact | | KY | K |
| 31 | C | | | | | | | | | | | | | | | | | | | | | |
| 32 | K | | | inact | | inact | | inact | >0.841 | inact | inact | inact | inact | inact | >0.823 | inact | inact | inact | inact | | WA | |
| 33 | Y | 0.76 | | 1.56 | | | | inact | 12.70 | | | 2.09 | 9.76 | 1.56 | 2.94 | 2.89 | | 2.88 | inact | | WT | WT |
| 34 | Q | 1.06 | 1.23 | | 0.59 | >1.808 | 2.01 | >4.379 | 5.20 | | | 4.41 | 3.36 | 5.77 | 5.40 | 2.24 | 1.18 | 0.71 | inact | | EFWGA | FGA |
| 35 | I | | inact | >1.020 | inact | inact | inact | | inact | | | inact | inact | | 1.34 | | 1.05 | | | | H | |
| 36 | G | 5.87 | 3.79 | 2.20 | inact | inact | inact | >2.972 | 1.87 | inact | 5.98 | | >4.905 | | 2.26 | >3.936 | 7.16 | 22.71 | 0.82 | | KFQTVLI | KFVLI |
| 37 | K | | 10.70 | 3.14 | 0.17 | inact | 4.37 | 2.60 | 2.04 | 3.54 | >3.238 | 7.01 | 5.42 | 1.40 | | 3.34 | | 1.34 | 7.72 | | RQSTP | RP |

FIG. 3B

| Peptide ID | Substitution | SEQ ID NO: | Sequence | $IC_{50}$ (Nav1.7) μM | $IC_{50}$ (Nav1.2) μM | Selectivity |
|---|---|---|---|---|---|---|
| HwTX-IV | Parent Synthetic | 1 | ECLEIFKACNPSNDQCCKSSKLVCSRKTRWCKYQI-NH2 | 0.04 | 0.07 | 1.66 |
| NV1D7 | Parent Recombinant | 2 | GPECLEIFKACNPSNDQCCKSSKLVCSRKTRWCKYQIGK | 0.16 | 0.34 | 2.14 |
| | | | | | | |
| NV1D2163 | E1N,E4R,Y33W,Q34S | 3 | GPNCLRIFKACNPSNDQCCKSSKLVCSRKTRWCKWSIGK | 0.01 | 0.02 | 1.58 |
| NV1D2142 | E1N,E4R,Q34S | 4 | GPNCLRIFKACNPSNDQCCKSSKLVCSRKTRWCKYSIGK | 0.01 | 0.02 | 1.77 |
| NV1D2161 | E1N,E4R,R26K,Q34S | 5 | GPNCLRIFKACNPSNDQCCKSSKLVCSKKTRWCKYSIGK | 0.01 | 0.11 | 8.33 |
| NV1D1780 | Q34F | 6 | GPECLEIFKACNPSNDQCCKSSKLVCSRKTRWCKYFIGK | 0.01 | >0.06 | >4.38 |
| NV1D2148 | E1N,Y33W,G36I | 7 | GPNCLEIFKACNPSNDQCCKSSKLVCSRKTRWCKWQIIK | 0.02 | 0.25 | 16.49 |
| NV1D2153 | E4R,Y33W,Q34S | 8 | GPECLRIFKACNPSNDQCCKSSKLVCSRKTRWCKWSIGK | 0.02 | 0.02 | 1.11 |
| NV1D1376 | E4Q | 9 | GPECLQIFKACNPSNDQCCKSSKLVCSRKTRWCKYQIGK | 0.02 | 0.02 | 1.20 |
| NV1D1783 | Q34S | 10 | GPECLEIFKACNPSNDQCCKSSKLVCSRKTRWCKYSIGK | 0.02 | 0.08 | 4.41 |
| NV1D1546 | Q15N | 11 | GPECLEIFKACNPSNDNCCKSSKLVCSRKTRWCKYQIGK | 0.02 | 0.06 | 3.44 |
| NV1D2143 | E1N,E4R,G36I | 12 | GPNCLRIFKACNPSNDQCCKSSKLVCSRKTRWCKYQIIK | 0.02 | 0.15 | 8.21 |
| NV1D1760 | Y33W | 13 | GPECLEIFKACNPSNDQCCKSSKLVCSRKTRWCKWQIGK | 0.02 | 0.26 | 12.70 |
| NV1D1608 | K21R | 14 | GPECLEIFKACNPSNDQCCKSSRLVCSRKTRWCKYQIGK | 0.02 | 0.04 | 2.00 |
| NV1D1448 | A8R | 15 | GPECLEIFKRCNPSNDQCCKSSKLVCSRKTRWCKYQIGK | 0.02 | 0.01 | 0.47 |
| NV1D2177 | E1N,E4R,R26K,Q34S,G36I | 16 | GPNCLRIFKACNPSNDQCCKSSKLVCSKKTRWCKYSIIK | 0.02 | 0.32 | 14.22 |
| NV1D2164 | E1N,E4R,Y33W,G36I | 17 | GPNCLRIFKACNPSNDQCCKSSKLVCSRKTRWCKWQIIK | 0.02 | 0.05 | 2.32 |
| NV1D1383 | E4R | 18 | GPECLRIFKACNPSNDQCCKSSKLVCSRKTRWCKYQIGK | 0.02 | 0.02 | 0.91 |
| NV1D2147 | E1N,Y33W,Q34S | 19 | GPNCLEIFKACNPSNDQCCKSSKLVCSRKTRWCKWSIGK | 0.02 | 0.01 | 0.57 |
| NV1D1594 | S20N | 20 | GPECLEIFKACNPSNDQCCKSNKLVCSRKTRWCKYQIGK | 0.02 | 0.07 | 2.81 |
| NV1D1569 | S19Q | 21 | GPECLEIFKACNPSNDQCCKQSKLVCSRKTRWCKYQIGK | 0.02 | 0.46 | 18.39 |
| NV1D2125 | E1N,E4R | 22 | GPNCLRIFKACNPSNDQCCKSSKLVCSRKTRWCKYQIGK | 0.03 | 0.03 | 1.10 |

FIG. 4(1)

| | | | | | | |
|---|---|---|---|---|---|---|
| NV1D93 | N13A | 23 | GPECLEIFKACNPSADQCCKSSKLVCSRKTRWCKYQIGK | 0.03 | 0.07 | 2.93 |
| NV1D1660 | S25I | 24 | GPECLEIFKACNPSNDQCCKSSKLVCIRKTRWCKYQIGK | 0.03 | 0.12 | 4.55 |
| NV1D1832 | K37R | 25 | GPECLEIFKACNPSNDQCCKSSKLVCSRKTRWCKYQIGR | 0.03 | 0.28 | 10.70 |
| NV1D1385 | E4N | 26 | GPECLNIFKACNPSNDQCCKSSKLVCSRKTRWCKYQIGK | 0.03 | 0.03 | 1.10 |
| NV1D1581 | S19P | 27 | GPECLEIFKACNPSNDQCCKPSKLVCSRKTRWCKYQIGK | 0.03 | 0.09 | 3.09 |
| NV1D1595 | S20D | 28 | GPECLEIFKACNPSNDQCCKSDKLVCSRKTRWCKYQIGK | 0.04 | 0.07 | 1.97 |
| NV1D1592 | S20R | 29 | GPECLEIFKACNPSNDQCCKSRKLVCSRKTRWCKYQIGK | 0.04 | 0.04 | 1.09 |
| NV1D1544 | Q15R | 30 | GPECLEIFKACNPSNDRCCKSSKLVCSRKTRWCKYQIGK | 0.04 | 0.05 | 1.22 |
| NV1D1790 | Q34L | 31 | GPECLEIFKACNPSNDQCCKSSKLVCSRKTRWCKYLIGK | 0.04 | 0.05 | 1.18 |
| NV1D2155 | E4R,Q34S,G36I | 32 | GPECLRIFKACNPSNDQCCKSSKLVCSRKTRWCKYSIIK | 0.04 | 0.04 | 1.00 |
| NV1D1604 | K21F | 33 | GPECLEIFKACNPSNDQCCKSSFLVCSRKTRWCKYQIGK | 0.04 | 0.13 | 3.33 |
| NV1D1606 | K21H | 34 | GPECLEIFKACNPSNDQCCKSSHLVCSRKTRWCKYQIGK | 0.04 | 0.12 | 3.01 |
| NV1D1597 | S20P | 35 | GPECLEIFKACNPSNDQCCKSPKLVCSRKTRWCKYQIGK | 0.04 | 0.13 | 3.31 |
| NV1D2162 | E1N,E4R,R26K,G36I | 36 | GPNCLRIFKACNPSNDQCCKSSKLVCSKKTRWCKYQIIK | 0.04 | 0.17 | 4.06 |
| NV1D1610 | K21N | 37 | GPECLEIFKACNPSNDQCCKSSNLVCSRKTRWCKYQIGK | 0.04 | 0.06 | 1.39 |
| NV1D1557 | K18Y | 38 | GPECLEIFKACNPSNDQCCYSSKLVCSRKTRWCKYQIGK | 0.04 | 0.08 | 1.81 |
| NV1D1397 | I5Y | 39 | GPECLEYFKACNPSNDQCCKSSKLVCSRKTRWCKYQIGK | 0.04 | 0.07 | 1.66 |
| NV1D2165 | E1N,E4R,Q34S,G36I | 40 | GPNCLRIFKACNPSNDQCCKSSKLVCSRKTRWCKYSIIK | 0.04 | 0.09 | 2.07 |
| NV1D1576 | S19R | 41 | GPECLEIFKACNPSNDQCCKRSKLVCSRKTRWCKYQIGK | 0.05 | 0.05 | 1.05 |
| NV1D1356 | E1P | 42 | GPPCLEIFKACNPSNDQCCKSSKLVCSRKTRWCKYQIGK | 0.05 | 0.03 | 0.72 |
| NV1D1625 | L22R | 43 | GPECLEIFKACNPSNDQCCKSSKRVCSRKTRWCKYQIGK | 0.05 | 0.10 | 2.06 |
| NV1D1381 | E4H | 44 | GPECLHIFKACNPSNDQCCKSSKLVCSRKTRWCKYQIGK | 0.05 | 0.06 | 1.28 |
| NV1D2130 | E4R,R26K | 45 | GPECLRIFKACNPSNDQCCKSSKLVCSKKTRWCKYQIGK | 0.05 | 0.25 | 5.15 |
| NV1D2134 | R26K,Y33W | 46 | GPECLEIFKACNPSNDQCCKSSKLVCSKKTRWCKWQIGK | 0.05 | 0.77 | 15.76 |
| NV1D1828 | K37F | 47 | GPECLEIFKACNPSNDQCCKSSKLVCSRKTRWCKYQIGF | 0.05 | 0.13 | 2.60 |
| NV1D2171 | E4R,R26K,Y33W,G36I | 48 | GPECLRIFKACNPSNDQCCKSSKLVCSKKTRWCKWQIIK | 0.05 | 0.34 | 6.63 |
| NV1D1785 | Q34T | 49 | GPECLEIFKACNPSNDQCCKSSKLVCSRKTRWCKYTIGK | 0.05 | 0.17 | 3.36 |

FIG. 4(2)

| | | | | | | |
|---|---|---|---|---|---|---|
| NV1D1351 | E1R | 50 | GPRCLEIFKACNPSNDQCCKSSKLVCSRKTRWCKYQIGK | 0.05 | 0.02 | 0.38 |
| NV1D1560 | K18R | 51 | GPECLEIFKACNPSNDQCCRSSKLVCSRKTRWCKYQIGK | 0.06 | 0.08 | 1.39 |
| NV1D2133 | E4R,G36I | 52 | GPECLRIFKACNPSNDQCCKSSKLVCSRKTRWCKYQIIK | 0.06 | 0.24 | 4.23 |
| NV1D1590 | S20Y | 53 | GPECLEIFKACNPSNDQCCKSYKLVCSRKTRWCKYQIGK | 0.06 | 0.10 | 1.81 |
| NV1D1441 | A8E | 54 | GPECLEIFKECNPSNDQCCKSSKLVCSRKTRWCKYQIGK | 0.06 | 0.14 | 2.33 |
| NV1D1712 | R29W | 55 | GPECLEIFKACNPSNDQCCKSSKLVCSRKTWWCKYQIGK | 0.06 | 0.41 | 6.87 |
| NV1D1423 | K7W | 56 | GPECLEIFWACNPSNDQCCKSSKLVCSRKTRWCKYQIGK | 0.06 | 0.08 | 1.36 |
| NV1D1680 | K27W | 57 | GPECLEIFKACNPSNDQCCKSSKLVCSRWTRWCKYQIGK | 0.06 | >0.92 | >14.75 |
| NV1D1821 | G36I | 58 | GPECLEIFKACNPSNDQCCKSSKLVCSRKTRWCKYQIIK | 0.06 | 1.42 | 22.71 |
| NV1D1345 | E1K | 59 | GPKCLEIFKACNPSNDQCCKSSKLVCSRKTRWCKYQIGK | 0.06 | 0.02 | 0.25 |
| NV1D1719 | R29H | 60 | GPECLEIFKACNPSNDQCCKSSKLVCSRKTHWCKYQIGK | 0.06 | 0.37 | 5.75 |
| NV1D1505 | N13Q | 61 | GPECLEIFKACNPSQDQCCKSSKLVCSRKTRWCKYQIGK | 0.06 | 0.49 | 7.67 |
| NV1D1380 | E4Y | 62 | GPECLYIFKACNPSNDQCCKSSKLVCSRKTRWCKYQIGK | 0.06 | 0.04 | 0.59 |
| NV1D1784 | Q34R | 63 | GPECLEIFKACNPSNDQCCKSSKLVCSRKTRWCKYRIGK | 0.06 | 0.08 | 1.23 |
| NV1D1580 | S19I | 64 | GPECLEIFKACNPSNDQCCKISKLVCSRKTRWCKYQIGK | 0.07 | 0.14 | 2.17 |
| NV1D2150 | E4R,R26K,Y33W | 65 | GPECLRIFKACNPSNDQCCKSSKLVCSKKTRWCKWQIGK | 0.07 | 0.04 | 0.62 |
| NV1D1582 | S19L | 66 | GPECLEIFKACNPSNDQCCKLSKLVCSRKTRWCKYQIGK | 0.07 | 0.19 | 2.89 |
| NV1D1353 | E1N | 67 | GPNCLEIFKACNPSNDQCCKSSKLVCSRKTRWCKYQIGK | 0.07 | 0.09 | 1.30 |
| NV1D1607 | K21S | 68 | GPECLEIFKACNPSNDQCCKSSSLVCSRKTRWCKYQIGK | 0.07 | 0.10 | 1.53 |
| NV1D1431 | K7R | 69 | GPECLEIFRACNPSNDQCCKSSKLVCSRKTRWCKYQIGK | 0.07 | 0.03 | 0.51 |
| NV1D1367 | L3S | 70 | GPECSEIFKACNPSNDQCCKSSKLVCSRKTRWCKYQIGK | 0.07 | 0.18 | 2.63 |
| NV1D1349 | E1H | 71 | GPHCLEIFKACNPSNDQCCKSSKLVCSRKTRWCKYQIGK | 0.07 | 0.03 | 0.44 |
| NV1D1664 | R26W | 72 | GPECLEIFKACNPSNDQCCKSSKLVCSWKTRWCKYQIGK | 0.07 | 0.40 | 5.64 |
| NV1D1355 | E1I | 73 | GPICLEIFKACNPSNDQCCKSSKLVCSRKTRWCKYQIGK | 0.07 | 0.03 | 0.43 |
| NV1D1504 | N13W | 74 | GPECLEIFKACNPSWDQCCKSSKLVCSRKTRWCKYQIGK | 0.07 | 0.37 | 5.15 |
| NV1D2152 | E4R,R26K,G36I | 75 | GPECLRIFKACNPSNDQCCKSSKLVCSKKTRWCKYQIIK | 0.07 | 0.33 | 4.60 |

FIG. 4(3)

| | | | | | | |
|---|---|---|---|---|---|---|
| NV1D1769 | Y33T | 76 | GPECLEIFKACNPSNDQCCKSSKLVCSRKTRWCKTQIGK | 0.07 | 0.70 | 9.76 |
| NV1D1386 | E4D | 77 | GPECLDIFKACNPSNDQCCKSSKLVCSRKTRWCKYQIGK | 0.07 | 0.12 | 1.60 |
| NV1D1823 | G36L | 78 | GPECLEIFKACNPSNDQCCKSSKLVCSRKTRWCKYQILK | 0.07 | 0.53 | 7.16 |
| NV1D1541 | Q15Y | 79 | GPECLEIFKACNPSNDYCCKSSKLVCSRKTRWCKYQIGK | 0.07 | 0.20 | 2.71 |
| NV1D1781 | Q34Y | 80 | GPECLEIFKACNPSNDQCCKSSKLVCSRKTRWCKYYIGK | 0.08 | 0.15 | 2.01 |
| NV1D1571 | S19K | 81 | GPECLEIFKACNPSNDQCCKKSKLVCSRKTRWCKYQIGK | 0.08 | 0.36 | 4.71 |
| NV1D1600 | K21W | 82 | GPECLEIFKACNPSNDQCCKSSWLVCSRKTRWCKYQIGK | 0.08 | 0.65 | 8.52 |
| NV1D2169 | E1N,Y33W,Q34S,G36I | 83 | GPNCLEIFKACNPSNDQCCKSSKLVCSRKTRWCKWSIIK | 0.08 | 0.50 | 6.38 |
| NV1D2175 | E1N,E4R,R26K,Y33W,Q34S | 84 | GPNCLRIFKACNPSNDQCCKSSKLVCSKKTRWCKWSIGK | 0.08 | 0.18 | 2.25 |
| NV1D1389 | E4L | 85 | GPECLLIFKACNPSNDQCCKSSKLVCSRKTRWCKYQIGK | 0.08 | 0.11 | 1.28 |
| NV1D1358 | E1G | 86 | GPGCLEIFKACNPSNDQCCKSSKLVCSRKTRWCKYQIGK | 0.08 | 0.02 | 0.29 |
| NV1D1545 | Q15T | 87 | GPECLEIFKACNPSNDTCCKSSKLVCSRKTRWCKYQIGK | 0.08 | 0.21 | 2.46 |
| NV1D1572 | S19V | 88 | GPECLEIFKACNPSNDQCCKVSKLVCSRKTRWCKYQIGK | 0.09 | 0.15 | 1.70 |
| NV1D1808 | G36W | 89 | GPECLEIFKACNPSNDQCCKSSKLVCSRKTRWCKYQIWK | 0.09 | 0.16 | 1.87 |
| NV1D1641 | V23T | 90 | GPECLEIFKACNPSNDQCCKSSKLTCSRKTRWCKYQIGK | 0.09 | 0.31 | 3.57 |
| NV1D2160 | E1N,E4R,R26K,Y33W | 91 | GPNCLRIFKACNPSNDQCCKSSKLVCSKKTRWCKWQIGK | 0.09 | 0.19 | 2.24 |
| NV1D1839 | K37G | 92 | GPECLEIFKACNPSNDQCCKSSKLVCSRKTRWCKYQIGG | 0.09 | 0.12 | 1.40 |
| NV1D1344 | E1Q | 93 | GPQCLEIFKACNPSNDQCCKSSKLVCSRKTRWCKYQIGK | 0.09 | 0.03 | 0.37 |
| NV1D2154 | E4R,Y33W,G36I | 94 | GPECLRIFKACNPSNDQCCKSSKLVCSRKTRWCKWQIIK | 0.09 | 0.16 | 1.80 |
| NV1D2173 | E4R,Y33W,Q34S,G36I | 95 | GPECLRIFKACNPSNDQCCKSSKLVCSRKTRWCKWSIIK | 0.09 | 0.18 | 2.03 |
| NV1D1811 | G36K | 96 | GPECLEIFKACNPSNDQCCKSSKLVCSRKTRWCKYQIKK | 0.09 | 0.53 | 5.87 |
| NV1D1578 | S19N | 97 | GPECLEIFKACNPSNDQCCKNSKLVCSRKTRWCKYQIGK | 0.09 | 0.19 | 2.08 |
| NV1D1593 | S20T | 98 | GPECLEIFKACNPSNDQCCKSTKLVCSRKTRWCKYQIGK | 0.09 | 0.19 | 2.10 |
| NV1D1614 | K21L | 99 | GPECLEIFKACNPSNDQCCKSSLLVCSRKTRWCKYQIGK | 0.09 | 0.20 | 2.15 |
| NV1D1591 | S20H | 100 | GPECLEIFKACNPSNDQCCKSHKLVCSRKTRWCKYQIGK | 0.09 | 0.23 | 2.40 |
| NV1D95 | Q15A | 101 | GPECLEIFKACNPSNDACCKSSKLVCSRKTRWCKYQIGK | 0.10 | 0.35 | 3.67 |

FIG. 4(4)

| | | | | | | |
|---|---|---|---|---|---|---|
| NV1D2128 | E1N,Q34S | 102 | GPNCLEIFKACNPSNDQCCKSSKLVCSRKTRWCKYSIGK | 0.10 | 0.25 | 2.58 |
| NV1D1830 | K37H | 103 | GPECLEIFKACNPSNDQCCKSSKLVCSRKTRWCKYQIGH | 0.10 | 0.31 | 3.14 |
| NV1D1574 | S19Y | 104 | GPECLEIFKACNPSNDQCCKYSKLVCSRKTRWCKYQIGK | 0.10 | 0.20 | 2.06 |
| NV1D1564 | K18I | 105 | GPECLEIFKACNPSNDQCCISSKLVCSRKTRWCKYQIGK | 0.10 | 0.32 | 3.24 |
| NV1D1573 | S19F | 106 | GPECLEIFKACNPSNDQCCKFSKLVCSRKTRWCKYQIGK | 0.10 | 0.31 | 3.03 |
| NV1D1514 | N13T | 107 | GPECLEIFKACNPSTDQCCKSSKLVCSRKTRWCKYQIGK | 0.10 | 0.19 | 1.88 |
| NV1D1515 | N13D | 108 | GPECLEIFKACNPSDDQCCKSSKLVCSRKTRWCKYQIGK | 0.10 | 0.43 | 4.18 |
| NV1D1730 | W30K | 109 | GPECLEIFKACNPSNDQCCKSSKLVCSRKTRKCKYQIGK | 0.10 | >2.95 | >28.65 |
| NV1D1772 | Y33I | 110 | GPECLEIFKACNPSNDQCCKSSKLVCSRKTRWCKIQIGK | 0.10 | 0.30 | 2.88 |
| NV1D111 | Q34A | 111 | GPECLEIFKACNPSNDQCCKSSKLVCSRKTRWCKYAIGK | 0.11 | 0.57 | 5.40 |
| NV1D2149 | E1N,Q34S,G36I | 112 | GPNCLEIFKACNPSNDQCCKSSKLVCSRKTRWCKYSIIK | 0.11 | 0.28 | 2.67 |
| NV1D1536 | Q15W | 113 | GPECLEIFKACNPSNDWCCKSSKLVCSRKTRWCKYQIGK | 0.11 | 0.79 | 7.44 |
| NV1D1357 | E1L | 114 | GPLCLEIFKACNPSNDQCCKSSKLVCSRKTRWCKYQIGK | 0.11 | 0.03 | 0.27 |
| NV1D1350 | E1S | 115 | GPSCLEIFKACNPSNDQCCKSSKLVCSRKTRWCKYQIGK | 0.11 | 0.05 | 0.47 |
| NV1D1388 | E4P | 116 | GPECLPIFKACNPSNDQCCKSSKLVCSRKTRWCKYQIGK | 0.11 | 0.15 | 1.37 |
| NV1D1561 | K18T | 117 | GPECLEIFKACNPSNDQCCTSSKLVCSRKTRWCKYQIGK | 0.11 | 0.23 | 2.11 |
| NV1D1445 | A8Y | 118 | GPECLEIFKYCNPSNDQCCKSSKLVCSRKTRWCKYQIGK | 0.11 | 0.05 | 0.50 |
| NV1D1370 | L3N | 119 | GPECNEIFKACNPSNDQCCKSSKLVCSRKTRWCKYQIGK | 0.11 | 0.07 | 0.64 |
| NV1D1465 | N10R | 120 | GPECLEIFKACRPSNDQCCKSSKLVCSRKTRWCKYQIGK | 0.11 | 0.09 | 0.84 |
| NV1D1824 | K37W | 121 | GPECLEIFKACNPSNDQCCKSSKLVCSRKTRWCKYQIGW | 0.11 | 0.23 | 2.04 |
| NV1D102 | V23A | 122 | GPECLEIFKACNPSNDQCCKSSKLACSRKTRWCKYQIGK | 0.11 | >1.51 | >13.25 |
| NV1D1510 | N13Y | 123 | GPECLEIFKACNPSYDQCCKSSKLVCSRKTRWCKYQIGK | 0.11 | 0.23 | 2.03 |
| NV1D1601 | K21Q | 124 | GPECLEIFKACNPSNDQCCKSSQLVCSRKTRWCKYQIGK | 0.12 | 0.50 | 4.28 |
| NV1D98 | S19A | 125 | GPECLEIFKACNPSNDQCCKASKLVCSRKTRWCKYQIGK | 0.12 | 0.19 | 1.58 |
| NV1D1596 | S20I | 126 | GPECLEIFKACNPSNDQCCKSIKLVCSRKTRWCKYQIGK | 0.12 | 0.21 | 1.76 |
| NV1D2159 | Y33W,Q34S,G36I | 127 | GPECLEIFKACNPSNDQCCKSSKLVCSRKTRWCKWSIIK | 0.12 | 0.68 | 5.70 |

FIG. 4(5)

| | | | | | | |
|---|---|---|---|---|---|---|
| NV1D1352 | E1T | 128 | GPTCLEIFKACNPSNDQCCKSSKLVCSRKTRWCKYQIGK | 0.12 | 0.06 | 0.50 |
| NV1D2166 | E1N,R26K,Y33W,Q34S | 129 | GPNCLEIFKACNPSNDQCCKSSKLVCSKKTRWCKWSIGK | 0.13 | 0.17 | 1.32 |
| NV1D1496 | S12R | 130 | GPECLEIFKACNPRNDQCCKSSKLVCSRKTRWCKYQIGK | 0.13 | 0.17 | 1.38 |
| NV1D1584 | S20W | 131 | GPECLEIFKACNPSNDQCCKSWKLVCSRKTRWCKYQIGK | 0.13 | 0.87 | 6.81 |
| NV1D2141 | E1N,E4R,Y33W | 132 | GPNCLRIFKACNPSNDQCCKSSKLVCSRKTRWCKWQIGK | 0.13 | 0.13 | 1.03 |
| NV1D1685 | K27Y | 133 | GPECLEIFKACNPSNDQCCKSSKLVCSRYTRWCKYQIGK | 0.13 | 0.10 | 0.77 |
| NV1D1588 | S20V | 134 | GPECLEIFKACNPSNDQCCKSVKLVCSRKTRWCKYQIGK | 0.13 | 0.73 | 5.60 |
| NV1D1646 | V23L | 135 | GPECLEIFKACNPSNDQCCKSSKLLCSRKTRWCKYQIGK | 0.13 | 0.24 | 1.79 |
| NV1D2139 | Q34S,G36I | 136 | GPECLEIFKACNPSNDQCCKSSKLVCSRKTRWCKYSIIK | 0.13 | 0.13 | 1.00 |
| NV1D2218 | N13Q,R29K,K37R | 137 | GPECLEIFKACNPSQDQCCKSSKLVCSRKTKWCKYQIGR | 0.13 | 0.73 | 5.52 |
| NV1D2156 | R26K,Y33W,Q34S | 138 | GPECLEIFKACNPSNDQCCKSSKLVCSKKTRWCKWSIGK | 0.13 | 0.32 | 2.38 |
| NV1D1347 | E1F | 139 | GPFCLEIFKACNPSNDQCCKSSKLVCSRKTRWCKYQIGK | 0.14 | 0.07 | 0.54 |
| NV1D1559 | K18S | 140 | GPECLEIFKACNPSNDQCCSSSKLVCSRKTRWCKYQIGK | 0.14 | 0.46 | 3.34 |
| NV1D1553 | K18Q | 141 | GPECLEIFKACNPSNDQCCQSSKLVCSRKTRWCKYQIGK | 0.14 | 0.79 | 5.58 |
| NV1D1516 | N13I | 142 | GPECLEIFKACNPSIDQCCKSSKLVCSRKTRWCKYQIGK | 0.14 | 0.95 | 6.70 |
| NV1D1630 | L22P | 143 | GPECLEIFKACNPSNDQCCKSSKPVCSRKTRWCKYQIGK | 0.14 | 0.25 | 1.76 |
| NV1D1460 | N10V | 144 | GPECLEIFKACVPSNDQCCKSSKLVCSRKTRWCKYQIGK | 0.14 | 0.16 | 1.14 |
| NV1D1430 | K7S | 145 | GPECLEIFSACNPSNDQCCKSSKLVCSRKTRWCKYQIGK | 0.14 | 0.09 | 0.61 |
| NV1D1622 | L22Y | 146 | GPECLEIFKACNPSNDQCCKSSKYVCSRKTRWCKYQIGK | 0.15 | 0.18 | 1.20 |
| NV1D1359 | L3W | 147 | GPECWEIFKACNPSNDQCCKSSKLVCSRKTRWCKYQIGK | 0.15 | 0.16 | 1.09 |
| NV1D1567 | K18G | 148 | GPECLEIFKACNPSNDQCCGSSKLVCSRKTRWCKYQIGK | 0.15 | 0.63 | 4.14 |
| NV1D1722 | R29N | 149 | GPECLEIFKACNPSNDQCCKSSKLVCSRKTNWCKYQIGK | 0.15 | >2.59 | >17.04 |
| NV1D1817 | G36R | 150 | GPECLEIFKACNPSNDQCCKSSKLVCSRKTRWCKYQIRK | 0.15 | 0.58 | 3.79 |
| NV1D1640 | V23R | 151 | GPECLEIFKACNPSNDQCCKSSKLRCSRKTRWCKYQIGK | 0.15 | 0.23 | 1.52 |
| NV1D1566 | K18L | 152 | GPECLEIFKACNPSNDQCCLSSKLVCSRKTRWCKYQIGK | 0.16 | 0.72 | 4.65 |
| NV1D1615 | K21G | 153 | GPECLEIFKACNPSNDQCCKSSGLVCSRKTRWCKYQIGK | 0.16 | 0.03 | 0.19 |
| NV1D1778 | Q34K | 154 | GPECLEIFKACNPSNDQCCKSSKLVCSRKTRWCKYKIGK | 0.16 | 0.17 | 1.06 |

FIG. 4(6)

| | | | | | | |
|---|---|---|---|---|---|---|
| NV1D2129 | E1N,G36I | 155 | GPNCLEIFKACNPSNDQCCKSSKLVCSRKTRWCKYQIIK | 0.16 | 0.16 | 1.00 |
| NV1D1364 | I3F | 156 | GPECFEIFKACNPSNDQCCKSSKLVCSRKTRWCKYQIGK | 0.16 | 0.29 | 1.83 |
| NV1D1395 | I5V | 157 | GPECLEVFKACNPSNDQCCKSSKLVCSRKTRWCKYQIGK | 0.16 | 0.12 | 0.72 |
| NV1D2145 | E1N,R26K,Q34S | 158 | GPNCLEIFKACNPSNDQCCKSSKLVCSKKTRWCKYSIGK | 0.16 | 0.27 | 1.68 |
| NV1D1585 | S20Q | 159 | GPECLEIFKACNPSNDQCCKSQKLVCSRKTRWCKYQIGK | 0.16 | 0.59 | 3.67 |
| NV1D1354 | E1D | 160 | GPDCLEIFKACNPSNDQCCKSSKLVCSRKTRWCKYQIGK | 0.16 | 0.22 | 1.35 |
| NV1D1348 | E1Y | 161 | GPYCLEIFKACNPSNDQCCKSSKLVCSRKTRWCKYQIGK | 0.16 | 0.07 | 0.41 |
| NV1D100 | K21A | 162 | GPECLEIFKACNPSNDQCCKSSALVCSRKTRWCKYQIGK | 0.16 | 0.37 | 2.31 |
| NV1D1492 | S12V | 163 | GPECLEIFKACNPVNDQCCKSSKLVCSRKTRWCKYQIGK | 0.16 | 0.15 | 0.93 |
| NV1D104 | R26A | 164 | GPECLEIFKACNPSNDQCCKSSKLVCSAKTRWCKYQIGK | 0.17 | >1.78 | >10.79 |
| NV1D1547 | Q15D | 165 | GPECLEIFKACNPSNDDCCKSSKLVCSRKTRWCKYQIGK | 0.18 | 1.08 | 6.17 |
| NV1D1511 | N13H | 166 | GPECLEIFKACNPSHDQCCKSSKLVCSRKTRWCKYQIGK | 0.18 | 0.77 | 4.36 |
| NV1D1444 | A8F | 167 | GPECLEIFKFCNPSNDQCCKSSKLVCSRKTRWCKYQIGK | 0.18 | 0.14 | 0.79 |
| NV1D1621 | L22F | 168 | GPECLEIFKACNPSNDQCCKSSKFVCSRKTRWCKYQIGK | 0.18 | 0.43 | 2.35 |
| NV1D1813 | G36F | 169 | GPECLEIFKACNPSNDQCCKSSKLVCSRKTRWCKYQIFK | 0.19 | >0.55 | >2.98 |
| NV1D1827 | K37V | 170 | GPECLEIFKACNPSNDQCCKSSKLVCSRKTRWCKYQIGV | 0.19 | 0.63 | 3.34 |
| NV1D1829 | K37Y | 171 | GPECLEIFKACNPSNDQCCKSSKLVCSRKTRWCKYQIGY | 0.19 | 0.82 | 4.37 |
| NV1D1519 | N13G | 172 | GPECLEIFKACNPSGDQCCKSSKLVCSRKTRWCKYQIGK | 0.19 | 3.74 | 19.79 |
| NV1D2140 | E1N,E4R,R26K | 173 | GPNCLRIFKACNPSNDQCCKSSKLVCSKKTRWCKYQIGK | 0.19 | 0.29 | 1.51 |
| NV1D1715 | R29K | 174 | GPECLEIFKACNPSNDQCCKSSKLVCSRKTKWCKYQIGK | 0.20 | 0.35 | 1.81 |
| NV1D1667 | R26K | 175 | GPECLEIFKACNPSNDQCCKSSKLVCSKKTRWCKYQIGK | 0.20 | 1.88 | 9.53 |
| NV1D1464 | N10S | 176 | GPECLEIFKACSPSNDQCCKSSKLVCSRKTRWCKYQIGK | 0.20 | 0.17 | 0.84 |
| NV1D1676 | R26I | 177 | GPECLEIFKACNPSNDQCCKSSKLVCSIKTRWCKYQIGK | 0.20 | 1.05 | 5.20 |
| NV1D2158 | R26K,Q34S,G36I | 178 | GPECLEIFKACNPSNDQCCKSSKLVCSKKTRWCKYSIIK | 0.20 | 1.22 | 6.04 |
| NV1D1387 | E4I | 179 | GPECLIIFKACNPSNDQCCKSSKLVCSRKTRWCKYQIGK | 0.20 | 0.19 | 0.92 |
| NV1D1727 | R29G | 180 | GPECLEIFKACNPSNDQCCKSSKLVCSRKTGWCKYQIGK | 0.21 | 1.59 | 7.67 |
| NV1D1727 | R29G | 181 | GPECLEIFKACNPSNDQCCKSSKLVCSRKTGWCKYQIGK | 0.21 | >2.79 | >13.5 |

FIG. 4(7)

| | | | | | | |
|---|---|---|---|---|---|---|
| NV1D1791 | Q34G | 182 | GPECLEIFKACNPSNDQCCKSSKLVCSRKTRWCKYGIGK | 0.21 | 1.20 | 5.77 |
| NV1D1700 | T28V | 183 | GPECLEIFKACNPSNDQCCKSSKLVCSRKVRWCKYQIGK | 0.21 | 0.43 | 2.06 |
| NV1D1815 | G36H | 184 | GPECLEIFKACNPSNDQCCKSSKLVCSRKTRWCKYQIHK | 0.22 | 0.47 | 2.20 |
| NV1D1461 | N10F | 185 | GPECLEIFKACFPSNDQCCKSSKLVCSRKTRWCKYQIGK | 0.22 | 0.26 | 1.22 |
| NV1D1462 | N10Y | 186 | GPECLEIFKACYPSNDQCCKSSKLVCSRKTRWCKYQIGK | 0.22 | 0.10 | 0.48 |
| NV1D1812 | G36V | 187 | GPECLEIFKACNPSNDQCCKSSKLVCSRKTRWCKYQIVK | 0.22 | >0.87 | >3.94 |
| NV1D1537 | Q15E | 188 | GPECLEIFKACNPSNDECCKSSKLVCSRKTRWCKYQIGK | 0.23 | 2.16 | 9.60 |
| NV1D1565 | K18P | 189 | GPECLEIFKACNPSNDQCCPSSKLVCSRKTRWCKYQIGK | 0.23 | 2.40 | 10.61 |
| NV1D1508 | N13V | 190 | GPECLEIFKACNPSVDQCCKSSKLVCSRKTRWCKYQIGK | 0.23 | 0.98 | 4.24 |
| NV1D1476 | P11V | 191 | GPECLEIFKACNVSNDQCCKSSKLVCSRKTRWCKYQIGK | 0.23 | 0.33 | 1.44 |
| NV1D2168 | E1N,R26K,Q34S,G36I | 192 | GPNCLEIFKACNPSNDQCCKSSKLVCSKKTRWCKYSIIK | 0.24 | >7.14 | >30.32 |
| NV1D1619 | L22K | 193 | GPECLEIFKACNPSNDQCCKSSKKVCSRKTRWCKYQIGK | 0.24 | 1.08 | 4.50 |
| NV1D1493 | S12F | 194 | GPECLEIFKACNPFNDQCCKSSKLVCSRKTRWCKYQIGK | 0.24 | 0.30 | 1.22 |
| NV1D1538 | Q15K | 195 | GPECLEIFKACNPSNDKCCKSSKLVCSRKTRWCKYQIGK | 0.24 | 0.30 | 1.22 |
| NV1D2135 | R26K,Q34S | 196 | GPECLEIFKACNPSNDQCCKSSKLVCSKKTRWCKYSIGK | 0.25 | 0.52 | 2.10 |
| NV1D1779 | Q34V | 197 | GPECLEIFKACNPSNDQCCKSSKLVCSRKTRWCKYVIGK | 0.25 | 0.56 | 2.24 |
| NV1D105 | K27A | 198 | GPECLEIFKACNPSNDQCCKSSKLVCSRATRWCKYQIGK | 0.26 | >2.95 | >11.57 |
| NV1D1609 | K21T | 199 | GPECLEIFKACNPSNDQCCKSSTLVCSRKTRWCKYQIGK | 0.26 | 0.44 | 1.71 |
| NV1D1489 | S12Q | 200 | GPECLEIFKACNPQNDQCCKSSKLVCSRKTRWCKYQIGK | 0.26 | 0.07 | 0.29 |
| NV1D107 | R29A | 201 | GPECLEIFKACNPSNDQCCKSSKLVCSRKTAWCKYQIGK | 0.26 | 1.03 | 3.99 |
| NV1D1837 | K37P | 202 | GPECLEIFKACNPSNDQCCKSSKLVCSRKTRWCKYQIGP | 0.26 | 2.00 | 7.72 |
| NV1D1512 | N13S | 203 | GPECLEIFKACNPSSDQCCKSSKLVCSRKTRWCKYQIGK | 0.26 | >0.98 | >3.75 |
| NV1D1550 | Q15L | 204 | GPECLEIFKACNPSNDLCCKSSKLVCSRKTRWCKYQIGK | 0.26 | 1.39 | 5.31 |
| NV1D1443 | A8V | 205 | GPECLEIFKVCNPSNDQCCKSSKLVCSRKTRWCKYQIGK | 0.26 | 0.25 | 0.93 |
| NV1D1458 | N10E | 206 | GPECLEIFKACEPSNDQCCKSSKLVCSRKTRWCKYQIGK | 0.26 | 0.28 | 1.05 |
| NV1D1517 | N13P | 207 | GPECLEIFKACNPSPDQCCKSSKLVCSRKTRWCKYQIGK | 0.26 | >0.85 | >3.22 |
| NV1D1368 | L3R | 208 | GPECREIFKACNPSNDQCCKSSKLVCSRKTRWCKYQIGK | 0.27 | 0.11 | 0.43 |

FIG. 4(8)

| | | | | | | |
|---|---|---|---|---|---|---|
| NV1D1459 | N10K | 209 | GPECLEIFKACKPSNDQCCKSSKLVCSRKTRWCKYQIGK | 0.27 | 0.24 | 0.89 |
| NV1D1583 | S19G | 210 | GPECLEIFKACNPSNDQCCKGSKLVCSRKTRWCKYQIGK | 0.27 | 0.33 | 1.22 |
| NV1D1834 | K37N | 211 | GPECLEIFKACNPSNDQCCKSSKLVCSRKTRWCKYQIGN | 0.27 | 0.97 | 3.54 |
| NV1D1518 | N13L | 212 | GPECLEIFKACNPSLDQCCKSSKLVCSRKTRWCKYQIGK | 0.28 | 1.33 | 4.84 |
| NV1D1533 | D14P | 213 | GPECLEIFKACNPSNPQCCKSSKLVCSRKTRWCKYQIGK | 0.28 | 2.71 | 9.72 |
| NV1D1788 | Q34I | 214 | GPECLEIFKACNPSNDQCCKSSKLVCSRKTRWCKYIIGK | 0.29 | 0.20 | 0.71 |
| NV1D1679 | R26G | 215 | GPECLEIFKACNPSNDQCCKSSKLVCSGKTRWCKYQIGK | 0.29 | 3.62 | 12.64 |
| NV1D1726 | R29L | 216 | GPECLEIFKACNPSNDQCCKSSKLVCSRKTLWCKYQIGK | 0.29 | >0.9 | >3.13 |
| NV1D1611 | K21D | 217 | GPECLEIFKACNPSNDQCCKSSDLVCSRKTRWCKYQIGK | 0.30 | 0.71 | 2.38 |
| NV1D1520 | D14W | 218 | GPECLEIFKACNPSNWQCCKSSKLVCSRKTRWCKYQIGK | 0.30 | 1.43 | 4.81 |
| NV1D1616 | L22W | 219 | GPECLEIFKACNPSNDQCCKSSKWVCSRKTRWCKYQIGK | 0.30 | 2.31 | 7.75 |
| NV1D1635 | V23K | 220 | GPECLEIFKACNPSNDQCCKSSKLKCSRKTRWCKYQIGK | 0.30 | 1.05 | 3.49 |
| NV1D1424 | K7Q | 221 | GPECLEIFQACNPSNDQCCKSSKLVCSRKTRWCKYQIGK | 0.30 | >0.27 | >0.9 |
| NV1D2126 | E1N,R26K | 222 | GPNCLEIFKACNPSNDQCCKSSKLVCSKKTRWCKYQIGK | 0.30 | 0.59 | 1.94 |

FIG. 4(9)

| Peptide ID | Substitution | SEQ ID NO: | Sequence | $IC_{50}$ (Nav1.7) µM | $IC_{50}$ (Nav1.2) µM | Selectivity |
|---|---|---|---|---|---|---|
| HwTX-IV | Parent Synthetic | 1 | ECLEIFKACNPSNDQCCKSSKLVCSRKTRWCKYQI-NH2 | 0.04 | 0.07 | 1.66 |
| NV1D7 | Parent Recombinant | 2 | GPECLEIFKACNPSNDQCCKSSKLVCSRKTRWCKYQIGK | 0.16 | 0.34 | 2.14 |
| | | | | | | |
| NV1D2168 | E1N,R26K,Q34S,G36I | 192 | GPNCLEIFKACNPSNDQCCKSSKLVCSKKTRWCKYSIIK | 0.24 | >7.14 | >30.32 |
| NV1D1730 | W30K | 109 | GPECLEIFKACNPSNDQCCKSSKLVCSRKTRKCKYQIGK | 0.10 | >2.95 | >28.65 |
| NV1D1821 | G36I | 58 | GPECLEIFKACNPSNDQCCKSSKLVCSRKTRWCKYQIIK | 0.06 | 1.42 | 22.71 |
| NV1D1733 | W30Y | 223 | GPECLEIFKACNPSNDQCCKSSKLVCSRKTRYCKYQIGK | 1.69 | 36.60 | 21.66 |
| NV1D1519 | N13G | 172 | GPECLEIFKACNPSGDQCCKSSKLVCSRKTRWCKYQIGK | 0.19 | 3.74 | 19.79 |
| NV1D1569 | S19Q | 21 | GPECLEIFKACNPSNDQCCKQSKLVCSRKTRWCKYQIGK | 0.02 | 0.46 | 18.39 |
| NV1D1722 | R29N | 149 | GPECLEIFKACNPSNDQCCKSSKLVCSRKTNWCKYQIGK | 0.15 | >2.59 | >17.04 |
| NV1D2148 | E1N,Y33W,G36I | 7 | GPNCLEIFKACNPSNDQCCKSSKLVCSRKTRWCKWQIIK | 0.02 | 0.25 | 16.49 |
| NV1D2134 | R26K,Y33W | 46 | GPECLEIFKACNPSNDQCCKSSKLVCSKKTRWCKWQIGK | 0.05 | 0.77 | 15.76 |
| NV1D1680 | K27W | 57 | GPECLEIFKACNPSNDQCCKSSKLVCSRWTRWCKYQIGK | 0.06 | >0.92 | >14.75 |
| NV1D2177 | E1N,E4R,R26K,Q34S,G36I | 16 | GPNCLRIFKACNPSNDQCCKSSKLVCSKKTRWCKYSIIK | 0.02 | 0.32 | 14.22 |
| NV1D102 | V23A | 122 | GPECLEIFKACNPSNDQCCKSSKLACSRKTRWCKYQIGK | 0.11 | >1.51 | >13.25 |
| NV1D1549 | Q15P | 224 | GPECLEIFKACNPSNDPCCKSSKLVCSRKTRWCKYQIGK | 0.35 | 4.63 | 13.23 |
| NV1D1760 | Y33W | 13 | GPECLEIFKACNPSNDQCCKSSKLVCSRKTRWCKWQIGK | 0.02 | 0.26 | 12.70 |
| NV1D1679 | R26G | 215 | GPECLEIFKACNPSNDQCCKSSKLVCSGKTRWCKYQIGK | 0.29 | 3.62 | 12.64 |
| NV1D2136 | R26K,G36I | 225 | GPECLEIFKACNPSNDQCCKSSKLVCSKKTRWCKYQIIK | 0.31 | >3.83 | >12.26 |
| NV1D105 | K27A | 198 | GPECLEIFKACNPSNDQCCKSSKLVCSRATRWCKYQIGK | 0.26 | >2.95 | >11.57 |

FIG. 5(1)

| | | | | | | |
|---|---|---|---|---|---|---|
| NV1D104 | R26A | 164 | GPECLEIFKACNPSNDQCCKSSKLVCSAKTRWCKYQIGK | 0.17 | >1.78 | >10.79 |
| NV1D1673 | R26T | 226 | GPECLEIFKACNPSNDQCCKSSKLVCSTKTRWCKYQIGK | 1.93 | >20.73 | >10.75 |
| NV1D1832 | K37R | 25 | GPECLEIFKACNPSNDQCCKSSKLVCSRKTRWCKYQIGR | 0.03 | 0.28 | 10.70 |
| NV1D1565 | K18P | 189 | GPECLEIFKACNPSNDQCCPSSKLVCSRKTRWCKYQIGK | 0.23 | 2.40 | 10.61 |
| NV1D1723 | R29D | 227 | GPECLEIFKACNPSNDQCCKSSKLVCSRKTDWCKYQIGK | 0.95 | >9.59 | >10.15 |
| NV1D1769 | Y33T | 76 | GPECLEIFKACNPSNDQCCKSSKLVCSRKTRWCKTQIGK | 0.07 | 0.70 | 9.76 |
| NV1D1533 | D14P | 213 | GPECLEIFKACNPSNPQCCKSSKLVCSRKTRWCKYQIGK | 0.28 | 2.71 | 9.72 |
| NV1D1537 | Q15E | 188 | GPECLEIFKACNPSNDECCKSSKLVCSRKTRWCKYQIGK | 0.23 | 2.16 | 9.60 |
| NV1D1556 | K18F | 228 | GPECLEIFKACNPSNDQCCFSSKLVCSRKTRWCKYQIGK | 0.36 | 3.46 | 9.56 |
| NV1D1667 | R26K | 175 | GPECLEIFKACNPSNDQCCKSSKLVCSKKTRWCKYQIGK | 0.20 | 1.88 | 9.53 |
| NV1D1600 | K21W | 82 | GPECLEIFKACNPSNDQCCKSSWLVCSRKTRWCKYQIGK | 0.08 | 0.65 | 8.52 |
| NV1D1671 | R26H | 229 | GPECLEIFKACNPSNDQCCKSSKLVCSHKTRWCKYQIGK | 0.74 | >6.3 | >8.47 |
| NV1D1521 | D14Q | 230 | GPECLEIFKACNPSNQQCCKSSKLVCSRKTRWCKYQIGK | 0.91 | 7.57 | 8.36 |
| NV1D2161 | E1N,E4R,R26K,Q34S | 5 | GPNCLRIFKACNPSNDQCCKSSKLVCSKKTRWCKYSIGK | 0.01 | 0.11 | 8.33 |
| NV1D2143 | E1N,E4R,G36I | 12 | GPNCLRIFKACNPSNDQCCKSSKLVCSRKTRWCKYQIIK | 0.02 | 0.15 | 8.21 |
| NV1D1668 | R26V | 231 | GPECLEIFKACNPSNDQCCKSSKLVCSVKTRWCKYQIGK | 0.41 | >3.19 | >7.86 |
| NV1D101 | L22A | 232 | GPECLEIFKACNPSNDQCCKSSKAVCSRKTRWCKYQIGK | 0.52 | >4.08 | >7.85 |
| NV1D1616 | L22W | 219 | GPECLEIFKACNPSNDQCCKSSKWVCSRKTRWCKYQIGK | 0.30 | 2.31 | 7.75 |
| NV1D1837 | K37P | 202 | GPECLEIFKACNPSNDQCCKSSKLVCSRKTRWCKYQIGP | 0.26 | 2.00 | 7.72 |
| NV1D1727 | R29G | 180 | GPECLEIFKACNPSNDQCCKSSKLVCSRKTGWCKYQIGK | 0.21 | 1.59 | 7.67 |
| NV1D1505 | N13Q | 61 | GPECLEIFKACNPSQDQCCKSSKLVCSRKTRWCKYQIGK | 0.06 | 0.49 | 7.67 |
| NV1D1536 | Q15W | 113 | GPECLEIFKACNPSNDWCCKSSKLVCSRKTRWCKYQIGK | 0.11 | 0.79 | 7.44 |
| NV1D1823 | G36L | 78 | GPECLEIFKACNPSNDQCCKSSKLVCSRKTRWCKYQILK | 0.07 | 0.53 | 7.16 |
| NV1D1535 | D14G | 233 | GPECLEIFKACNPSNGQCCKSSKLVCSRKTRWCKYQIGK | 0.72 | >5.18 | >7.16 |
| NV1D1831 | K37S | 234 | GPECLEIFKACNPSNDQCCKSSKLVCSRKTRWCKYQIGS | 1.47 | 10.30 | 7.01 |
| NV1D1712 | R29W | 55 | GPECLEIFKACNPSNDQCCKSSKLVCSRKTWWCKYQIGK | 0.06 | 0.41 | 6.87 |

FIG. 5(2)

| | | | | | | |
|---|---|---|---|---|---|---|
| NV1D1584 | S20W | 131 | GPECLEIFKACNPSNDQCCKSWKLVCSRKTRWCKYQIGK | 0.13 | 0.87 | 6.81 |
| NV1D1516 | N13I | 142 | GPECLEIFKACNPSIDQCCKSSKLVCSRKTRWCKYQIGK | 0.14 | 0.95 | 6.70 |
| NV1D2171 | E4R,R26K,Y33W,G36I | 48 | GPECLRIFKACNPSNDQCCKSSKLVCSKKTRWCKWQIIK | 0.05 | 0.34 | 6.63 |
| NV1D1539 | Q15V | 235 | GPECLEIFKACNPSNDVCCKSSKLVCSRKTRWCKYQIGK | 0.75 | 4.91 | 6.58 |
| NV1D2169 | E1N,Y33W,Q34S,G36I | 83 | GPNCLEIFKACNPSNDQCCKSSKLVCSRKTRWCKWSIIK | 0.08 | 0.50 | 6.38 |
| NV1D1547 | Q15D | 165 | GPECLEIFKACNPSNDDCCKSSKLVCSRKTRWCKYQIGK | 0.18 | 1.08 | 6.17 |
| NV1D1840 | F6M | 236 | GPECLEIMKACNPSNDQCCKSSKLVCSRKTRWCKYQIGK | 1.10 | 6.68 | 6.07 |
| NV1D2158 | R26K,Q34S,G36I | 178 | GPECLEIFKACNPSNDQCCKSSKLVCSKKTRWCKYSIIK | 0.20 | 1.22 | 6.04 |
| NV1D1809 | G36Q | 237 | GPECLEIFKACNPSNDQCCKSSKLVCSRKTRWCKYQIQK | 1.74 | 10.40 | 5.98 |
| NV1D1811 | G36K | 96 | GPECLEIFKACNPSNDQCCKSSKLVCSRKTRWCKYQIKK | 0.09 | 0.53 | 5.87 |
| NV1D1791 | Q34G | 182 | GPECLEIFKACNPSNDQCCKSSKLVCSRKTRWCKYGIGK | 0.21 | 1.20 | 5.77 |
| NV1D1719 | R29H | 60 | GPECLEIFKACNPSNDQCCKSSKLVCSRKTHWCKYQIGK | 0.06 | 0.37 | 5.75 |
| NV1D2159 | Y33W,Q34S,G36I | 127 | GPECLEIFKACNPSNDQCCKSSKLVCSRKTRWCKWSIIK | 0.12 | 0.68 | 5.70 |
| NV1D1664 | R26W | 72 | GPECLEIFKACNPSNDQCCKSSKLVCSWKTRWCKYQIGK | 0.07 | 0.40 | 5.64 |
| NV1D1588 | S20V | 134 | GPECLEIFKACNPSNDQCCKSVKLVCSRKTRWCKYQIGK | 0.13 | 0.73 | 5.60 |
| NV1D1553 | K18Q | 141 | GPECLEIFKACNPSNDQCCQSSKLVCSRKTRWCKYQIGK | 0.14 | 0.79 | 5.58 |
| NV1D2218 | N13Q,R29K,K37R | 137 | GPECLEIFKACNPSQDQCCKSSKLVCSRKTKWCKYQIGR | 0.13 | 0.73 | 5.52 |
| NV1D1833 | K37T | 238 | GPECLEIFKACNPSNDQCCKSSKLVCSRKTRWCKYQIGT | 0.37 | 2.02 | 5.42 |
| NV1D111 | Q34A | 111 | GPECLEIFKACNPSNDQCCKSSKLVCSRKTRWCKYAIGK | 0.11 | 0.57 | 5.40 |
| NV1D1550 | Q15L | 204 | GPECLEIFKACNPSNDLCCKSSKLVCSRKTRWCKYQIGK | 0.26 | 1.39 | 5.31 |
| NV1D1552 | K18W | 239 | GPECLEIFKACNPSNDQCCWSSKLVCSRKTRWCKYQIGK | 0.46 | 2.38 | 5.21 |
| NV1D1776 | Q34W | 240 | GPECLEIFKACNPSNDQCCKSSKLVCSRKTRWCKYWIGK | 1.32 | 6.87 | 5.20 |
| NV1D1676 | R26I | 177 | GPECLEIFKACNPSNDQCCKSSKLVCSIKTRWCKYQIGK | 0.20 | 1.05 | 5.20 |
| NV1D1504 | N13W | 74 | GPECLEIFKACNPSWDQCCKSSKLVCSRKTRWCKYQIGK | 0.07 | 0.37 | 5.15 |
| NV1D2130 | E4R,R26K | 45 | GPECLRIFKACNPSNDQCCKSSKLVCSKKTRWCKYQIGK | 0.05 | 0.25 | 5.15 |

FIG. 5(3)

| Peptide ID | Substitution | SEQ ID NO: | Sequence | $IC_{50}$ (Nav1.7) μM | $IC_{50}$ (Nav1.2) μM | Selectivity |
|---|---|---|---|---|---|---|
| NV1D7 | Parent Recombinant | 2 | GPECLEIFKACNPSNDQCCKSSKLVCSRKTRWCKYQIGK | 0.05 | 0.05 | 0.92 |
| | | | | | | |
| NV1D1383 | E4R | 18 | GPECLRIFKACNPSNDQCCKSSKLVCSRKTRWCKYQIGK | 0.01 | 0.01 | 2.42 |
| NV1D2133 | E4R, G36I | 52 | GPECLRIFKACNPSNDQCCKSSKLVCSRKTRWCKYQIIK | 0.01 | 0.05 | 8.00 |
| NV1D2163 | E1N, E4R, Y33W, Q34S | 3 | GPNCLRIFKACNPSNDQCCKSSKLVCSRKTRWCKWSIGK | 0.01 | 0.02 | 2.46 |
| NV1D1760 | Y33W | 13 | GPECLEIFKACNPSNDQCCKSSKLVCSRKTRWCKWQIGK | 0.01 | 0.01 | 1.90 |
| NV1D2142 | E1N, E4R, Q34S | 4 | GPNCLRIFKACNPSNDQCCKSSKLVCSRKTRWCKYSIGK | 0.01 | 0.03 | 3.49 |
| NV1D2150 | E4R, R26K, Y33W | 65 | GPECLRIFKACNPSNDQCCKSSKLVCSKKTRWCKWQIGK | 0.01 | 0.02 | 1.61 |
| NV1D2165 | E1N, E4R, Q34S, G36I | 40 | GPNCLRIFKACNPSNDQCCKSSKLVCSRKTRWCKYSIIK | 0.01 | 0.06 | 5.00 |
| NV1D2137 | Y33W, Q34S | 241 | GPECLEIFKACNPSNDQCCKSSKLVCSRKTRWCKWSIGK | 0.01 | 0.04 | 2.93 |
| NV1D85 | E4A | 242 | GPECLAIFKACNPSNDQCCKSSKLVCSRKTRWCKYQIGK | 0.02 | 0.03 | 1.36 |
| NV1D1353 | E1N | 67 | GPNCLEIFKACNPSNDQCCKSSKLVCSRKTRWCKYQIGK | 0.02 | 0.03 | 1.24 |
| NV1D1783 | Q34S | 10 | GPECLEIFKACNPSNDQCCKSSKLVCSRKTRWCKYSIGK | 0.03 | 0.04 | 1.41 |
| NV1D82 | E1A | 243 | GPACLEIFKACNPSNDQCCKSSKLVCSRKTRWCKYQIGK | 0.04 | 0.05 | 1.20 |
| NV1D2177 | E1N, E4R, R26K, Q34S, G36I | 16 | GPNCLRIFKACNPSNDQCCKSSKLVCSKKTRWCKYSIIK | 0.04 | 0.87 | 21.15 |
| NV1D1441 | A8E | 54 | GPECLEIFKECNPSNDQCCKSSKLVCSRKTRWCKYQIGK | 0.04 | 0.02 | 0.52 |
| NV1D97 | K18A | 244 | GPECLEIFKACNPSNDQCCASSKLVCSRKTRWCKYQIGK | 0.05 | 0.52 | 10.71 |
| NV1D95 | Q15A | 101 | GPECLEIFKACNPSNDACCKSSKLVCSRKTRWCKYQIGK | 0.05 | 0.07 | 1.35 |
| NV1D107 | R29A | 201 | GPECLEIFKACNPSNDQCCKSSKLVCSRKTAWCKYQIGK | 0.05 | 0.20 | 3.96 |
| NV1D1439 | A8W | 245 | GPECLEIFKWCNPSNDQCCKSSKLVCSRKTRWCKYQIGK | 0.05 | 0.01 | 0.22 |
| NV1D106 | T28A | 246 | GPECLEIFKACNPSNDQCCKSSKLVCSRKARWCKYQIGK | 0.06 | 0.10 | 1.71 |

FIG. 6(1)

| | | | | | | |
|---|---|---|---|---|---|---|
| NV1D2149 | E1N, Q34S, G36I | 112 | GPNCLEIFKACNPSNDQCCKSSKLVCSRKTRWCKYSIIK | 0.07 | 0.11 | 1.55 |
| NV1D99 | S20A | 247 | GPECLEIFKACNPSNDQCCKSAKLVCSRKTRWCKYQIGK | 0.07 | 0.12 | 1.69 |
| NV1D111 | Q34A | 111 | GPECLEIFKACNPSNDQCCKSSKLVCSRKTRWCKYAIGK | 0.09 | 0.11 | 1.21 |
| NV1D98 | S19A | 125 | GPECLEIFKACNPSNDQCCKASKLVCSRKTRWCKYQIGK | 0.10 | 0.05 | 0.48 |
| NV1D93 | N13A | 23 | GPECLEIFKACNPSADQCCKSSKLVCSRKTRWCKYQIGK | 0.10 | 0.15 | 1.56 |
| NV1D114 | K37A | 248 | GPECLEIFKACNPSNDQCCKSSKLVCSRKTRWCKYQIGA | 0.10 | 0.21 | 2.13 |
| NV1D90 | N10A | 249 | GPECLEIFKACAPSNDQCCKSSKLVCSRKTRWCKYQIGK | 0.10 | 0.18 | 1.78 |
| NV1D1505 | N13Q | 61 | GPECLEIFKACNPSQDQCCKSSKLVCSRKTRWCKYQIGK | 0.10 | 0.06 | 0.58 |
| NV1D92 | S12A | 250 | GPECLEIFKACNPANDQCCKSSKLVCSRKTRWCKYQIGK | 0.11 | 0.15 | 1.39 |
| NV1D102 | V23A | 122 | GPECLEIFKACNPSNDQCCKSSKLACSRKTRWCKYQIGK | 0.12 | 0.06 | 0.49 |
| NV1D100 | K21A | 162 | GPECLEIFKACNPSNDQCCKSSALVCSRKTRWCKYQIGK | 0.13 | 0.10 | 0.80 |
| NV1D104 | R26A | 164 | GPECLEIFKACNPSNDQCCKSSKLVCSAKTRWCKYQIGK | 0.14 | 1.87 | 13.55 |
| NV1D88 | K7A | 251 | GPECLEIFAACNPSNDQCCKSSKLVCSRKTRWCKYQIGK | 0.14 | 0.08 | 0.54 |
| NV1D1821 | G36I | 58 | GPECLEIFKACNPSNDQCCKSSKLVCSRKTRWCKYQIIK | 0.14 | 0.22 | 1.56 |
| NV1D105 | K27A | 198 | GPECLEIFKACNPSNDQCCKSSKLVCSRATRWCKYQIGK | 0.19 | 1.22 | 6.29 |
| NV1D86 | I5A | 252 | GPECLEAFKACNPSNDQCCKSSKLVCSRKTRWCKYQIGK | 0.22 | 0.18 | 0.79 |
| NV1D1569 | S19Q | 21 | GPECLEIFKACNPSNDQCCKQSKLVCSRKTRWCKYQIGK | 0.23 | 0.07 | 0.29 |
| NV1D84 | L3A | 253 | GPECAEIFKACNPSNDQCCKSSKLVCSRKTRWCKYQIGK | 0.23 | 0.13 | 0.55 |
| NV1D1667 | R26K | 175 | GPECLEIFKACNPSNDQCCKSSKLVCSKKTRWCKYQIGK | 0.23 | 0.22 | 0.96 |
| NV1D113 | Q36A | 254 | GPECLEIFKACNPSNDQCCKSSKLVCSRKTRWCKYQIAK | 0.39 | 0.32 | 0.83 |
| NV1D87 | F6A | 255 | GPECLEIAKACNPSNDQCCKSSKLVCSRKTRWCKYQIGK | 0.52 | 5.53 | 10.55 |
| NV1D112 | I35A | 256 | GPECLEIFKACNPSNDQCCKSSKLVCSRKTRWCKYQAGK | 0.59 | 0.16 | 0.28 |
| NV1D110 | Y33A | 257 | GPECLEIFKACNPSNDQCCKSSKLVCSRKTRWCKAQIGK | 0.86 | 1.01 | 1.18 |
| NV1D101 | L22A | 232 | GPECLEIFKACNPSNDQCCKSSKAVCSRKTRWCKYQIGK | 0.88 | 3.49 | 3.99 |
| NV1D91 | P11A | 258 | GPECLEIFKACNASNDQCCKSSKLVCSRKTRWCKYQIGK | 1.09 | 1.23 | 1.13 |
| NV1D94 | D14A | 259 | GPECLEIFKACNPSNAQCCKSSKLVCSRKTRWCKYQIGK | 1.33 | 2.34 | 1.76 |
| NV1D103 | S25A | 260 | GPECLEIFKACNPSNDQCCKSSKLVCARKTRWCKYQIGK | 8.24 | 1.89 | 0.23 |
| NV1D108 | W30A | 261 | GPECLEIFKACNPSNDQCCKSSKLVCSRKTRACKYQIGK | Inactive | Inactive | Inactive |
| NV1D109 | K32A | 262 | GPECLEIFKACNPSNDQCCKSSKLVCSRKTRWCAYQIGK | Inactive | Inactive | Inactive |

FIG. 6(2)

Mean AUC of Paw Pressure Responses for Huwentoxin IV

| NV1D2168 Mutants | | Mutation | Sequence |
|---|---|---|---|
| peptide name | SEQ ID NO: | | |
| NV1D2168 | 281 | E1N,R26K,Q34S,G36I | GPNCLEIFKACNPSNDQCCKSSKLVCSKKTRWCKYSIIK |
| NV1G554 | 282 | E1N,R26K,Q34S,G36I,K37F | GPNCLEIFKACNPSNDQCCKSSKLVCSKKTRWCKYSIIF |
| NV1G555 | 283 | E1N,R26K,Q34S,G36I,K37R | GPNCLEIFKACNPSNDQCCKSSKLVCSKKTRWCKYSIIR |
| NV1G556 | 284 | E1N,S25I,R26K,Q34S,G36I | GPNCLEIFKACNPSNDQCCKSSKLVCIKKTRWCKYSIIK |
| NV1G557 | 285 | E1N,K21N,R26K,Q34S,G36I | GPNCLEIFKACNPSNDQCCKSSNLVCSKKTRWCKYSIIK |
| NV1G558 | 286 | E1N,K21H,R26K,Q34S,G36I | GPNCLEIFKACNPSNDQCCKSSHLVCSKKTRWCKYSIIK |
| NV1G559 | 287 | E1N,K21F,R26K,Q34S,G36I | GPNCLEIFKACNPSNDQCCKSSFLVCSKKTRWCKYSIIK |
| NV1G560 | 288 | E1N,K21R,R26K,Q34S,G36I | GPNCLEIFKACNPSNDQCCKSSRLVCSKKTRWCKYSIIK |
| NV1G561 | 289 | E1N,L22R,R26K,Q34S,G36I | GPNCLEIFKACNPSNDQCCKSSKRVCSKKTRWCKYSIIK |
| NV1G563 | 290 | E1N,S19P,R26K,Q34S,G36I | GPNCLEIFKACNPSNDQCCKPSKLVCSKKTRWCKYSIIK |
| NV1G565 | 291 | E1N,K18Y,R26K,Q34S,G36I | GPNCLEIFKACNPSNDQCCYSSKLVCSKKTRWCKYSIIK |
| NV1G566 | 292 | E1N,S20N,R26K,Q34S,G36I | GPNCLEIFKACNPSNDQCCKSNKLVCSKKTRWCKYSIIK |
| NV1G567 | 293 | E1N,S20P,R26K,Q34S,G36I | GPNCLEIFKACNPSNDQCCKSPKLVCSKKTRWCKYSIIK |
| NV1G569 | 294 | E1N,S20R,R26K,Q34S,G36I | GPNCLEIFKACNPSNDQCCKSRKLVCSKKTRWCKYSIIK |
| NV1G550 | 295 | E1N,E4N, A8R,R26K,Q34S,G36I | GPNCLNIFKRCNPSNDQCCKSSKLVCSKKTRWCKYSIIK |
| NV1G551 | 296 | E1N,E4Q, A8R,R26K,Q34S,G36I | GPNCLNIFKRCNPSNDQCCKSSKLVCSKKTRWCKYSIIK |
| NV1G552 | 297 | E1N,E4H, A8Q,R26K,Q34S,G36I | GPNCLHIFKQCNPSNDQCCKSSKLVCSKKTRWCKYSIIK |
| NV1G553 | 298 | E1N,E4Q, A8Q,R26K,Q34S,G36I | GPNCLHIFKQCNPSNDQCCKSSKLVCSKKTRWCKYSIIK |
| NV1G564 | 299 | E1N,Q15R,R26K,Q34S,G36I | GPNCLEIFKACNPSNDRCCKSSKLVCSKKTRWCKYSIIK |
| NV1G570 | 300 | E1N,N13A,R26K,Q34S,G36I | GPNCLEIFKACNPSADQCCKSSKLVCSKKTRWCKYSIIK |
| NV1G571 | 301 | E1N,A8Q,R26K,Q34S,G36I | GPNCLEIFKQCNPSNDQCCKSSKLVCSKKTRWCKYSIIK |
| NV1G572 | 302 | E1N,A8N,R26K,Q34S,G36I | GPNCLEIFKNCNPSNDQCCKSSKLVCSKKTRWCKYSIIK |
| NV1G573 | 303 | E1N,E4Q,R26K,Q34S,G36I | GPNCLQIFKACNPSNDQCCKSSKLVCSKKTRWCKYSIIK |
| NV1G562 | 304 | E1N,Q15N,R26K,Q34S,G36I | GPNCLEIFKACNPSNDNCCKSSKLVCSKKTRWCKYSIIK |
| NV1G568 | 305 | E1N,S19R,R26K,Q34S,G36I | GPNCLEIFKACNPSNDQCCKRSKLVCSKKTRWCKYSIIK |
| NV1G651 | 306 | E1N,S20V,R26K,Q34S,G36I | GPNCLEIFKACNPSNDQCCKSVKLVCSKKTRWCKYSIIK |

FIG. 13A

| NV1D2168 Mutants | | hNav1.1 $IC_{50}$ (nM) | | hNav1.2 $IC_{50}$ (nM) | | hNav1.3 $IC_{50}$ (nM) | | hNav1.4 $IC_{50}$ (nM) | | hNav1.5 $IC_{50}$ (nM) | | hNav1.6 $IC_{50}$ (nM) | | hNav1.7 $IC_{50}$ (nM) | |
|---|---|---|---|---|---|---|---|---|---|---|---|---|---|---|---|
| peptide name | SEQ ID NO: | TETRA | QP | TETRA | QP | TETRA | QP | TETRA | QP | TETRA | QP | TETRA | QP | TETRA | QP |
| NV1D2168 | 281 | 187 | 75 | | 871 | | 724 | >1000 | >10000 | >1000 | >10000 | >1000 | 67 | 67 | 41 |
| NV1G554 | 282 | 215 | | | | | | >1000 | | >1000 | | >1000 | | 38 | |
| NV1G555 | 283 | 37 | | | | | | >525 | | >1000 | | >525 | | 34 | |
| NV1G556 | 284 | 166 | | | | | | >1000 | | >1000 | | >1000 | | >1000 | |
| NV1G557 | 285 | 168 | 90 | | 76 | | | >1000 | | >1000 | | >1000 | 88 | 118 | 36 |
| NV1G558 | 286 | 71 | 90 | | 86 | | | >1000 | | >1000 | | 3850 | 91 | 73 | 24 |
| NV1G559 | 287 | >1000 | 81 | | 601 | | | >1000 | | >1000 | | >1000 | 267 | 145 | 17 |
| NV1G560 | 288 | >1000 | 87 | | 85 | | | >1000 | | >1000 | | 2300 | 87 | 55 | 21 |
| NV1G561 | 289 | >1000 | | | | | | >1000 | | >1000 | | 4170 | | >1000 | |
| NV1G563 | 290 | >1000 | 80 | | 44 | | | >1000 | | >1000 | | 2780 | 231 | 203 | 64 |
| NV1G565 | 291 | >1000 | | | | | | >1000 | | >1000 | | >1000 | | 846 | |
| NV1G566 | 292 | >1000 | 89 | | 567 | | | >1000 | | >1000 | | >1000 | 202 | 208 | 32 |
| NV1G567 | 293 | >1000 | | | 41 | | | >1000 | | >1000 | | >1000 | 86 | 446 | 207 |
| NV1G569 | 294 | 704 | | | | | | >1000 | | >1000 | | 206 | | 32 | |
| NV1G550 | 295 | 157 | | | | | | 1370 | | >1000 | | 41 | | 22 | |
| NV1G551 | 296 | 128 | | | | | | 1370 | | >1000 | | 69 | | 34 | |
| NV1G552 | 297 | 360 | | | | | | 2770 | | >1000 | | 145 | | 34 | |
| NV1G553 | 298 | 524 | | | | | | >1000 | | | | 681 | | 162 | |
| NV1G564 | 299 | 833 | | | | | | >1000 | | | | 1110 | | 276 | |
| NV1G570 | 300 | >1000 | | | | | | >1000 | | | | 1190 | | 406 | |
| NV1G571 | 301 | >1000 | | | | | | >1000 | | | | 1200 | | 440 | |
| NV1G572 | 302 | >1000 | | | | | | >1000 | | | | 1340 | | >1000 | |
| NV1G573 | 303 | 579 | | | | | | >1000 | | | | 672 | | 158 | |
| NV1G562 | 304 | | | | | | | | | | | | | | 45.8%* |
| NV1G568 | 305 | | | | | | | | | | | | 36.9%* | | 27 |
| NV1G651 | 306 | | | | | | | | | | | | | | 0%* |
| | | *% Inhibiton at single point 100 nM concentration | | | | | | | | | | | | | |

FIG. 13B

| NV1D2168 Mutants | | | |
|---|---|---|---|
| | | | |
| ID | SEQ ID NO: | Mutation | Sequence |
| NV1D2163 | 307 | E1N,E4R,Y33W,Q34S | GPNCLRIFKACNPSNDQCCKSSKLVCSRKTRWCKWSIGK |
| NV1G600 | 308 | E1N,E4R,S19Q, Y33W,Q34S | GPNCLRIFKACNPSNDQCCKQSKLVCSRKTRWCKWSIGK |
| NV1G601 | 309 | E1N,E4R,Q15D, Y33W,Q34S | GPNCLRIFKACNPSNDDCCKSSKLVCSRKTRWCKWSIGK |
| NV1G602 | 310 | E1N,E4R,K18Q, Y33W,Q34S | GPNCLRIFKACNPSNDQCCQSSKLVCSRKTRWCKWSIGK |
| NV1G603 | 311 | E1N,E4R,D14S, Y33W,Q34S | GPNCLRIFKACNPSNSQCCKSSKLVCSRKTRWCKWSIGK |
| NV1G604 | 312 | E1N,E4R,D14Q, Y33W,Q34S | GPNCLRIFKACNPSNQQCCKSSKLVCSRKTRWCKWSIGK |
| NV1G605 | 313 | E1N,E4R,Q15P,Y33W,Q34S | GPNCLRIFKACNPSNDPCCKSSKLVCSRKTRWCKWSIGK |
| NV1G607 | 314 | E1N,E4R,K32A,Y33W,Q34S | GPNCLRIFKACNPSNDQCCKSSKLVCSRKTRWCAWSIGK |
| NV1G608 | 315 | E1N,E4R,K32W,Y33W,Q34S | GPNCLRIFKACNPSNDQCCKSSKLVCSRKTRWCWWSIGK |
| NV1G610 | 316 | E1N,E4R,K27A,Y33W,Q34S | GPNCLRIFKACNPSNDQCCKSSKLVCSRATRWCKWSIGK |
| NV1G611 | 317 | E1N,E4R,R26D,Y33W,Q34S | GPNCLRIFKACNPSNDQCCKSSKLVCSDKTRWCKWSIGK |
| NV1G612 | 318 | E1N,E4R,K27H,Y33W,Q34S | GPNCLRIFKACNPSNDQCCKSSKLVCSRHTRWCKWSIGK |
| NV1G613 | 319 | E1N,E4R,R26H,Y33W,Q34S | GPNCLRIFKACNPSNDQCCKSSKLVCSHKTRWCKWSIGK |
| NV1G614 | 320 | E1N,E4R,Y33W,Q34S,K37R | GPNCLRIFKACNPSNDQCCKSSKLVCSRKTRWCKWSIGR |
| NV1G615 | 321 | E1N,E4R,Y33W,Q34S,K37P | GPNCLRIFKACNPSNDQCCKSSKLVCSRKTRWCKWSIGP |
| NV1G616 | 322 | E1N,E4R,K18W,Y33W,Q34S | GPNCLRIFKACNPSNDQCCWSSKLVCSRKTRWCKWSIGK |
| NV1G617 | 323 | E1N,E4R,D14L,Y33W,Q34S | GPNCLRIFKACNPSNLQCCKSSKLVCSRKTRWCKWSIGK |
| NV1G618 | 324 | E1N,E4R,Q15W,Y33W,Q34S | GPNCLRIFKACNPSNDWCCKSSKLVCSRKTRWCKWSIGK |
| NV1G619 | 325 | E1N,E4R,Y33W,Q34S,G36V | GPNCLRIFKACNPSNDQCCKSSKLVCSRKTRWCKWSIVK |
| NV1G620 | 326 | E1N,E4R,R29G,Y33W,Q34S | GPNCLRIFKACNPSNDQCCKSSKLVCSRKTGWCKWSIGK |
| NV1G621 | 327 | E1N,E4R,R29W,Y33W,Q34S | GPNCLRIFKACNPSNDQCCKSSKLVCSRKTWWCKWSIGK |
| NV1G622 | 328 | E1N,E4R,Y33W,Q34S,G36T | GPNCLRIFKACNPSNDQCCKSSKLVCSRKTRWCKWSITK |
| NV1G623 | 329 | E1N,E4R,W30K,Y33W,Q34S | GPNCLRIFKACNPSNDQCCKSSKLVCSRKTRKCKWSIGK |
| NV1G624 | 330 | E1N,E4R,R29L,Y33W,Q34S | GPNCLRIFKACNPSNDQCCKSSKLVCSRKTLWCKWSIGK |
| NV1G625 | 331 | E1N,E4R,W30Y,Y33W,Q34S | GPNCLRIFKACNPSNDQCCKSSKLVCSRKTRYCKWSIGK |
| NV1G626 | 332 | E1N,E4R,R26P,Y33W,Q34S | GPNCLRIFKACNPSNDQCCKSSKLVCSPKTRWCKWSIGK |
| NV1G627 | 333 | E1N,E4R,L22A,Y33W,Q34S | GPNCLRIFKACNPSNDQCCKSSKAVCSRKTRWCKWSIGK |
| NV1G628 | 334 | E1N,E4R,L22W,Y33W,Q34S | GPNCLRIFKACNPSNDQCCKSSKWVCSRKTRWCKWSIGK |
| NV1G629 | 335 | E1N,E4R,T28L,Y33W,Q34S | GPNCLRIFKACNPSNDQCCKSSKLVCSRKLRWCKWSIGK |
| NV1G630 | 336 | E1N,E4R,K27P,Y33W,Q34S | GPNCLRIFKACNPSNDQCCKSSKLVCSRPTRWCKWSIGK |
| NV1G631 | 337 | E1N,E4R,R26V,Y33W,Q34S | GPNCLRIFKACNPSNDQCCKSSKLVCSVKTRWCKWSIGK |
| NV1G632 | 338 | E1N,E4R,R26G,Y33W,Q34S | GPNCLRIFKACNPSNDQCCKSSKLVCSGKTRWCKWSIGK |
| NV1G633 | 339 | E1N,E4R,K21W,Y33W,Q34S | GPNCLRIFKACNPSNDQCCKSSWLVCSRKTRWCKWSIGK |
| NV1G634 | 340 | E1N,E4R,R26I,Y33W,Q34S | GPNCLRIFKACNPSNDQCCKSSKLVCSIKTRWCKWSIGK |
| NV1G635 | 341 | E1N,E4R,K27W,Y33W,Q34S | GPNCLRIFKACNPSNDQCCKSSKLVCSRWTRWCKWSIGK |
| NV1G636 | 342 | E1N,E4R,R26A,Y33W,Q34S | GPNCLRIFKACNPSNDQCCKSSKLVCSAKTRWCKWSIGK |
| NV1G637 | 343 | E1N,E4R,S20W,Y33W,Q34S | GPNCLRIFKACNPSNDQCCKSWKLVCSRKTRWCKWSIGK |
| NV1G638 | 344 | E1N,E4R,Q15E,Y33W,Q34S | GPNCLRIFKACNPSNDECCKSSKLVCSRKTRWCKWSIGK |
| NV1G639 | 345 | E1N,E4R,K18P,Y33W,Q34S | GPNCLRIFKACNPSNDQCCPSSKLVCSRKTRWCKWSIGK |
| NV1G640 | 346 | E1N,E4R,Q15V,Y33W,Q34S | GPNCLRIFKACNPSNDVCCKSSKLVCSRKTRWCKWSIGK |
| NV1G641 | 347 | E1N,E4R,D14G,Y33W,Q34S | GPNCLRIFKACNPSNGQCCKSSKLVCSRKTRWCKWSIGK |
| NV1G642 | 348 | E1N,E4R,K18F,Y33W,Q34S | GPNCLRIFKACNPSNDQCCFSSKLVCSRKTRWCKWSIGK |
| NV1G644 | 349 | E1N,E4R,Y33W,Q34S,K37T | GPNCLRIFKACNPSNDQCCKSSKLVCSRKTRWCKWSIGT |
| NV1G645 | 350 | E1N,E4R,Y33W,Q34S,K37Q | GPNCLRIFKACNPSNDQCCKSSKLVCSRKTRWCKWSIGQ |
| NV1G646 | 351 | E1N,E4R,Y33W,Q34S,K37S | GPNCLRIFKACNPSNDQCCKSSKLVCSRKTRWCKWSIGS |
| NV1G647 | 352 | E1N,E4R,F6M,Y33W,Q34S | GPNCLRIMKACNPSNDQCCKSSKLVCSRKTRWCKWSIGK |
| NV1G648 | 353 | E1N,E4R,K7Q,Y33W,Q34S | GPNCLRIFQACNPSNDQCCKSSKLVCSRKTRWCKWSIGK |
| NV1G649 | 354 | E1N,E4R,P11R,Y33W,Q34S | GPNCLRIFKACNRSNDQCCKSSKLVCSRKTRWCKWSIGK |
| NV1G650 | 355 | E1N,E4R,S19Q,Y33W,Q34S | GPNCLRIFKACNPSNDQCCKQSKLVCSRKTRWCKWSIGK |

*FIG. 14A*

| NV1D2168 Mutants | | | hNav1.6 IC50 (nM) | | | hNav1.7 IC50 (nM) | |
|---|---|---|---|---|---|---|---|
| | | | TETRA | QP | | TETRA | QP |
| ID | SEQ ID NO: | | | | | | |
| NV1D2163 | 307 | | | 98.6%I @ 300 nM | | 14 | 32 |
| NV1G600 | 308 | | | | | 941 | |
| NV1G601 | 309 | | | | | 797 | |
| NV1G602 | 310 | | | | | | 37.7%I @ 100 nM |
| NV1G603 | 311 | | | | | 4490 | |
| NV1G604 | 312 | | | | | | 17.7%I @ 100 nM |
| NV1G605 | 313 | | | | | | -23.7%I @ 100 nM |
| NV1G607 | 314 | | | | | | -3.3%I @ 100 nM |
| NV1G608 | 315 | | | | | | -12.5%I @ 100 nM |
| NV1G610 | 316 | | | 149 | | | 13 |
| NV1G611 | 317 | | | 85 | | | 8 |
| NV1G612 | 318 | | | 47.3%I @ 30 nM | | | 8 |
| NV1G613 | 319 | | | 77.2%I @ 30 nM | | | 5 |
| NV1G614 | 320 | | | 70.3%I @ 100 nM | | | 14 |
| NV1G615 | 321 | | | 66.8%I @ 100 nM | | | 16 |
| NV1G616 | 322 | | | 91.6%I @ 300 nM | | | 25 |
| NV1G617 | 323 | | | 72.8%I @ 300 nM | | | 31 |
| NV1G618 | 324 | | | 14.9%I @ 100 nM | | | 6.1%I @ 30 nM |
| NV1G619 | 325 | | | 86.8%I @ 300 nM | | | 30 |
| NV1G620 | 326 | | | 67.2%I @ 30 nM | | | 9 |
| NV1G621 | 327 | | | 96.2%I @ 100 nM | | | 20 |
| NV1G622 | 328 | | | | | 4720 | |
| NV1G623 | 329 | | | 58.3%I @ 30 nM | | | 7 |
| NV1G624 | 330 | | | | | 406 | |
| NV1G625 | 331 | | | 75.5%I @ 100 nM | | | 13 |
| NV1G626 | 332 | | | 74.1%I @ 300 nM | | | 38 |
| NV1G627 | 333 | | | 77.9%I @ 100 nM | | | 18 |
| NV1G628 | 334 | | | | | 1780 | |
| NV1G629 | 335 | | | 86.0%I @ 300 nM | | | 26 |
| NV1G630 | 336 | | | 74.9%I @ 100 nM | | | 19 |
| NV1G631 | 337 | | | | | | 53 |
| NV1G632 | 338 | | | 57.9%I @ 30 nM | | | 11 |
| NV1G633 | 339 | | | 76.5%I @ 300 nM | | | 46 |
| NV1G634 | 340 | | | 68.3%I @ 100 nM | | | 21 |
| NV1G635 | 341 | | | | | 2180 | |
| NV1G636 | 342 | | | 75.9%I @ 300 nM | | | 24 |
| NV1G637 | 343 | | | | | 1980 | |
| NV1G638 | 344 | | | | | | 80 |
| NV1G639 | 345 | | | | | | -8.6%I @ 30 nM |
| NV1G640 | 346 | | | | | | 17.8%I @ 30 nM |
| NV1G641 | 347 | | | | | | 83 |
| NV1G642 | 348 | | | 75.0%I @ 30 nM | | 65 | 3 |
| NV1G644 | 349 | | | 81.9%I @ 30 nM | | 19 | 2 |
| NV1G645 | 350 | | | 95.6%I @ 30 nM | | 22 | 3 |
| NV1G646 | 351 | | | 92.5%I @ 300 nM | | 66 | 48 |
| NV1G647 | 352 | | | 95.0%I @ 30 nM | | 13 | 3 |
| NV1G648 | 353 | | | | | 131 | |
| NV1G649 | 354 | | | | | 587 | |
| NV1G650 | 355 | | | 81.9%I @ 30 nM | | 19 | 2 |

*FIG. 14B*

Mean AUC of Paw Pressure Responses for Huwentoxin IV

Tactile Allodynia Following 50% Intraplantar CFA in Rat

P<0.001 Overall: Two-way ANOVA with Bonferroni Post-hoc Test

P<0.001 Overall: Two-way ANOVA with Bonferroni Post-hoc Test

Intraplantar Protoxin II Reduces CFA-Induced Tactile Allodynia

P<0.01 Overall: Two-way ANOVA with Bonferroni Post-hoc Test 3 nmoles Intraplantar Protoxin II Reduces CFA-Induced Tactile Allodynia-Mouse P<0.001 Overall: Two-way ANOVA with Bonferroni Post-hoc Test

SEQUENCE LISTING

```
<160> NUMBER OF SEQ ID NOS: 357

<210> SEQ ID NO 1
<211> LENGTH: 35
<212> TYPE: PRT
<213> ORGANISM: Ornithoctonus huwena
<220> FEATURE:
<221> NAME/KEY: MOD_RES
<222> LOCATION: (35)..(35)
<223> OTHER INFORMATION: AMIDATION

<400> SEQUENCE: 1

Glu Cys Leu Glu Ile Phe Lys Ala Cys Asn Pro Ser Asn Asp Gln Cys
1               5                   10                  15

Cys Lys Ser Ser Lys Leu Val Cys Ser Arg Lys Thr Arg Trp Cys Lys
            20                  25                  30

Tyr Gln Ile
        35
```

<210> SEQ ID NO 2
<211> LENGTH: 39
<212> TYPE: PRT
<213> ORGANISM: Ornithoctonus huwena

<400> SEQUENCE: 2

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 3
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 3

Gly Pro Asn Cys Leu Arg Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Trp Ser Ile Gly Lys
35

<210> SEQ ID NO 4
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 4

Gly Pro Asn Cys Leu Arg Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Ser Ile Gly Lys
35

<210> SEQ ID NO 5
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 5

Gly Pro Asn Cys Leu Arg Ile Phe Lys Ala Cys Asn Pro Ser Asn Asp
1 5 10 15

Gln Cys Cys Lys Ser Ser Lys Leu Val Cys Ser Lys Lys Thr Arg Trp
20 25 30

Cys Lys Tyr Ser Ile Gly Lys
35

<210> SEQ ID NO 6
<211> LENGTH: 39
<212> TYPE: PRT

-continued

```
<213> ORGANISM: Artificial sequence
<220> FEATURE:
<223> OTHER INFORMATION: Huwentoxin-IV variant

<400> SEQUENCE: 6

Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Phe Ile Gly Lys
        35


<210> SEQ ID NO 7
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 7

Gly Pro Asn Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Trp Gln Ile Ile Lys
        35


<210> SEQ ID NO 8
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 8

Gly Pro Glu Cys Leu Arg Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Trp Ser Ile Gly Lys
        35


<210> SEQ ID NO 9
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 9

Gly Pro Glu Cys Leu Gln Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35


<210> SEQ ID NO 10
<211> LENGTH: 39
<212> TYPE: PRT
<213> ORGANISM: Artificial sequence
<220> FEATURE:
<223> OTHER INFORMATION: Huwentoxin-IV variant
```

<400> SEQUENCE: 10

```
Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Ser Ile Gly Lys
        35
```

<210> SEQ ID NO 11
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 11

```
Gly Pro Glu Cys Leu Glu Ile Phe Lys Ala Cys Asn Pro Ser Asn Asp
1               5                   10                  15

Asn Cys Cys Lys Ser Ser Lys Leu Val Cys Ser Arg Lys Thr Arg Trp
            20                  25                  30

Cys Lys Tyr Gln Ile Gly Lys
        35
```

<210> SEQ ID NO 12
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 12

```
Gly Pro Asn Cys Leu Arg Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Ile Lys
        35
```

<210> SEQ ID NO 13
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 13

```
Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Trp Gln Ile Gly Lys
        35
```

<210> SEQ ID NO 14
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 14

-continued

Gly Pro Glu Cys Leu Glu Ile Phe Lys Ala Cys Asn Pro Ser Asn Asp
1 5 10 15

Gln Cys Cys Lys Ser Ser Arg Leu Val Cys Ser Arg Lys Thr Arg Trp
20 25 30

Cys Lys Tyr Gln Ile Gly Lys
35

<210> SEQ ID NO 15
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 15

Gly Pro Glu Cys Leu Glu Ile Phe Lys Arg Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 16
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 16

Gly Pro Asn Cys Leu Arg Ile Phe Lys Ala Cys Asn Pro Ser Asn Asp
1 5 10 15

Gln Cys Cys Lys Ser Ser Lys Leu Val Cys Ser Lys Lys Thr Arg Trp
20 25 30

Cys Lys Tyr Ser Ile Ile Lys
35

<210> SEQ ID NO 17
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 17

Gly Pro Asn Cys Leu Arg Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Trp Gln Ile Ile Lys
35

<210> SEQ ID NO 18
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 18

Gly Pro Glu Cys Leu Arg Ile Phe Lys Ala Cys Asn Pro Ser Asn Asp
1 5 10 15

```
Gln Cys Cys Lys Ser Ser Lys Leu Val Cys Ser Arg Lys Thr Arg Trp
            20                  25                  30

Cys Lys Tyr Gln Ile Gly Lys
        35


<210> SEQ ID NO 19
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 19

Gly Pro Asn Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Trp Ser Ile Gly Lys
        35


<210> SEQ ID NO 20
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 20

Gly Pro Glu Cys Leu Glu Ile Phe Lys Ala Cys Asn Pro Ser Asn Asp
1               5                   10                  15

Gln Cys Cys Lys Ser Asn Lys Leu Val Cys Ser Arg Lys Thr Arg Trp
            20                  25                  30

Cys Lys Tyr Gln Ile Gly Lys
        35


<210> SEQ ID NO 21
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 21

Gly Pro Glu Cys Leu Glu Ile Phe Lys Ala Cys Asn Pro Ser Asn Asp
1               5                   10                  15

Gln Cys Cys Lys Gln Ser Lys Leu Val Cys Ser Arg Lys Thr Arg Trp
            20                  25                  30

Cys Lys Tyr Gln Ile Gly Lys
        35


<210> SEQ ID NO 22
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 22

Gly Pro Asn Cys Leu Arg Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30
```

Cys Lys Tyr Gln Ile Gly Lys
35

<210> SEQ ID NO 23
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 23

Gly Pro Glu Cys Leu Glu Ile Phe Lys Ala Cys Asn Pro Ser Ala Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 24
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 24

Gly Pro Glu Cys Leu Glu Ile Phe Lys Ala Cys Asn Pro Ser Asn Asp
1 5 10 15

Gln Cys Cys Lys Ser Ser Lys Leu Val Cys Ile Arg Lys Thr Arg Trp
20 25 30

Cys Lys Tyr Gln Ile Gly Lys
35

<210> SEQ ID NO 25
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 25

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Arg
35

<210> SEQ ID NO 26
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 26

Gly Pro Glu Cys Leu Asn Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 27
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 27

```
Gly Pro Glu Cys Leu Glu Ile Phe Lys Ala Cys Asn Pro Ser Asn Asp
1               5                   10                  15

Gln Cys Cys Lys Pro Ser Lys Leu Val Cys Ser Arg Lys Thr Arg Trp
            20                  25                  30

Cys Lys Tyr Gln Ile Gly Lys
        35
```

<210> SEQ ID NO 28
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 28

```
Gly Pro Glu Cys Leu Glu Ile Phe Lys Ala Cys Asn Pro Ser Asn Asp
1               5                   10                  15

Gln Cys Cys Lys Ser Asp Lys Leu Val Cys Ser Arg Lys Thr Arg Trp
            20                  25                  30

Cys Lys Tyr Gln Ile Gly Lys
        35
```

<210> SEQ ID NO 29
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 29

```
Gly Pro Glu Cys Leu Glu Ile Phe Lys Ala Cys Asn Pro Ser Asn Asp
1               5                   10                  15

Gln Cys Cys Lys Ser Arg Lys Leu Val Cys Ser Arg Lys Thr Arg Trp
            20                  25                  30

Cys Lys Tyr Gln Ile Gly Lys
        35
```

<210> SEQ ID NO 30
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 30

```
Gly Pro Glu Cys Leu Glu Ile Phe Lys Ala Cys Asn Pro Ser Asn Asp
1               5                   10                  15

Arg Cys Cys Lys Ser Ser Lys Leu Val Cys Ser Arg Lys Thr Arg Trp
            20                  25                  30

Cys Lys Tyr Gln Ile Gly Lys
        35
```

<210> SEQ ID NO 31
<211> LENGTH: 39

<212> TYPE: PRT
<213> ORGANISM: Artificial sequence
<220> FEATURE:
<223> OTHER INFORMATION: Huwentoxin-IV variant

<400> SEQUENCE: 31

```
Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Leu Ile Gly Lys
        35
```

<210> SEQ ID NO 32
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 32

```
Gly Pro Glu Cys Leu Arg Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Ser Ile Ile Lys
        35
```

<210> SEQ ID NO 33
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 33

```
Gly Pro Glu Cys Leu Glu Ile Phe Lys Ala Cys Asn Pro Ser Asn Asp
1               5                   10                  15

Gln Cys Cys Lys Ser Ser Phe Leu Val Cys Ser Arg Lys Thr Arg Trp
            20                  25                  30

Cys Lys Tyr Gln Ile Gly Lys
        35
```

<210> SEQ ID NO 34
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 34

```
Gly Pro Glu Cys Leu Glu Ile Phe Lys Ala Cys Asn Pro Ser Asn Asp
1               5                   10                  15

Gln Cys Cys Lys Ser Ser His Leu Val Cys Ser Arg Lys Thr Arg Trp
            20                  25                  30

Cys Lys Tyr Gln Ile Gly Lys
        35
```

<210> SEQ ID NO 35
<211> LENGTH: 39
<212> TYPE: PRT
<213> ORGANISM: Artificial sequence
<220> FEATURE:

<223> OTHER INFORMATION: Huwentoxin-IV variant

<400> SEQUENCE: 35

```
Gly Pro Glu Cys Leu Glu Ile Phe Lys Ala Cys Asn Pro Ser Asn Asp
1               5                   10                  15

Gln Cys Cys Lys Ser Pro Lys Leu Val Cys Ser Arg Lys Thr Arg Trp
            20                  25                  30

Cys Lys Tyr Gln Ile Gly Lys
        35
```

<210> SEQ ID NO 36
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 36

```
Gly Pro Asn Cys Leu Arg Ile Phe Lys Ala Cys Asn Pro Ser Asn Asp
1               5                   10                  15

Gln Cys Cys Lys Ser Ser Lys Leu Val Cys Ser Lys Lys Thr Arg Trp
            20                  25                  30

Cys Lys Tyr Gln Ile Ile Lys
        35
```

<210> SEQ ID NO 37
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 37

```
Gly Pro Glu Cys Leu Glu Ile Phe Lys Ala Cys Asn Pro Ser Asn Asp
1               5                   10                  15

Gln Cys Cys Lys Ser Ser Asn Leu Val Cys Ser Arg Lys Thr Arg Trp
            20                  25                  30

Cys Lys Tyr Gln Ile Gly Lys
        35
```

<210> SEQ ID NO 38
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 38

```
Gly Pro Glu Cys Leu Glu Ile Phe Lys Ala Cys Asn Pro Ser Asn Asp
1               5                   10                  15

Gln Cys Cys Tyr Ser Ser Lys Leu Val Cys Ser Arg Lys Thr Arg Trp
            20                  25                  30

Cys Lys Tyr Gln Ile Gly Lys
        35
```

<210> SEQ ID NO 39
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 39

Gly Pro Glu Cys Leu Glu Tyr Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 40
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 40

Gly Pro Asn Cys Leu Arg Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Ser Ile Ile Lys
35

<210> SEQ ID NO 41
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 41

Gly Pro Glu Cys Leu Glu Ile Phe Lys Ala Cys Asn Pro Ser Asn Asp
1 5 10 15

Gln Cys Cys Lys Arg Ser Lys Leu Val Cys Ser Arg Lys Thr Arg Trp
20 25 30

Cys Lys Tyr Gln Ile Gly Lys
35

<210> SEQ ID NO 42
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 42

Gly Pro Pro Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 43
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 43

Gly Pro Glu Cys Leu Glu Ile Phe Lys Ala Cys Asn Pro Ser Asn Asp
1 5 10 15

-continued

```
Gln Cys Cys Lys Ser Ser Lys Arg Val Cys Ser Arg Lys Thr Arg Trp
            20                  25                  30

Cys Lys Tyr Gln Ile Gly Lys
        35


<210> SEQ ID NO 44
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 44

Gly Pro Glu Cys Leu His Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35


<210> SEQ ID NO 45
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 45

Gly Pro Glu Cys Leu Arg Ile Phe Lys Ala Cys Asn Pro Ser Asn Asp
1               5                   10                  15

Gln Cys Cys Lys Ser Ser Lys Leu Val Cys Ser Lys Lys Thr Arg Trp
            20                  25                  30

Cys Lys Tyr Gln Ile Gly Lys
        35


<210> SEQ ID NO 46
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 46

Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Lys Lys Thr Arg Trp
            20                  25                  30

Cys Lys Trp Gln Ile Gly Lys
        35


<210> SEQ ID NO 47
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 47

Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30
```

```
Cys Lys Tyr Gln Ile Gly Phe
        35


<210> SEQ ID NO 48
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 48

Gly Pro Glu Cys Leu Arg Ile Phe Lys Ala Cys Asn Pro Ser Asn Asp
1               5                   10                  15

Gln Cys Cys Lys Ser Ser Lys Leu Val Cys Ser Lys Lys Thr Arg Trp
            20                  25                  30

Cys Lys Trp Gln Ile Ile Lys
        35


<210> SEQ ID NO 49
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 49

Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Thr Ile Gly Lys
        35


<210> SEQ ID NO 50
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 50

Gly Pro Arg Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35


<210> SEQ ID NO 51
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 51

Gly Pro Glu Cys Leu Glu Ile Phe Lys Ala Cys Asn Pro Ser Asn Asp
1               5                   10                  15

Gln Cys Cys Arg Ser Ser Lys Leu Val Cys Ser Arg Lys Thr Arg Trp
            20                  25                  30

Cys Lys Tyr Gln Ile Gly Lys
        35
```

<210> SEQ ID NO 52
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 52

```
Gly Pro Glu Cys Leu Arg Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Ile Lys
        35
```

<210> SEQ ID NO 53
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 53

```
Gly Pro Glu Cys Leu Glu Ile Phe Lys Ala Cys Asn Pro Ser Asn Asp
1               5                   10                  15

Gln Cys Cys Lys Ser Tyr Lys Leu Val Cys Ser Arg Lys Thr Arg Trp
            20                  25                  30

Cys Lys Tyr Gln Ile Gly Lys
        35
```

<210> SEQ ID NO 54
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 54

```
Gly Pro Glu Cys Leu Glu Ile Phe Lys Glu Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35
```

<210> SEQ ID NO 55
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 55

```
Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Trp Trp
            20                  25                  30

Cys Lys Tyr Gln Ile Gly Lys
        35
```

<210> SEQ ID NO 56

<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 56

Gly Pro Glu Cys Leu Glu Ile Phe Trp Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 57
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 57

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Trp Thr Arg Trp
20 25 30

Cys Lys Tyr Gln Ile Gly Lys
35

<210> SEQ ID NO 58
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 58

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Ile Lys
35

<210> SEQ ID NO 59
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 59

Gly Pro Lys Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 60
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 60

```
Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr His Trp
            20                  25                  30

Cys Lys Tyr Gln Ile Gly Lys
        35
```

<210> SEQ ID NO 61
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 61

```
Gly Pro Glu Cys Leu Glu Ile Phe Lys Ala Cys Asn Pro Ser Gln Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35
```

<210> SEQ ID NO 62
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 62

```
Gly Pro Glu Cys Leu Tyr Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35
```

<210> SEQ ID NO 63
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 63

```
Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Arg Ile Gly Lys
        35
```

<210> SEQ ID NO 64
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 64

Gly Pro Glu Cys Leu Glu Ile Phe Lys Ala Cys Asn Pro Ser Asn Asp
1 5 10 15

Gln Cys Cys Lys Ile Ser Lys Leu Val Cys Ser Arg Lys Thr Arg Trp
20 25 30

Cys Lys Tyr Gln Ile Gly Lys
35

<210> SEQ ID NO 65
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 65

Gly Pro Glu Cys Leu Arg Ile Phe Lys Ala Cys Asn Pro Ser Asn Asp
1 5 10 15

Gln Cys Cys Lys Ser Ser Lys Leu Val Cys Ser Lys Lys Thr Arg Trp
20 25 30

Cys Lys Trp Gln Ile Gly Lys
35

<210> SEQ ID NO 66
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 66

Gly Pro Glu Cys Leu Glu Ile Phe Lys Ala Cys Asn Pro Ser Asn Asp
1 5 10 15

Gln Cys Cys Lys Leu Ser Lys Leu Val Cys Ser Arg Lys Thr Arg Trp
20 25 30

Cys Lys Tyr Gln Ile Gly Lys
35

<210> SEQ ID NO 67
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 67

Gly Pro Asn Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 68
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 68

Gly Pro Glu Cys Leu Glu Ile Phe Lys Ala Cys Asn Pro Ser Asn Asp

```
1               5                   10                  15

Gln Cys Cys Lys Ser Ser Ser Leu Val Cys Ser Arg Lys Thr Arg Trp
            20                  25                  30

Cys Lys Tyr Gln Ile Gly Lys
        35
```

<210> SEQ ID NO 69
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 69

```
Gly Pro Glu Cys Leu Glu Ile Phe Arg Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35
```

<210> SEQ ID NO 70
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 70

```
Gly Pro Glu Cys Ser Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35
```

<210> SEQ ID NO 71
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 71

```
Gly Pro His Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35
```

<210> SEQ ID NO 72
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 72

```
Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Trp Lys Thr Arg Trp
```

```
            20                  25                  30

Cys Lys Tyr Gln Ile Gly Lys
        35


<210> SEQ ID NO 73
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 73

Gly Pro Ile Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35


<210> SEQ ID NO 74
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 74

Gly Pro Glu Cys Leu Glu Ile Phe Lys Ala Cys Asn Pro Ser Trp Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35


<210> SEQ ID NO 75
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 75

Gly Pro Glu Cys Leu Arg Ile Phe Lys Ala Cys Asn Pro Ser Asn Asp
1               5                   10                  15

Gln Cys Cys Lys Ser Ser Lys Leu Val Cys Ser Lys Lys Thr Arg Trp
            20                  25                  30

Cys Lys Tyr Gln Ile Ile Lys
        35


<210> SEQ ID NO 76
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 76

Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Thr Gln Ile Gly Lys
```

35

<210> SEQ ID NO 77
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 77

Gly Pro Glu Cys Leu Asp Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 78
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 78

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Leu Lys
35

<210> SEQ ID NO 79
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 79

Gly Pro Glu Cys Leu Glu Ile Phe Lys Ala Cys Asn Pro Ser Asn Asp
1 5 10 15

Tyr Cys Cys Lys Ser Ser Lys Leu Val Cys Ser Arg Lys Thr Arg Trp
20 25 30

Cys Lys Tyr Gln Ile Gly Lys
35

<210> SEQ ID NO 80
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 80

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Tyr Ile Gly Lys
35

-continued

<210> SEQ ID NO 81
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 81

Gly Pro Glu Cys Leu Glu Ile Phe Lys Ala Cys Asn Pro Ser Asn Asp
1 5 10 15

Gln Cys Cys Lys Lys Ser Lys Leu Val Cys Ser Arg Lys Thr Arg Trp
20 25 30

Cys Lys Tyr Gln Ile Gly Lys
35

<210> SEQ ID NO 82
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 82

Gly Pro Glu Cys Leu Glu Ile Phe Lys Ala Cys Asn Pro Ser Asn Asp
1 5 10 15

Gln Cys Cys Lys Ser Ser Trp Leu Val Cys Ser Arg Lys Thr Arg Trp
20 25 30

Cys Lys Tyr Gln Ile Gly Lys
35

<210> SEQ ID NO 83
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 83

Gly Pro Asn Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Trp Ser Ile Ile Lys
35

<210> SEQ ID NO 84
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 84

Gly Pro Asn Cys Leu Arg Ile Phe Lys Ala Cys Asn Pro Ser Asn Asp
1 5 10 15

Gln Cys Cys Lys Ser Ser Lys Leu Val Cys Ser Lys Lys Thr Arg Trp
20 25 30

Cys Lys Trp Ser Ile Gly Lys
35

<210> SEQ ID NO 85
<211> LENGTH: 39
<212> TYPE: PRT

<213> ORGANISM: Artificial sequence
<220> FEATURE:
<223> OTHER INFORMATION: Huwentoxin-IV variant

<400> SEQUENCE: 85

```
Gly Pro Glu Cys Leu Leu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35
```

<210> SEQ ID NO 86
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 86

```
Gly Pro Gly Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35
```

<210> SEQ ID NO 87
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 87

```
Gly Pro Glu Cys Leu Glu Ile Phe Lys Ala Cys Asn Pro Ser Asn Asp
1               5                   10                  15

Thr Cys Cys Lys Ser Ser Lys Leu Val Cys Ser Arg Lys Thr Arg Trp
            20                  25                  30

Cys Lys Tyr Gln Ile Gly Lys
        35
```

<210> SEQ ID NO 88
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 88

```
Gly Pro Glu Cys Leu Glu Ile Phe Lys Ala Cys Asn Pro Ser Asn Asp
1               5                   10                  15

Gln Cys Cys Lys Val Ser Lys Leu Val Cys Ser Arg Lys Thr Arg Trp
            20                  25                  30

Cys Lys Tyr Gln Ile Gly Lys
        35
```

<210> SEQ ID NO 89
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 89

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Trp Lys
35

<210> SEQ ID NO 90
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 90

Gly Pro Glu Cys Leu Glu Ile Phe Lys Ala Cys Asn Pro Ser Asn Asp
1 5 10 15

Gln Cys Cys Lys Ser Ser Lys Leu Thr Cys Ser Arg Lys Thr Arg Trp
20 25 30

Cys Lys Tyr Gln Ile Gly Lys
35

<210> SEQ ID NO 91
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 91

Gly Pro Asn Cys Leu Arg Ile Phe Lys Ala Cys Asn Pro Ser Asn Asp
1 5 10 15

Gln Cys Cys Lys Ser Ser Lys Leu Val Cys Ser Lys Lys Thr Arg Trp
20 25 30

Cys Lys Trp Gln Ile Gly Lys
35

<210> SEQ ID NO 92
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 92

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Gly
35

<210> SEQ ID NO 93
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 93

-continued

Gly Pro Gln Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35

<210> SEQ ID NO 94
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 94

Gly Pro Glu Cys Leu Arg Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Trp Gln Ile Ile Lys
        35

<210> SEQ ID NO 95
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 95

Gly Pro Glu Cys Leu Arg Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Trp Ser Ile Ile Lys
        35

<210> SEQ ID NO 96
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 96

Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Lys Lys
        35

<210> SEQ ID NO 97
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 97

Gly Pro Glu Cys Leu Glu Ile Phe Lys Ala Cys Asn Pro Ser Asn Asp
1               5                   10                  15

```
Gln Cys Cys Lys Asn Ser Lys Leu Val Cys Ser Arg Lys Thr Arg Trp
            20                  25                  30

Cys Lys Tyr Gln Ile Gly Lys
        35


<210> SEQ ID NO 98
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 98

Gly Pro Glu Cys Leu Glu Ile Phe Lys Ala Cys Asn Pro Ser Asn Asp
1               5                   10                  15

Gln Cys Cys Lys Ser Thr Lys Leu Val Cys Ser Arg Lys Thr Arg Trp
            20                  25                  30

Cys Lys Tyr Gln Ile Gly Lys
        35


<210> SEQ ID NO 99
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 99

Gly Pro Glu Cys Leu Glu Ile Phe Lys Ala Cys Asn Pro Ser Asn Asp
1               5                   10                  15

Gln Cys Cys Lys Ser Ser Leu Leu Val Cys Ser Arg Lys Thr Arg Trp
            20                  25                  30

Cys Lys Tyr Gln Ile Gly Lys
        35


<210> SEQ ID NO 100
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 100

Gly Pro Glu Cys Leu Glu Ile Phe Lys Ala Cys Asn Pro Ser Asn Asp
1               5                   10                  15

Gln Cys Cys Lys Ser His Lys Leu Val Cys Ser Arg Lys Thr Arg Trp
            20                  25                  30

Cys Lys Tyr Gln Ile Gly Lys
        35


<210> SEQ ID NO 101
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 101

Gly Pro Glu Cys Leu Glu Ile Phe Lys Ala Cys Asn Pro Ser Asn Asp
1               5                   10                  15

Ala Cys Cys Lys Ser Ser Lys Leu Val Cys Ser Arg Lys Thr Arg Trp
            20                  25                  30
```

-continued

```
Cys Lys Tyr Gln Ile Gly Lys
        35


<210> SEQ ID NO 102
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 102

Gly Pro Asn Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Ser Ile Gly Lys
        35


<210> SEQ ID NO 103
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 103

Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly His
        35


<210> SEQ ID NO 104
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 104

Gly Pro Glu Cys Leu Glu Ile Phe Lys Ala Cys Asn Pro Ser Asn Asp
1               5                   10                  15

Gln Cys Cys Lys Tyr Ser Lys Leu Val Cys Ser Arg Lys Thr Arg Trp
            20                  25                  30

Cys Lys Tyr Gln Ile Gly Lys
        35


<210> SEQ ID NO 105
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 105

Gly Pro Glu Cys Leu Glu Ile Phe Lys Ala Cys Asn Pro Ser Asn Asp
1               5                   10                  15

Gln Cys Cys Ile Ser Ser Lys Leu Val Cys Ser Arg Lys Thr Arg Trp
            20                  25                  30

Cys Lys Tyr Gln Ile Gly Lys
        35
```

<210> SEQ ID NO 106
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 106

```
Gly Pro Glu Cys Leu Glu Ile Phe Lys Ala Cys Asn Pro Ser Asn Asp
1               5                   10                  15

Gln Cys Cys Lys Phe Ser Lys Leu Val Cys Ser Arg Lys Thr Arg Trp
            20                  25                  30

Cys Lys Tyr Gln Ile Gly Lys
        35
```

<210> SEQ ID NO 107
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 107

```
Gly Pro Glu Cys Leu Glu Ile Phe Lys Ala Cys Asn Pro Ser Thr Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35
```

<210> SEQ ID NO 108
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 108

```
Gly Pro Glu Cys Leu Glu Ile Phe Lys Ala Cys Asn Pro Ser Asp Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35
```

<210> SEQ ID NO 109
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 109

```
Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Lys
            20                  25                  30

Cys Lys Tyr Gln Ile Gly Lys
        35
```

<210> SEQ ID NO 110
<211> LENGTH: 39

-continued

<212> TYPE: PRT
<213> ORGANISM: Artificial sequence
<220> FEATURE:
<223> OTHER INFORMATION: Huwentoxin-IV variant

<400> SEQUENCE: 110

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Ile Gln Ile Gly Lys
35

<210> SEQ ID NO 111
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 111

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Ala Ile Gly Lys
35

<210> SEQ ID NO 112
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 112

Gly Pro Asn Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Ser Ile Ile Lys
35

<210> SEQ ID NO 113
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 113

Gly Pro Glu Cys Leu Glu Ile Phe Lys Ala Cys Asn Pro Ser Asn Asp
1 5 10 15

Trp Cys Cys Lys Ser Ser Lys Leu Val Cys Ser Arg Lys Thr Arg Trp
20 25 30

Cys Lys Tyr Gln Ile Gly Lys
35

<210> SEQ ID NO 114
<211> LENGTH: 39
<212> TYPE: PRT
<213> ORGANISM: Artificial sequence
<220> FEATURE:

<223> OTHER INFORMATION: Huwentoxin-IV variant

<400> SEQUENCE: 114

Gly Pro Leu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 115
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 115

Gly Pro Ser Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 116
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 116

Gly Pro Glu Cys Leu Pro Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 117
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 117

Gly Pro Glu Cys Leu Glu Ile Phe Lys Ala Cys Asn Pro Ser Asn Asp
1 5 10 15

Gln Cys Cys Thr Ser Ser Lys Leu Val Cys Ser Arg Lys Thr Arg Trp
20 25 30

Cys Lys Tyr Gln Ile Gly Lys
35

<210> SEQ ID NO 118
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 118

Gly Pro Glu Cys Leu Glu Ile Phe Lys Tyr Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 119
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 119

Gly Pro Glu Cys Asn Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 120
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 120

Gly Pro Glu Cys Leu Glu Ile Phe Lys Ala Cys Arg Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 121
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 121

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Trp
35

<210> SEQ ID NO 122
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 122

Gly Pro Glu Cys Leu Glu Ile Phe Lys Ala Cys Asn Pro Ser Asn Asp
1 5 10 15

Gln Cys Cys Lys Ser Ser Lys Leu Ala Cys Ser Arg Lys Thr Arg Trp
20 25 30

Cys Lys Tyr Gln Ile Gly Lys
35

<210> SEQ ID NO 123
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 123

Gly Pro Glu Cys Leu Glu Ile Phe Lys Ala Cys Asn Pro Ser Tyr Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 124
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 124

Gly Pro Glu Cys Leu Glu Ile Phe Lys Ala Cys Asn Pro Ser Asn Asp
1 5 10 15

Gln Cys Cys Lys Ser Ser Gln Leu Val Cys Ser Arg Lys Thr Arg Trp
20 25 30

Cys Lys Tyr Gln Ile Gly Lys
35

<210> SEQ ID NO 125
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 125

Gly Pro Glu Cys Leu Glu Ile Phe Lys Ala Cys Asn Pro Ser Asn Asp
1 5 10 15

Gln Cys Cys Lys Ala Ser Lys Leu Val Cys Ser Arg Lys Thr Arg Trp
20 25 30

Cys Lys Tyr Gln Ile Gly Lys
35

<210> SEQ ID NO 126
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 126

Gly Pro Glu Cys Leu Glu Ile Phe Lys Ala Cys Asn Pro Ser Asn Asp
1 5 10 15

Gln Cys Cys Lys Ser Ile Lys Leu Val Cys Ser Arg Lys Thr Arg Trp
20 25 30

```
Cys Lys Tyr Gln Ile Gly Lys
        35


<210> SEQ ID NO 127
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 127

Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Trp Ser Ile Ile Lys
        35


<210> SEQ ID NO 128
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 128

Gly Pro Thr Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35


<210> SEQ ID NO 129
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 129

Gly Pro Asn Cys Leu Glu Ile Phe Lys Ala Cys Asn Pro Ser Asn Asp
1               5                   10                  15

Gln Cys Cys Lys Ser Ser Lys Leu Val Cys Ser Lys Lys Thr Arg Trp
            20                  25                  30

Cys Lys Trp Ser Ile Gly Lys
        35


<210> SEQ ID NO 130
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 130

Gly Pro Glu Cys Leu Glu Ile Phe Lys Ala Cys Asn Pro Arg Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35
```

<210> SEQ ID NO 131
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 131

Gly Pro Glu Cys Leu Glu Ile Phe Lys Ala Cys Asn Pro Ser Asn Asp
1 5 10 15

Gln Cys Cys Lys Ser Trp Lys Leu Val Cys Ser Arg Lys Thr Arg Trp
20 25 30

Cys Lys Tyr Gln Ile Gly Lys
35

<210> SEQ ID NO 132
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 132

Gly Pro Asn Cys Leu Arg Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Trp Gln Ile Gly Lys
35

<210> SEQ ID NO 133
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 133

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Tyr Thr Arg Trp
20 25 30

Cys Lys Tyr Gln Ile Gly Lys
35

<210> SEQ ID NO 134
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 134

Gly Pro Glu Cys Leu Glu Ile Phe Lys Ala Cys Asn Pro Ser Asn Asp
1 5 10 15

Gln Cys Cys Lys Ser Val Lys Leu Val Cys Ser Arg Lys Thr Arg Trp
20 25 30

Cys Lys Tyr Gln Ile Gly Lys
35

<210> SEQ ID NO 135

<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 135

Gly Pro Glu Cys Leu Glu Ile Phe Lys Ala Cys Asn Pro Ser Asn Asp
1 5 10 15

Gln Cys Cys Lys Ser Ser Lys Leu Leu Cys Ser Arg Lys Thr Arg Trp
20 25 30

Cys Lys Tyr Gln Ile Gly Lys
35

<210> SEQ ID NO 136
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 136

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Ser Ile Ile Lys
35

<210> SEQ ID NO 137
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 137

Gly Pro Glu Cys Leu Glu Ile Phe Lys Ala Cys Asn Pro Ser Gln Asp
1 5 10 15

Gln Cys Cys Lys Ser Ser Lys Leu Val Cys Ser Arg Lys Thr Lys Trp
20 25 30

Cys Lys Tyr Gln Ile Gly Arg
35

<210> SEQ ID NO 138
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 138

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Lys Lys Thr Arg Trp
20 25 30

Cys Lys Trp Ser Ile Gly Lys
35

<210> SEQ ID NO 139
<211> LENGTH: 39
<212> TYPE: PRT
<213> ORGANISM: Artificial sequence

```
<220> FEATURE:
<223> OTHER INFORMATION: Huwentoxin-IV variant

<400> SEQUENCE: 139

Gly Pro Phe Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35


<210> SEQ ID NO 140
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 140

Gly Pro Glu Cys Leu Glu Ile Phe Lys Ala Cys Asn Pro Ser Asn Asp
1               5                   10                  15

Gln Cys Cys Ser Ser Ser Lys Leu Val Cys Ser Arg Lys Thr Arg Trp
            20                  25                  30

Cys Lys Tyr Gln Ile Gly Lys
        35


<210> SEQ ID NO 141
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 141

Gly Pro Glu Cys Leu Glu Ile Phe Lys Ala Cys Asn Pro Ser Asn Asp
1               5                   10                  15

Gln Cys Cys Gln Ser Ser Lys Leu Val Cys Ser Arg Lys Thr Arg Trp
            20                  25                  30

Cys Lys Tyr Gln Ile Gly Lys
        35


<210> SEQ ID NO 142
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 142

Gly Pro Glu Cys Leu Glu Ile Phe Lys Ala Cys Asn Pro Ser Ile Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35


<210> SEQ ID NO 143
<211> LENGTH: 39
<212> TYPE: PRT
<213> ORGANISM: Artificial sequence
<220> FEATURE:
<223> OTHER INFORMATION: Huwentoxin-IV variant
```

<400> SEQUENCE: 143

Gly Pro Glu Cys Leu Glu Ile Phe Lys Ala Cys Asn Pro Ser Asn Asp
1 5 10 15

Gln Cys Cys Lys Ser Ser Lys Pro Val Cys Ser Arg Lys Thr Arg Trp
20 25 30

Cys Lys Tyr Gln Ile Gly Lys
35

<210> SEQ ID NO 144
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 144

Gly Pro Glu Cys Leu Glu Ile Phe Lys Ala Cys Val Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 145
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 145

Gly Pro Glu Cys Leu Glu Ile Phe Ser Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 146
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 146

Gly Pro Glu Cys Leu Glu Ile Phe Lys Ala Cys Asn Pro Ser Asn Asp
1 5 10 15

Gln Cys Cys Lys Ser Ser Lys Tyr Val Cys Ser Arg Lys Thr Arg Trp
20 25 30

Cys Lys Tyr Gln Ile Gly Lys
35

<210> SEQ ID NO 147
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 147

Gly Pro Glu Cys Trp Glu Ile Phe Lys Ala Cys Asn Pro Ser Asn Asp 1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 148
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 148

Gly Pro Glu Cys Leu Glu Ile Phe Lys Ala Cys Asn Pro Ser Asn Asp
1 5 10 15

Gln Cys Cys Gly Ser Ser Lys Leu Val Cys Ser Arg Lys Thr Arg Trp
20 25 30

Cys Lys Tyr Gln Ile Gly Lys
35

<210> SEQ ID NO 149
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 149

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Asn Trp
20 25 30

Cys Lys Tyr Gln Ile Gly Lys
35

<210> SEQ ID NO 150
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 150

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Arg Lys
35

<210> SEQ ID NO 151
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 151

Gly Pro Glu Cys Leu Glu Ile Phe Lys Ala Cys Asn Pro Ser Asn Asp
1 5 10 15

Gln Cys Cys Lys Ser Ser Lys Leu Arg Cys Ser Arg Lys Thr Arg Trp 20 25 30

Cys Lys Tyr Gln Ile Gly Lys
35

<210> SEQ ID NO 152
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 152

Gly Pro Glu Cys Leu Glu Ile Phe Lys Ala Cys Asn Pro Ser Asn Asp
1 5 10 15

Gln Cys Cys Leu Ser Ser Lys Leu Val Cys Ser Arg Lys Thr Arg Trp
20 25 30

Cys Lys Tyr Gln Ile Gly Lys
35

<210> SEQ ID NO 153
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 153

Gly Pro Glu Cys Leu Glu Ile Phe Lys Ala Cys Asn Pro Ser Asn Asp
1 5 10 15

Gln Cys Cys Lys Ser Ser Gly Leu Val Cys Ser Arg Lys Thr Arg Trp
20 25 30

Cys Lys Tyr Gln Ile Gly Lys
35

<210> SEQ ID NO 154
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 154

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Lys Ile Gly Lys
35

<210> SEQ ID NO 155
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 155

Gly Pro Asn Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Ile Lys

35

<210> SEQ ID NO 156
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 156

```
Gly Pro Glu Cys Phe Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35
```

<210> SEQ ID NO 157
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 157

```
Gly Pro Glu Cys Leu Glu Val Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35
```

<210> SEQ ID NO 158
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 158

```
Gly Pro Asn Cys Leu Glu Ile Phe Lys Ala Cys Asn Pro Ser Asn Asp
1               5                   10                  15

Gln Cys Cys Lys Ser Ser Lys Leu Val Cys Ser Lys Lys Thr Arg Trp
            20                  25                  30

Cys Lys Tyr Ser Ile Gly Lys
        35
```

<210> SEQ ID NO 159
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 159

```
Gly Pro Glu Cys Leu Glu Ile Phe Lys Ala Cys Asn Pro Ser Asn Asp
1               5                   10                  15

Gln Cys Cys Lys Ser Gln Lys Leu Val Cys Ser Arg Lys Thr Arg Trp
            20                  25                  30

Cys Lys Tyr Gln Ile Gly Lys
        35
```

<210> SEQ ID NO 160
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 160

Gly Pro Asp Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35

<210> SEQ ID NO 161
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 161

Gly Pro Tyr Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35

<210> SEQ ID NO 162
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 162

Gly Pro Glu Cys Leu Glu Ile Phe Lys Ala Cys Asn Pro Ser Asn Asp
1               5                   10                  15

Gln Cys Cys Lys Ser Ser Ala Leu Val Cys Ser Arg Lys Thr Arg Trp
            20                  25                  30

Cys Lys Tyr Gln Ile Gly Lys
        35

<210> SEQ ID NO 163
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 163

Gly Pro Glu Cys Leu Glu Ile Phe Lys Ala Cys Asn Pro Val Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35

<210> SEQ ID NO 164
<211> LENGTH: 39
<212> TYPE: PRT

<213> ORGANISM: Artificial sequence
<220> FEATURE:
<223> OTHER INFORMATION: Huwentoxin-IV variant

<400> SEQUENCE: 164

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Ala Lys Thr Arg Trp
20 25 30

Cys Lys Tyr Gln Ile Gly Lys
35

<210> SEQ ID NO 165
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 165

Gly Pro Glu Cys Leu Glu Ile Phe Lys Ala Cys Asn Pro Ser Asn Asp
1 5 10 15

Asp Cys Cys Lys Ser Ser Lys Leu Val Cys Ser Arg Lys Thr Arg Trp
20 25 30

Cys Lys Tyr Gln Ile Gly Lys
35

<210> SEQ ID NO 166
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 166

Gly Pro Glu Cys Leu Glu Ile Phe Lys Ala Cys Asn Pro Ser His Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 167
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 167

Gly Pro Glu Cys Leu Glu Ile Phe Lys Phe Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 168
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 168

Gly Pro Glu Cys Leu Glu Ile Phe Lys Ala Cys Asn Pro Ser Asn Asp
1 5 10 15

Gln Cys Cys Lys Ser Ser Lys Phe Val Cys Ser Arg Lys Thr Arg Trp
20 25 30

Cys Lys Tyr Gln Ile Gly Lys
35

<210> SEQ ID NO 169
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 169

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Phe Lys
35

<210> SEQ ID NO 170
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 170

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Val
35

<210> SEQ ID NO 171
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 171

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Tyr
35

<210> SEQ ID NO 172
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 172

Gly Pro Glu Cys Leu Glu Ile Phe Lys Ala Cys Asn Pro Ser Gly Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35

<210> SEQ ID NO 173
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 173

Gly Pro Asn Cys Leu Arg Ile Phe Lys Ala Cys Asn Pro Ser Asn Asp
1               5                   10                  15

Gln Cys Cys Lys Ser Ser Lys Leu Val Cys Ser Lys Lys Thr Arg Trp
            20                  25                  30

Cys Lys Tyr Gln Ile Gly Lys
        35

<210> SEQ ID NO 174
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 174

Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Lys Trp
            20                  25                  30

Cys Lys Tyr Gln Ile Gly Lys
        35

<210> SEQ ID NO 175
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 175

Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Lys Lys Thr Arg Trp
            20                  25                  30

Cys Lys Tyr Gln Ile Gly Lys
        35

<210> SEQ ID NO 176
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 176

Gly Pro Glu Cys Leu Glu Ile Phe Lys Ala Cys Ser Pro Ser Asn Asp
1               5                   10                  15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 177
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 177

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Ile Lys Thr Arg Trp
20 25 30

Cys Lys Tyr Gln Ile Gly Lys
35

<210> SEQ ID NO 178
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 178

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Lys Lys Thr Arg Trp
20 25 30

Cys Lys Tyr Ser Ile Ile Lys
35

<210> SEQ ID NO 179
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 179

Gly Pro Glu Cys Leu Ile Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 180
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 180

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Gly Trp
20 25 30

```
Cys Lys Tyr Gln Ile Gly Lys
        35


<210> SEQ ID NO 181
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 181

Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Gly Trp
            20                  25                  30

Cys Lys Tyr Gln Ile Gly Lys
        35


<210> SEQ ID NO 182
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 182

Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gly Ile Gly Lys
        35


<210> SEQ ID NO 183
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 183

Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Arg Lys Val Arg Trp
            20                  25                  30

Cys Lys Tyr Gln Ile Gly Lys
        35


<210> SEQ ID NO 184
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 184

Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile His Lys
        35
```

<210> SEQ ID NO 185
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 185

Gly Pro Glu Cys Leu Glu Ile Phe Lys Ala Cys Phe Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 186
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 186

Gly Pro Glu Cys Leu Glu Ile Phe Lys Ala Cys Tyr Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 187
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 187

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Val Lys
35

<210> SEQ ID NO 188
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 188

Gly Pro Glu Cys Leu Glu Ile Phe Lys Ala Cys Asn Pro Ser Asn Asp
1 5 10 15

Glu Cys Cys Lys Ser Ser Lys Leu Val Cys Ser Arg Lys Thr Arg Trp
20 25 30

Cys Lys Tyr Gln Ile Gly Lys
35

<210> SEQ ID NO 189
<211> LENGTH: 39

<212> TYPE: PRT
<213> ORGANISM: Artificial sequence
<220> FEATURE:
<223> OTHER INFORMATION: Huwentoxin-IV variant

<400> SEQUENCE: 189

```
Gly Pro Glu Cys Leu Glu Ile Phe Lys Ala Cys Asn Pro Ser Asn Asp
1               5                   10                  15

Gln Cys Cys Pro Ser Ser Lys Leu Val Cys Ser Arg Lys Thr Arg Trp
            20                  25                  30

Cys Lys Tyr Gln Ile Gly Lys
        35
```

<210> SEQ ID NO 190
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 190

```
Gly Pro Glu Cys Leu Glu Ile Phe Lys Ala Cys Asn Pro Ser Val Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35
```

<210> SEQ ID NO 191
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 191

```
Gly Pro Glu Cys Leu Glu Ile Phe Lys Ala Cys Asn Val Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35
```

<210> SEQ ID NO 192
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 192

```
Gly Pro Asn Cys Leu Glu Ile Phe Lys Ala Cys Asn Pro Ser Asn Asp
1               5                   10                  15

Gln Cys Cys Lys Ser Ser Lys Leu Val Cys Ser Lys Lys Thr Arg Trp
            20                  25                  30

Cys Lys Tyr Ser Ile Ile Lys
        35
```

<210> SEQ ID NO 193
<211> LENGTH: 39
<212> TYPE: PRT
<213> ORGANISM: Artificial sequence
<220> FEATURE:

<223> OTHER INFORMATION: Huwentoxin-IV variant

<400> SEQUENCE: 193

```
Gly Pro Glu Cys Leu Glu Ile Phe Lys Ala Cys Asn Pro Ser Asn Asp
1               5                   10                  15

Gln Cys Cys Lys Ser Ser Lys Lys Val Cys Ser Arg Lys Thr Arg Trp
            20                  25                  30

Cys Lys Tyr Gln Ile Gly Lys
        35
```

<210> SEQ ID NO 194
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 194

```
Gly Pro Glu Cys Leu Glu Ile Phe Lys Ala Cys Asn Pro Phe Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35
```

<210> SEQ ID NO 195
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 195

```
Gly Pro Glu Cys Leu Glu Ile Phe Lys Ala Cys Asn Pro Ser Asn Asp
1               5                   10                  15

Lys Cys Cys Lys Ser Ser Lys Leu Val Cys Ser Arg Lys Thr Arg Trp
            20                  25                  30

Cys Lys Tyr Gln Ile Gly Lys
        35
```

<210> SEQ ID NO 196
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 196

```
Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Lys Lys Thr Arg Trp
            20                  25                  30

Cys Lys Tyr Ser Ile Gly Lys
        35
```

<210> SEQ ID NO 197
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 197

```
Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Val Ile Gly Lys
        35


<210> SEQ ID NO 198
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 198

Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Arg Ala Thr Arg Trp
            20                  25                  30

Cys Lys Tyr Gln Ile Gly Lys
        35


<210> SEQ ID NO 199
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 199

Gly Pro Glu Cys Leu Glu Ile Phe Lys Ala Cys Asn Pro Ser Asn Asp
1               5                   10                  15

Gln Cys Cys Lys Ser Ser Thr Leu Val Cys Ser Arg Lys Thr Arg Trp
            20                  25                  30

Cys Lys Tyr Gln Ile Gly Lys
        35


<210> SEQ ID NO 200
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 200

Gly Pro Glu Cys Leu Glu Ile Phe Lys Ala Cys Asn Pro Gln Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35


<210> SEQ ID NO 201
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 201

Gly Pro Glu Cys Leu Glu Ile Phe Lys Ala Cys Asn Pro Ser Asn Asp
1               5                   10                  15
```

```
Gln Cys Cys Lys Ser Ser Lys Leu Val Cys Ser Arg Lys Thr Ala Trp
            20                  25                  30

Cys Lys Tyr Gln Ile Gly Lys
        35


<210> SEQ ID NO 202
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 202

Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Pro
        35


<210> SEQ ID NO 203
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 203

Gly Pro Glu Cys Leu Glu Ile Phe Lys Ala Cys Asn Pro Ser Ser Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35


<210> SEQ ID NO 204
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 204

Gly Pro Glu Cys Leu Glu Ile Phe Lys Ala Cys Asn Pro Ser Asn Asp
1               5                   10                  15

Leu Cys Cys Lys Ser Ser Lys Leu Val Cys Ser Arg Lys Thr Arg Trp
            20                  25                  30

Cys Lys Tyr Gln Ile Gly Lys
        35


<210> SEQ ID NO 205
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 205

Gly Pro Glu Cys Leu Glu Ile Phe Lys Val Cys Asn Pro Ser Asn Asp
1               5                   10                  15

Gln Cys Cys Lys Ser Ser Lys Leu Val Cys Ser Arg Lys Thr Arg Trp
            20                  25                  30
```

```
Cys Lys Tyr Gln Ile Gly Lys
        35


<210> SEQ ID NO 206
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 206

Gly Pro Glu Cys Leu Glu Ile Phe Lys Ala Cys Glu Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35


<210> SEQ ID NO 207
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 207

Gly Pro Glu Cys Leu Glu Ile Phe Lys Ala Cys Asn Pro Ser Pro Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35


<210> SEQ ID NO 208
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 208

Gly Pro Glu Cys Arg Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35


<210> SEQ ID NO 209
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 209

Gly Pro Glu Cys Leu Glu Ile Phe Lys Ala Cys Lys Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35
```

<210> SEQ ID NO 210
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 210

```
Gly Pro Glu Cys Leu Glu Ile Phe Lys Ala Cys Asn Pro Ser Asn Asp
1               5                   10                  15

Gln Cys Cys Lys Gly Ser Lys Leu Val Cys Ser Arg Lys Thr Arg Trp
            20                  25                  30

Cys Lys Tyr Gln Ile Gly Lys
        35
```

<210> SEQ ID NO 211
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 211

```
Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Asn
        35
```

<210> SEQ ID NO 212
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 212

```
Gly Pro Glu Cys Leu Glu Ile Phe Lys Ala Cys Asn Pro Ser Leu Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35
```

<210> SEQ ID NO 213
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 213

```
Gly Pro Glu Cys Leu Glu Ile Phe Lys Ala Cys Asn Pro Ser Asn Pro
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35
```

<210> SEQ ID NO 214

<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 214

```
Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Ile Ile Gly Lys
        35
```

<210> SEQ ID NO 215
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 215

```
Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Gly Lys Thr Arg Trp
            20                  25                  30

Cys Lys Tyr Gln Ile Gly Lys
        35
```

<210> SEQ ID NO 216
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 216

```
Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Leu Trp
            20                  25                  30

Cys Lys Tyr Gln Ile Gly Lys
        35
```

<210> SEQ ID NO 217
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 217

```
Gly Pro Glu Cys Leu Glu Ile Phe Lys Ala Cys Asn Pro Ser Asn Asp
1               5                   10                  15

Gln Cys Cys Lys Ser Ser Asp Leu Val Cys Ser Arg Lys Thr Arg Trp
            20                  25                  30

Cys Lys Tyr Gln Ile Gly Lys
        35
```

<210> SEQ ID NO 218
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 218

Gly Pro Glu Cys Leu Glu Ile Phe Lys Ala Cys Asn Pro Ser Asn Trp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 219
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 219

Gly Pro Glu Cys Leu Glu Ile Phe Lys Ala Cys Asn Pro Ser Asn Asp
1 5 10 15

Gln Cys Cys Lys Ser Ser Lys Trp Val Cys Ser Arg Lys Thr Arg Trp
20 25 30

Cys Lys Tyr Gln Ile Gly Lys
35

<210> SEQ ID NO 220
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 220

Gly Pro Glu Cys Leu Glu Ile Phe Lys Ala Cys Asn Pro Ser Asn Asp
1 5 10 15

Gln Cys Cys Lys Ser Ser Lys Leu Lys Cys Ser Arg Lys Thr Arg Trp
20 25 30

Cys Lys Tyr Gln Ile Gly Lys
35

<210> SEQ ID NO 221
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 221

Gly Pro Glu Cys Leu Glu Ile Phe Gln Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 222
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 222

```
Gly Pro Asn Cys Leu Glu Ile Phe Lys Ala Cys Asn Pro Ser Asn Asp
1               5                   10                  15

Gln Cys Cys Lys Ser Ser Lys Leu Val Cys Ser Lys Lys Thr Arg Trp
            20                  25                  30

Cys Lys Tyr Gln Ile Gly Lys
        35
```

<210> SEQ ID NO 223
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 223

```
Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Tyr
            20                  25                  30

Cys Lys Tyr Gln Ile Gly Lys
        35
```

<210> SEQ ID NO 224
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 224

```
Gly Pro Glu Cys Leu Glu Ile Phe Lys Ala Cys Asn Pro Ser Asn Asp
1               5                   10                  15

Pro Cys Cys Lys Ser Ser Lys Leu Val Cys Ser Arg Lys Thr Arg Trp
            20                  25                  30

Cys Lys Tyr Gln Ile Gly Lys
        35
```

<210> SEQ ID NO 225
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 225

```
Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Lys Lys Thr Arg Trp
            20                  25                  30

Cys Lys Tyr Gln Ile Ile Lys
        35
```

<210> SEQ ID NO 226
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 226

```
Gly Pro Glu Cys Leu Glu Ile Phe Lys Ala Cys Asn Pro Ser Asn Asp
```

-continued

```
1               5                   10                  15

Gln Cys Cys Lys Ser Ser Lys Leu Val Cys Ser Thr Lys Thr Arg Trp
            20                  25                  30

Cys Lys Tyr Gln Ile Gly Lys
        35
```

<210> SEQ ID NO 227
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 227

```
Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Asp Trp
            20                  25                  30

Cys Lys Tyr Gln Ile Gly Lys
        35
```

<210> SEQ ID NO 228
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 228

```
Gly Pro Glu Cys Leu Glu Ile Phe Lys Ala Cys Asn Pro Ser Asn Asp
1               5                   10                  15

Gln Cys Cys Phe Ser Ser Lys Leu Val Cys Ser Arg Lys Thr Arg Trp
            20                  25                  30

Cys Lys Tyr Gln Ile Gly Lys
        35
```

<210> SEQ ID NO 229
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 229

```
Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser His Lys Thr Arg Trp
            20                  25                  30

Cys Lys Tyr Gln Ile Gly Lys
        35
```

<210> SEQ ID NO 230
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 230

```
Gly Pro Glu Cys Leu Glu Ile Phe Lys Ala Cys Asn Pro Ser Asn Gln
1               5                   10                  15

Gln Cys Cys Lys Ser Ser Lys Leu Val Cys Ser Arg Lys Thr Arg Trp
```

20 25 30

Cys Lys Tyr Gln Ile Gly Lys
35

<210> SEQ ID NO 231
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 231

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Val Lys Thr Arg Trp
20 25 30

Cys Lys Tyr Gln Ile Gly Lys
35

<210> SEQ ID NO 232
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 232

Gly Pro Glu Cys Leu Glu Ile Phe Lys Ala Cys Asn Pro Ser Asn Asp
1 5 10 15

Gln Cys Cys Lys Ser Ser Lys Ala Val Cys Ser Arg Lys Thr Arg Trp
20 25 30

Cys Lys Tyr Gln Ile Gly Lys
35

<210> SEQ ID NO 233
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 233

Gly Pro Glu Cys Leu Glu Ile Phe Lys Ala Cys Asn Pro Ser Asn Gly
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 234
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 234

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Ser

35

<210> SEQ ID NO 235
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 235

Gly Pro Glu Cys Leu Glu Ile Phe Lys Ala Cys Asn Pro Ser Asn Asp
1 5 10 15

Val Cys Cys Lys Ser Ser Lys Leu Val Cys Ser Arg Lys Thr Arg Trp
20 25 30

Cys Lys Tyr Gln Ile Gly Lys
35

<210> SEQ ID NO 236
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 236

Gly Pro Glu Cys Leu Glu Ile Met Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 237
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 237

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gln Lys
35

<210> SEQ ID NO 238
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 238

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Thr
35

-continued

<210> SEQ ID NO 239
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 239

Gly Pro Glu Cys Leu Glu Ile Phe Lys Ala Cys Asn Pro Ser Asn Asp
1 5 10 15

Gln Cys Cys Trp Ser Ser Lys Leu Val Cys Ser Arg Lys Thr Arg Trp
20 25 30

Cys Lys Tyr Gln Ile Gly Lys
35

<210> SEQ ID NO 240
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 240

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Trp Ile Gly Lys
35

<210> SEQ ID NO 241
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 241

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Trp Ser Ile Gly Lys
35

<210> SEQ ID NO 242
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 242

Gly Pro Glu Cys Leu Ala Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 243
<211> LENGTH: 39
<212> TYPE: PRT

<213> ORGANISM: Artificial sequence
<220> FEATURE:
<223> OTHER INFORMATION: Huwentoxin-IV variant

<400> SEQUENCE: 243

Gly Pro Ala Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 244
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 244

Gly Pro Glu Cys Leu Glu Ile Phe Lys Ala Cys Asn Pro Ser Asn Asp
1 5 10 15

Gln Cys Cys Ala Ser Ser Lys Leu Val Cys Ser Arg Lys Thr Arg Trp
20 25 30

Cys Lys Tyr Gln Ile Gly Lys
35

<210> SEQ ID NO 245
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 245

Gly Pro Glu Cys Leu Glu Ile Phe Lys Trp Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 246
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 246

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Ala Arg Trp
20 25 30

Cys Lys Tyr Gln Ile Gly Lys
35

<210> SEQ ID NO 247
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 247

Gly Pro Glu Cys Leu Glu Ile Phe Lys Ala Cys Asn Pro Ser Asn Asp
1 5 10 15

Gln Cys Cys Lys Ser Ala Lys Leu Val Cys Ser Arg Lys Thr Arg Trp
20 25 30

Cys Lys Tyr Gln Ile Gly Lys
35

<210> SEQ ID NO 248
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 248

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Ala
35

<210> SEQ ID NO 249
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 249

Gly Pro Glu Cys Leu Glu Ile Phe Lys Ala Cys Ala Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 250
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 250

Gly Pro Glu Cys Leu Glu Ile Phe Lys Ala Cys Asn Pro Ala Asn Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 251
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 251

```
Gly Pro Glu Cys Leu Glu Ile Phe Ala Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35


<210> SEQ ID NO 252
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 252

Gly Pro Glu Cys Leu Glu Ala Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35


<210> SEQ ID NO 253
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 253

Gly Pro Glu Cys Ala Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Gly Lys
        35


<210> SEQ ID NO 254
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 254

Gly Pro Glu Cys Leu Glu Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Tyr Gln Ile Ala Lys
        35


<210> SEQ ID NO 255
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 255

Gly Pro Glu Cys Leu Glu Ile Ala Lys Ala Cys Asn Pro Ser Asn Asp
1               5                   10                  15
```

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 256
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 256

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Tyr Gln Ala Gly Lys
35

<210> SEQ ID NO 257
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 257

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Ala Gln Ile Gly Lys
35

<210> SEQ ID NO 258
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 258

Gly Pro Glu Cys Leu Glu Ile Phe Lys Ala Cys Asn Ala Ser Asn Asp
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 259
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 259

Gly Pro Glu Cys Leu Glu Ile Phe Lys Ala Cys Asn Pro Ser Asn Ala
1 5 10 15

Gln Cys Cys Lys Ser Ser Lys Leu Val Cys Ser Arg Lys Thr Arg Trp
20 25 30

Cys Lys Tyr Gln Ile Gly Lys
35

<210> SEQ ID NO 260
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 260

Gly Pro Glu Cys Leu Glu Ile Phe Lys Ala Cys Asn Pro Ser Asn Asp
1 5 10 15

Gln Cys Cys Lys Ser Ser Lys Leu Val Cys Ala Arg Lys Thr Arg Trp
20 25 30

Cys Lys Tyr Gln Ile Gly Lys
35

<210> SEQ ID NO 261
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 261

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Ala
20 25 30

Cys Lys Tyr Gln Ile Gly Lys
35

<210> SEQ ID NO 262
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 262

Gly Pro Glu Cys Leu Glu Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Ala Tyr Gln Ile Gly Lys
35

<210> SEQ ID NO 263
<211> LENGTH: 1977
<212> TYPE: PRT
<213> ORGANISM: Homo sapiens

<400> SEQUENCE: 263

Met Ala Met Leu Pro Pro Pro Gly Pro Gln Ser Phe Val His Phe Thr
1 5 10 15

Lys Gln Ser Leu Ala Leu Ile Glu Gln Arg Ile Ala Glu Arg Lys Ser
20 25 30

Lys Glu Pro Lys Glu Glu Lys Lys Asp Asp Asp Glu Glu Ala Pro Lys
35 40 45

Pro Ser Ser Asp Leu Glu Ala Gly Lys Gln Leu Pro Phe Ile Tyr Gly
50 55 60

```
Asp Ile Pro Pro Gly Met Val Ser Glu Pro Leu Glu Asp Leu Asp Pro
65                  70                  75                  80

Tyr Tyr Ala Asp Lys Lys Thr Phe Ile Val Leu Asn Lys Gly Lys Thr
                85                  90                  95

Ile Phe Arg Phe Asn Ala Thr Pro Ala Leu Tyr Met Leu Ser Pro Phe
            100                 105                 110

Ser Pro Leu Arg Arg Ile Ser Ile Lys Ile Leu Val His Ser Leu Phe
        115                 120                 125

Ser Met Leu Ile Met Cys Thr Ile Leu Thr Asn Cys Ile Phe Met Thr
    130                 135                 140

Met Asn Asn Pro Pro Asp Trp Thr Lys Asn Val Glu Tyr Thr Phe Thr
145                 150                 155                 160

Gly Ile Tyr Thr Phe Glu Ser Leu Val Lys Ile Leu Ala Arg Gly Phe
                165                 170                 175

Cys Val Gly Glu Phe Thr Phe Leu Arg Asp Pro Trp Asn Trp Leu Asp
            180                 185                 190

Phe Val Val Ile Val Phe Ala Tyr Leu Thr Glu Phe Val Asn Leu Gly
        195                 200                 205

Asn Val Ser Ala Leu Arg Thr Phe Arg Val Leu Arg Ala Leu Lys Thr
    210                 215                 220

Ile Ser Val Ile Pro Gly Leu Lys Thr Ile Val Gly Ala Leu Ile Gln
225                 230                 235                 240

Ser Val Lys Lys Leu Ser Asp Val Met Ile Leu Thr Val Phe Cys Leu
                245                 250                 255

Ser Val Phe Ala Leu Ile Gly Leu Gln Leu Phe Met Gly Asn Leu Lys
            260                 265                 270

His Lys Cys Phe Arg Asn Ser Leu Glu Asn Asn Glu Thr Leu Glu Ser
        275                 280                 285

Ile Met Asn Thr Leu Glu Ser Glu Glu Asp Phe Arg Lys Tyr Phe Tyr
    290                 295                 300

Tyr Leu Glu Gly Ser Lys Asp Ala Leu Leu Cys Gly Phe Ser Thr Asp
305                 310                 315                 320

Ser Gly Gln Cys Pro Glu Gly Tyr Thr Cys Val Lys Ile Gly Arg Asn
                325                 330                 335

Pro Asp Tyr Gly Tyr Thr Ser Phe Asp Thr Phe Ser Trp Ala Phe Leu
            340                 345                 350

Ala Leu Phe Arg Leu Met Thr Gln Asp Tyr Trp Glu Asn Leu Tyr Gln
        355                 360                 365

Gln Thr Leu Arg Ala Ala Gly Lys Thr Tyr Met Ile Phe Phe Val Val
    370                 375                 380

Val Ile Phe Leu Gly Ser Phe Tyr Leu Ile Asn Leu Ile Leu Ala Val
385                 390                 395                 400

Val Ala Met Ala Tyr Glu Glu Gln Asn Gln Ala Asn Ile Glu Glu Ala
                405                 410                 415

Lys Gln Lys Glu Leu Glu Phe Gln Gln Met Leu Asp Arg Leu Lys Lys
            420                 425                 430

Glu Gln Glu Glu Ala Glu Ala Ile Ala Ala Ala Ala Ala Glu Tyr Thr
        435                 440                 445

Ser Ile Arg Arg Ser Arg Ile Met Gly Leu Ser Glu Ser Ser Ser Glu
    450                 455                 460

Thr Ser Lys Leu Ser Ser Lys Ser Ala Lys Glu Arg Arg Asn Arg Arg
465                 470                 475                 480
```

-continued

```
Lys Lys Lys Asn Gln Lys Lys Leu Ser Ser Gly Glu Glu Lys Gly Asp
                485                 490                 495

Ala Glu Lys Leu Ser Lys Ser Glu Ser Glu Asp Ser Ile Arg Arg Lys
            500                 505                 510

Ser Phe His Leu Gly Val Glu Gly His Arg Arg Ala His Glu Lys Arg
        515                 520                 525

Leu Ser Thr Pro Asn Gln Ser Pro Leu Ser Ile Arg Gly Ser Leu Phe
    530                 535                 540

Ser Ala Arg Arg Ser Ser Arg Thr Ser Leu Phe Ser Phe Lys Gly Arg
545                 550                 555                 560

Gly Arg Asp Ile Gly Ser Glu Thr Glu Phe Ala Asp Asp Glu His Ser
                565                 570                 575

Ile Phe Gly Asp Asn Glu Ser Arg Arg Gly Ser Leu Phe Val Pro His
            580                 585                 590

Arg Pro Gln Glu Arg Arg Ser Ser Asn Ile Ser Gln Ala Ser Arg Ser
        595                 600                 605

Pro Pro Met Leu Pro Val Asn Gly Lys Met His Ser Ala Val Asp Cys
    610                 615                 620

Asn Gly Val Val Ser Leu Val Asp Gly Arg Ser Ala Leu Met Leu Pro
625                 630                 635                 640

Asn Gly Gln Leu Leu Pro Glu Gly Thr Thr Asn Gln Ile His Lys Lys
                645                 650                 655

Arg Arg Cys Ser Ser Tyr Leu Leu Ser Glu Asp Met Leu Asn Asp Pro
            660                 665                 670

Asn Leu Arg Gln Arg Ala Met Ser Arg Ala Ser Ile Leu Thr Asn Thr
        675                 680                 685

Val Glu Glu Leu Glu Glu Ser Arg Gln Lys Cys Pro Pro Trp Trp Tyr
    690                 695                 700

Arg Phe Ala His Lys Phe Leu Ile Trp Asn Cys Ser Pro Tyr Trp Ile
705                 710                 715                 720

Lys Phe Lys Lys Cys Ile Tyr Phe Ile Val Met Asp Pro Phe Val Asp
                725                 730                 735

Leu Ala Ile Thr Ile Cys Ile Val Leu Asn Thr Leu Phe Met Ala Met
            740                 745                 750

Glu His His Pro Met Thr Glu Glu Phe Lys Asn Val Leu Ala Ile Gly
        755                 760                 765

Asn Leu Val Phe Thr Gly Ile Phe Ala Ala Glu Met Val Leu Lys Leu
    770                 775                 780

Ile Ala Met Asp Pro Tyr Glu Tyr Phe Gln Val Gly Trp Asn Ile Phe
785                 790                 795                 800

Asp Ser Leu Ile Val Thr Leu Ser Leu Val Glu Leu Phe Leu Ala Asp
                805                 810                 815

Val Glu Gly Leu Ser Val Leu Arg Ser Phe Arg Leu Leu Arg Val Phe
            820                 825                 830

Lys Leu Ala Lys Ser Trp Pro Thr Leu Asn Met Leu Ile Lys Ile Ile
        835                 840                 845

Gly Asn Ser Val Gly Ala Leu Gly Asn Leu Thr Leu Val Leu Ala Ile
    850                 855                 860

Ile Val Phe Ile Phe Ala Val Val Gly Met Gln Leu Phe Gly Lys Ser
865                 870                 875                 880

Tyr Lys Glu Cys Val Cys Lys Ile Asn Asp Asp Cys Thr Leu Pro Arg
                885                 890                 895

Trp His Met Asn Asp Phe Phe His Ser Phe Leu Ile Val Phe Arg Val
```

-continued

```
            900                 905                 910

Leu Cys Gly Glu Trp Ile Glu Thr Met Trp Asp Cys Met Glu Val Ala
        915                 920                 925

Gly Gln Ala Met Cys Leu Ile Val Tyr Met Met Val Met Val Ile Gly
    930                 935                 940

Asn Leu Val Val Leu Asn Leu Phe Leu Ala Leu Leu Leu Ser Ser Phe
945                 950                 955                 960

Ser Ser Asp Asn Leu Thr Ala Ile Glu Glu Asp Pro Asp Ala Asn Asn
                965                 970                 975

Leu Gln Ile Ala Val Thr Arg Ile Lys Lys Gly Ile Asn Tyr Val Lys
            980                 985                 990

Gln Thr Leu Arg Glu Phe Ile Leu  Lys Ala Phe Ser Lys  Lys Pro Lys
        995                 1000                1005

Ile Ser  Arg Glu Ile Arg Gln  Ala Glu Asp Leu Asn  Thr Lys Lys
    1010                1015                1020

Glu Asn  Tyr Ile Ser Asn His  Thr Leu Ala Glu Met  Ser Lys Gly
    1025                1030                1035

His Asn  Phe Leu Lys Glu Lys  Asp Lys Ile Ser Gly  Phe Gly Ser
    1040                1045                1050

Ser Val  Asp Lys His Leu Met  Glu Asp Ser Asp Gly  Gln Ser Phe
    1055                1060                1065

Ile His  Asn Pro Ser Leu Thr  Val Thr Val Pro Ile  Ala Pro Gly
    1070                1075                1080

Glu Ser  Asp Leu Glu Asn Met  Asn Ala Glu Glu Leu  Ser Ser Asp
    1085                1090                1095

Ser Asp  Ser Glu Tyr Ser Lys  Val Arg Leu Asn Arg  Ser Ser Ser
    1100                1105                1110

Ser Glu  Cys Ser Thr Val Asp  Asn Pro Leu Pro Gly  Glu Gly Glu
    1115                1120                1125

Glu Ala  Glu Ala Glu Pro Met  Asn Ser Asp Glu Pro  Glu Ala Cys
    1130                1135                1140

Phe Thr  Asp Gly Cys Val Arg  Arg Phe Ser Cys Cys  Gln Val Asn
    1145                1150                1155

Ile Glu  Ser Gly Lys Gly Lys  Ile Trp Trp Asn Ile  Arg Lys Thr
    1160                1165                1170

Cys Tyr  Lys Ile Val Glu His  Ser Trp Phe Glu Ser  Phe Ile Val
    1175                1180                1185

Leu Met  Ile Leu Leu Ser Ser  Gly Ala Leu Ala Phe  Glu Asp Ile
    1190                1195                1200

Tyr Ile  Glu Arg Lys Lys Thr  Ile Lys Ile Ile Leu  Glu Tyr Ala
    1205                1210                1215

Asp Lys  Ile Phe Thr Tyr Ile  Phe Ile Leu Glu Met  Leu Leu Lys
    1220                1225                1230

Trp Ile  Ala Tyr Gly Tyr Lys  Thr Tyr Phe Thr Asn  Ala Trp Cys
    1235                1240                1245

Trp Leu  Asp Phe Leu Ile Val  Asp Val Ser Leu Val  Thr Leu Val
    1250                1255                1260

Ala Asn  Thr Leu Gly Tyr Ser  Asp Leu Gly Pro Ile  Lys Ser Leu
    1265                1270                1275

Arg Thr  Leu Arg Ala Leu Arg  Pro Leu Arg Ala Leu  Ser Arg Phe
    1280                1285                1290

Glu Gly  Met Arg Val Val Val  Asn Ala Leu Ile Gly  Ala Ile Pro
    1295                1300                1305
```

-continued

```
Ser Ile  Met Asn Val Leu Leu  Val Cys Leu Ile Phe  Trp Leu Ile
    1310                 1315                 1320

Phe Ser  Ile Met Gly Val Asn  Leu Phe Ala Gly Lys  Phe Tyr Glu
    1325                 1330                 1335

Cys Ile  Asn Thr Thr Asp Gly  Ser Arg Phe Pro Ala  Ser Gln Val
    1340                 1345                 1350

Pro Asn  Arg Ser Glu Cys Phe  Ala Leu Met Asn Val  Ser Gln Asn
    1355                 1360                 1365

Val Arg  Trp Lys Asn Leu Lys  Val Asn Phe Asp Asn  Val Gly Leu
    1370                 1375                 1380

Gly Tyr  Leu Ser Leu Leu Gln  Val Ala Thr Phe Lys  Gly Trp Thr
    1385                 1390                 1395

Ile Ile  Met Tyr Ala Ala Val  Asp Ser Val Asn Val  Asp Lys Gln
    1400                 1405                 1410

Pro Lys  Tyr Glu Tyr Ser Leu  Tyr Met Tyr Ile Tyr  Phe Val Val
    1415                 1420                 1425

Phe Ile  Ile Phe Gly Ser Phe  Phe Thr Leu Asn Leu  Phe Ile Gly
    1430                 1435                 1440

Val Ile  Ile Asp Asn Phe Asn  Gln Gln Lys Lys Lys  Leu Gly Gly
    1445                 1450                 1455

Gln Asp  Ile Phe Met Thr Glu  Glu Gln Lys Lys Tyr  Tyr Asn Ala
    1460                 1465                 1470

Met Lys  Lys Leu Gly Ser Lys  Lys Pro Gln Lys Pro  Ile Pro Arg
    1475                 1480                 1485

Pro Gly  Asn Lys Ile Gln Gly  Cys Ile Phe Asp Leu  Val Thr Asn
    1490                 1495                 1500

Gln Ala  Phe Asp Ile Ser Ile  Met Val Leu Ile Cys  Leu Asn Met
    1505                 1510                 1515

Val Thr  Met Met Val Glu Lys  Glu Gly Gln Ser Gln  His Met Thr
    1520                 1525                 1530

Glu Val  Leu Tyr Trp Ile Asn  Val Val Phe Ile Ile  Leu Phe Thr
    1535                 1540                 1545

Gly Glu  Cys Val Leu Lys Leu  Ile Ser Leu Arg His  Tyr Tyr Phe
    1550                 1555                 1560

Thr Val  Gly Trp Asn Ile Phe  Asp Phe Val Val Val  Ile Ile Ser
    1565                 1570                 1575

Ile Val  Gly Met Phe Leu Ala  Asp Leu Ile Glu Thr  Tyr Phe Val
    1580                 1585                 1590

Ser Pro  Thr Leu Phe Arg Val  Ile Arg Leu Ala Arg  Ile Gly Arg
    1595                 1600                 1605

Ile Leu  Arg Leu Val Lys Gly  Ala Lys Gly Ile Arg  Thr Leu Leu
    1610                 1615                 1620

Phe Ala  Leu Met Met Ser Leu  Pro Ala Leu Phe Asn  Ile Gly Leu
    1625                 1630                 1635

Leu Leu  Phe Leu Val Met Phe  Ile Tyr Ala Ile Phe  Gly Met Ser
    1640                 1645                 1650

Asn Phe  Ala Tyr Val Lys Lys  Glu Asp Gly Ile Asn  Asp Met Phe
    1655                 1660                 1665

Asn Phe  Glu Thr Phe Gly Asn  Ser Met Ile Cys Leu  Phe Gln Ile
    1670                 1675                 1680

Thr Thr  Ser Ala Gly Trp Asp  Gly Leu Leu Ala Pro  Ile Leu Asn
    1685                 1690                 1695
```

-continued

```
Ser Lys  Pro Pro Asp Cys Asp  Pro Lys Lys Val His  Pro Gly Ser
    1700                 1705                 1710

Ser Val  Glu Gly Asp Cys Gly  Asn Pro Ser Val Gly  Ile Phe Tyr
    1715                 1720                 1725

Phe Val  Ser Tyr Ile Ile Ile  Ser Phe Leu Val Val  Val Asn Met
    1730                 1735                 1740

Tyr Ile  Ala Val Ile Leu Glu  Asn Phe Ser Val Ala  Thr Glu Glu
    1745                 1750                 1755

Ser Thr  Glu Pro Leu Ser Glu  Asp Asp Phe Glu Met  Phe Tyr Glu
    1760                 1765                 1770

Val Trp  Glu Lys Phe Asp Pro  Asp Ala Thr Gln Phe  Ile Glu Phe
    1775                 1780                 1785

Ser Lys  Leu Ser Asp Phe Ala  Ala Ala Leu Asp Pro  Pro Leu Leu
    1790                 1795                 1800

Ile Ala  Lys Pro Asn Lys Val  Gln Leu Ile Ala Met  Asp Leu Pro
    1805                 1810                 1815

Met Val  Ser Gly Asp Arg Ile  His Cys Leu Asp Ile  Leu Phe Ala
    1820                 1825                 1830

Phe Thr  Lys Arg Val Leu Gly  Glu Ser Gly Glu Met  Asp Ser Leu
    1835                 1840                 1845

Arg Ser  Gln Met Glu Glu Arg  Phe Met Ser Ala Asn  Pro Ser Lys
    1850                 1855                 1860

Val Ser  Tyr Glu Pro Ile Thr  Thr Thr Leu Lys Arg  Lys Gln Glu
    1865                 1870                 1875

Asp Val  Ser Ala Thr Val Ile  Gln Arg Ala Tyr Arg  Arg Tyr Arg
    1880                 1885                 1890

Leu Arg  Gln Asn Val Lys Asn  Ile Ser Ser Ile Tyr  Ile Lys Asp
    1895                 1900                 1905

Gly Asp  Arg Asp Asp Asp Leu  Leu Asn Lys Lys Asp  Met Ala Phe
    1910                 1915                 1920

Asp Asn  Val Asn Glu Asn Ser  Ser Pro Glu Lys Thr  Asp Ala Thr
    1925                 1930                 1935

Ser Ser  Thr Thr Ser Pro Pro  Ser Tyr Asp Ser Val  Thr Lys Pro
    1940                 1945                 1950

Asp Lys  Glu Lys Tyr Glu Gln  Asp Arg Thr Glu Lys  Glu Asp Lys
    1955                 1960                 1965

Gly Lys  Asp Ser Lys Glu Ser  Lys Lys
    1970                 1975
```

<210> SEQ ID NO 264
<211> LENGTH: 2005
<212> TYPE: PRT
<213> ORGANISM: Homo sapiens

<400> SEQUENCE: 264

```
Met Ala Gln Ser Val Leu Val Pro Pro Gly Pro Asp Ser Phe Arg Phe
1               5                   10                  15

Phe Thr Arg Glu Ser Leu Ala Ala Ile Glu Gln Arg Ile Ala Glu Glu
            20                  25                  30

Lys Ala Lys Arg Pro Lys Gln Glu Arg Lys Asp Glu Asp Asp Glu Asn
        35                  40                  45

Gly Pro Lys Pro Asn Ser Asp Leu Glu Ala Gly Lys Ser Leu Pro Phe
    50                  55                  60

Ile Tyr Gly Asp Ile Pro Pro Glu Met Val Ser Val Pro Leu Glu Asp
65                  70                  75                  80
```

```
Leu Asp Pro Tyr Tyr Ile Asn Lys Lys Thr Phe Ile Val Leu Asn Lys
                85                  90                  95

Gly Lys Ala Ile Ser Arg Phe Ser Ala Thr Pro Ala Leu Tyr Ile Leu
            100                 105                 110

Thr Pro Phe Asn Pro Ile Arg Lys Leu Ala Ile Lys Ile Leu Val His
        115                 120                 125

Ser Leu Phe Asn Met Leu Ile Met Cys Thr Ile Leu Thr Asn Cys Val
    130                 135                 140

Phe Met Thr Met Ser Asn Pro Pro Asp Trp Thr Lys Asn Val Glu Tyr
145                 150                 155                 160

Thr Phe Thr Gly Ile Tyr Thr Phe Glu Ser Leu Ile Lys Ile Leu Ala
                165                 170                 175

Arg Gly Phe Cys Leu Glu Asp Phe Thr Phe Leu Arg Asp Pro Trp Asn
            180                 185                 190

Trp Leu Asp Phe Thr Val Ile Thr Phe Ala Tyr Val Thr Glu Phe Val
        195                 200                 205

Asp Leu Gly Asn Val Ser Ala Leu Arg Thr Phe Arg Val Leu Arg Ala
    210                 215                 220

Leu Lys Thr Ile Ser Val Ile Pro Gly Leu Lys Thr Ile Val Gly Ala
225                 230                 235                 240

Leu Ile Gln Ser Val Lys Lys Leu Ser Asp Val Met Ile Leu Thr Val
                245                 250                 255

Phe Cys Leu Ser Val Phe Ala Leu Ile Gly Leu Gln Leu Phe Met Gly
            260                 265                 270

Asn Leu Arg Asn Lys Cys Leu Gln Trp Pro Pro Asp Asn Ser Ser Phe
        275                 280                 285

Glu Ile Asn Ile Thr Ser Phe Phe Asn Asn Ser Leu Asp Gly Asn Gly
    290                 295                 300

Thr Thr Phe Asn Arg Thr Val Ser Ile Phe Asn Trp Asp Glu Tyr Ile
305                 310                 315                 320

Glu Asp Lys Ser His Phe Tyr Phe Leu Glu Gly Gln Asn Asp Ala Leu
                325                 330                 335

Leu Cys Gly Asn Ser Ser Asp Ala Gly Gln Cys Pro Glu Gly Tyr Ile
            340                 345                 350

Cys Val Lys Ala Gly Arg Asn Pro Asn Tyr Gly Tyr Thr Ser Phe Asp
        355                 360                 365

Thr Phe Ser Trp Ala Phe Leu Ser Leu Phe Arg Leu Met Thr Gln Asp
    370                 375                 380

Phe Trp Glu Asn Leu Tyr Gln Leu Thr Leu Arg Ala Ala Gly Lys Thr
385                 390                 395                 400

Tyr Met Ile Phe Phe Val Leu Val Ile Phe Leu Gly Ser Phe Tyr Leu
                405                 410                 415

Ile Asn Leu Ile Leu Ala Val Val Ala Met Ala Tyr Glu Glu Gln Asn
            420                 425                 430

Gln Ala Thr Leu Glu Glu Ala Glu Gln Lys Glu Ala Glu Phe Gln Gln
        435                 440                 445

Met Leu Glu Gln Leu Lys Lys Gln Gln Glu Glu Ala Gln Ala Ala Ala
    450                 455                 460

Ala Ala Ala Ser Ala Glu Ser Arg Asp Phe Ser Gly Ala Gly Gly Ile
465                 470                 475                 480

Gly Val Phe Ser Glu Ser Ser Ser Val Ala Ser Lys Leu Ser Ser Lys
                485                 490                 495
```

-continued

```
Ser Glu Lys Glu Leu Lys Asn Arg Arg Lys Lys Lys Lys Gln Lys Glu
            500                 505                 510

Gln Ser Gly Glu Glu Glu Lys Asn Asp Arg Val Arg Lys Ser Glu Ser
        515                 520                 525

Glu Asp Ser Ile Arg Arg Lys Gly Phe Arg Phe Ser Leu Glu Gly Ser
    530                 535                 540

Arg Leu Thr Tyr Glu Lys Arg Phe Ser Ser Pro His Gln Ser Leu Leu
545                 550                 555                 560

Ser Ile Arg Gly Ser Leu Phe Ser Pro Arg Arg Asn Ser Arg Ala Ser
                565                 570                 575

Leu Phe Ser Phe Arg Gly Arg Ala Lys Asp Ile Gly Ser Glu Asn Asp
            580                 585                 590

Phe Ala Asp Asp Glu His Ser Thr Phe Glu Asp Asn Asp Ser Arg Arg
        595                 600                 605

Asp Ser Leu Phe Val Pro His Arg His Gly Glu Arg Arg His Ser Asn
    610                 615                 620

Val Ser Gln Ala Ser Arg Ala Ser Arg Val Leu Pro Ile Leu Pro Met
625                 630                 635                 640

Asn Gly Lys Met His Ser Ala Val Asp Cys Asn Gly Val Val Ser Leu
                645                 650                 655

Val Gly Gly Pro Ser Thr Leu Thr Ser Ala Gly Gln Leu Leu Pro Glu
            660                 665                 670

Gly Thr Thr Thr Glu Thr Glu Ile Arg Lys Arg Arg Ser Ser Ser Tyr
        675                 680                 685

His Val Ser Met Asp Leu Leu Glu Asp Pro Thr Ser Arg Gln Arg Ala
    690                 695                 700

Met Ser Ile Ala Ser Ile Leu Thr Asn Thr Met Glu Glu Leu Glu Glu
705                 710                 715                 720

Ser Arg Gln Lys Cys Pro Pro Cys Trp Tyr Lys Phe Ala Asn Met Cys
                725                 730                 735

Leu Ile Trp Asp Cys Cys Lys Pro Trp Leu Lys Val Lys His Leu Val
            740                 745                 750

Asn Leu Val Val Met Asp Pro Phe Val Asp Leu Ala Ile Thr Ile Cys
        755                 760                 765

Ile Val Leu Asn Thr Leu Phe Met Ala Met Glu His Tyr Pro Met Thr
    770                 775                 780

Glu Gln Phe Ser Ser Val Leu Ser Val Gly Asn Leu Val Phe Thr Gly
785                 790                 795                 800

Ile Phe Thr Ala Glu Met Phe Leu Lys Ile Ile Ala Met Asp Pro Tyr
                805                 810                 815

Tyr Tyr Phe Gln Glu Gly Trp Asn Ile Phe Asp Gly Phe Ile Val Ser
            820                 825                 830

Leu Ser Leu Met Glu Leu Gly Leu Ala Asn Val Glu Gly Leu Ser Val
        835                 840                 845

Leu Arg Ser Phe Arg Leu Leu Arg Val Phe Lys Leu Ala Lys Ser Trp
    850                 855                 860

Pro Thr Leu Asn Met Leu Ile Lys Ile Ile Gly Asn Ser Val Gly Ala
865                 870                 875                 880

Leu Gly Asn Leu Thr Leu Val Leu Ala Ile Ile Val Phe Ile Phe Ala
                885                 890                 895

Val Val Gly Met Gln Leu Phe Gly Lys Ser Tyr Lys Glu Cys Val Cys
            900                 905                 910

Lys Ile Ser Asn Asp Cys Glu Leu Pro Arg Trp His Met His Asp Phe
```

```
        915                 920                 925

Phe His Ser Phe Leu Ile Val Phe Arg Val Leu Cys Gly Glu Trp Ile
    930                 935                 940

Glu Thr Met Trp Asp Cys Met Glu Val Ala Gly Gln Thr Met Cys Leu
945                 950                 955                 960

Thr Val Phe Met Met Val Met Val Ile Gly Asn Leu Val Val Leu Asn
                965                 970                 975

Leu Phe Leu Ala Leu Leu Leu Ser Ser Phe Ser Ser Asp Asn Leu Ala
            980                 985                 990

Ala Thr Asp Asp Asp Asn Glu Met  Asn Asn Leu Gln Ile  Ala Val Gly
        995                 1000                1005

Arg Met  Gln Lys Gly Ile Asp  Phe Val Lys Arg Lys  Ile Arg Glu
    1010                1015                1020

Phe Ile  Gln Lys Ala Phe Val  Arg Lys Gln Lys Ala  Leu Asp Glu
    1025                1030                1035

Ile Lys  Pro Leu Glu Asp Leu  Asn Asn Lys Lys Asp  Ser Cys Ile
    1040                1045                1050

Ser Asn  His Thr Thr Ile Glu  Ile Gly Lys Asp Leu  Asn Tyr Leu
    1055                1060                1065

Lys Asp  Gly Asn Gly Thr Thr  Ser Gly Ile Gly Ser  Ser Val Glu
    1070                1075                1080

Lys Tyr  Val Val Asp Glu Ser  Asp Tyr Met Ser Phe  Ile Asn Asn
    1085                1090                1095

Pro Ser  Leu Thr Val Thr Val  Pro Ile Ala Val Gly  Glu Ser Asp
    1100                1105                1110

Phe Glu  Asn Leu Asn Thr Glu  Glu Phe Ser Ser Glu  Ser Asp Met
    1115                1120                1125

Glu Glu  Ser Lys Glu Lys Leu  Asn Ala Thr Ser Ser  Ser Glu Gly
    1130                1135                1140

Ser Thr  Val Asp Ile Gly Ala  Pro Ala Glu Gly Glu  Gln Pro Glu
    1145                1150                1155

Val Glu  Pro Glu Glu Ser Leu  Glu Pro Glu Ala Cys  Phe Thr Glu
    1160                1165                1170

Asp Cys  Val Arg Lys Phe Lys  Cys Cys Gln Ile Ser  Ile Glu Glu
    1175                1180                1185

Gly Lys  Gly Lys Leu Trp Trp  Asn Leu Arg Lys Thr  Cys Tyr Lys
    1190                1195                1200

Ile Val  Glu His Asn Trp Phe  Glu Thr Phe Ile Val  Phe Met Ile
    1205                1210                1215

Leu Leu  Ser Ser Gly Ala Leu  Ala Phe Glu Asp Ile  Tyr Ile Glu
    1220                1225                1230

Gln Arg  Lys Thr Ile Lys Thr  Met Leu Glu Tyr Ala  Asp Lys Val
    1235                1240                1245

Phe Thr  Tyr Ile Phe Ile Leu  Glu Met Leu Leu Lys  Trp Val Ala
    1250                1255                1260

Tyr Gly  Phe Gln Val Tyr Phe  Thr Asn Ala Trp Cys  Trp Leu Asp
    1265                1270                1275

Phe Leu  Ile Val Asp Val Ser  Leu Val Ser Leu Thr  Ala Asn Ala
    1280                1285                1290

Leu Gly  Tyr Ser Glu Leu Gly  Ala Ile Lys Ser Leu  Arg Thr Leu
    1295                1300                1305

Arg Ala  Leu Arg Pro Leu Arg  Ala Leu Ser Arg Phe  Glu Gly Met
    1310                1315                1320
```

-continued

```
Arg Val  Val Val Asn Ala Leu  Leu Gly Ala Ile Pro  Ser Ile Met
    1325                 1330                 1335

Asn Val  Leu Leu Val Cys Leu  Ile Phe Trp Leu Ile  Phe Ser Ile
    1340                 1345                 1350

Met Gly  Val Asn Leu Phe Ala  Gly Lys Phe Tyr His  Cys Ile Asn
    1355                 1360                 1365

Tyr Thr  Thr Gly Glu Met Phe  Asp Val Ser Val Val  Asn Asn Tyr
    1370                 1375                 1380

Ser Glu  Cys Lys Ala Leu Ile  Glu Ser Asn Gln Thr  Ala Arg Trp
    1385                 1390                 1395

Lys Asn  Val Lys Val Asn Phe  Asp Asn Val Gly Leu  Gly Tyr Leu
    1400                 1405                 1410

Ser Leu  Leu Gln Val Ala Thr  Phe Lys Gly Trp Met  Asp Ile Met
    1415                 1420                 1425

Tyr Ala  Ala Val Asp Ser Arg  Asn Val Glu Leu Gln  Pro Lys Tyr
    1430                 1435                 1440

Glu Asp  Asn Leu Tyr Met Tyr  Leu Tyr Phe Val Ile  Phe Ile Ile
    1445                 1450                 1455

Phe Gly  Ser Phe Phe Thr Leu  Asn Leu Phe Ile Gly  Val Ile Ile
    1460                 1465                 1470

Asp Asn  Phe Asn Gln Gln Lys  Lys Lys Phe Gly Gly  Gln Asp Ile
    1475                 1480                 1485

Phe Met  Thr Glu Glu Gln Lys  Lys Tyr Tyr Asn Ala  Met Lys Lys
    1490                 1495                 1500

Leu Gly  Ser Lys Lys Pro Gln  Lys Pro Ile Pro Arg  Pro Ala Asn
    1505                 1510                 1515

Lys Phe  Gln Gly Met Val Phe  Asp Phe Val Thr Lys  Gln Val Phe
    1520                 1525                 1530

Asp Ile  Ser Ile Met Ile Leu  Ile Cys Leu Asn Met  Val Thr Met
    1535                 1540                 1545

Met Val  Glu Thr Asp Asp Gln  Ser Gln Glu Met Thr  Asn Ile Leu
    1550                 1555                 1560

Tyr Trp  Ile Asn Leu Val Phe  Ile Val Leu Phe Thr  Gly Glu Cys
    1565                 1570                 1575

Val Leu  Lys Leu Ile Ser Leu  Arg Tyr Tyr Tyr Phe  Thr Ile Gly
    1580                 1585                 1590

Trp Asn  Ile Phe Asp Phe Val  Val Val Ile Leu Ser  Ile Val Gly
    1595                 1600                 1605

Met Phe  Leu Ala Glu Leu Ile  Glu Lys Tyr Phe Val  Ser Pro Thr
    1610                 1615                 1620

Leu Phe  Arg Val Ile Arg Leu  Ala Arg Ile Gly Arg  Ile Leu Arg
    1625                 1630                 1635

Leu Ile  Lys Gly Ala Lys Gly  Ile Arg Thr Leu Leu  Phe Ala Leu
    1640                 1645                 1650

Met Met  Ser Leu Pro Ala Leu  Phe Asn Ile Gly Leu  Leu Leu Phe
    1655                 1660                 1665

Leu Val  Met Phe Ile Tyr Ala  Ile Phe Gly Met Ser  Asn Phe Ala
    1670                 1675                 1680

Tyr Val  Lys Arg Glu Val Gly  Ile Asp Asp Met Phe  Asn Phe Glu
    1685                 1690                 1695

Thr Phe  Gly Asn Ser Met Ile  Cys Leu Phe Gln Ile  Thr Thr Ser
    1700                 1705                 1710
```

```
Ala Gly  Trp Asp Gly Leu Leu  Ala Pro Ile Leu Asn  Ser Gly Pro
    1715                 1720                 1725

Pro Asp  Cys Asp Pro Asp Lys  Asp His Pro Gly Ser  Ser Val Lys
    1730                 1735                 1740

Gly Asp  Cys Gly Asn Pro Ser  Val Gly Ile Phe Phe  Phe Val Ser
    1745                 1750                 1755

Tyr Ile  Ile Ile Ser Phe Leu  Val Val Val Asn Met  Tyr Ile Ala
    1760                 1765                 1770

Val Ile  Leu Glu Asn Phe Ser  Val Ala Thr Glu Glu  Ser Ala Glu
    1775                 1780                 1785

Pro Leu  Ser Glu Asp Asp Phe  Glu Met Phe Tyr Glu  Val Trp Glu
    1790                 1795                 1800

Lys Phe  Asp Pro Asp Ala Thr  Gln Phe Ile Glu Phe  Ala Lys Leu
    1805                 1810                 1815

Ser Asp  Phe Ala Asp Ala Leu  Asp Pro Pro Leu Leu  Ile Ala Lys
    1820                 1825                 1830

Pro Asn  Lys Val Gln Leu Ile  Ala Met Asp Leu Pro  Met Val Ser
    1835                 1840                 1845

Gly Asp  Arg Ile His Cys Leu  Asp Ile Leu Phe Ala  Phe Thr Lys
    1850                 1855                 1860

Arg Val  Leu Gly Glu Ser Gly  Glu Met Asp Ala Leu  Arg Ile Gln
    1865                 1870                 1875

Met Glu  Glu Arg Phe Met Ala  Ser Asn Pro Ser Lys  Val Ser Tyr
    1880                 1885                 1890

Glu Pro  Ile Thr Thr Thr Leu  Lys Arg Lys Gln Glu  Glu Val Ser
    1895                 1900                 1905

Ala Ile  Ile Ile Gln Arg Ala  Tyr Arg Arg Tyr Leu  Leu Lys Gln
    1910                 1915                 1920

Lys Val  Lys Lys Val Ser Ser  Ile Tyr Lys Lys Asp  Lys Gly Lys
    1925                 1930                 1935

Glu Cys  Asp Gly Thr Pro Ile  Lys Glu Asp Thr Leu  Ile Asp Lys
    1940                 1945                 1950

Leu Asn  Glu Asn Ser Thr Pro  Glu Lys Thr Asp Met  Thr Pro Ser
    1955                 1960                 1965

Thr Thr  Ser Pro Pro Ser Tyr  Asp Ser Val Thr Lys  Pro Glu Lys
    1970                 1975                 1980

Glu Lys  Phe Glu Lys Asp Lys  Ser Glu Lys Glu Asp  Lys Gly Lys
    1985                 1990                 1995

Asp Ile  Arg Glu Ser Lys Lys
    2000                 2005
```

<210> SEQ ID NO 265
<211> LENGTH: 37
<212> TYPE: PRT
<213> ORGANISM: Artificial sequence
<220> FEATURE:
<223> OTHER INFORMATION: Huwentoxin-IV variant
<220> FEATURE:
<221> NAME/KEY: MISC_FEATURE
<222> LOCATION: (1)..(1)
<223> OTHER INFORMATION: Xaa1 is any amino acid
<220> FEATURE:
<221> NAME/KEY: MISC_FEATURE
<222> LOCATION: (3)..(5)
<223> OTHER INFORMATION: Xaa is any amino acid
<220> FEATURE:
<221> NAME/KEY: MISC_FEATURE
<222> LOCATION: (7)..(8)
<223> OTHER INFORMATION: Xaa is any amino acid
<220> FEATURE:
<221> NAME/KEY: MISC_FEATURE
<222> LOCATION: (10)..(15)
<223> OTHER INFORMATION: Xaa is any amino acid
<220> FEATURE:
<221> NAME/KEY: MISC_FEATURE
<222> LOCATION: (18)..(23)
<223> OTHER INFORMATION: Xaa is any amino acid
<220> FEATURE:
<221> NAME/KEY: MISC_FEATURE
<222> LOCATION: (25)..(30)
<223> OTHER INFORMATION: Xaa is any amino acid
<220> FEATURE:
<221> NAME/KEY: MISC_FEATURE
<222> LOCATION: (33)..(34)
<223> OTHER INFORMATION: Xaa is any amino acid
<220> FEATURE:
<221> NAME/KEY: MISC_FEATURE
<222> LOCATION: (36)..(37)
<223> OTHER INFORMATION: Xaa is any amino acid or deleted

<400> SEQUENCE: 265

```
Xaa Cys Xaa Xaa Xaa Phe Xaa Xaa Cys Xaa Xaa Xaa Xaa Xaa Xaa Cys
1               5                   10                  15

Cys Xaa Xaa Xaa Xaa Xaa Xaa Cys Xaa Xaa Xaa Xaa Xaa Xaa Cys Lys
            20                  25                  30

Xaa Xaa Ile Xaa Xaa
        35
```

<210> SEQ ID NO 266
<211> LENGTH: 30
<212> TYPE: PRT
<213> ORGANISM: Artificial sequence
<220> FEATURE:
<223> OTHER INFORMATION: Linker

<400> SEQUENCE: 266

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30
```

<210> SEQ ID NO 267
<211> LENGTH: 37
<212> TYPE: PRT
<213> ORGANISM: Artificial sequence
<220> FEATURE:
<223> OTHER INFORMATION: Reference huwentoxin-IV sequence

<400> SEQUENCE: 267

```
Glu Cys Leu Glu Ile Phe Lys Ala Cys Asn Pro Ser Asn Asp Gln Cys
1               5                   10                  15

Cys Lys Ser Ser Lys Leu Val Cys Ser Arg Lys Thr Arg Trp Cys Lys
            20                  25                  30

Tyr Gln Ile Gly Lys
        35
```

<210> SEQ ID NO 268
<211> LENGTH: 35
<212> TYPE: PRT
<213> ORGANISM: Ornithoctonus huwena

<400> SEQUENCE: 268

```
Glu Cys Leu Glu Ile Phe Lys Ala Cys Asn Pro Ser Asn Asp Gln Cys
1               5                   10                  15

Cys Lys Ser Ser Lys Leu Val Cys Ser Arg Lys Thr Arg Trp Cys Lys
```

20 25 30

Tyr Gln Ile
35

<210> SEQ ID NO 269
<211> LENGTH: 20
<212> TYPE: PRT
<213> ORGANISM: Artificial sequence
<220> FEATURE:
<223> OTHER INFORMATION: Linker

<400> SEQUENCE: 269

Gly Gly Gly Gly Ser Gly Gly Gly Gly Ser Gly Gly Gly Gly Ser Gly
1 5 10 15

Gly Gly Gly Ser
20

<210> SEQ ID NO 270
<211> LENGTH: 8
<212> TYPE: PRT
<213> ORGANISM: Artificial sequence
<220> FEATURE:
<223> OTHER INFORMATION: Linker

<400> SEQUENCE: 270

Leu Glu Val Leu Phe Gln Gly Pro
1 5

<210> SEQ ID NO 271
<211> LENGTH: 111
<212> TYPE: DNA
<213> ORGANISM: Artificial sequence
<220> FEATURE:
<223> OTHER INFORMATION: Huwentoxin-IV variant

<400> SEQUENCE: 271
aactgcttac ggatttttaa ggcatgcaac ccttcaaatg accagtgctg caagagctcg 60
aaattagttt gcagtcgaaa aaccaggtgg tgtaaatgga gcataggtaa a 111

<210> SEQ ID NO 272
<211> LENGTH: 111
<212> TYPE: DNA
<213> ORGANISM: Artificial sequence
<220> FEATURE:
<223> OTHER INFORMATION: Huwentoxin-IV variant

<400> SEQUENCE: 272
aactgcttac ggatttttaa ggcatgcaac ccttcaaatg accagtgctg caagagctcg 60
aaattagttt gcagtcgaaa aaccaggtgg tgtaaataca gcataggtaa a 111

<210> SEQ ID NO 273
<211> LENGTH: 111
<212> TYPE: DNA
<213> ORGANISM: Artificial sequence
<220> FEATURE:
<223> OTHER INFORMATION: Huwentoxin-IV variant

<400> SEQUENCE: 273
aactgcttac ggatttttaa ggcatgcaac ccttcaaatg accagtgctg caagagctcg 60
aaattagttt gcagtaagaa aaccaggtgg tgtaaataca gcataggtaa a 111

<210> SEQ ID NO 274
<211> LENGTH: 111

<212> TYPE: DNA
<213> ORGANISM: Artificial sequence
<220> FEATURE:
<223> OTHER INFORMATION: Huwentoxin-IV variant

<400> SEQUENCE: 274
gagtgcttag agatttttaa ggcatgcaac ccttcaaatg accagtgctg caagagctcg 60
aaattagttt gcagtcgaaa aaccaggtgg tgtaaatact ttataggtaa a 111

<210> SEQ ID NO 275
<211> LENGTH: 111
<212> TYPE: DNA
<213> ORGANISM: Artificial sequence
<220> FEATURE:
<223> OTHER INFORMATION: Huwentoxin-IV variant

<400> SEQUENCE: 275
aactgcttag agatttttaa ggcatgcaac ccttcaaatg accagtgctg caagagctcg 60
aaattagttt gcagtcgaaa aaccaggtgg tgtaaatggc aaataatcaa a 111

<210> SEQ ID NO 276
<211> LENGTH: 37
<212> TYPE: PRT
<213> ORGANISM: Artificial sequence
<220> FEATURE:
<223> OTHER INFORMATION: Huwentoxin-IV variant
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (3)..(5)
<223> OTHER INFORMATION: Xaa is any amino acid
<220> FEATURE:
<221> NAME/KEY: MISC_FEATURE
<222> LOCATION: (7)..(8)
<223> OTHER INFORMATION: Xaa is any amino acid
<220> FEATURE:
<221> NAME/KEY: MISC_FEATURE
<222> LOCATION: (10)..(15)
<223> OTHER INFORMATION: Xaa is any amino acid
<220> FEATURE:
<221> NAME/KEY: MISC_FEATURE
<222> LOCATION: (18)..(23)
<223> OTHER INFORMATION: Xaa is any amino acid
<220> FEATURE:
<221> NAME/KEY: MISC_FEATURE
<222> LOCATION: (25)..(27)
<223> OTHER INFORMATION: Xaa is any amino acid
<220> FEATURE:
<221> NAME/KEY: MISC_FEATURE
<222> LOCATION: (29)..(29)
<223> OTHER INFORMATION: Xaa is any amino acid
<220> FEATURE:
<221> NAME/KEY: MISC_FEATURE
<222> LOCATION: (34)..(35)
<223> OTHER INFORMATION: Xaa is any amino acid
<220> FEATURE:
<221> NAME/KEY: MISC_FEATURE
<222> LOCATION: (36)..(37)
<223> OTHER INFORMATION: Xaa is any amino acid or deleted

<400> SEQUENCE: 276

Xaa Cys Xaa Xaa Xaa Phe Xaa Xaa Cys Xaa Xaa Xaa Xaa Xaa Xaa Cys
1               5                   10                  15

Cys Xaa Xaa Xaa Xaa Xaa Xaa Cys Xaa Xaa Xaa Thr Xaa Trp Cys Lys
            20                  25                  30

Tyr Xaa Xaa Xaa Xaa
        35

<210> SEQ ID NO 277
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 277

```
Gly Pro Asn Cys Leu Glu Ile Phe Lys Ala Cys Asn Pro Ser Asn Asp
1               5                   10                  15

Gln Cys Cys Lys Ser Ser Phe Leu Val Cys Ser Lys Lys Thr Arg Trp
            20                  25                  30

Cys Lys Tyr Ser Ile Ile Lys
        35
```

<210> SEQ ID NO 278
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 278

```
Gly Pro Asn Cys Leu Glu Ile Phe Lys Ala Cys Asn Pro Ser Asn Asp
1               5                   10                  15

Gln Cys Cys Lys Ser Asn Lys Leu Val Cys Ser Lys Lys Thr Arg Trp
            20                  25                  30

Cys Lys Tyr Ser Ile Ile Lys
        35
```

<210> SEQ ID NO 279
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 279

```
Gly Pro Asn Cys Leu Arg Ile Phe Lys Ala Cys Asn Pro Ser Asn Asp
1               5                   10                  15

Gln Cys Cys Lys Ser Ser Lys Leu Val Cys Ser Asp Lys Thr Arg Trp
            20                  25                  30

Cys Lys Trp Ser Ile Gly Lys
        35
```

<210> SEQ ID NO 280
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 280

```
Gly Pro Asn Cys Leu Arg Ile Phe Lys Ala Cys Asn Pro Ser Asn Asp
1               5                   10                  15

Gln Cys Cys Lys Ser Ser Lys Leu Val Cys Ser Arg His Thr Arg Trp
            20                  25                  30

Cys Lys Trp Ser Ile Gly Lys
        35
```

<210> SEQ ID NO 281

<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 281

Gly Pro Asn Cys Leu Glu Ile Phe Lys Ala Cys Asn Pro Ser Asn Asp
1 5 10 15

Gln Cys Cys Lys Ser Ser Lys Leu Val Cys Ser Lys Lys Thr Arg Trp
20 25 30

Cys Lys Tyr Ser Ile Ile Lys
35

<210> SEQ ID NO 282
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 282

Gly Pro Asn Cys Leu Glu Ile Phe Lys Ala Cys Asn Pro Ser Asn Asp
1 5 10 15

Gln Cys Cys Lys Ser Ser Lys Leu Val Cys Ser Lys Lys Thr Arg Trp
20 25 30

Cys Lys Tyr Ser Ile Ile Phe
35

<210> SEQ ID NO 283
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 283

Gly Pro Asn Cys Leu Glu Ile Phe Lys Ala Cys Asn Pro Ser Asn Asp
1 5 10 15

Gln Cys Cys Lys Ser Ser Lys Leu Val Cys Ser Lys Lys Thr Arg Trp
20 25 30

Cys Lys Tyr Ser Ile Ile Arg
35

<210> SEQ ID NO 284
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 284

Gly Pro Asn Cys Leu Glu Ile Phe Lys Ala Cys Asn Pro Ser Asn Asp
1 5 10 15

Gln Cys Cys Lys Ser Ser Lys Leu Val Cys Ile Lys Lys Thr Arg Trp
20 25 30

Cys Lys Tyr Ser Ile Ile Lys
35

<210> SEQ ID NO 285
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 285

Gly Pro Asn Cys Leu Glu Ile Phe Lys Ala Cys Asn Pro Ser Asn Asp
1               5                   10                  15

Gln Cys Cys Lys Ser Ser Asn Leu Val Cys Ser Lys Lys Thr Arg Trp
            20                  25                  30

Cys Lys Tyr Ser Ile Ile Lys
        35

<210> SEQ ID NO 286
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 286

Gly Pro Asn Cys Leu Glu Ile Phe Lys Ala Cys Asn Pro Ser Asn Asp
1               5                   10                  15

Gln Cys Cys Lys Ser Ser His Leu Val Cys Ser Lys Lys Thr Arg Trp
            20                  25                  30

Cys Lys Tyr Ser Ile Ile Lys
        35

<210> SEQ ID NO 287
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 287

Gly Pro Asn Cys Leu Glu Ile Phe Lys Ala Cys Asn Pro Ser Asn Asp
1               5                   10                  15

Gln Cys Cys Lys Ser Ser Phe Leu Val Cys Ser Lys Lys Thr Arg Trp
            20                  25                  30

Cys Lys Tyr Ser Ile Ile Lys
        35

<210> SEQ ID NO 288
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 288

Gly Pro Asn Cys Leu Glu Ile Phe Lys Ala Cys Asn Pro Ser Asn Asp
1               5                   10                  15

Gln Cys Cys Lys Ser Ser Arg Leu Val Cys Ser Lys Lys Thr Arg Trp
            20                  25                  30

Cys Lys Tyr Ser Ile Ile Lys
        35

<210> SEQ ID NO 289
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 289

Gly Pro Asn Cys Leu Glu Ile Phe Lys Ala Cys Asn Pro Ser Asn Asp
1               5                   10                  15

Gln Cys Cys Lys Ser Ser Lys Arg Val Cys Ser Lys Lys Thr Arg Trp
            20                  25                  30

Cys Lys Tyr Ser Ile Ile Lys
        35

<210> SEQ ID NO 290
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 290

Gly Pro Asn Cys Leu Glu Ile Phe Lys Ala Cys Asn Pro Ser Asn Asp
1               5                   10                  15

Gln Cys Cys Lys Pro Ser Lys Leu Val Cys Ser Lys Lys Thr Arg Trp
            20                  25                  30

Cys Lys Tyr Ser Ile Ile Lys
        35

<210> SEQ ID NO 291
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 291

Gly Pro Asn Cys Leu Glu Ile Phe Lys Ala Cys Asn Pro Ser Asn Asp
1               5                   10                  15

Gln Cys Cys Tyr Ser Ser Lys Leu Val Cys Ser Lys Lys Thr Arg Trp
            20                  25                  30

Cys Lys Tyr Ser Ile Ile Lys
        35

<210> SEQ ID NO 292
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 292

Gly Pro Asn Cys Leu Glu Ile Phe Lys Ala Cys Asn Pro Ser Asn Asp
1               5                   10                  15

Gln Cys Cys Lys Ser Asn Lys Leu Val Cys Ser Lys Lys Thr Arg Trp
            20                  25                  30

Cys Lys Tyr Ser Ile Ile Lys
        35

<210> SEQ ID NO 293
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 293

Gly Pro Asn Cys Leu Glu Ile Phe Lys Ala Cys Asn Pro Ser Asn Asp 1 5 10 15

Gln Cys Cys Lys Ser Pro Lys Leu Val Cys Ser Lys Lys Thr Arg Trp
20 25 30

Cys Lys Tyr Ser Ile Ile Lys
35

<210> SEQ ID NO 294
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 294

Gly Pro Asn Cys Leu Glu Ile Phe Lys Ala Cys Asn Pro Ser Asn Asp
1 5 10 15

Gln Cys Cys Lys Ser Arg Lys Leu Val Cys Ser Lys Lys Thr Arg Trp
20 25 30

Cys Lys Tyr Ser Ile Ile Lys
35

<210> SEQ ID NO 295
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 295

Gly Pro Asn Cys Leu Asn Ile Phe Lys Arg Cys Asn Pro Ser Asn Asp
1 5 10 15

Gln Cys Cys Lys Ser Ser Lys Leu Val Cys Ser Lys Lys Thr Arg Trp
20 25 30

Cys Lys Tyr Ser Ile Ile Lys
35

<210> SEQ ID NO 296
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 296

Gly Pro Asn Cys Leu Asn Ile Phe Lys Arg Cys Asn Pro Ser Asn Asp
1 5 10 15

Gln Cys Cys Lys Ser Ser Lys Leu Val Cys Ser Lys Lys Thr Arg Trp
20 25 30

Cys Lys Tyr Ser Ile Ile Lys
35

<210> SEQ ID NO 297
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 297

Gly Pro Asn Cys Leu His Ile Phe Lys Gln Cys Asn Pro Ser Asn Asp
1 5 10 15

Gln Cys Cys Lys Ser Ser Lys Leu Val Cys Ser Lys Lys Thr Arg Trp 20 25 30

Cys Lys Tyr Ser Ile Ile Lys
35

<210> SEQ ID NO 298
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 298

Gly Pro Asn Cys Leu His Ile Phe Lys Gln Cys Asn Pro Ser Asn Asp
1 5 10 15

Gln Cys Cys Lys Ser Ser Lys Leu Val Cys Ser Lys Lys Thr Arg Trp
20 25 30

Cys Lys Tyr Ser Ile Ile Lys
35

<210> SEQ ID NO 299
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 299

Gly Pro Asn Cys Leu Glu Ile Phe Lys Ala Cys Asn Pro Ser Asn Asp
1 5 10 15

Arg Cys Cys Lys Ser Ser Lys Leu Val Cys Ser Lys Lys Thr Arg Trp
20 25 30

Cys Lys Tyr Ser Ile Ile Lys
35

<210> SEQ ID NO 300
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 300

Gly Pro Asn Cys Leu Glu Ile Phe Lys Ala Cys Asn Pro Ser Ala Asp
1 5 10 15

Gln Cys Cys Lys Ser Ser Lys Leu Val Cys Ser Lys Lys Thr Arg Trp
20 25 30

Cys Lys Tyr Ser Ile Ile Lys
35

<210> SEQ ID NO 301
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 301

Gly Pro Asn Cys Leu Glu Ile Phe Lys Gln Cys Asn Pro Ser Asn Asp
1 5 10 15

Gln Cys Cys Lys Ser Ser Lys Leu Val Cys Ser Lys Lys Thr Arg Trp
20 25 30

Cys Lys Tyr Ser Ile Ile Lys

35

<210> SEQ ID NO 302
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 302

Gly Pro Asn Cys Leu Glu Ile Phe Lys Asn Cys Asn Pro Ser Asn Asp
1 5 10 15

Gln Cys Cys Lys Ser Ser Lys Leu Val Cys Ser Lys Lys Thr Arg Trp
20 25 30

Cys Lys Tyr Ser Ile Ile Lys
35

<210> SEQ ID NO 303
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 303

Gly Pro Asn Cys Leu Gln Ile Phe Lys Ala Cys Asn Pro Ser Asn Asp
1 5 10 15

Gln Cys Cys Lys Ser Ser Lys Leu Val Cys Ser Lys Lys Thr Arg Trp
20 25 30

Cys Lys Tyr Ser Ile Ile Lys
35

<210> SEQ ID NO 304
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 304

Gly Pro Asn Cys Leu Glu Ile Phe Lys Ala Cys Asn Pro Ser Asn Asp
1 5 10 15

Asn Cys Cys Lys Ser Ser Lys Leu Val Cys Ser Lys Lys Thr Arg Trp
20 25 30

Cys Lys Tyr Ser Ile Ile Lys
35

<210> SEQ ID NO 305
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 305

Gly Pro Asn Cys Leu Glu Ile Phe Lys Ala Cys Asn Pro Ser Asn Asp
1 5 10 15

Gln Cys Cys Lys Arg Ser Lys Leu Val Cys Ser Lys Lys Thr Arg Trp
20 25 30

Cys Lys Tyr Ser Ile Ile Lys
35

<210> SEQ ID NO 306
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 306

```
Gly Pro Asn Cys Leu Glu Ile Phe Lys Ala Cys Asn Pro Ser Asn Asp
1               5                   10                  15

Gln Cys Cys Lys Ser Val Lys Leu Val Cys Ser Lys Lys Thr Arg Trp
            20                  25                  30

Cys Lys Tyr Ser Ile Ile Lys
        35
```

<210> SEQ ID NO 307
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 307

```
Gly Pro Asn Cys Leu Arg Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Trp Ser Ile Gly Lys
        35
```

<210> SEQ ID NO 308
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 308

```
Gly Pro Asn Cys Leu Arg Ile Phe Lys Ala Cys Asn Pro Ser Asn Asp
1               5                   10                  15

Gln Cys Cys Lys Gln Ser Lys Leu Val Cys Ser Arg Lys Thr Arg Trp
            20                  25                  30

Cys Lys Trp Ser Ile Gly Lys
        35
```

<210> SEQ ID NO 309
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 309

```
Gly Pro Asn Cys Leu Arg Ile Phe Lys Ala Cys Asn Pro Ser Asn Asp
1               5                   10                  15

Asp Cys Cys Lys Ser Ser Lys Leu Val Cys Ser Arg Lys Thr Arg Trp
            20                  25                  30

Cys Lys Trp Ser Ile Gly Lys
        35
```

<210> SEQ ID NO 310
<211> LENGTH: 39
<212> TYPE: PRT

-continued

<213> ORGANISM: Artificial sequence
<220> FEATURE:
<223> OTHER INFORMATION: Huwentoxin-IV variant

<400> SEQUENCE: 310

Gly Pro Asn Cys Leu Arg Ile Phe Lys Ala Cys Asn Pro Ser Asn Asp
1 5 10 15

Gln Cys Cys Gln Ser Ser Lys Leu Val Cys Ser Arg Lys Thr Arg Trp
20 25 30

Cys Lys Trp Ser Ile Gly Lys
35

<210> SEQ ID NO 311
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 311

Gly Pro Asn Cys Leu Arg Ile Phe Lys Ala Cys Asn Pro Ser Asn Ser
1 5 10 15

Gln Cys Cys Lys Ser Ser Lys Leu Val Cys Ser Arg Lys Thr Arg Trp
20 25 30

Cys Lys Trp Ser Ile Gly Lys
35

<210> SEQ ID NO 312
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 312

Gly Pro Asn Cys Leu Arg Ile Phe Lys Ala Cys Asn Pro Ser Asn Gln
1 5 10 15

Gln Cys Cys Lys Ser Ser Lys Leu Val Cys Ser Arg Lys Thr Arg Trp
20 25 30

Cys Lys Trp Ser Ile Gly Lys
35

<210> SEQ ID NO 313
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 313

Gly Pro Asn Cys Leu Arg Ile Phe Lys Ala Cys Asn Pro Ser Asn Asp
1 5 10 15

Pro Cys Cys Lys Ser Ser Lys Leu Val Cys Ser Arg Lys Thr Arg Trp
20 25 30

Cys Lys Trp Ser Ile Gly Lys
35

<210> SEQ ID NO 314
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 314

Gly Pro Asn Cys Leu Arg Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Ala Trp Ser Ile Gly Lys
35

<210> SEQ ID NO 315
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 315

Gly Pro Asn Cys Leu Arg Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Trp Trp Ser Ile Gly Lys
35

<210> SEQ ID NO 316
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 316

Gly Pro Asn Cys Leu Arg Ile Phe Lys Ala Cys Asn Pro Ser Asn Asp
1 5 10 15

Gln Cys Cys Lys Ser Ser Lys Leu Val Cys Ser Arg Ala Thr Arg Trp
20 25 30

Cys Lys Trp Ser Ile Gly Lys
35

<210> SEQ ID NO 317
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 317

Gly Pro Asn Cys Leu Arg Ile Phe Lys Ala Cys Asn Pro Ser Asn Asp
1 5 10 15

Gln Cys Cys Lys Ser Ser Lys Leu Val Cys Ser Asp Lys Thr Arg Trp
20 25 30

Cys Lys Trp Ser Ile Gly Lys
35

<210> SEQ ID NO 318
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 318

Gly Pro Asn Cys Leu Arg Ile Phe Lys Ala Cys Asn Pro Ser Asn Asp
1               5                   10                  15

Gln Cys Cys Lys Ser Ser Lys Leu Val Cys Ser Arg His Thr Arg Trp
            20                  25                  30

Cys Lys Trp Ser Ile Gly Lys
        35

<210> SEQ ID NO 319
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 319

Gly Pro Asn Cys Leu Arg Ile Phe Lys Ala Cys Asn Pro Ser Asn Asp
1               5                   10                  15

Gln Cys Cys Lys Ser Ser Lys Leu Val Cys Ser His Lys Thr Arg Trp
            20                  25                  30

Cys Lys Trp Ser Ile Gly Lys
        35

<210> SEQ ID NO 320
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 320

Gly Pro Asn Cys Leu Arg Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Trp Ser Ile Gly Arg
        35

<210> SEQ ID NO 321
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 321

Gly Pro Asn Cys Leu Arg Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Trp Ser Ile Gly Pro
        35

<210> SEQ ID NO 322
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 322

Gly Pro Asn Cys Leu Arg Ile Phe Lys Ala Cys Asn Pro Ser Asn Asp
1               5                   10                  15

```
Gln Cys Cys Trp Ser Ser Lys Leu Val Cys Ser Arg Lys Thr Arg Trp
            20                  25                  30

Cys Lys Trp Ser Ile Gly Lys
        35


<210> SEQ ID NO 323
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 323

Gly Pro Asn Cys Leu Arg Ile Phe Lys Ala Cys Asn Pro Ser Asn Leu
1               5                   10                  15

Gln Cys Cys Lys Ser Ser Lys Leu Val Cys Ser Arg Lys Thr Arg Trp
            20                  25                  30

Cys Lys Trp Ser Ile Gly Lys
        35


<210> SEQ ID NO 324
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 324

Gly Pro Asn Cys Leu Arg Ile Phe Lys Ala Cys Asn Pro Ser Asn Asp
1               5                   10                  15

Trp Cys Cys Lys Ser Ser Lys Leu Val Cys Ser Arg Lys Thr Arg Trp
            20                  25                  30

Cys Lys Trp Ser Ile Gly Lys
        35


<210> SEQ ID NO 325
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 325

Gly Pro Asn Cys Leu Arg Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Trp Ser Ile Val Lys
        35


<210> SEQ ID NO 326
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 326

Gly Pro Asn Cys Leu Arg Ile Phe Lys Ala Cys Asn Pro Ser Asn Asp
1               5                   10                  15

Gln Cys Cys Lys Ser Ser Lys Leu Val Cys Ser Arg Lys Thr Gly Trp
            20                  25                  30
```

```
Cys Lys Trp Ser Ile Gly Lys
        35


<210> SEQ ID NO 327
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 327

Gly Pro Asn Cys Leu Arg Ile Phe Lys Ala Cys Asn Pro Ser Asn Asp
1               5                   10                  15

Gln Cys Cys Lys Ser Ser Lys Leu Val Cys Ser Arg Lys Thr Trp Trp
            20                  25                  30

Cys Lys Trp Ser Ile Gly Lys
        35


<210> SEQ ID NO 328
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 328

Gly Pro Asn Cys Leu Arg Ile Phe Lys Ala Cys Asn Pro Ser Asn Asp
1               5                   10                  15

Gln Cys Cys Lys Ser Ser Lys Leu Val Cys Ser Arg Lys Thr Arg Trp
            20                  25                  30

Cys Lys Trp Ser Ile Thr Lys
        35


<210> SEQ ID NO 329
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 329

Gly Pro Asn Cys Leu Arg Ile Phe Lys Ala Cys Asn Pro Ser Asn Asp
1               5                   10                  15

Gln Cys Cys Lys Ser Ser Lys Leu Val Cys Ser Arg Lys Thr Arg Lys
            20                  25                  30

Cys Lys Trp Ser Ile Gly Lys
        35


<210> SEQ ID NO 330
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 330

Gly Pro Asn Cys Leu Arg Ile Phe Lys Ala Cys Asn Pro Ser Asn Asp
1               5                   10                  15

Gln Cys Cys Lys Ser Ser Lys Leu Val Cys Ser Arg Lys Thr Leu Trp
            20                  25                  30

Cys Lys Trp Ser Ile Gly Lys
        35
```

-continued

<210> SEQ ID NO 331
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 331

```
Gly Pro Asn Cys Leu Arg Ile Phe Lys Ala Cys Asn Pro Ser Asn Asp
1               5                   10                  15

Gln Cys Cys Lys Ser Ser Lys Leu Val Cys Ser Arg Lys Thr Arg Tyr
            20                  25                  30

Cys Lys Trp Ser Ile Gly Lys
        35
```

<210> SEQ ID NO 332
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 332

```
Gly Pro Asn Cys Leu Arg Ile Phe Lys Ala Cys Asn Pro Ser Asn Asp
1               5                   10                  15

Gln Cys Cys Lys Ser Ser Lys Leu Val Cys Ser Pro Lys Thr Arg Trp
            20                  25                  30

Cys Lys Trp Ser Ile Gly Lys
        35
```

<210> SEQ ID NO 333
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 333

```
Gly Pro Asn Cys Leu Arg Ile Phe Lys Ala Cys Asn Pro Ser Asn Asp
1               5                   10                  15

Gln Cys Cys Lys Ser Ser Lys Ala Val Cys Ser Arg Lys Thr Arg Trp
            20                  25                  30

Cys Lys Trp Ser Ile Gly Lys
        35
```

<210> SEQ ID NO 334
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 334

```
Gly Pro Asn Cys Leu Arg Ile Phe Lys Ala Cys Asn Pro Ser Asn Asp
1               5                   10                  15

Gln Cys Cys Lys Ser Ser Lys Trp Val Cys Ser Arg Lys Thr Arg Trp
            20                  25                  30

Cys Lys Trp Ser Ile Gly Lys
        35
```

<210> SEQ ID NO 335
<211> LENGTH: 39

<212> TYPE: PRT
<213> ORGANISM: Artificial sequence
<220> FEATURE:
<223> OTHER INFORMATION: Huwentoxin-IV variant

<400> SEQUENCE: 335

Gly Pro Asn Cys Leu Arg Ile Phe Lys Ala Cys Asn Pro Ser Asn Asp
1 5 10 15

Gln Cys Cys Lys Ser Ser Lys Leu Val Cys Ser Arg Lys Leu Arg Trp
20 25 30

Cys Lys Trp Ser Ile Gly Lys
35

<210> SEQ ID NO 336
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 336

Gly Pro Asn Cys Leu Arg Ile Phe Lys Ala Cys Asn Pro Ser Asn Asp
1 5 10 15

Gln Cys Cys Lys Ser Ser Lys Leu Val Cys Ser Arg Pro Thr Arg Trp
20 25 30

Cys Lys Trp Ser Ile Gly Lys
35

<210> SEQ ID NO 337
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 337

Gly Pro Asn Cys Leu Arg Ile Phe Lys Ala Cys Asn Pro Ser Asn Asp
1 5 10 15

Gln Cys Cys Lys Ser Ser Lys Leu Val Cys Ser Val Lys Thr Arg Trp
20 25 30

Cys Lys Trp Ser Ile Gly Lys
35

<210> SEQ ID NO 338
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 338

Gly Pro Asn Cys Leu Arg Ile Phe Lys Ala Cys Asn Pro Ser Asn Asp
1 5 10 15

Gln Cys Cys Lys Ser Ser Lys Leu Val Cys Ser Gly Lys Thr Arg Trp
20 25 30

Cys Lys Trp Ser Ile Gly Lys
35

<210> SEQ ID NO 339
<211> LENGTH: 39
<212> TYPE: PRT
<213> ORGANISM: Artificial sequence
<220> FEATURE:

<223> OTHER INFORMATION: Huwentoxin-IV variant

<400> SEQUENCE: 339

```
Gly Pro Asn Cys Leu Arg Ile Phe Lys Ala Cys Asn Pro Ser Asn Asp
1               5                   10                  15

Gln Cys Cys Lys Ser Ser Trp Leu Val Cys Ser Arg Lys Thr Arg Trp
            20                  25                  30

Cys Lys Trp Ser Ile Gly Lys
        35
```

<210> SEQ ID NO 340
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 340

```
Gly Pro Asn Cys Leu Arg Ile Phe Lys Ala Cys Asn Pro Ser Asn Asp
1               5                   10                  15

Gln Cys Cys Lys Ser Ser Lys Leu Val Cys Ser Ile Lys Thr Arg Trp
            20                  25                  30

Cys Lys Trp Ser Ile Gly Lys
        35
```

<210> SEQ ID NO 341
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 341

```
Gly Pro Asn Cys Leu Arg Ile Phe Lys Ala Cys Asn Pro Ser Asn Asp
1               5                   10                  15

Gln Cys Cys Lys Ser Ser Lys Leu Val Cys Ser Arg Trp Thr Arg Trp
            20                  25                  30

Cys Lys Trp Ser Ile Gly Lys
        35
```

<210> SEQ ID NO 342
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 342

```
Gly Pro Asn Cys Leu Arg Ile Phe Lys Ala Cys Asn Pro Ser Asn Asp
1               5                   10                  15

Gln Cys Cys Lys Ser Ser Lys Leu Val Cys Ser Ala Lys Thr Arg Trp
            20                  25                  30

Cys Lys Trp Ser Ile Gly Lys
        35
```

<210> SEQ ID NO 343
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 343

Gly Pro Asn Cys Leu Arg Ile Phe Lys Ala Cys Asn Pro Ser Asn Asp
1 5 10 15

Gln Cys Cys Lys Ser Trp Lys Leu Val Cys Ser Arg Lys Thr Arg Trp
20 25 30

Cys Lys Trp Ser Ile Gly Lys
35

<210> SEQ ID NO 344
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 344

Gly Pro Asn Cys Leu Arg Ile Phe Lys Ala Cys Asn Pro Ser Asn Asp
1 5 10 15

Glu Cys Cys Lys Ser Ser Lys Leu Val Cys Ser Arg Lys Thr Arg Trp
20 25 30

Cys Lys Trp Ser Ile Gly Lys
35

<210> SEQ ID NO 345
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 345

Gly Pro Asn Cys Leu Arg Ile Phe Lys Ala Cys Asn Pro Ser Asn Asp
1 5 10 15

Gln Cys Cys Pro Ser Ser Lys Leu Val Cys Ser Arg Lys Thr Arg Trp
20 25 30

Cys Lys Trp Ser Ile Gly Lys
35

<210> SEQ ID NO 346
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 346

Gly Pro Asn Cys Leu Arg Ile Phe Lys Ala Cys Asn Pro Ser Asn Asp
1 5 10 15

Val Cys Cys Lys Ser Ser Lys Leu Val Cys Ser Arg Lys Thr Arg Trp
20 25 30

Cys Lys Trp Ser Ile Gly Lys
35

<210> SEQ ID NO 347
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 347

Gly Pro Asn Cys Leu Arg Ile Phe Lys Ala Cys Asn Pro Ser Asn Gly
1 5 10 15

Gln Cys Cys Lys Ser Ser Lys Leu Val Cys Ser Arg Lys Thr Arg Trp
20 25 30

Cys Lys Trp Ser Ile Gly Lys
35

<210> SEQ ID NO 348
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 348

Gly Pro Asn Cys Leu Arg Ile Phe Lys Ala Cys Asn Pro Ser Asn Asp
1 5 10 15

Gln Cys Cys Phe Ser Ser Lys Leu Val Cys Ser Arg Lys Thr Arg Trp
20 25 30

Cys Lys Trp Ser Ile Gly Lys
35

<210> SEQ ID NO 349
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 349

Gly Pro Asn Cys Leu Arg Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Trp Ser Ile Gly Thr
35

<210> SEQ ID NO 350
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 350

Gly Pro Asn Cys Leu Arg Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Trp Ser Ile Gly Gln
35

<210> SEQ ID NO 351
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 351

Gly Pro Asn Cys Leu Arg Ile Phe Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Trp Ser Ile Gly Ser
35

<210> SEQ ID NO 352
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 352

Gly Pro Asn Cys Leu Arg Ile Met Lys Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Trp Ser Ile Gly Lys
35

<210> SEQ ID NO 353
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 353

Gly Pro Asn Cys Leu Arg Ile Phe Gln Ala Cys Asn Pro Ser Asn Asp
1 5 10 15

Gln Cys Cys Lys Ser Ser Lys Leu Val Cys Ser Arg Lys Thr Arg Trp
20 25 30

Cys Lys Trp Ser Ile Gly Lys
35

<210> SEQ ID NO 354
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 354

Gly Pro Asn Cys Leu Arg Ile Phe Lys Ala Cys Asn Arg Ser Asn Asp
1 5 10 15

Gln Cys Cys Lys Ser Ser Lys Leu Val Cys Ser Arg Lys Thr Arg Trp
20 25 30

Cys Lys Trp Ser Ile Gly Lys
35

<210> SEQ ID NO 355
<211> LENGTH: 39
<212> TYPE: PRT
<213> ORGANISM: Artificial sequence
<220> FEATURE:
<223> OTHER INFORMATION: Huwentoxin-IV variant

<400> SEQUENCE: 355

Gly Pro Asn Cys Leu Arg Ile Phe Lys Ala Cys Asn Pro Ser Asn Asp
1 5 10 15

Gln Cys Cys Lys Gln Ser Lys Leu Val Cys Ser Arg Lys Thr Arg Trp
20 25 30

Cys Lys Trp Ser Ile Gly Lys
35

-continued

```
<210> SEQ ID NO 356
<211> LENGTH: 30
<212> TYPE: PRT
<213> ORGANISM: Thrixopelma pruriens

<400> SEQUENCE: 356

Tyr Cys Gln Lys Trp Met Trp Thr Cys Asp Ser Glu Arg Lys Cys Cys
1               5                   10                  15

Glu Gly Met Val Cys Arg Leu Trp Cys Lys Lys Lys Leu Trp
            20                  25                  30


<210> SEQ ID NO 357
<211> LENGTH: 16
<212> TYPE: PRT
<213> ORGANISM: Conus kinoshitai
<220> FEATURE:
<221> NAME/KEY: MOD_RES
<222> LOCATION: (16)..(16)
<223> OTHER INFORMATION: AMIDATION

<400> SEQUENCE: 357

Cys Cys Asn Cys Ser Ser Lys Trp Cys Arg Asp His Ser Arg Cys Cys
1               5                   10                  15
```

HUWENTOXIN-IV VARIANTS AND METHODS OF USE

CROSS-REFERENCE TO RELATED APPLICATIONS

This application is a U.S. National Stage Entry of International Patent Application No. PCT/US2013/041572 filed Mar. 15, 2013, which is a Continuation-in-Part of U.S. patent application Ser. No. 13/833,555, filed Mar. 15, 2013, which claims the benefit of U.S. Provisional Application Nos. 61/648,871 filed May 18, 2012, and 61/702,538 filed Sep. 18, 2012. Additionally, International Patent Application No. PCT/US2013/041572 claims the benefit of U.S. Provisional Application No. 61/781,276 filed Mar. 14, 2013. The complete disclosures of the aforementioned related patent applications are hereby incorporated herein by reference for all purposes.

SEQUENCE LISTING

The instant application contains a Sequence Listing which has been submitted in ASCII format via EFS-WEB and is hereby incorporated herein by reference in its entirety. Said ASCII copy, created on Oct. 31, 2014, is named JBI5008USPCT_substitute seqlist_10-31-2014.txt and is 195,895 bytes in size and contains no new matter.

FIELD OF THE INVENTION

The present invention relates to Huwentoxin-IV variants, polynucleotides encoding them, methods of making and using the foregoing, and methods of alleviating pain with peptide inhibitors of Nav1.7.

BACKGROUND OF THE INVENTION

Voltage-gated sodium channels (VGSC) are present in all excitable cells including cardiac and skeletal muscle cells and central and peripheral neurons. In neuronal cells, sodium channels are responsible for amplifying sub-threshold depolarizations and generating the rapid upstroke of the action potential. As such, sodium channels are essential to the initiation and propagation of electrical signals in the nervous system. Aberrant sodium channel function is thought to underlie a variety of medical disorders (Hubner and Jentsch, Hum Mol Genet 11:2435-45, 2002) including epilepsy (Yogeeswari et al., Curr Drug Targets 5:589-602, 2004), arrhythmia (Tfelt-Hansen et al., J Cardiovasc Electrophysiol 21:107-15, 2010) myotonia (Cannon and Bean, J Clin Invest 120:80-3, 2010), and pain (Cregg et al., J Physiol 588:1897-904, 2010). Sodium channels are typically a complex of various subunits, the principle one being the pore-forming alpha-subunit, which is alone sufficient for function.

Nine known members of the family of voltage-gated sodium channel (VGSC) alpha subunits exist in humans, Nav1.1-Nav1.9. The Nav1.x subfamily can be pharmacologically subdivided into tetrodotoxin (TTX)-sensitive or TTX-resistant. Nav1.7, (also named as PN1, SCN9A or hNE) is TTX-sensitive and is primarily expressed in peripheral sympathetic and sensory neurons. Nav1.7 accumulates at nerve fiber endings and amplifies small sub-threshold depolarizations and acts as a threshold channel that regulates excitability.

Nav1.7 function is implicated in various pain states, including acute, inflammatory and/or neuropathic pain. In man, gain of function mutations of Nav1.7 have been linked to primary erythermalgia (PE), a disease characterized by burning pain and inflammation of the extremities (Yang et al., J Med Genet 41:171-4, 2004), and paroxysmal extreme pain disorder (PEPD) (Fertleman et al., Neuron 52:767-74, 2006). Consistent with this observation, non-selective sodium channel blockers lidocaine, mexiletine and carbamazepine can provide symptomatic relief in these painful disorders (Legroux-Crespel et al., Ann Dermatol Venereol 130:429-33, 2003; Fertleman et al., Neuron 52:767-74, 2006).

Loss-of-function mutations of SNC9A in humans cause congenital indifference to pain (CIP), a rare autosomal recessive disorder characterized by a complete indifference or insensitivity to painful stimuli (Cox et al., Nature 444: 894-8, 2006; Goldberg et al, Clin Genet 71:311-9, 2007; Ahmad et al., Hum Mol Genet 16:2114-21, 2007).

Single nucleotide polymorphisms in the coding region of SCN9A have been associated with increased nociceptor excitability and pain sensitivity. For example, a polymorphism rs6746030 resulting in R1150W substitution in human Nav1.7 has been associated with osteoarthritis pain, lumbar discectomy pain, phantom pain, and pancreatitis pain (Reimann et al., Proc Natl Acad Sci USA 107:5148-53, 2010). DRG neurons expressing the R1150W Nav1.7 display increased firing frequency in response to depolarization (Estacion et al., Ann Neurol 66:862-6, 2009). A disabling form of fibromyalgia has been associated with SCN9A sodium channel polymorphism rs6754031, indicating that some patients with severe fibromyalgia may have a dorsal root ganglia sodium channelopathy (Vargas-Alarcon et al., BMC Musculoskelet Disord 13:23, 2012).

In mice, deletion of the SCN9A gene in nociceptive neurons lead to reduction in mechanical and thermal pain thresholds and reduction or abolition of inflammatory pain responses (Nassar et al., Proc Natl Acad Sci USA 101: 12706-11, 2004). Ablating Nav1.7 gene expression in all sensory neurons abolished mechanical pain, inflammatory pain and reflex withdrawal responses to heat. Deleting SCN9A in both sensory and sympathetic neurons abolished mechanical, thermal and neuropathic pain, and recapitulated the pain-free phenotype seen in humans with SCN9A loss-of-function mutations (Minett et al., Nat Commun 3:791, 2012). Nav1.7 inhibitors or blockers may therefore be useful in the treatment of a wide range of pain associated with various disorders.

Spider venoms are known to contain a large number of sodium channel blocking peptides, including Huwentoxin-IV (HwTx-IV) (Peng et al., J Biol Chem 277:47564-71, 2002), Protoxin-I, Protoxin-II (Middleton et al., Biochemistry 41:14734-47, 2002) and Phrixotoxin-III (Bosmans et al., Mol Pharmacol 69:419-29, 2006). Huwentoxin-IV (HWTx-IV), from the Chinese bird spider *Ornithoctonus huwena*, is a potent blocker of Nav1.7 and other TTX-sensitive voltage-gated sodium channels and likely functions as a gating modifier by trapping the voltage sensor of domain II in an inward, closed conformation (Xiao et al., J Biol Chem 283:27300-13, 2008). Protoxin-II, due to its favorable potency and selectivity profile, has been the subject of various in vivo studies aimed at demonstrating analgesia, none of which have reported success without disrupting the perineurium. Only through subversion of the blood-nerve barrier via desheathing of cutaneous nerves (Schmalhofer et al., Mol Pharm 74:1476-1484, 2008) or perineurial injection of hypertonic saline leading to down-regulation of tight junction protein claudin-1 (Hackel et. al., PNAS 109:29 E2018-27, 2012) was any efficacy observed for Protoxin-II. There is a need for identification of additional Nav1.7 blockers for treatment of a wide range of pain indications. In particular, there is a need for new Nav1.7 blockers with selectivity for Nav1.7 over other VGSC isoforms.

BRIEF DESCRIPTION OF THE DRAWINGS

FIGS. 1 *a*) and *b*) shows $IC_{50}$ values for inhibition of veratridine-induced membrane depolarization for Nav1.7 for generated Huwentoxin-IV variants having specific substitutions at designated residue positions. Reference Huwentoxin-IV residue corresponds to residues in polypeptide of SEQ ID NO: 267. Substitutions highlighted in gray result in variants having $IC_{50}$ values $\leq 300\times10^{-9}$ M. Values beginning with > indicate that the particular variant was inactive at the concentration indicated.

FIGS. 2 *a*) and *b*) shows $IC_{50}$ values for inhibition of veratridine-induced membrane depolarization for Nav1.2 for generated Huwentoxin-IV variants having specific substitutions at designated residue positions. Reference Huwentoxin-IV residue corresponds to residues in polypeptide of SEQ ID NO: 267. Values beginning with > indicate that the particular variant was inactive at the concentration indicated.

FIGS. 3 *a*) and *b*) shows selectivity of generated Huwentoxin-IV variants as ratios of $IC_{50}$ values for Nav1.2 to $IC_{50}$ values for Nav1.7 for each variant having specific substitutions at designated residue positions ($IC_{50}$ values calculated for inhibition of veratridine-induced membrane depolarization). Reference Huwentoxin-IV residue corresponds to residues in polypeptide of SEQ ID NO: 267. Substitutions highlighted in gray result in variants having $IC_{50}$ (Nav1.2)/ $IC_{50}$ (Nav1.7) ratio equal or over 5.0. Values beginning with > indicate that the particular variant was inactive at the concentration indicated. "Inact" indicates that the peptide was inactive on Nav1.7.

FIG. 4 shows sequences of Huwentoxin-IV variants having $EC_{50}$ for Nav1.7$\leq 300\times10^{-9}$ M ($IC_{50}$ values calculated for inhibition of veratridine-induced membrane depolarization).

FIG. 5 shows sequences of Huwentoxin-IV variants that are at least 5-fold more selective for Nav1.7 than Nav1.2, assessed using the $IC_{50}$ (Nav1.2)/$IC_{50}$ (Nav1.7) ratio, of are inactive at Nav1.2 ($IC_{50}$ values calculated for inhibition of veratridine-induced membrane depolarization).

FIG. 6 shows $IC_{50}$ values and selectivity for select Huwentoxin-IV variants in whole cell patch-clamp assay (QPatch).

FIG. 13 shows A) sequences and B) $IC_{50}$ values for NV1D2168 (SEQ ID NO: 102) variants. TETRA: FLIPR® Tetra; QP: QPatch.

FIG. 14 shows A) sequences and B) $IC_{50}$ values for NV1D2163 (SEQ ID NO: 3) variants. TETRA: FLIPR® Tetra; QP: QPatch.

SUMMARY OF THE INVENTION

Figure 7A:
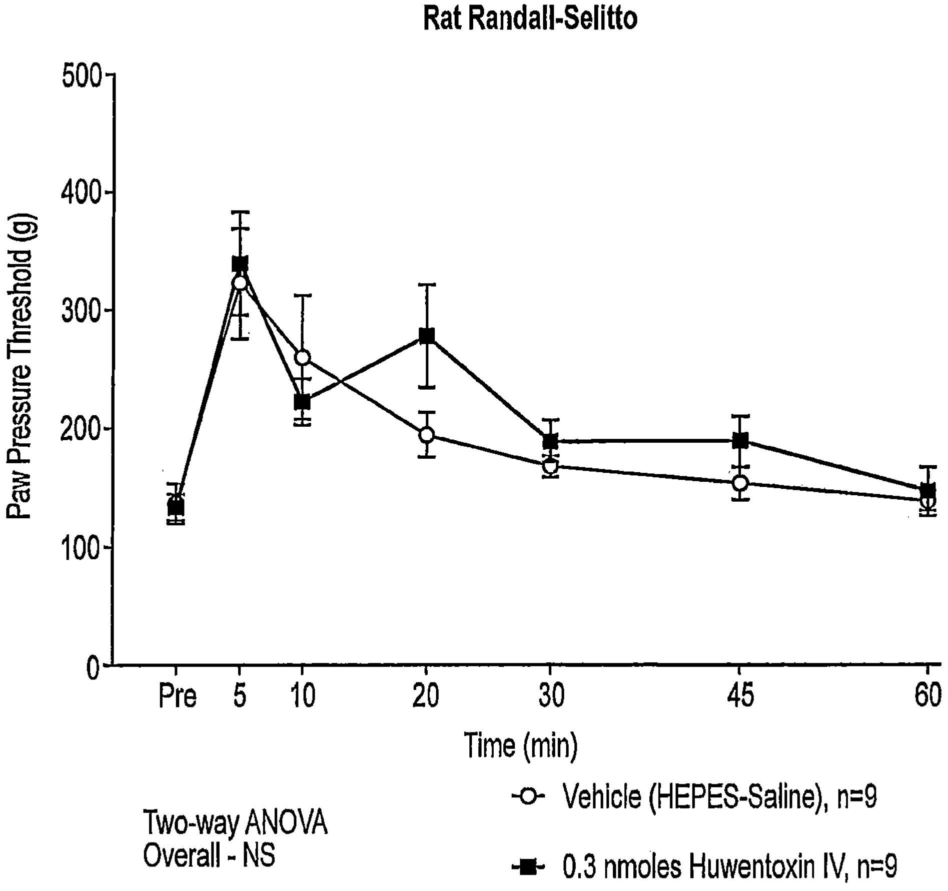
FIG. 7 shows line graph of Randall-Selitto paw pressure thresholds in grams (g) before (Pre) and 5, 10, 20, 30, 45 and 60 minutes following dorsal hind paw injections of vehicle (n=9) or a) 0.3 nmoles, b) 3 nmoles or c) 30 nmoles of huwentoxin IV (n=9) in rat. Data are represented as mean±s.e.m using Two-way ANOVA with Bonferroni posttests. NS=not significant; =$p<0.01$; *=$p<0.001$.

One embodiment of the invention is an isolated Huwentoxin-IV variant comprising a sequence $X_1CX_2X_3X_4FX_5X_6CX_7X_8X_9X_{10}X_{11}X_{12}CCX_{13}X_{14}X_{15}$-$X_{16}X_{17}X_{18}CX_{19}X_{20}X_{21}X_{22}X_{23}X_{24}CKX_{25}X_{26}IX_{27}X_{28}$ (SEQ ID NO: 265); wherein $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{16}$, $X_{12}$, $X_{18}$, $X_{19}$, $X_{20}$, $X_{21}$, $X_{22}$, $X_{23}$, $X_{24}$, $X_{25}$, and $X_{26}$ are any amino acid; $X_{27}$ and $X_{28}$ are any amino acid or deleted; and the Huwentoxin-IV variant has an $IC_{50}$ value about $300 \times 10^{-9}$ M or less for human Nav1.7 (SEQ ID NO: 263), with the proviso that the Huwentoxin-IV variant is not a polypeptide comprising a sequence shown in SEQ ID NO: 1.

Another embodiment of the invention is an isolated Huwentoxin-IV variant comprising a sequence $X_1CX_2X_3X_4FX_5X_6CX_7X_8X_9X_{10}X_{11}X_{12}CCX_{13}X_{14}X_{15}$-$X_{16}X_{17}X_{18}CX_{19}X_{20}X_{21}X_{22}X_{23}X_{24}CKX_{25}X_{26}IX_{27}X_{28}$ (SEQ ID NO: 265); wherein $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{16}$, $X_{17}$, $X_{18}$, $X_{19}$, $X_{20}$, $X_{21}$, $X_{22}$, $X_{23}$, $X_{24}$, $X_{25}$, and $X_{26}$ are any amino acid; $X_{27}$ and $X_{28}$ are any amino acid or deleted; and the Huwentoxin-IV variant selectively inhibits Nav1.7, with the proviso that the Huwentoxin-IV variant is not a polypeptide comprising a sequence shown in SEQ ID NO: 1.

Another embodiment of the invention is an isolated Huwentoxin-IV variant comprising a sequence $X_1CX_2X_3X_4FX_5X_6CX_7X_8X_9X_{10}X_{11}X_{12}CCX_{13}X_{14}X_{15}$-$X_{16}X_{17}X_{18}CX_{19}X_{20}X_{21}TX_{22}WCKYX_{23}X_{24}X_{25}X_{26}$ (SEQ ID NO: 276); wherein $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{16}$, $X_{17}$, $X_{18}$, $X_{19}$, $X_{20}$, $X_{21}$, $X_{22}$, $X_{23}$ and $X_{24}$ are any amino acid; $X_{25}$ and $X_{26}$ are any amino acid or deleted; and the Huwentoxin-IV variant has an $IC_{50}$ value about $300 \times 10^{-9}$ M or less for human Nav1.7 (SEQ ID NO: 263), with the proviso that the Huwentoxin-IV variant is not a polypeptide comprising a sequence shown in SEQ ID NO: 1.

Another embodiment of the invention is an isolated polynucleotide encoding the Huwentoxin-IV variants of the invention.

Another embodiment of the invention is a vector comprising the isolated polynucleotides of the invention.

Another embodiment of the invention is a host cell comprising a vector of the invention.

Another embodiment of the invention is a method of producing the isolated Huwentoxin-IV variant polypeptide of the invention comprising culturing the host cell of the invention and recovering the Huwentoxin-IV variant polypeptide by the host cell.

Another embodiment of the invention is a pharmaceutical composition comprising the isolated Huwentoxin-IV variant of the invention and a pharmaceutically acceptable excipient.

Another embodiment of the invention is a method of treating pain in a subject, comprising administering to the subject an effective amount of the Huwentoxin-IV variant of the invention to treat pain, other disorders of sensory or sympathetic neuron dysfunction.

Another embodiment of the invention is a method of alleviating Nav1.7-mediated pain by administering a therapeutically effective amount of a peptide inhibitor of Nav1.7 in a subject in need thereof for a time sufficient to treat or alleviate the Nav1.7-mediated pain.

In the other aspects of the invention, the peptide inhibitor of Nav1.7 is administered peripherally.

In the other aspects of the invention, the peptide inhibitor of Nav1.7 is Protoxin-II or Huwentoxin-IV or variants thereof.

DETAILED DESCRIPTION OF THE INVENTION

All publications, including but not limited to patents and patent applications, cited in this specification are herein incorporated by reference as though fully set forth.

As used herein and in the claims, the singular forms "a," "and," and "the" include plural reference unless the context clearly dictates otherwise.

Unless defined otherwise, all technical and scientific terms used herein have the same meaning as commonly understood by one of ordinary skill in the art to which an invention belongs. Although any compositions and methods similar or equivalent to those described herein can be used in the practice or testing of the invention, exemplary compositions and methods are described herein.

The term "polypeptide" means a molecule that comprises at least two amino acid residues linked by a peptide bond to form a polypeptide. Small polypeptides of less than 50 amino acids may be referred to as "peptides". Polypeptides may also be referred as "proteins".

The term "polynucleotide" means a molecule comprising a chain of nucleotides covalently linked by a sugar-phosphate backbone or other equivalent covalent chemistry. Double and single-stranded DNAs and RNAs are typical examples of polynucleotides.

The term "complementary sequence" means a second isolated polynucleotide sequence that is antiparallel to a first isolated polynucleotide sequence and that comprises nucleotides complementary to the nucleotides in the first polynucleotide sequence.

The term "vector" means a polynucleotide capable of being duplicated within a biological system or that can be moved between such systems. Vector polynucleotides typically contain elements, such as origins of replication, polyadenylation signal or selection markers, that function to facilitate the duplication or maintenance of these polynucleotides in a biological system. Examples of such biological systems may include a cell, virus, animal, plant, and reconstituted biological systems utilizing biological components capable of duplicating a vector. The polynucleotides comprising a vector may be DNA or RNA molecules or hybrids of these.

The term "expression vector" means a vector that can be utilized in a biological system or a reconstituted biological system to direct the translation of a polypeptide encoded by a polynucleotide sequence present in the expression vector.

The term "wild type Huwentoxin-IV" or "wild type HwTx-IV" as used herein refers to Chinese bird spider *Ornithoctonus huwena* Huwentoxin-IV polypeptide having a sequence shown in SEQ ID NO: 1 (ECLEIFKACNPSNDQCCKSSKLVCSRKTRWCKYQI). The term "recombinant Huwentoxin-IV" or recombinant HwTx-IV" as used herein refers to the recombinantly expressed Huwentoxin-IV having a sequence shown in SEQ ID NO: 2 (GPECLEIFKACNPSNDQCCKSSKLVCSRKTRWCKY-QIGK). Recombinant Huwentoxin-IV incorporates a two amino acid N- and C-terminal tail when compared to the wild type Huwentoxin-IV. The term "reference Huwentoxin-IV" refers to a polypeptide sequence of SEQ ID NO: 267 (ECLEIFKACNPSNDQCCKSSKLVCSRKTRWCKY-QIGK). Throughout the specification, residue numbering is according to SEQ ID NO: 267. For example, "F6" in the specification refers to Phenylalanine residues at position 6 of SEQ ID NO: 267.

The term "variant" as used herein refers to a polypeptide or a polynucleotide that differs from the wild type Huwentoxin-IV polypeptide of SEQ ID NO: 1 or the wild type Huwentoxin-IV polynucleotide of SEQ ID NO: 268 sequence by one or more modifications for example, substitutions, insertions or deletions of nucleotides or amino acids.

"Nav1.7" (also called as SCN9A, hNE, PN1) as used herein refers to the well known sodium channel protein type 9 subunit alpha having a sequence shown in GenBank accession number NP 002968.1 and in SEQ ID NO: 263.

"Nav1.2" as used herein refers to the well known sodium channel protein type 2 subunit alpha (SCN2A) having a sequence shown in GenBank accession number NP 001035232.1 and in SEQ ID NO: 264.

"Blocks activity" or "inhibits activity" as used herein refers to an ability of Huwentoxin-IV variants to reduce membrane depolarization induced by veratridine (3-Veratroylveracevine) by at least 10%, 20%, 30%, 40%, 50%, 60%, 70%, 75%, 80%, 85%, 90%, 95% or 100% in an in vitro membrane depolarization assay using FRET (fluorescence resonance energy transfer), where veratridine-induced depolarization is measured as a reduction in FRET signal using DISBAC2(3) ([bis-(1,3-diethylthiobarbituric acid) trimethine oxonol]) as an acceptor and PTS18 (trisodium 8-octadecyloxypyrene-1,3, 6-trisulfonate) as a donor by exciting the donor at 390-420 nm and measuring FRET at 515-575 nm using cell lines stably expressing Nav1.7.

The term "Protoxin-II" or "ProTx-II" as used herein refers to the tarantula *Thrixopelma pruriens* (Peruvian green velvet tarantula) toxin peptide having the amino acid sequence YCQKWMWTCDSERKCCEGMVCRLWCKKKLW-COOH (SEQ ID NO: 356) as described in Middleton et al., Biochemistry 41(50):14734-47, 2002. ProTx-II is a potent and selective Nav1.7 inhibitor in vitro with a reported $IC_{50}$ value of 0.3 nM and selectivity of over 100-fold when compared to other Nav1.x subtypes (Schmalhofer et al., Mol Pharmacol 74:1476-1484, 2008).

The term "μ-conotoxin KIIIA" or "conotoxin KIIIA" as used herein refers to the *Conus kinoshitai* toxin having the sequence CCNCSSKWCRDHSRCC-$NH_2$ (SEQ ID NO: 357) as described in Zhang et al., J Biol Chem 282(42): 30699-706, 2007.

"Nav1.7 inhibitor" or "peptide inhibitor of Nav1.7" or "blocker of Nav1.7" as used herein refers to a peptide that inhibits, reduces or blocks Nav1.7 channel activity. Peptide inhibitors of Nav1.7 can be tested for their Nav1.7 blocking activity using electrophysiological assays known in the art and assays disclosed herein. For example see Clare et al., drug Discovery Today 5:506-520, 2000.

The present invention provides isolated Huwentoxin-IV (HwTx-IV) variant polypeptides that inhibit Nav1.7, polynucleotides encoding them, vectors, host cells, and methods of using the polynucleotides and polypeptides of the invention. The variants of the invention may be more potent or more selective towards Nav1.7 when compared to the recombinant Huwentoxin-IV polypeptide. The polypeptides of the invention inhibit depolarization resulting from Nav1.7 activation, and therefore may be useful in the treatment of various conditions associated with pain and conditions associated with sensory or sympathetic neuron dysfunction. The current invention is based, at least in part, on the finding that certain residues in Huwentoxin-IV are intolerant to substitutions, specifically F6, K32 and I35, and additionally residues I5, P11, D14, S25, K27, T28, W30 and Y33 (residue numbering according to SEQ ID NO: 267) are substantially intolerant to substitutions, while other residues may be substituted to enhance potency and/or selectivity of Huwentoxin-IV variants for Nav1.7 as long as the cysteine residues at positions C2, C9, C16, C17, C24 and C31 remain intact.

One embodiment of the invention is an isolated Huwentoxin-IV variant comprising a sequence $X_1CX_2X_3X_4FX_5X_6CX_7X_8X_9X_{10}X_{11}X_{12}CCX_{13}X_{14}X_{15}X_{16}X_{17}X_{18}CX_{19}X_{20}X_{21}X_{22}X_{23}X_{24}CKX_{25}X_{26}IX_{27}X_{28}$ (SEQ ID NO: 265); wherein a) $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{16}$, $X_{17}$, $X_{18}$, $X_{19}$, $X_{20}$, $X_{21}$, $X_{22}$, $X_{23}$, $X_{24}$, $X_{25}$, and $X_{26}$ are any amino acid;

b) $X_{27}$ and $X_{28}$ are any amino acid or deleted; and c) the Huwentoxin-IV variant has an $IC_{50}$ value about $300\times10^{-9}$ M or less for human Nav1.7 (SEQ ID NO: 263), with the proviso that the Huwentoxin-IV variant is not a polypeptide comprising a sequence shown in SEQ ID NOs: 1.

The Huwentoxin-IV variants of the invention are equally potent or more potent Nav1.7 inhibitors when compared to recombinant Huwentoxin-IV (SEQ ID NO: 2). Recombinant Huwentoxin-IV has an $IC_{50}$ value of about $160\times10^{-9}$ M for human Nav1.7 in a veratridine-induced depolarization inhibition assay measuring decline in FRET (fluorescence resonance energy transfer) in cells stably expressing Nav1.7 using FLIPR® Tetra instrument (Molecular Devices). A Huwentoxin-IV variant is "equally potent or more potent" Nav1.7 inhibitor when the $IC_{50}$ value in the assay described above is about $300\times10^{-9}$ M or less. This $IC_{50}$ value is set higher than the measured $IC_{50}$ for the recombinantly expressed Huwentoxin-IV due to the intrinsic variability (½ log) of the assay itself. For clarity, an $IC_{50}$ of $300\times10^{-9}$ M is identical to $IC_{50}$ of $3.0\times10^{-7}$ M.

The Huwentoxin-IV variants of the invention retain the native disulfide bridges between C2-C17, C9-C24 and C16-C31 in addition to invariant residues F6, K32 and I35 (residue numbering according to SEQ ID NO: 267), while the remaining residues can be substituted with any amino acid as long as the resulting variant in the above Nav1.7 inhibition assay has an $IC_{50}$ of about $300\times10^{-9}$ M or less.

The Huwentoxin-IV variant polypeptides of the invention may be produced by chemical synthesis, such as solid phase peptide synthesis, on an automated peptide synthesizer. Alternatively, the polypeptides of the invention can be obtained from polynucleotides encoding the polypeptides by the use of cell-free expression systems such as reticulocyte lysate based expression systems, or by standard recombinant expression systems. Those skilled in the art will recognize other techniques for obtaining the polypeptides of the invention. In an exemplary method, the Huwentoxin-IV variants of the invention are generated by expressing them as human serum albumin (HSA) fusion proteins utilizing a glycine-rich linker such as $(GGGGS)_4$ (SEQ ID NO: 269) or $(GGGGS)_6$ (SEQ ID NO: 266) coupled to a protease cleavable linker such as a recognition sequence for HRV3C protease (Recombinant type 14 3C protease from human rhinovirus) LEVLFQGP (HRV3C linker) (SEQ ID NO: 270)). Hexahistidine or other tags may be used to facilitate purification using well known methods.

Generation of the Huwentoxin-IV variants is typically achieved at the nucleic acid level. The polynucleotides can be synthesized using chemical gene synthesis according to methods described in U.S. Pat. Nos. 6,521,427 and 6,670,127, utilizing degenerate oligonucleotides to generate the desired variants, or by standard PCR cloning and mutagenesis. Libraries of variants can be generated by standard cloning techniques to clone the polynucleotides encoding the Huwentoxin-IV variants into the vector for expression.

The Huwentoxin-IV variants may incorporate additional N- and/or C-terminal amino acids when compared to the wild type HwTx-IV of SEQ ID NO: 1, for example resulting from cloning and/or expression schemes. For example, cleavage from HSA after expression of the variant as HSA-$(GGGGS)_4$-HRV3C linker-HwTx-IV variant fusion protein may result in the incorporation of additional two residues to the N-terminus of each HwTx-IV variant, such as G and P.

Additional residues may be incorporated to the C-terminus of the HwTx-IV variants, such as G and K to generate an endogenous amidation recognition sequence.

The HwTx-IV variants of the invention are tested for their ability to inhibit Nav1.7 using methods described herein. An exemplary assay is a veratridine-induced depolarization inhibition assay measuring decline in FRET (fluorescence resonance energy transfer) in cells stably expressing Nav1.7. Another exemplary assay employs electrophysiological recordings to measure the total influx of sodium ions ($Na^+$) across the cell membrane by way of voltage differential using well known patch clamp techniques and described herein.

In another embodiment, an isolated Huwentoxin-IV variant comprises a sequence $X_1cX_2X_3X_4FX_5X_6cX_7X_8X_9X_{10}X_{11}X_{12}CCX_{13}X_{14}X_{15x}$-$X_{16}X_{17}X_{18}CX_{19}X_{20}X_{21}X_{22}X_{23}X_{24}CKX_{25}X_{26}IX_{27}X_{28}$ (SEQ ID NO: 265); wherein a) $X_4$ is Y, V or I;
b) $X_8$ is P or V;
c) $X_{11}$ is D, P or W;
d) $X_{19}$ is S or I;
e) $X_{21}$ is Y, W, A, H or K;
f) $X_{22}$ is T or V;
g) $X_{24}$ is W or K;
h) $X_{25}$ is W, T, I or Y;
i) $X_1$, $X_2$, $X_3$, $X_5$, $X_6$, $X_7$, $X_9$, $X_{10}$, $X_{12}$, $X_{13}$, $X_{14}$, $X_{15}$, $X_{16}$, $X_{17}$, $X_{18}$, $X_{20}$, $X_{23}$ and $X_{26}$ are any amino acid;
j) $X_{27}$ and $X_{28}$ are any amino acid or deleted; and
k) the Huwentoxin-IV variant has an $IC_{50}$ value about $300\times10^{-9}$ M or less for human Nav1.7 (SEQ ID NO: 263), with the proviso that the Huwentoxin-IV variant is not a polypeptide comprising a sequence shown in SEQ ID NO: 1.

In another embodiment, the isolated Huwentoxin-IV variant comprises a sequence $X_1CX_2X_3X_4FX_5X_6CX_7X_8X_9X_{10}X_{11}X_{12}CCX_{13}$-$X_{14}X_{15}X_{16}X_{17}X_{18}CX_{19}X_{20}X_{21}X_{22}X_{23}X_{24}CKX_{25}$-$X_{26}IX_{27}X_{28}$ (SEQ ID NO: 265); wherein a) $X_1$ is K, R, H, D, Y, F, N, Q, S, T, G, L, I, P or E;
b) $X_2$ is R, F, W, N, S or L;
c) $X_3$ is R, H, D, Y, N, Q, L, I, P or E;
d) $X_4$ is Y, V or I;
e) $X_5$ is R, W, Q, S or K;
f) $X_6$ is R, E, Y, F, V or A;
g) $X_7$ is K, R, E, Y, F, S, V or N;
h) $X_8$ is P or V;
i) $X_9$ is R, F, Q, V or S;
j) $X_{10}$ is H, D, Y, W, Q, S, T, G, A, V, L, I, P or N;
k) $X_{11}$ is D, P or W;
l) $X_{12}$ is K, R, D, E, Y, W, N, T, A, L or Q;
m) $X_{13}$ is R, Y, Q, S, T, G, L, I, P or K;
n) $X_{14}$ is K, R, Y, F, N, Q, G, A, V, L, I, P or S;
o) $X_{15}$ is R, H, D, Y, W, N, Q, T, V, I, P or S;
p) $X_{16}$ is R, H, D, F, W, N, Q, S, T, G, A, L or K;
q) $X_{17}$ is K, R, Y, F, W, P or L;
r) $X_{18}$ is K, R, T, A, L or V;
s) $X_{19}$ is S or I;
t) $X_{20}$ is K, W, G, A, I, D or R;
u) $X_{21}$ is Y, W, A or K;
v) $X_{22}$ is T or V;
w) $X_{23}$ is K, H, W, N, G, A, L or R;
x) $X_{24}$ is W or K;
y) $X_{25}$ is W, T, I or Y;
z) $X_{26}$ is K, R, Y, F, S, T, G, A, V, L, I or Q;
aa) $X_{27}$ is K, R, H, F, W, V, L, I, G or deleted; and
bb) $X_{28}$ is R, H, Y, F, W, N, G, V, P, K or deleted; and the Huwentoxin-IV variant has an $IC_{50}$ value about $300\times10^{-9}$ M or less for human Nav1.7 (SEQ ID NO: 263), with the proviso that the Huwentoxin-IV variant is not a polypeptide comprising a sequence shown in SEQ ID NO: 1.

The Huwentoxin-IV variants of the invention may inhibit Nav1.7 with an $IC_{50}$ value of between about $12\times10^{-9}$ M to about $300\times10^{-9}$ M. Exemplary variants demonstrating the range of $IC_{50}$ values are polypeptides of SEQ ID NOs: 3-222 shown in FIG. 4.

Another embodiment of the invention is an isolated Huwentoxin-IV variant comprising a sequence $X_1CX_2X_3X_4FX_5X_6CX_7X_8X_9X_{10}X_{11}X_{12}CCX_{13}X_{14}$-$X_{15}X_{16}X_{17}X_{18}CX_{19}X_{20}X_{21}X_{22}X_{23}X_{24}CKX_{25}X_{26}$-$IX_{27}X_{28}$ (SEQ ID NO: 265); wherein a) $X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{16}$, $X_{17}$, $X_{18}$, $X_{19}$, $X_{20}$, $X_{21}$, $X_{22}$, $X_{23}$, $X_{24}$, $X_{25}$, and $X_{26}$ are any amino acid;
b) $X_{27}$ and $X_{28}$ are any amino acid or deleted; and
c) the Huwentoxin-IV variant selectively inhibits Nav1.7, with the proviso that the Huwentoxin-IV variant is not a polypeptide comprising a sequence shown in SEQ ID NO: 1.

The Huwentoxin-IV variants of the invention may be more selective towards Nav1.7 when compared to the recombinant Huwentoxin-IV (SEQ ID NO: 2). Recombinant Huwentoxin-IV has an $IC_H$ of about $159\times10^{-9}$ M for Nav1.7 and an $IC_{50}$ of about $342\times10^{-9}$M for Nav1.2, and therefore the ratio of $IC_{50}$ for Nav1.2 to $IC_{50}$ for Nav1.7 about 2.143. "Selectivity" or "selective" or "more selective" or "selectively blocks" or "selectively inhibits" when used herein refers to a Huwentoxin-IV variant that has a ratio of $IC_{50}$ for Nav1.2 to $IC_{50}$ for Nav1.7 ($IC_{50}$(Nav1.2)/$IC_{50}$ (Nav1.7)) equal or over about 5.0. In addition, a Huwentoxin-IV variant "selectively inhibits" Nav1.7 in instances when the variant does not inhibit Nav1.2 at a peptide concentration of at least $0.8\times10^{-6}$ M even if the $IC_{50}$ ratio is less than 5. $IC_{50}$ for Nav1.2 can be assayed in a veratridine-induced depolarization inhibition assay using cell lines stably expressing Nav1.2 according to methods described for Nav1.7.

Residue positions in Huwentoxin-IV that can be mutagenized to improve selectivity include residues N13, D14, Q15, K18, S19, S20, K21, L22, R26, K27, R29, W30, Y33 and Q34 (residue numbering according to SEQ ID NO: 267). Exemplary substitutions to improve selectivity are N13G, N13I, Q15E, Q15W, Q15P, K18F, K18P, S19Q, R26K and R26I. Exemplary Huwentoxin-IV variants with improved selectivity are variants of SEQ ID NOs: 5, 7, 12, 13, 16, 21, 25, 45, 46, 48, 55, 57, 58, 60, 61, 72, 74, 76, 78, 82, 83, 96, 109, 111, 113, 122, 127, 131, 134, 137, 141, 142, 149, 164, 165, 172, 175, 177, 178, 180, 182, 188, 189, 192, 198, 202, 204, 213, 215, 219, 223, 224, 225, 226, 227, 228, 229, 230, 231, 232, 233, 234, 235, 236, 237, 238, 239 and 240.

Residues K7, N13, D14, Q15, K18, S19, S20, K21, L22, V23, R26, K27, R29, W30, Y33, and Q34, G36 and K37 (residue number according to SEQ ID NO: 267) may be substituted to improve both potency and selectivity of the resulting Huwentoxin-IV variants (FIGS. 1 and 3). Exemplary substitutions increasing both potency and selectivity are R26K, Y33W, G36I, N13Q, S19Q, and K37R (residue numbering according to SEQ ID NO: 267). Exemplary variants with improved potency and selectivity are variants of SEQ ID NOs: 5, 6, 7, 12, 13, 16, 21, 25, 45, 46, 48, 55, 57, 58, 60, 61, 72, 74, 76, 78, 82, 83, 96, 109, 111, 113, 122, 127, 131, 134, 137, 141, 142, 149, 164, 165, 169, 172, 175, 177, 178, 180, 181, 182, 187, 188, 189, 192, 198, 202, 203, 204, 207, 213, 215, 216, 219 and 221.

Another embodiment of the invention is a Huwentoxin-IV variant having the amino acid sequence shown in SEQ ID NOs: 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354 and 355.

Selectivity and/or potency of the Huwentoxin-IV variants of the invention can further be improved by selective substitutions (grafting) at positions identified to modulate selectivity and/or potency into existing variants. Exemplary variants that can further be modified and/or improved are variants NV1G387 (E1N, R26K, Q34S, G36I; NV1D2168, SEQ ID NO: 192) and NV1G327 (E1N, E4R, Y33W, Q34S; NV1D2163, SEQ ID NO: 3). NV1G387 demonstrated high selectivity towards Nav1.7. The potency of NV1G387 can be potentially improved by diversifying positions E4, A8, N13, Q15, K18, S19, S20, K21, L22, S25, K37 and G36. Exemplary substitutions are shown in FIG. 13A and FIG. 14A. NV1G327 demonstrated higher potency towards Nav1.7. The selectivity of NG1G327 can be potentially improved by diversifying positions F6, P11, D14, Q15, K18, S19, R26, K27, R29, K32 and Y33. Exemplary substitutions are shown in FIG. 13A and FIG. 14A. Those skilled in the art will recognize that substitutions at any Huwentoxin-IV variant described herein may be combined and the effect of the combination on the potency, selectivity or other characteristics can be assessed using methods described herein.

Another embodiment of the invention is an isolated Huwentoxin-IV variant comprising a sequence $X_1CX_2X_3X_4FX_5X_6CX_7X_8X_9X_{10}X_{11}X_{12}CCX_{13}X_{14}X_{15}X_{16}X_{17}X_{18}CX_{19}X_{20}X_{21}TX_{22}WCKYX_{23}X_{24}X_{25}X_{26}$ (SEQ ID NO: 276); wherein $X_1$, $X_2$, $X_3$, $X_4$, $X_5$, $X_6$, $X_7X_8$, $X_9$, $X_{10}$, $X_{11}$, $X_{12}X_{13}X_{14}$, $X_{15}$, $X_{16}$, $X_{17}$, $X_{18}X_{19}$, $X_{20}X_{21}$, $X_{22}$, $X_{23}$ and $X_{24}$ are any amino acid;

$X_{25}$ and $X_{26}$ are any amino acid or deleted; and the Huwentoxin-IV variant has an $IC_{50}$ value about $300\times10^{-9}$ M or less for human Nav1.7 (SEQ ID NO: 263), with the proviso that the Huwentoxin-IV variant is not a polypeptide comprising a sequence shown in SEQ ID NO: 1.

Huwentoxin-IV variant of SEQ ID NO: 276 may comprise following substitutions:

$X_4$ is Y, V or I;
$X_8$ is P or V;
$X_{11}$ is D, P or W;
$X_{19}$ is S or I;
$X_{21}$ is Y, W, A, H or K; and
$X_{24}$ is I in SEQ ID NO: 276.

Huwentoxin-IV variant of SEQ ID NO: 276 may further comprise following substitutions:

$X_1$ is K, R, H, D, Y, F, N, Q, S, T, G, L, I, P or E;
$X_2$ is R, F, W, N, S or L;
$X_3$ is R, H, D, Y, N, Q, L, I, P or E;
$X_5$ is R, W, Q, S or K;
$X_6$ is R, E, Y, F, V or A;
$X_7$ is K, R, E, Y, F, S, V or N;
$X_9$ is R, F, Q, V or S;
$X_{10}$ is H, D, Y, W, Q, S, T, G, A, V, L, I, P or N;
$X_{12}$ is K, R, D, E, Y, W, N, T, A, L or Q;
$X_{11}$ is R, Y, Q, S, T, G, L, I, P or K;
$X_{14}$ is K, R, Y, F, N, Q, G, A, V, L, I, P or S;
$X_{15}$ is R, H, D, Y, W, N, Q, T, V, I, P or S;
$X_{16}$ is R, H, D, F, W, N, Q, S, T, G, A, L or K;
$X_{17}$ is K, R, Y, F, W, P or L;
$X_{18}$ is K, R, T, A, L or V;
$X_{20}$ is K, W, G, A, I, D or R;
$X_{22}$ is K, H, W, N, G, A, L or R;
$X_{23}$ is K, R, Y, F, S, T, G, A, V, L, I or Q;
$X_{25}$ is K, R, H, F, W, V, L, I, G or deleted; and
$X_{26}$ is R, H, Y, F, W, N, G, V, P, K or deleted.

The isolated Huwentoxin-IV variant of SEQ ID NO: 276 may have an $IC_{50}$ of less than about $160\times10^{-9}$ M for human Nav1.7.

The Huwentoxin-IV variant of SEQ ID NO: 276 may bind human Nav1.7 at residues F6, T28, W30, K32 and Y33. As long as these residues are kept invariant, other residues in the Huwentoxin-IV may be altered to improve properties, such as affinity and/or selectivity using methods described herein.

Another embodiment of the invention is an isolated fusion protein comprising the Huwentoxin-IV variant of SEQ ID NOs: 3-253 or 277-355 fused with a second polypeptide. Such second polypeptides may be leader or secretory signal sequences, partially or completely synthetic sequences resulting for example from cloning steps, or tags such as hexahistidine tag.

Additional moieties may be incorporated into the Huwentoxin-IV variants of the invention such as polyethylene glycol (PEG) molecules, such as PEG5000 or PEG20000, fatty acids and fatty acid esters of different chain lengths, for example laurate, myristate, stearate, arachidate, behenate, oleate, arachidonate, octanedioic acid, tetradecanedioic acid, octadecanedioic acid, docosanedioic acid, and the like, polylysine, octane, carbohydrates (dextran, cellulose, oligo- or polysaccharides) for desired properties. These moieties may be direct fusions with the Huwentoxin-IV variant polypeptides and may be generated by standard cloning and expression techniques. Alternatively, well known chemical coupling methods may be used to attach the moieties to recombinantly produced HwTx-IV variants of the invention.

Huwentoxin-IV variants incorporating additional moieties may be compared for functionality by several well known assays. For example, pharmacokinetic properties of Huwentoxin-IV variants coupled to PEG may be evaluated in well known in vivo models.

Another embodiment of the invention is an isolated Huwentoxin-IV variant comprising a polypeptide sequence of SEQ ID NOs: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354 or 355.

Another embodiment of the invention is an isolated polynucleotide comprising a polynucleotide encoding the Huwentoxin-IV variant polypeptide of the invention.

The polynucleotides of the invention may be produced by chemical synthesis such as solid phase polynucleotide synthesis on an automated polynucleotide synthesizer. Alternatively, the polynucleotides of the invention may be produced by other techniques such as PCR based duplication, vector based duplication, or restriction enzyme based DNA manipulation techniques. Techniques for producing or obtaining polynucleotides of a given known sequence are well known in the art.

The polynucleotides of the invention may also comprise at least one non-coding sequence, such as transcribed but not translated sequences, termination signals, ribosome binding sites, mRNA stabilizing sequences, introns and polyadenylation signals. The polynucleotide sequences may also comprise additional sequences encoding additional amino acids. These additional polynucleotide sequences may, for example, encode a marker or well known tag sequences such as a hexa-histidine or a HA tag which facilitate the purification of fused polypeptides. Certain exemplary polynucleotides are disclosed herein, however, other polynucleotides which, given the degeneracy of the genetic code or codon preferences in a given expression system, encode the antibody antagonists of the invention are also within the scope of the invention. Exemplary polynucleotides are polynucleotides comprising a sequence shown in SEQ ID NOs: 271, 272, 273, 274 and 275.

Another embodiment of the invention is a vector comprising an isolated polynucleotide encoding the Huwentoxin-IV variants of the invention. The vectors of the invention are useful for maintaining polynucleotides, duplicating polynucleotides, or driving expression of a polypeptide encoded by a vector of the invention in biological systems, including reconstituted biological systems. Vectors may be chromosomal-, episomal- and virus-derived such as vectors derived from bacterial plasmids, bacteriophages, transposons, yeast episomes, insertion elements, yeast chromosomal elements, baculoviruses, papova viruses such as SV40, vaccinia viruses, adenoviruses, fowl pox viruses, pseudorabies viruses, picornaviruses and retroviruses and vectors derived from combinations thereof, such as cosmids and phagemids.

In one embodiment of the invention the vector is an expression vector. Expression vectors typically comprise nucleic acid sequence elements that can control, regulate, cause or permit expression of a polypeptide encoded by such a vector. Such elements may comprise transcriptional enhancer binding sites, RNA polymerase initiation sites, ribosome binding sites, and other sites that facilitate the expression of encoded polypeptides in a given expression system. Such expression systems may be cell-based, or cell-free systems well known in the art. Nucleic acid sequence elements and parent vector sequences suitable for use in the expression of encoded polypeptides are also well known. An exemplary plasmid-derived expression vector useful for expression of the polypeptides of the invention comprises an *E. coli* origin of replication, an ampicillin resistance (Amp) gene, a CMV promoter, a signal sequence, and a SV40 polyadenlyation site.

Another embodiment of the invention is an isolated host cell comprising a vector of the invention. Exemplary host cells include Archaea cells; bacterial cells such as Streptococci, Staphylococci, Enterococci, *E. coli, Streptomyces*, cyanobacteria, *B. subtilis* and *S. aureus*; fungal cells such as *Kluveromyces, Saccharomyces, Basidomycete, Candida albicans* or *Aspergillus*; insect cells such as *Drosophila* S2 and *Spodoptera* Sf9; animal cells such as CHO, COS, HeLa, C127, 3T3, BHK, HEK293, CV-1, Bowes melanoma and myeloma; and plant cells, such as gymnosperm or angiosperm cells. The host cells in the methods of the invention may be provided as individual cells, or populations of cells. Populations of cells may comprise an isolated or cultured population of cells or cells present in a matrix such as a tissue.

Introduction of a polynucleotide, such as a vector, into a host cell can be effected by methods well known to those skilled in the art. These methods include calcium phosphate transfection, DEAE-Dextran mediated transfection, microinjection, cationic lipid-mediated transfection and electroporation.

Another embodiment of the invention is a method for expressing the Huwentoxin-IV variant of the invention comprising the steps of providing a host cell of the invention; and culturing the host cell under conditions sufficient for the expression of at least one Huwentoxin-IV variant of the invention.

Host cells can be cultured under any conditions suitable for maintaining or propagating a given type of host cell and sufficient for expressing a polypeptide. Culture conditions, media, and related methods sufficient for the expression of polypeptides are well known in the art. For example, many mammalian cell types can be aerobically cultured at 37° C. using appropriately buffered DMEM media while bacterial, yeast and other cell types may be cultured at 37° C. under appropriate atmospheric conditions in LB media.

In the methods of the invention the expression of the Huwentoxin-IV variant can be confirmed using a variety of well known methods. For example, expression of a polypeptide can be confirmed using detection reagents, such as antibodies using for example FACS or immunofluorescent techniques, or using SDS-PAGE or HPLC.

Another aspect of the invention is a method of modulating the activity of Nav1.7 in a biological tissue, the method comprising contacting a biological tissue expressing Nav1.7 with a Nav1.7 modulating amount of a Huwentoxin-IV variant of the invention, or a pharmaceutically acceptable salt thereof.

Methods of Treatment

Huwentoxin-IV variants of the invention may be utilized in any therapy where it is desired to treat, reduce or alleviate symptoms of pain or other disorders of sensory or sympathetic neuron dysfunction.

Pain treated with the Huwentoxin-IV variants of the invention may be any type of pain, such as chronic pain, acute pain, neuropathic pain, nociceptive pain, visceral pain, back pain, pain associated with inflammatory conditions, post-operative pain, thermal pain or pain associated with disease and degeneration.

Pain treated with the Huwentoxin-IV variants of the invention may be Nav1.7-mediated pain.

Nav1.7-mediated pain as used herein refers to pain resulting at least partially from increased Nav1.7 channel activity.

The methods of the invention may be used to treat an animal patient belonging to any classification. Examples of such animals include mammals such as humans, rodents, dogs, cats and farm animals.

The pain and/or Nav1.7-mediated pain may result from one or more causes, such as peripheral neuropathy, central neuropathy, nerve compression or entrapment syndromes such as carpal tunnel syndrome, tarsus tunnel syndrome, ulnar nerve entrapment, compression radiculopathy, lumbar spinal stenosis, sciatic nerve compression, spinal root compression, intercostal neuralgia, compression radiculopathy and radicular lower back pain, spinal root lesions, neuritis, automimmune diseases, general inflammation, chronic inflammatory conditions, arthritis, rheumatic diseases, lupus, osteoarthritis, general gastrointestinal disorders, colitis, gastric ulceration, duodenal ulcers, inflammatory bowel disorders, irritable bowel syndrome, pain associated with diarrhea, inflammatory eye disorders, inflammatory or unstable bladder disorders, psoriasis, skin complaints with inflammatory components, sunburn, carditis, dermatitis, myositis, neuritis, collagen vascular diseases, inflammatory pain and associated hyperalgesia and allodynia, neuropathic pain and associated hyperalgesia and allodynia, multiple sclerosis, demyelinating diseases, diabetes, diabetic neuropathy pain, causalgia, pain resulting from amputation or abscess, phantom limb pain, fracture pain, bone injury, direct trauma, HIV infection, acquired immune deficiency syndrome ("AIDS"), small pox infection, herpes infection, exposure to toxins or other foreign particles or molecules, invasive cancer, cancer, chemotherapy, radiotherapy, hormonal therapy, burns, congenital defect, dental pain, gout pain, fibromyalgias, encephalitis, chronic alcoholism, hypothyroidism, uremia and vitamin deficiencies, trigeminal neuralgia, stroke, thalamic pain syndrome, general headache, migraine, cluster headache, tension headache, mixed-vascular and non vascular syndromes, sympathetically maintained pain, deafferentation syndromes, asthma, epithelial tissue damage or dysfunction, disturbances of visceral motility at respiratory, genitourinary, gastrointestinal or vascular regions, wounds, burns, allergic skin reactions, pruritis, vasomotor or allergic rhinitis, or bronchial disorders, dysmenorrhoea, pain during labor and delivery, dyspepsia, gastroesophageal reflux, pancreatitis, and visceralgia.

Other disorders of sensory or sympathetic neuron dysfunction that may be alleviated by peptide Nav1.7 blockers include itch, cough and asthma. In mice, global deletion of the SCN9A gene leads to complete insensitivity to histamine-induced itch (Gingras et al., American Pain Society Meeting Abstract 2013 and U.S. Pat. Publ. No. 20120185956). This finding suggests that peptide Nav1.7 blockers may have utility in the treatment of itch, which may arise from various sources, such as dermatological or inflammatory disorders; or inflammatory disorders such as renal or hepatobiliary disorders, immunological disorders, medication reactions and unknown/idiopathic conditions, including dermatitis, psoriasis, eczema, insect sting or bite. Nav1.7 is also expressed in sensory nerves innervating the airways (Muroi et al., J Physiol. 2011 Dec. 1; 589(Pt 23):5663-76; Muroi et al., Am J Physiol Regul Integr Comp Physiol. 2013 Apr. 10), suggesting that peptide Nav1.7 blockers may be beneficial in the treatment of cough e.g., acute or chronic cough, or cough caused by irritation from gastroesophageal reflux disease, and inflammatory diseases of the airways such as asthma and allergy-related immune responses, bronchospasm, chronic obstructive pulmonary disease, chronic bronchitis, emphysema, and hiccups (hiccoughs, singultus). Silencing Nav1.7 in vivo in nodose ganglia of guinea pigs using shRNA nearly abolished the cough reflex induced by mechanical probing (Muroi et al., Am J Physiol Regul Integr Comp Physiol. 2013 Apr. 10).

One aspect of the invention is a method of alleviating or treating itch, cough or asthma in a subject by administering a therapeutically effective amount of the Huwentoxin-IV variant of the invention to a subject in need thereof for a time sufficient to alleviate the itch, cough or asthma.

Huwentoxin-IV variants of the invention can be tested for their effect in reducing or alleviating pain using animal models described herein, and models such as the SNL (spinal nerve ligation) rat model of neuropathic pain, carageenan induced allodynia model, the Freund's complete adjuvant (CFA)-induced allodynia model, the thermal injury model, the formalin model and the Bennett Model and other modes as described in U.S. Pat. Appl. No. 2011/0124711A1 and U.S. Pat. No. 7,998,980. Carageenan induced allodynia and (CFA)-induced allodynia are models of inflammatory pain. The Bennett model provides an animal model for chronic pain including post-operative pain, complex regional pain syndrome, and reflex sympathetic dystrophy.

Any of the foregoing animal models may be used to evaluate the efficacy of Huwentoxin-IV variants of the invention inhibitor in treating pain associated with the animal models. The efficacy can be compared to a no treatment or placebo control. Additionally or alternatively, efficacy can be evaluated in comparison to one or more known pain relieving medicaments.

The present invention provides methods of treating Nav1.7-mediated pain using peptide inhibitors of Nav1.7. The invention is based on the surprising finding that administration of Nav1.7 blocking peptides are efficacious in treating and/or alleviating pain in various animal models of pain, contrary to what is disclosed and suggested in the literature. While peptide inhibitors of Nav1.7 are potent and/or selective towards Nav1.7 in in vitro cell culture models using overexpressed Nav1.7 or on isolated neurons in which the blood-nerve barrier is subverted through desheathing or hypertonic saline injection, the peptide inhibitors have proven non-efficacious in in vivo animal models of pain, which lack of efficacy has been reported to result from inability of the peptides to pass the blood-nerve barrier. Several publications describe lack of efficacy of Nav1.7 blocking peptides in animal models of pain or in isolated nerves. For example Hackel et al., Proc Natl Acad Sci 109:E2018-27, 2012, describes the inability of ProTx-II to inhibit action potential firing in isolated nerves unless the perineural barrier, which provides a diffusion barrier in this model, is compromised. ProTx-II was found non-efficacious in rodent models of acute and inflammatory pain; a likely explanation stated the inability of ProTx-II to cross the blood-nerve barrier (Schmalhofer et al., Mol Pharmacol 74:1476-1484, 2008). It has been proposed that Nav1.7 peptide toxin blockers have poor oral bioavailability and they are difficult to deliver to nerve endings, implying that their use as therapeutic agents remain limited (Dib-Hajj et al., Nature Rev Neuroscience 14, 49-62, 2013).

$Na_v1.7$ is expressed in the peripheral nervous system i.e., in nociceptive dorsal root ganglions (DRG), most notably in nociceptive small-diameter DRG neurons, in particular in peripheral terminals in the skin, with little representation in the brain. $Na_v1.7$ distribution (e.g. sensory ending) and physiology predispose it to a major role in transmitting painful stimuli.

One embodiment of the invention is a method of alleviating Nav1.7-mediated pain by administering a therapeutically effective amount of a peptide inhibitor of Nav1.7 to a subject in need thereof for a time sufficient to alleviate the Nav1.7-mediated pain.

The peptide inhibitors of Nav1.7 may be utilized in any therapy where it is desired to alleviate symptoms of Nav1.7-mediated pain or other disorders of sensory or sympathetic neuron dysfunction. Alleviation of pain is meant to include complete reduction as well as partial reduction of pain sensations.

In one embodiment, pain alleviated with the peptide inhibitor of Nav1.7 may be any type of Nav1.7-mediated pain, such as chronic pain, acute pain, neuropathic pain, nociceptive pain, visceral pain, back pain, pain associated with inflammatory conditions, post-operative pain, thermal pain or pain associated with disease and degeneration.

Neuropathic pain includes for example painful diabetic neuropathy (PDN), post-herpetic neuropathy (PHN) or trigeminal neuralgia (TN). Other causes of neuropathic pain include spinal cord injuries, multiple sclerosis, phantom limb pain, post-stroke pain and HIV-associated pain. Conditions such as chronic back pain, osteoarthritis and cancer may also result in the generation of neuropathic-related pain and thus are potentially suitable for treatment with the peptide inhibitors of Nav1.7.

The peptide inhibitors of Nav1.7 can be tested for their effect in reducing or alleviating pain using animal models such as those described herein.

Any of the foregoing animal models may be used to evaluate the efficacy of the peptide inhibitors of Nav1.7 in treating or reducing pain associated with the animal models. The efficacy can be compared to a no treatment or placebo control. Additionally or alternatively, efficacy can be evaluated in comparison to one or more known pain relieving medicaments.

In another embodiment, the Nav1.7-mediated pain is associated with primary erythemalgia (PE), paraoxysmal extreme pain disorder (PEPD), osteoarthritis, rheumatoid arthritis, lumbar discectomy, pancreatitis or fibromyalgia.

Peptide inhibitors of Nav1.7 include Protoxin-II (ProTx-II) (SEQ ID NO: 356) and Huwentoxin-IV (HwTx-IV) (SEQ ID NO: 1). Protoxin-II variants (ProTx-II variants) can be used in the methods of the invention as long as they block Nav1.7 activity and preferably have a selectivity towards Nav1.7 comparable to that of ProTx-II. Such variants are described for example in U.S. Pat. Publ. No. US2011/0065647, Int. Pat. Publ. No. WO2008/088422, and Int. Pat. Publ. No. WO2012/004664. Huwenotoxin-IV variants (HwTx-IV variants) can be used in the methods of the invention as long as they block Nav1.7 activity and preferably have selectivity towards Nav1.7 comparable to that of HwTx-IV. Such variants are described for example in U.S. Provisional Pat. Appl. Ser. No. 61/702,538 and as described herein.

In the methods of the invention, the peptide inhibitors of Nav1.7 may be conjugated to a second polypeptide to form a fusion protein. Such fusion proteins are for example the well known Fc fusions or fusions to human serum albumin to extend half life of the peptide inhibitors. The conjugation can be a direct conjugation of via a linker, such as a glycine-serine rich linker. Such linkers are well known in the art.

In the methods of the invention, additional moieties may be incorporated into the peptide inhibitors of Nav1.7, such as polyethylene glycol (PEG) molecules, such as PEG5000 or PEG20000, fatty acids and fatty acid esters of different chain lengths, for example laurate, myristate, stearate, arachidate, behenate, oleate, arachidonate, octanedioic acid, tetradecanedioic acid, octadecanedioic acid, docosanedioic acid, and the like, polylysine, octane, carbohydrates (dextran, cellulose, oligo- or polysaccharides) for desired properties. These moieties may be direct fusions with the peptide inhibitors of Nav1.7 and are commercially available or may be generated by known chemical synthetic routes and known chemical coupling methods may be used to attach the moieties to the peptide inhibitors of Nav1.7

The peptide inhibitors of Nav1.7 incorporating additional moieties may be compared for their Nav1.7 blocking ability and efficacy in treatment or reducing pain using well known methods and those described herein.

Other disorders of sensory or sympathetic neuron dysfunction that can be treated with the peptide inhibitors of Nav1.7, including asthma, cough, heart-burn, itch, dermatitis, bladder instability, and Reynaud's disease.

Pharmaceutical Compositions

The Huwentoxin-IV variants of the invention or other peptide inhibitors of Nav1.7 can be formulated in a pharmaceutically acceptable vehicle or carrier. A suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. These solutions are sterile and generally free of particulate matter, and may be sterilized by conventional, well-known sterilization techniques (e.g., filtration). The compositions may contain pharmaceutically acceptable excipients as required to approximate physiological conditions, such as pH adjusting and buffering agents, stabilizing, thickening, lubricating and coloring agents, etc. Suitable vehicles and their formulation and packaging are described, for example, in Remington: The Science and Practice of Pharmacy (21st ed., Troy, D. ed., Lippincott Williams & Wilkins, Baltimore, Md. (2005) Chapters 40 and 41).

In the methods of the invention, the Huwentoxin-IV variants or the invention or other peptide inhibitors of Nav1.7 may be administered by peripheral administration. "Peripheral administration" or "administered peripherally" means introducing an agent into a subject outside of the central nervous system. Peripheral administration encompasses any route of administration other than direct administration to the spine or brain.

Peripheral administration can be local or systemic. Local administration of the peptide inhibitors of Nav1.7 may be suitable for less selective Nav1.7 inhibitors, such as Mu-conotoxins, family 1(HwTx-like) and family 3 (ProTx-II like). Local administration may be used to concentrate the therapeutic to the site of action, such as local administration to joints, spinal cord, surgical wounds, sites of injury/trauma, peripheral nerve fibers, various organs (GI, urogenital, etc) or inflamed tissues. Systemic administration results in delivery of a pharmaceutical composition to essentially the entire peripheral nervous system of the subject and may also result in delivery to the central nervous system depending on the properties of the composition.

Routes of peripheral administration encompass, without limitation, topical administration, intravenous or other injection, and implanted mini-pumps or other extended release devices or formulations.

Pharmaceutical compositions of the invention include formulations involving Huwentoxin-IV variants or other peptide inhibitors of Nav1.7 in sustained- or controlled-delivery formulations. These formulations may be achieved through use of for example injectable microspheres, bio-erodible particles, microemulsions, nanoparticles, nanocapsules, macroemulsions, polymeric compounds (such as polyesters, polyamino acids, hydrogels, poly(lactic acid), polyglycolic acid or ethylene vinylacetate copolymers), beads or liposomes, that may provide controlled or sustained release of the Huwentoxin-IV variants or other peptide inhibitors of Nav1.7 which can be delivered via depot injection, known to those skilled in the art. For example, hyaluronic acid or implantable drug delivery device may be used, having the effect of promoting sustained duration in the circulation.

Pharmaceutical compositions of the invention may be formulated for inhalation as a dry, inhalable powder. The inhalation solutions may also be formulated with a propellant for aerosol delivery, or a nebulizer.

Pharmaceutical compositions of the invention may be formulated for oral delivery. Huwentoxin IV variants or other peptide inhibitors of Nav1.7 that that are administered in this fashion may be formulated with or without carriers customarily used in the compounding of solid dosage forms such as tablets and capsules. A capsule may be designed to release the active portion of the formulation at the point in the gastrointestinal tract when bioavailability is maximized and pre-systemic degradation is minimized. Additional agents can be included to facilitate absorption of the Huwentoxin-IV variants. Diluents, flavorings, low melting point waxes, vegetable oils, lubricants, suspending agents, tablet disintegrating agents, and binders may also be employed. A pharmaceutical composition of the invention is preferably provided to comprise an effective quantity of one or a plurality of Huwentoxin-IV variants in a mixture with non toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or *acacia*; or lubricating agents such as magnesium stearate, stearic acid, or talc.

The Huwentoxin-IV variants of the invention or other peptide inhibitors of Nav1.7 may be prepared for use for parenteral (subcutaneous, intramuscular or intravenous), intracerebral (intra-parenchymal), intracerebroventricular, intramuscular, intra-ocular, intra-arterial, intraportal, or intralesional routes; by sustained release systems or by implantation devices, or any other administration, particularly in the form of liquid solutions or suspensions; for buccal or sublingual administration such as in the form of tablets or capsules; or intranasally such as in form of powders, nasal drops or aerosols or certain agents; transdermally in a form of a gel, ointment, lotion, cream or dusting powder, suspension or patch delivery system with chemical enhancers to either modify the skin structure or to increase the drug concentration in the transdermal patch, or with agents that enable the application of formulations containing proteins and peptides onto the skin (WO98/53847), or applications of electric fields to create transient transport pathways such as electroporation, or to increase the mobility of charged drugs through the skin such as iontophoresis, or application of ultrasound such as sonophoresis (U.S. Pat. Nos. 4,309,989 and 4,767,402). The composition also may be administered locally via implantation of a membrane, sponge or another appropriate material onto which the desired molecule has been absorbed or encapsulated.

In certain embodiments, where an implantation device is used, the device may be implanted into any suitable tissue or organ, and delivery of the desired molecule may be via diffusion, timed-release bolus, or continuous administration.

The concentration of the Huwentoxin-IV variants of the invention or other peptide inhibitors of Nav1.7 in such pharmaceutical formulation can vary widely, i.e., from less than about 0.5%, usually at or at least about 1% to as much as 15%, 20%, 30%, 40%, 50%, 60% or 70% by weight and will be selected primarily based on fluid volumes, viscosities and other factors, according to the particular mode of administration selected. The Huwentoxin-IV variants of the invention or other peptide inhibitors of Nav1.7 can be lyophilized for storage and reconstituted in a suitable vehicle prior to use. This technique has been shown to be effective with conventional protein preparations. Lyophilization and reconstitution techniques are well known in the art.

An exemplary pharmaceutical compositions of the present invention may comprise Tris buffer of about pH 7.0-8.5, or acetate buffer of about pH 4.0-5.5, and may further include sorbitol, sucrose, Tween-20 and/or a suitable substitute thereof.

The appropriate therapeutically effective dose can be determined readily by those of skill in the art. Effective dose refers to an amount or dosage sufficient to produce a desired result, i.e. to partially or completely prevent, stop, inhibit, reduce, or delay the perception of pain associated with any painful medical condition. The effective amount may vary depending on the specific vehicle and Huwentoxin-IV variant or other peptide inhibitors of Nav1.7 selected, and is also dependent on a variety of factors and conditions related to the subject to be treated and the severity of the pain. For example, factors such as the age, weight and health of the subject to be administered with the pharmaceutical compositions of the invention as well as dose response curves and toxicity data obtained in preclinical animal work would be among those considered. A determined dose may, if necessary, be repeated at appropriate time intervals selected as appropriate by a physician or other person skilled in the relevant art (e.g. nurse, veterinarian, or veterinary technician) during the treatment period. The determination of an effective amount or a therapeutically effective amount for a given agent is well within the ability of those skilled in the art.

Thus, a pharmaceutical composition of the invention for intramuscular injection could be prepared to contain 1 ml sterile buffered water, and between about 1 ng to about 100 mg, about 50 ng to about 30 mg or about 5 mg to about 25 mg of a Huwentoxin-IV variant of the invention. Similarly, a pharmaceutical composition of the invention for intravenous infusion could be made up to contain about 250 ml of sterile Ringer's solution, and about 1 mg to about 30 mg or about 5 mg to about 25 mg of a Huwentoxin-IV variant of the invention or other peptide inhibitors of Nav1.7. Actual methods for preparing parenterally administrable compositions are well known and are described in more detail in, for example, "Remington's Pharmaceutical Science", 15th ed., Mack Publishing Company, Easton, Pa.

The present invention will now be described with reference to the following specific, non-limiting examples.

EXAMPLE 1

Design and Generation of Huwentoxin-IV Variants

Single position amino acid scanning library substituting Ala, Asp, Glu, Phe, Gly, His, Ile, Lys, Leu, Asn, Pro, Gln, Arg, Ser, Thr, Val, Trp, and Tyr at every non-cysteine residue within the wild type Huwentoxin-IV (ECLEIFKACNPSNDQCCKSSKLVCSRKTRWCKYQI; SEQ ID NO: 1) derived from the venom of the Chinese bird spider, *Ornithoctonus huwena* was generated. The Huwentoxin-IV variants were encoded as HRV3C protease cleavable human serum albumin (HSA) fusion proteins in the following format from N- to C-terminus: $His_6$-HSA-$(GGGGS)_4$-HRV3C cleavage site-Huwentoxin-IV variant. Every variant peptide, following cleavage from HSA had a residual N-terminal GP from the cleavage site as well as a C-terminal GK which is the endogenous amidation recognition sequence. The single position variants were tested in fluorescence-based screening assays measuring their ability to inhibit Veratridine-induced membrane potential and hits were confirmed in Qpatch electrophysiology. The C-terminal GK residues in the recombinantly expressed cleaved Huwentoxin-IV variants were also substituted.

Combinatorial libraries were designed to test for additive effects of select single position hits in an attempt to generate Nav1.7 antagonists with further improved potency and selectivity profile compared to the native peptide. Two combinatorial libraries were produced, one that combined E1N, E4R, R26K, Y33W, Q34S, and G36I (library NV1D7L5), the other combined N13Q, S19Q, V23R, K27Y, R29K, and K37R (library NV1D7L6).

Construction of Expression Vectors cDNAs encoding the designed Huwentoxin-IV variant polypeptides were generated using a gene assembly technology described in U.S. Pat. No. 6,521,427. Briefly, the amino acid sequences of the designed peptide variants were back-translated to DNA sequences using human-high frequency codons. The DNA sequence of each variant gene, together with a portion of vector DNA including the DNA cloning sites, was synthesized as multiple oligonucleotides, some of which contained degenerate codons, and assembled into full-length DNA fragments. The assembled DNA fragments were amplified by PCR and PCR products were subsequently cloned as a pool. Pooled PCR products were digested with the appropriate restriction enzymes and cloned into the designed expression vector in such as manner as to fuse each toxin variant gene to the signal peptide and the fusion partner contained in the vector. Standard molecular biology techniques were used to identify a positive clone for each designed variant. The plasmid DNA from these positive clones was purified and sequence confirmed before expressing each Huwentoxin-IV peptide variant.

Protein Expression

HEK293F cells maintained in 293 Freestyle™ media (Invitrogen) were transiently transfected with plasmids encoding Huwentoxin-IV variants using Freestyle™ transfection reagent (Invitrogen) according to standard protocols. Transfected cells were placed in a humidified incubator set at 37'C. and 8% $CO_2$ for 4 days shaking at 125 RPM. The supernatant was separated from the cells by centrifugation at 5,000 g for 10 minutes and filtered through a 0.2 μm filter and concentrated 10 and 50 fold using an Amicon Ultra Concentrator 10K (Cat #UFC901096), and centrifuging for approximately 10 minutes at 3,750 g.

Protein Purification

The secreted Huwentoxin-IV variant proteins were purified via IMAC using 1 ml HisTrap HP columns (GE Healthcare). The chromatography method was run using an AKTA Xpress and protein was eluted from the column using a step gradient of Imidazole. Peak fractions were pooled and digested overnight with HRV3C protease (EMD cat#71493; 1 unit/100 μg protein). Cleaved peptide was purified via RP-HPLC using a C18(2) column (Phenomenex, cat#00G-4252-N0). The chromatography method was run on a Dionex HPLC system and the bound peptide was eluted using a linear gradient of acetonitrile. Peak fractions were collected, pooled and lyophilized.

Lyophilized peptides were re-suspended in HEPES buffered saline, pH7.4 (10 mM HEPES, 137 mM NaCl, 5.4 mM KCl, 5 mM glucose, 2 mM $CaCl_2$, 1 mM $MgCl_2$). Absorbance was measured at 280 nm, and concentrations calculated using each peptide's extinction coefficient. Peptides were analyzed by non-reducing SDS-PAGE.

For scale-up, proteins were purified in IMAC using 5 ml HisTrap HP columns (GE Healthcare, cat#17-5248-02). The chromatography method was run using an AKTA Explorer or FPLC and protein was eluted from the column using a step gradient of Imidazole. Peak fractions were pooled and concentrated using Amicon Ultra-15 centrifugal concentrators (Millipore, cat# UFC901096) and dialyzed overnight against 2 changes of Dulbecco's phosphate buffered saline, pH7.2 (Invitrogen, cat#14190). The fusion was then digested overnight with HRV3C (EMD cat#71493; 1 unit/100 μg protein). The cleaved fusion was purified by IMAC using 5 ml HisTrap HP columns. The peptide was collected in the flow through fraction. Pooled peptide was concentrated and polished via RP-HPLC using a C18(2) column (Phenomenex, cat#00G-4252-N0). The chromatography method was run on an Agilent 1100 HPLC system and the bound peptide was eluted using a linear gradient of acetonitrile.

Each peak fraction was analyzed by RP-HPLC on an analytical C18(2) column (Phenomenex, cat#00G-4252-E0) using an acetonitrile linear gradient. Fractions with the same retention times were pooled and lyophilized. Lyophilized peptides were re-suspended in HEPES buffered saline, pH7.4 (10 mM HEPES, 137 mM NaCl, 5.4 mM KCl, 5 mM glucose, 2 mM $CaCl_2$, 1 mM $MgCl_2$). Absorbance was measured at 280 nm, and concentrations calculated using each peptide's extinction coefficient. Final peptides were analyzed by electrospray ionization mass spectrometry on a Waters system.

EXAMPLE 2

Characterization of Huwentoxin-IV Variants Membrane Depolarization Assays

Ability of the generated Huwentoxin-IV variants to inhibit membrane depolarization induced by Nav1.7 agonist veratridine (3-Veratroylveracevine; Biomol, Catalog# NA125) was measured using FRET assay (fluorescence resonance energy transfer) on FLIPR® Tetra using DISBAC2(3) (Invitrogen, K1018) as an electron acceptor and PTS18 (Trisodium 8-octadecyloxypyrene-1,3,6-trisulfonate) (Sigma) as a donor by exciting the donor at 390-420 nm and measuring FRET at 515-575 nm.

HEK293F cells stably expressing the hNav1.7 channel under G418 selection (Invitrogen) were cultured in DMEM/F12 supplemented with glutamine, 10% FBS, 1% NEAAs, and 400 μg/ml G-418. 50 μl of harvested cells were plated at 25,000 cells/well into poly-lysine coated 384-well black clear bottom plates. The plates were incubated at room temperature (RT) for 15 min followed by an overnight incubation at 37° C. All incubations were done in the dark unless otherwise stated. The next day, the wells were washed 4 times with assay buffer, and resuspended in 25 μl of assay buffer (137 mM NaCl, 4 mM KCl, 2 mM $MgCl_2$, 2 mM $CaCl_2$, 5 mM Glucose, 10 mM HEPES). 2× stock (6 μM) of the PTS18 dye was prepared by suspending the dye in 10% pluronic F127 in DMSO at 1:1 (v/v ratio). 25 μl of the 2× PTS18 stock was added into the wells and the cells were stained for 30 min at RT, after which the dye was washed off with the assay buffer.

Huwentoxin-IV peptides were suspended at 3× their final concentration in the assay buffer containing 10 μM DISBAC2(3) and 400 μM VABSC-1 to suppress background fluorescence (Sigma, cat#201987). 25 μl/well of the suspended Huwentoxin-IV peptides were added onto each well, and incubated for 60 minutes at RT. Depolarization was induced by 25 μM final concentration of veratridine (by adding 25 μl/well of 75 mM (3×) stock solution), and the reduction in the mean intensity of FRET dye fluorescence was measured 30 seconds after adding the agonist. A 1.3× dilution of each measured Huwentoxin-IV peptide occurred after adding veratridine by convention, the concentration at the beginning of the FLIPR® Tetra assay is reported. Tetracaine, TTX, Protoxin-II and Huwentoxin-IV are established sodium channel blockers and were used as controls in each experimental series.

Fluorescence counts for each well were converted to % inhibition by normalizing the signal to the negative control (response to agonist veratridine alone) and positive control (response to veratridine in the presence of 10 μM tetracaine)

For measurements, "spatial uniformity correction" (all fluorescence traces are normalized to the average initial starting intensity) and "subtract bias value" (subtract the initial starting intensity from each trace) are turned on in FLIPR® Tetra.

For screening mode, no averaging was performed and each uploaded data point represents the response in an individual well.

For concentration-response mode, all individual data points were used in a non-linear least-squares procedure to find the best fit to a Hill function using Origin software (Microcal). $IC_{50}$ values were extrapolated from the resultant fitted curve.

The mean and standard deviations of the positive (P±dP) and negative (N±dN) controls were used to calculate the amount of block (B) in a well with a response (R) as follows:

$$s = 100\%\left(\frac{N-R}{N-P}\right)$$

The screening window (a measure of the data quality) is defined as:

$$z' = 1 - 3\left|\frac{(\delta N + \delta P)}{N-P}\right|$$

Assay plates were accepted if (1) the screening window based on the controls was z'>0.5, and (2) the potency of control antagonists for that day were within ±0.5 log units of their historical mean.

Selectivity of Huwentoxin-IV variants were assessed by ability of the variants to inhibit NaV1.2-induced membrane depolarization using HEK293F cells stably expressing the hNav1.2 channel under G418 selection (Invitrogen cat #11330) as described for Nav1.7, except that depolarization was induced by about 8.35 μM final concentration of veratridine (by adding 25 μl/well of 25 μM (3×) stock solution). Selectivity was measured as a ratio of $IC_{50}$(Nav1.2)/$IC_{50}$ (Nav1.7).

QPatch Assay

HEK293 cells stably expressing human Nav1.7 were cultured in DMEM/F-12 media (1:1), supplemented with 10% fetal bovine serum, 400 μg/mL Geneticin and 100 μM NEAAs (all reagents from Invitrogen). The cells were maintained at 37° C. and in 5% $CO_2$ and assayed upon reaching ~70-90% confluency. Before testing in QPatch (Sophion), cells were first dissociated using 0.05% trypsin (5 min at 37° C.), resuspended in CHO-S-SFM media (Life Technologies) and gently triturated to break up cell clumps. Cell density was adjusted to 1-2×$10^6$/mL with the same media and cells were transferred to a cell "hotel" in QPatch HT and used in experiments for several hours.

For giga-ohm seal formation and whole-cell patch clamp recording, the extracellular solution contained 137 mM NaCl, 5.4 mM KCl, 1 mM $MgCl_2$, 2 mM $CaCl_2$, 5 mM glucose, and 10 mM HEPES, pH=7.4 and osmolarity=315 mOsm. The intracellular solution contained 135 mM CsF, 10 mM CsCl, 5 mM EGTA, 5 mM NaCl and 10 mM HEPES, pH=7.3 and osmolarity=290 mOsm.

The voltage protocol used in the assay was as follows. From a holding potential of −75 mV, cells were first hyperpolarized to −120 mV for 2 sec and then depolarized to 0 mV for 5 ms before returning to the holding potential (−75 mV). This protocol was repeated once every 60 sec during liquid applications (see below). Cells were otherwise held at −75 mV when the above voltage protocol was not executed.

Upon establishment of the whole-cell recording configuration, a total of five applications of the extracellular solution (all containing 0.1% bovine serum albumin (BSA) with or without test compound, except for the last application, which contained 1 μM TTX without BSA) were made on to cells being recorded. The first application contained only the control buffer (5 μl). The voltage protocol was executed 10 times (for a total duration of 10 min) five sec after the application. The next three applications (5 μl each) contained a test compound (same compound at the same concentration for all three applications) or control buffer (for control cells only). Five seconds after each of these applications, the voltage protocol was again executed 10 times (also once per min). The last application contained 1 μM TTX (composed of three 10 μl sub-applications, each separated by 2 sec), five seconds after which the same voltage protocol was executed twice to obtain the baseline current.

Currents were sampled at 25 kHz and filtered at 5 kHz with an 8-pole Bessle filter. The series resistance compensation level was set at 80%. For each cell, the peak current amplitude at 0 mV for each current trace in the first four liquid applications was first subtracted from that of the last trace in the presence of TTX and then normalized to that of the last trace in the first (control buffer) application as % inhibition. To control for current rundown, this (% inhibition) value for each cell in the presence of a test compound was further normalized to the average % inhibition value for control (typically 5-6) cells in the same experiment. The mean value of the last two such values in the last compound application (i.e., the corrected % inhibition value for each concentration of a test compound) was used in concentration response calculations. All experiments were performed at room temperature (~22° C.). Data are expressed as mean±se.

For reference compounds, results obtained from QPatch using this protocol, e.g., potency/kinetics, were in good accord with that from manual patch clamp.

Results

Library matrix for single substitution variants and their $IC_{50}$ values for Nav1.7 obtained using the depolarization assay on FLIPR® Tetra is shown in FIG. 1. Library matrix for single substitution variants and the $IC_{50}$ for Nav1.2 obtained using the depolarization assay on FLIPR® Tetra is shown in FIG. 2. Selectivity measured as a ratio of the obtained $IC_{50}$ for Nav1.2 to the obtained $IC_H$ for Nav1.7 of the single substitution variants is shown in FIG. 3. FIGS. 4 and 5 show sequences of the variants ranked by potency on Nav1.7 (FIG. 4) or selectivity (FIG. 5).

Select variants were tested in whole cell patch clamp experiments. The recombinant Huwentoxin-IV and Huwentoxin-IV variants were tested against Nav1.7 and Nav1.2 stably expressed in HEK293 cells using the QPatch assay described above. The $IC_{50}$ values obtained for each huwentoxin-IV variant for Nav1.7 and Nav1.2 using the whole cell patch clamp methods is shown in FIG. 6. Selectivity of the Huwentoxin-IV variants was calculated as above using the $IC_{50}$ values obtained from the whole cell patch-clamp experiments.

Using Huwentoxin-IV as a starting point single-position amino acid scanning library was designed to identify variants with improved potency or selectivity. Select single position variants with interesting properties were included into combinatorial libraries. Single-position variants that were used in the design of the combinatorial libraries included E1N, E4R, R26K, Y33W, Q34S, G36I, N13Q, S19Q, V23R, K27Y, R29K, and K37R (residue numbering according to SEQ ID NO: 267), all of which showed improvements in potency, selectivity or both. Additional single-position variants with improved properties include R26W (SEQ ID NO: 72), K27W (SEQ ID NO: 57), Q34F (SEQ ID NO: 6) and R29W (SEQ ID NO: 55). In addition, variants (E1N,E4R,R26K,Q34S) (SEQ ID NO: 5), (E1N, E4R,R26K,Q34S,G36I) (SEQ ID NO: 16), (E4R,R26K, Y33W,G36I) (SEQ ID NO: 48), (E1N,Y33W,Q34S,G36I) (SEQ ID NO: 83), (N13Q,R29K,K37R) (SEQ ID NO: 137), (E1N,R26K,Q34S,G36I) (SEQ ID NO: 192) and (R26K, Y33W)(SEQ ID NO: 46) identified from combinatorial libraries demonstrate improved potency and/or selectivity.

EXAMPLE 3

Analgesic Activity of Huwentoxin-IV Following Intraplantar Administration in Rats Methods Male Sprague-Dawley (CD) rats (Charles River, San Diego) weighing >300 grams were used in this study. Naive animals were trained for two days prior to the day of testing (in order to reduce the variability in responses). Training consisted of performing actual tests multiple times on each animal over a duration of ~1 hour for each rat. Animals first received a mark with a Sharpie in the center of the dorsal aspect of the left paw just proximal to the toes to enable consistently testing the same site of the paw. Rats were then loosely wrapped in a towel leaving the hind paws uncovered, the left hind paw was placed in the Randall Selitto device with the maximum threshold set at 500 grams (Ugo-Basile Randall-Selitto Device, Analgesy-Meter) with the Sharpie mark just beneath the point of the cone on the test device that comes in contact with the paw and pressure was increased at a steady rate via electronic ramp with foot control until the animal responded. A 'response' for training followed the same criteria as that on the day of testing and consisted of any one of the following: 1) removal of the hind paw from the device, 2) a clear attempt at removal or 3) vocalization. Rats were tested up to 3 times consecutively unless they responded to a threshold greater than or equal to 100 grams. Over the course of the hour/day of training, 1-3 consecutive tests were made for each rat with 5-20 minutes apart.

For compound testing, trained, un-injured rats were tested once for the pre-compound thresholds. Animals were assigned into peptide- or vehicle-treated groups in such a manner as to produce comparable pre-administration threshold means. Experiments were conducted blind to treatment groups where possible. One test for each time point following injection (5, 10, 20, 30 45, 60 min) was taken and recorded.

Material Preparation and Local Administration in Hindpaw

Amidated Huwentoxin IV (Peptides International, Louisville, Ky.) was received in lyophilized form and reconstituted with HEPES-buffered saline, aliquoted and frozen at −20° C. Just prior to administration in the left dorsal hind paw, aliquots were thawed and diluted to appropriate concentrations using HEPES-buffered saline as the diluent. Because stress related to handling and paw injections may itself produce an increase in paw pressure threshold (stress-induced analgesia), rats were briefly anesthetized with isoflurane for the injection (5% induction; 2-3% maintenance). Animals were injected s.c. (100 μL of peptide solution or vehicle) in the dorsal aspect of the paw with the needle inserted left of center toward the ankle such that the tip of the needle ended just underneath the Sharpie mark in the center of the dorsal paw proximal to the toes.

Data Analysis

Gram thresholds were recorded and entered into Prism 5.01 (Graphpad Software Inc., LaJolla, Calif.) for graphing, generating area under the curve (AUC) values and statistical analysis. For comparison of gram values over time, a two-way ANOVA was used with a significance level of $p<0.05$. For generation of mean AUC values, the AUC for each rat in the peptide group was individually obtained and the mean AUC of the vehicle group was subtracted from it. The vehicle subtracted AUCs for each peptide-treated animal were averaged and compared either by Student's T-test or one-way ANOVA, each with a significance level of $p<0.05$.

Results

Figure 7B:
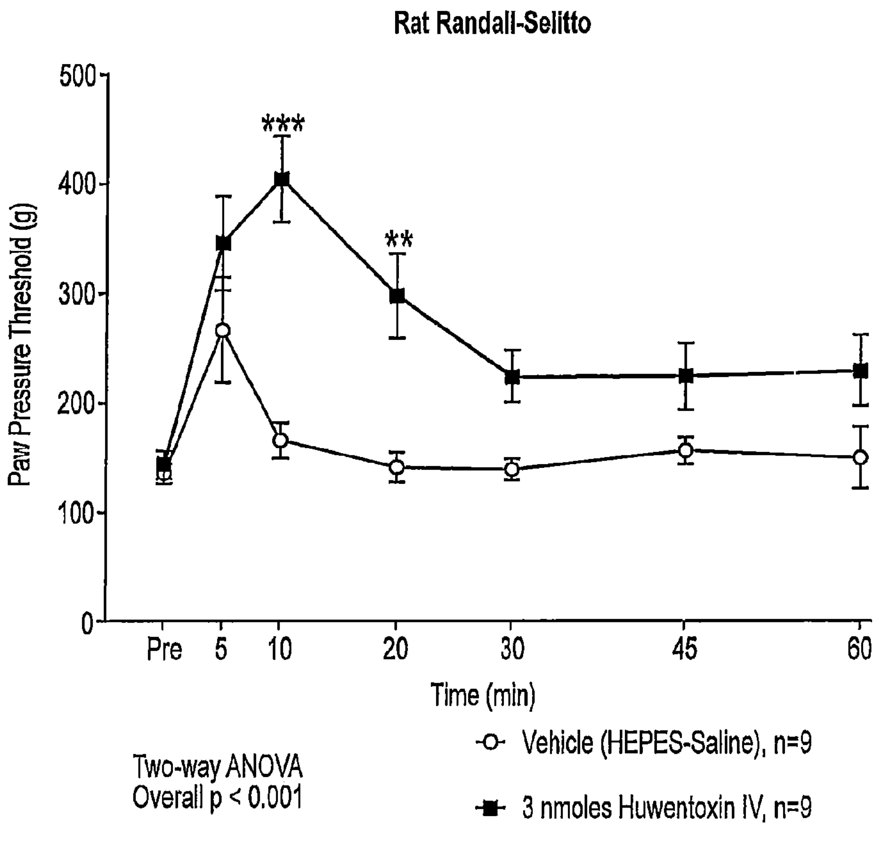
Figure 7C:
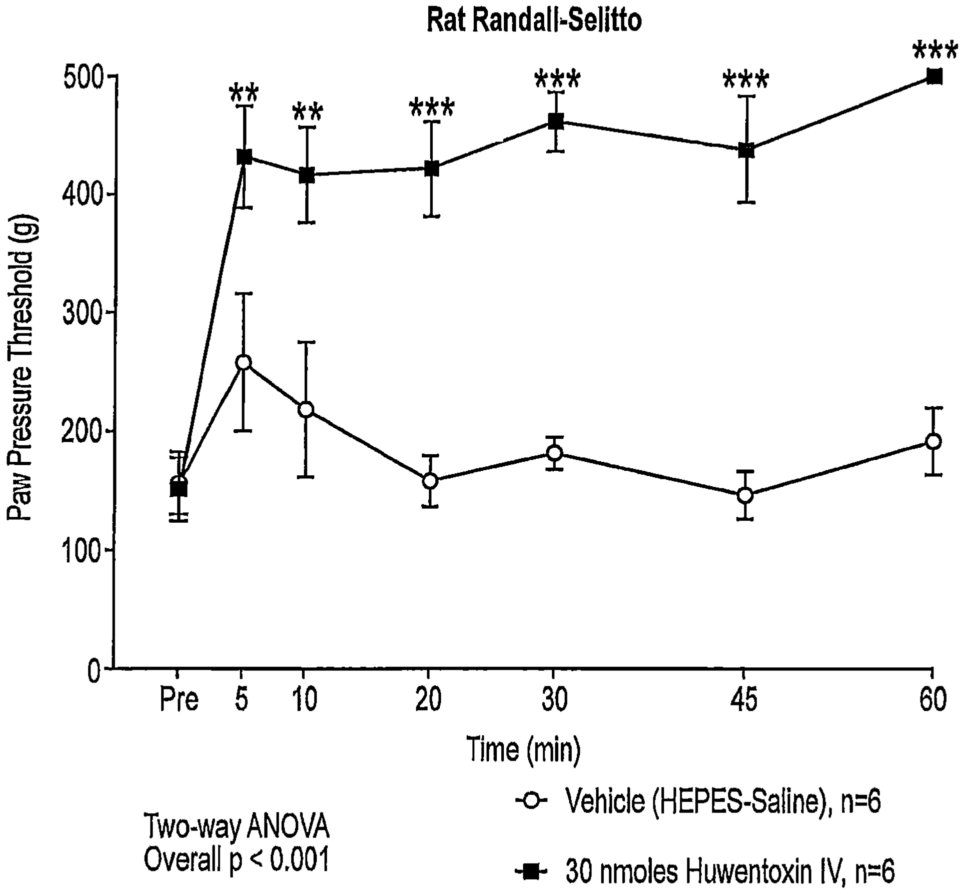
Figure 8:
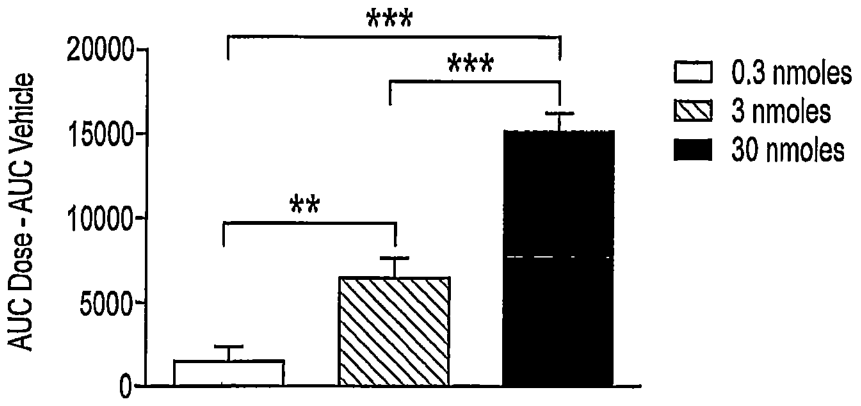
FIG. 8 shows mean area under the curve (AUC) of gram thresholds for huwentoxin IV-treated rats with subtraction (for each individual huwentoxin IV-treated rat) of the mean AUC for vehicle-treated animals. Using one-way ANOVA, there was a significant effect of dose ($p<0.001$) demonstrating dose-dependent responses. Bonferroni post tests showed significant differences between each dose group, =$p<0.01$; *=$p<0.001$.

Huwentoxin-IV administered locally into the dorsal aspect of the paw produced a dose-dependent increase in paw pressure threshold in the Randall-Selitto test. Three and 30 nmoles Huwentoxin IV, but not 0.3 nmoles, increased thresholds significantly above those observed for vehicle-treated animals (FIG. 7). AUCs were significantly different between all 3 peptide treated groups (with mean vehicle AUC subtracted from the AUC for each animal) (FIG. 8). Some local edema was also noted following administration of each dose of Huwentoxin-IV. Similar edema was not noted in the vehicle injected rats.

EXAMPLE 4

Molecular Modeling of Huwentoxin-IV Interaction With Nav1.7

NMR Structure Determination

All NMR experiments were performed using Bruker Avance 600, 700, or 950 MHz spectrometers. The peptides were dissolved in aqueous buffer containing 10% $D_2O$. The buffer maintained a pH of 6.7 using 20 mM phosphate, 0.1 mM dEDTA, and 0.002% $NaN_3$. All spectra were collected at 298 K, unless otherwise stated. Individual residue spin systems were assigned using TOCSY (Bax and Davis, Mag. Reson. 1985, 65, 355-360) spectra using spin-lock (MLEV) with mixing times of 75 ms. Sequential residue assignments were made from NOESY (Jeener et al., J. Chem. Phys. 1979, 71, 4546-4553; Kumar et al., Biochem. Biophys. Res. Commun. 1980, 95, 1-6) experiments collected with a mixing time of 150 ms. In addition, $^{15}N$-HSQC (Bodenhausen et al., Chem. Phys. Lett. 1980, 69, 185-189) experiments aided assignment, and Cysteine oxidation states were elucidated via $^{13}C$-HSQC spectra using routine methods (Cavanagh et al., Protein NMR Spectroscopy: Principles and Practice 1995 Academic Press). Shifted sinebell squared weighting and zero filling was applied before Fourier transformation using NMRPipe (Delaglio et al., J. Biomol. NMR 6, 277-293, 1995) during data processing. Interproton distance restraints were derived from through-space interactions observed in the NOESY spectra, and automatically assigned by CYANA (Guntert et al., J. Mol. Biol. 273, 283-298, 1997). In addition, peptides containing W32 that showed significant (>0.2 ppm) ring current anisotropy on neighboring amino acids have aromatic side-chain restraints applied. The applications PREDITOR (Berjanskii et al., Nuc. Acid. Res. 2006, 34, W63-W69) and DANGLE (Cheung et al., J. Mag. Reson. 202, 223-233, 2010) were used to predict phi and psi angle ranges based on chemical shift data. Backbone omega angle restraints were set to 180°. Based on data derived from the NOESY and $^{13}$C-HSQC experiments disulfide bonds were fixed between, C9-C24, C2-C17, and C16-C31.

Homology models of the peptides were used as input (Cycle 1) to CYANA followed by six cycles of combined automated NOESY assignment and structure calculation. During each cycle 1000 conformers were calculated using a standard simulated annealing schedule with 10000 torsion angle dynamics steps per conformer followed by 50000 steps of energy minimization. Ensembles of 20 conformers with the lowest target function values were then used as input into an explicit water, distance restrained minimization refinement routine using MOE (Chemical Computing Group Inc., www://_chemcomp_com).

Molecular Dynamics

An NMR structure of native HwTx-IV (structure at Protein Data Bank http://_www_rcsb_org/pdb/home/home_do; pdb 1MB6) was used as the starting point to characterize the stability of HwTx-IV using molecular dynamics simulations. In addition to simulations of the native HwTx-IV, simulations were performed to discern the importance of each of the three disulfide bonds and to determine the changes in peptide stability due to single alanine point mutations. To characterize the importance of the three disulfide bonds, separate molecular dynamics simulations (total of 7 simulations) were performed with the C2-C17, C9-C24, C16-C31, C2-C17/C9-C24, C2-C17/C16-C31, C9-C24/C16-C31 and C2-C17/C9-C24/C16-C31 cysteines converted into individual cysteine residues. To determine the effects of a single alanine point mutation an in silico molecular dynamics alanine scan (of all non-cysteine positions) was performed (total of 28 simulations).

For each molecular dynamics simulation, the HwTx-IV was solvated in explicit water (with a minimum of 12 Å padding) and neutralized to 0.1M NaCl. The protein was minimized and equilibrated for 50 ns using NAMD 2.8 [James et al., Journal of Computational Chemistry, 26:1781-1802, 2005). CHARMM 22 CMAP [MacKerell, Jr. et al., J Comput Chem 25: 1400-1415, 2004) parameters were used for the simulations with a multiple time stepping algorithm for evaluating electrostatics with bonded interactions computed every 1 fs, short-range non-bonded interactions computed every 2 fs, and long-range interactions computed every 4 fs. Long range electrostatic forces were evaluated using the particle mesh Ewald summation method with a grid spacing of less than 1 Å. Temperature was maintained at 300K using Langevin dynamics and a constant pressure of 1 atm was maintained using a Nose-Hoover Langevin piston. Periodic boundary conditions were assumed and non-bonded interactions were calculated using scaled 1-4 exclusion with shifting starting at 8 Å and a complete cut-off at 12 Å. Following simulation, the molecular dynamics trajectories were aligned based on the backbone C-alpha (CA) atoms and the root mean square deviation (RMSD) per residue calculated over the entire simulation relative to the initial NMR structure using Visual Molecular Dynamics (VMD) (Humphrey et al., J. Molec. Graphics, 1996, vol. 14, pp. 33-38).

Homology Modeling of Nav1.7 and Docking of HwTx-IV

A homology model of Nav1.7 Domain 2 (DII) segments S1-S4 was built with the structure NavAb (voltage-gated Na(+) channel from *Arcobacter butzleri*; structure at Protein Data Bank http://_www_rcsb_org/pdb/home/home_do; pdb 3RVY) as a template using the Modeller component in Discovery Studio 3.1 (Accelrys). The model was then further refined to generate a resting state Nav1.7 structure. S4 was manually moved down into a resting state configuration, the S1-S2 and S3-S4 loops were regenerated and the entire model was energy minimized. Native HwTx-IV was manually docked into the Nav1.7 homology model based on the results of the alanine scan of HwTx-IV inhibition against Nav1.7 and on published Nav1.7 mutations that effect HwTx-IV binding (Xiao et al., J Biol Chem. 286:27301-10, 2011. Epub 2011 Jun. 9.).

Following the manual docking, the entire Nav1.7 DII S1-S4 with docked HwTx-IV system was minimized and an implicit membrane molecular dynamics simulation performed using the CHARMm forcefield with Generalized Born Implicit Membrane (Discovery Studio (Spassov et al., *J. Phys. Chem. B*, 106, 8726-8738, 2002) to further refine the docked structure.

Results

Molecular Dynamic Simulations

A series of molecular dynamics simulations were conducted to help understand the molecular basis for changes in the activity of the HwTx-IV mutants that lead to significant loss of activity (F6A, P11A, D14A, L22A, S25A, W30A, K32A, Y33A) or channel selectivity (K18A, R26A and K27A) based on structural changes of the toxins alone. The previously generated NMR structure for HwTx-IV (pdb code 1MB6) was used as a template for building the various alanine mutant peptides and each toxin variant was subjected to 50 ns of molecular dynamics simulations.

Figure 9A:
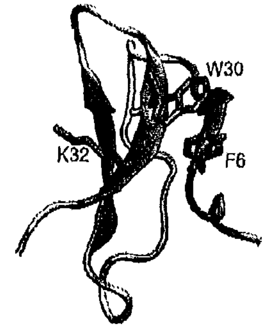
FIG. 9 shows various Huwentoxin-IV alanine mutants that cause significant (>10×) reduction in function (QPatch) colored by average per residue C-alpha (CA) atoms root mean square deviation (RMSD) calculated from their respective molecular dynamics simulations (50 ns each). The CA RMSDs are colored on a gradient from 0.5 Å in red to 2.2 Å in blue. (a) WT (b) F6A, (c) P11A, (d) D14A, (e) L22A, (f) S25A, (g) W30A, (h) K32A and (i) Y33A Huwentoxin-IV mutants.
Figure 9B:
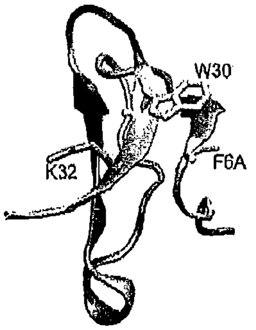
Figure 9C:
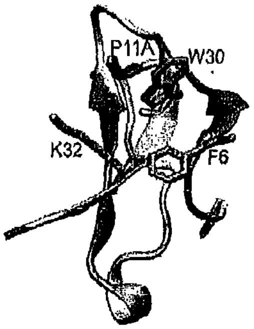
Figure 9D:
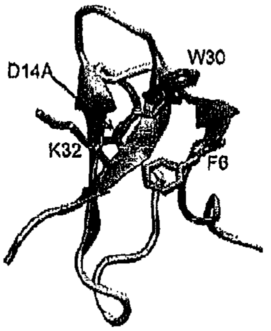
Figure 9E:
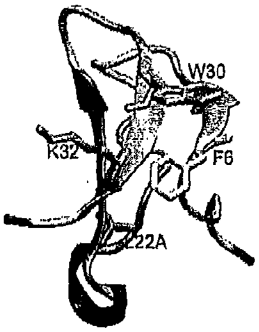
Figure 9F:
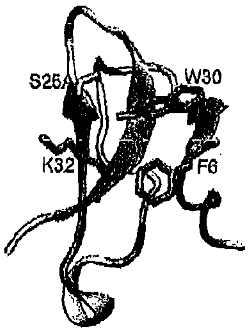
Figure 9G:
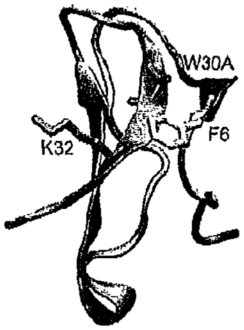
Figure 9H:
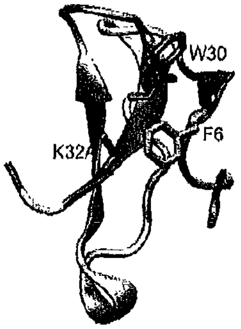
Figure 9I:
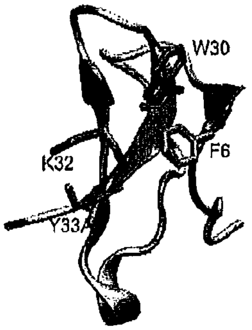
Figure 10A:
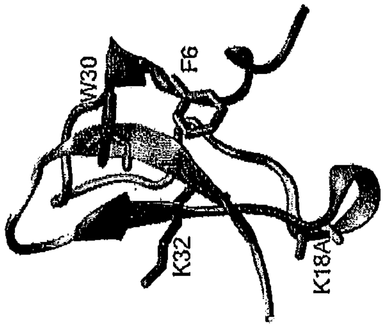
FIG. 10 shows various Huwentoxin-IV alanine mutants that appear to cause isoform specific changes in function (QPatch) colored by average per residue CA RMSD calculated from their respective molecular dynamics simulations (50 ns each). The CA RMSDs are colored on a gradient from 0.5 Å in red to 2.2 Å in blue. (a) K18A, (b) R26A, (c) K27A.
Figure 10B:
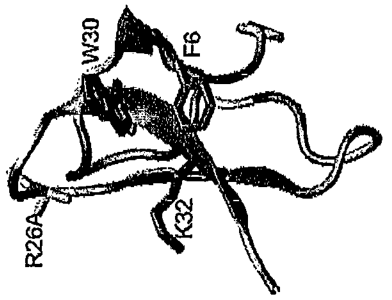
Figure 10C:
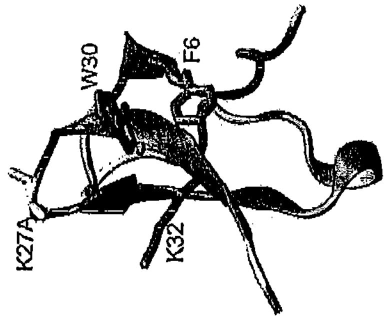
Figure 11:
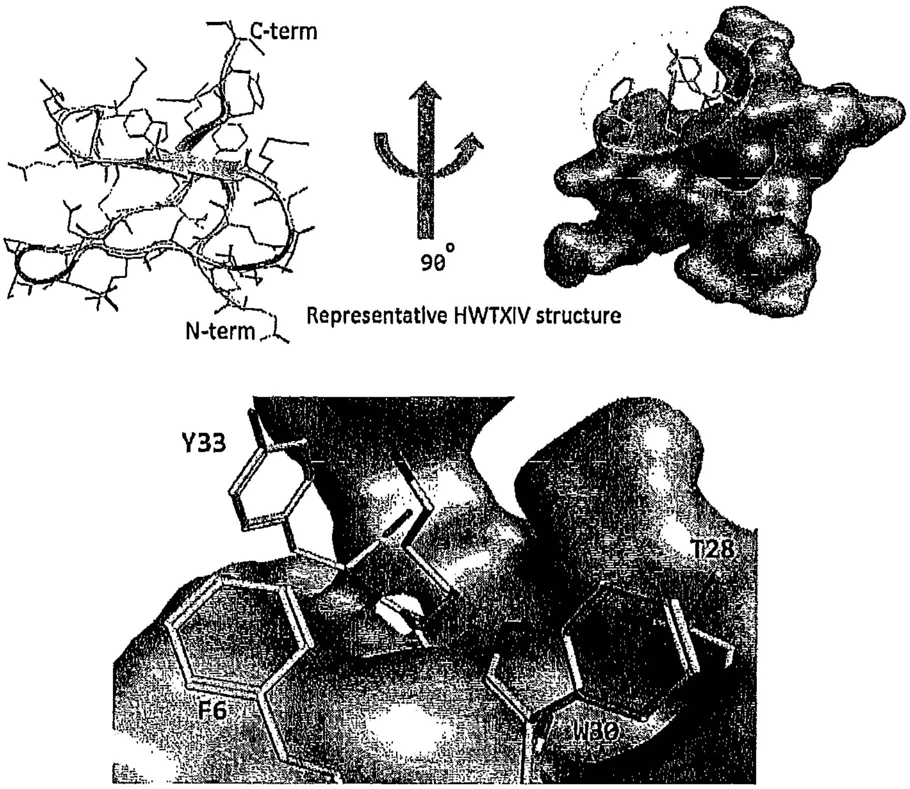
FIG. 11 shows NMR solution structure of recombinant Huwentoxin-IV (SEQ ID NO:1). The NMR structure reveals 5 residues in HwTx-IV (F6, T28, W30, K32 and Y33) that form a twisted β-sheet (cyan) to create a polar-aryl face, a putative interacting surface between Huwentoxin-IV and Nav1.7.

The average CA RMSD of native HwTx-IV peptide was only 1.007 Å indicating a highly stable peptide. Molecular dynamics simulations revealed that only W30A (FIG. 9*g*), F6A (FIG. 9*b*) (which normally form a pi-pi interaction) and L22A (FIG. 9*e*) could influence the core stability of HwTx-IV. All other loss of function mutants exerted little to no effect on core stability. On the contrary, all loss of function mutants, as well as the mutants that differentially affected Nav1.7 and Nav1.2 activity were able to influence the flexibility of the loop regions. For example, W30A (FIG. 9*g*), F6A (FIGS. 9*b*) and L22A (FIG. 9*e*), increased the flexibility of loops 3 and 4, K32A (FIG. 9*h*) increased loop 3 flexibility and D14A (FIGS. 9*d*) and P11A (FIG. 9*c*) showed a pronounced increase in loop 2 flexibility. K27A (FIGS. 10*c*) and R26A (FIG. 10*b*) were found to increase loop 4 flexibility. K18A (FIGS. 10*a*) and S25A (FIG. 9*f*) mutations did not impact the flexibility of any loops.

NMR

To gain additional insight into the structural features of HwTX-IV and to directly test some of the main predictions of the molecular dynamic simulations we determined the NMR structure of recombinant WT HwTX-IV and compared it to the structure of W30A and K32A.

Despite the complete loss of activity measured in the QPatch and binding assays, but largely in keeping with the molecular dynamic simulations, W30A and K32A exhibit a similar global structure to WT recombinant HwTX-IV. Although interproton NOESY's and backbone chemical shift values indicate W30A, K32A, and the wild type peptides have very similar folds and structure, local differences are apparent near the solvent exposed face of the twisted beta-sheet. These differences include the observation of strong ring current anisotropy within a 5 angstrom radius of W30 in the K32A and wild type peptides. This anisotropy, most notably affecting F6 and T28, is indicative of a close spatial interaction that may affect the conformation/dynamics of the β-turn as well as the orientations of the side-chains. The solution structures imply another local difference, based on side-chain geometry, a potential cation-π interaction between the protonated amine of K32 and the π electrons of Y33, available to the W30A and wild type peptides. The side-chains of the five residues involved with these local differences, F6, T28, W30, K32, Y33 all reside in close proximity to each other lending to the aforementioned intra-molecular interactions as well as to form a potential 'pharmacophore' for inter-molecular interactions with Nav1.7.

Homology Modeling and Docking

In order to explore the specific interactions made between HwTx-IV and the Nav1.7 channel, a homology model of Nav1.7 domain II (DII) voltage sensor domain (VSD; segments S1-S4) was constructed using NavAB as a template. The model was further refined to produce a resting state structure into which to manually dock the HwTx-IV peptide using available SAR data along with published channel mutation data (Xiao et al., Biol Chem. 286:27301-10, 2011. Epub 2011 Jun. 9.).

Figure 12:
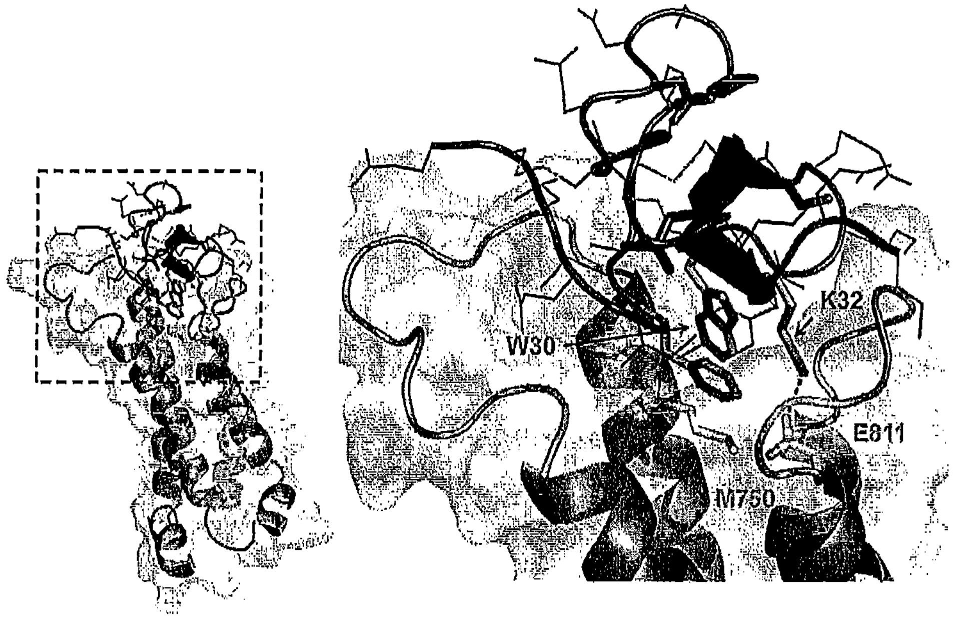
FIG. 12 shows Homology model of the domain 2 (DII) voltage sensing domain (VSD) of hNav1.7 with Huwentoxin-IV docked. Based on this model, Huwentoxin-IV docks in a grove made by segments S1-S2 and S3-S4. Huwentoxin-IV (SEQ ID NO:1) residues K32 and W30 are predicted to interact with Nav1.7 (SEQ ID NO:263) residues E811 and M750, respectively.

The published channel mutation data suggested that HwTx-IV binds in the DII voltage sensor domain with interactions with the S1-S2 and S3-S4 loops (specifically with residues E753, E811, D816, and E818). The resulting docked structure is presented in FIG. 12, with the hydrophobic patch comprised of W30 and F6 along with the basic K32 residue oriented in the groove formed by Nav1.7 S1-S2 and S3-S4 loops. The docked model places the W30 and F6 hydrophobic patch interacting with the channel groove with corresponding hydrophobic residue M750. While charged interactions along the edge of the S1-S2 loop and S3-S4 loop allow the HwTx-IV to orient itself in the binding site. Specifically on S1-S2 loop, charge-charge interactions are made between K7-E753 and E4-K762 of the HwTx-IV and the Nav1.7 channel respectively. Likewise, a series of charge-charge interactions between the HwTx-IV and the S3-S4 Nav1.7 loop also occur, R26-D816, K27-818, and K32-E811.

EXAMPLE 5

Design and Generation of Additional Huwentoxin-IV Variants

Two grafting libraries were generated based on the obtained Huwentoxin-IV variants NV1G387 (E1N, R26K, Q34S, G36I; NV1D2168, SEQ ID NO: 192) and NV1G327 (E1N, E4R, Y33W, Q34S; NV1D2163, SEQ ID NO: 3).

Peptides were recombinantly expressed as described in Example 2, and IC50 values were measured using FLIPR® Tetra and QPatch as described in Example 2. Selectivity to voltage-gated sodium channels Nav1.1, Nav1.2, Hav1.3, Nav1.4, Nav1.5 and Nav1.7 were assessed using both methods.

The variant NV1G387 (NV1D2168) demonstrated high selectivity towards Nav1.7 (FIG. 5) and was grafted with substitutions that in the original Huwentoxin-IV scan enhanced potency (Nav1.7 IC50>0.05 μM). The library design for NV1G387 is shown in Table 1.

TABLE 1

| | Favorable potency mutations E1N, R26K, Q34S, G26I NV1G387 (NV1D2168) |
|---|---|
| | ≤0.05 |
| E1 | |
| C2 | |
| L3 | |
| E4 | R, H, N, Q |
| I5 | Y |
| F6 | |
| K7 | |
| A8 | R, H, N, Q |
| C9 | |
| N10 | |
| P11 | |
| S12 | |
| N13 | A |
| D14 | |
| Q15 | R, N |
| C16 | |
| C17 | |
| K18 | Y |
| S19 | R, Q, P |
| S20 | R, D, N, P |
| K21 | R, H, F, N |
| L22 | R |
| V23 | |
| C24 | |
| S25 | I |
| R26 | |
| K27 | |
| T28 | |
| R29 | |
| W30 | |
| C31 | |
| K32 | |
| Y33 | W |
| Q34 | |
| I35 | |
| G36 | |
| K37 | R, F |

The variant NV1G327 (NV1D2163) demonstrated high potency (FIG. 4) and was grafted with substitutions that in the original Huwentoxin-IV scan enhanced selectivity (in this experiment defined as >5× selectivity over NaV1.2 or undefined). The library design for NV1G327 is shown in Table

TABLE 2

| | Favorable potency mutations E1N, R26K, Q34S, G26I NV1G387 (NV1D2168) | |
|---|---|---|
| | >5x or undef. | >5x |
| E1 | | |
| C2 | | |
| L3 | | |
| E4 | | |
| I5 | | |
| F6 | V, M | M |
| K7 | Q | |
| A8 | | |
| C9 | | |
| N10 | | |
| P11 | R | |
| S12 | | |
| N13 | W, Q, S, G, I, P | W, Q, G, I |
| D14 | Q, S, G, L, P | Q, S, G, P |
| Q15 | D, E, W, V, P | D, E, W, V, P |
| C16 | | |

TABLE 2-continued

| | Favorable potency mutations E1N, R26K, Q34S, G26I NV1G387 (NV1D2168) | |
|---|---|---|
| | >5x or undef. | >5x |
| C17 | | |
| K18 | F, W, Q, P | F, W, Q, P |
| S19 | Q | Q, S, G, P |
| S20 | W, V | W, V |
| K21 | W | W |
| L22 | E, W, Q, A | W, A |
| V23 | A | A |
| C24 | | |
| S25 | | |
| R26 | K, H, D, W, T, G, A, V, I, P | K, H, D, W, T, G, A, V, I, P |
| K27 | H, W, A, I, P | H, W, A |
| T28 | K, L | |
| R29 | H, D, W, N, G, L | H, D, W, N, G |
| W30 | K, Y | K, Y |
| C31 | | |
| K32 | W, A | |
| Y33 | | |
| Q34 | | |
| I35 | H | |
| G36 | F, T, V, I | I |
| K37 | R, Q, S, T, P | R, S, P |

FIG. 13A shows the sequences and FIG. 13B characteristics of mutants based on the NV1G387 (NV1D2168) scaffold. All values are $IC_{50}$ values in nM unless only a single point assay was performed. In the latter case, the percent inhibition (% I) achieved at a given peptide concentration is listed.

FIG. 14A shows sequences and FIG. 14B characteristics of mutants based on the NV1G327 (NV1D2163) scaffold. Values in FIG. 14B are as in FIG. 13B.

The Huwentoxin-IV variants from the bidirectional grafting libraries demonstrated improved selectivity and/or include variants

```
>NV1G559
                                    (SEQ ID NO: 277)
GPNCLEIFKACNPSNDQCCKSSFLVCSKKTRWCKYSIIK
(E1N, R26K, Q34S, G36I, grafted with K21F)

>NV1G566
                                    (SEQ ID NO: 278)
GPNCLEIFKACNPSNDQCCKSNKLVCSKKTRWCKYSIIK
(E1N, R26K, Q34S, G36I, grafted with S20N)

>NV1G611
                                    (SEQ ID NO: 279)
GPNCLRIFKACNPSNDQCCKSSKLVCSDKTRWCKWSIGK
(E1N, E4R, Y33W, Q34S, grafted with R26D)

>NV1G612
(SEQ ID NO: 280)
GPNCLRIFKACNPSNDQCCKSSKLVCSRHTRWCKWSIGK
(E1N, E4R, Y33W, Q34S, grafted with K27H)
```

EXAMPLE 6

Local Administration of Nav1.7 Inhibitors Provide Analgesic Effects in a Model of Nociceptive Pain in Rats The analgesic effects of three Nav1.7 blocking peptides were evaluated in rat and mouse models of acute nociceptive pain. The peptides evaluated were Huwentoxin-IV (HwTx-IV) (Peng et al., J Biol Chem 277:47564-71, 2002), Protoxin II (Middleton et al., Biochemistry 41:14734-47, 2002) and conotoxin KIIIA (Zhang et al., J Biol Chem. 2007 282(42): 30699-706). These peptides were applied locally since HwTX-IV and KIIIA block several voltage-gated sodium channel isoforms and are expected to induce significant side-effects when administered systemically. The rank order of potency for Nav1.7 block for these three peptides is ProTX-II>HwTX-IV>KIIIA.

Animals. Male Sprague-Dawley (CD) rats (Charles River, San Diego) were ordered ~190-200 grams and used at >300 grams.

Material Preparation and Local Administration in Hindpaw. Amidated Huwentoxin IV (Peptides International, Louisville, Ky.), Protoxin II (Peptides Institute, Japan) or KIIIA were received in lyophilized form and reconstituted with HEPES-buffered saline, aliquoted and frozen at −20° C. Just prior to administration in the left dorsal hind paw, aliquots were thawed and diluted to appropriate concentrations using HEPES-buffered saline as the diluent. Because stress related to handling and paw injections may itself produce an increase in paw pressure threshold (stress-induced analgesia), rats were briefly anesthetized with isoflurane for the injection (5% induction; 2-3% maintenance). Animals were injected s.c. 100 μL of peptide solution or vehicle) in the dorsal aspect of the paw with the needle inserted left of center toward the ankle such that the tip of the needle ended just underneath a mark made with an indelible marker in the center of the dorsal paw proximal to the toes.

Randall-Selitto Test

A Ugo-Basile Randall-Selitto Device (Analgesy-Meter) was used with the maximum threshold set at 500 grams.

Training. Naive animals were trained for two days prior to the day of testing (in order to reduce the variability in responses) as in commonly reported in the literature. Training consisted of performing actual tests multiple times on each animal over duration of −1 hour for each rat. Animals first received a mark with an indelible marker in the center of the dorsal aspect of the left paw just proximal to the toes to enable consistently testing the same site of the paw. Rats were then loosely wrapped in a towel leaving the hind paws uncovered, the left hind paw was placed in the Randall-Selitto device with the indelible mark just beneath the point of the cone on the test device that comes in contact with the paw and pressure was increased at a steady rate via electronic ramp with foot control until the animal responded. A ‘response’ for training followed the same criteria as that on the day of testing and consisted of any one of the following: 1) removal of the hind paw from the device, 2) a clear attempt at removal or 3) vocalization. Rats were tested up to 3 times consecutively unless they responded to a threshold greater than or equal to 100 grams. Over the course of the hour/day of training, 1-3 consecutive tests were made for each rat with 5-20 minutes apart.

Testing. Prior to application of peptides or vehicle, trained, un-injured rats were tested once for the pre-compound thresholds. Animals were assigned into peptide- or vehicle-treated groups in such a manner as to produce comparable pre-administration threshold means. Experiments were conducted blind to treatment groups whenever possible (i.e. whenever starting with testing a new peptide or new dose). One test for each time point following injection (5, 10, 20, 30 45, 60 and 120 min) was taken and recorded. Responses were defined identically as responses during training (see Training above).

Data Analysis. Gram thresholds were recorded on paper and entered into Prism 5.01 (Graphpad Software Inc., LaJolla, Calif.) for graphing, generating area under the curve (AUC) values and statistical analysis. For comparison of gram values over time, a two-way ANOVA was used with a significance level of $p<0.05$. For generation of mean AUC values, the AUC for each rat in the peptide group was individually obtained and the mean AUC of the vehicle group was subtracted from it. Next, the vehicle subtracted AUCs for each peptide-treated animal were averaged together and compared either by Student's T-test or one-way ANOVA, each with a significance level of $p<0.05$. Responses at 120 min are not shown and were not included in the AUC calculations. Instead, values from prior to administration (Pre) and 5-60 min were used.

Figure 15A:
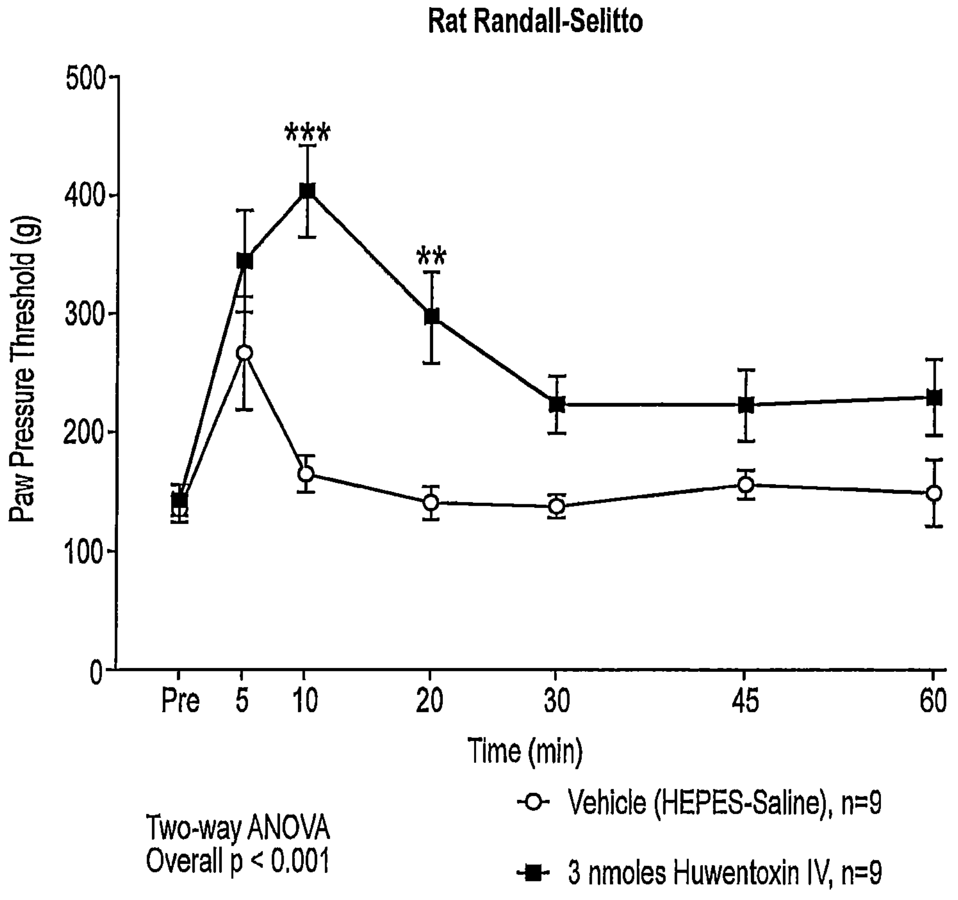
FIG. 15 shows local administration of A) 3 nmoles and B) 30 nmoles Huwentoxin-IV (HwTx-IV) provides analgesic effect in a rat model of nociceptive pain as measured by an increase in paw pressure threshold after HwTx-IV administration. C) Mean area under the curve (AUC) of paw pressure response for HwTx-IV at indicated concentrations. In C), $p<0.01$; *$p<0.001$.
Figure 15B:
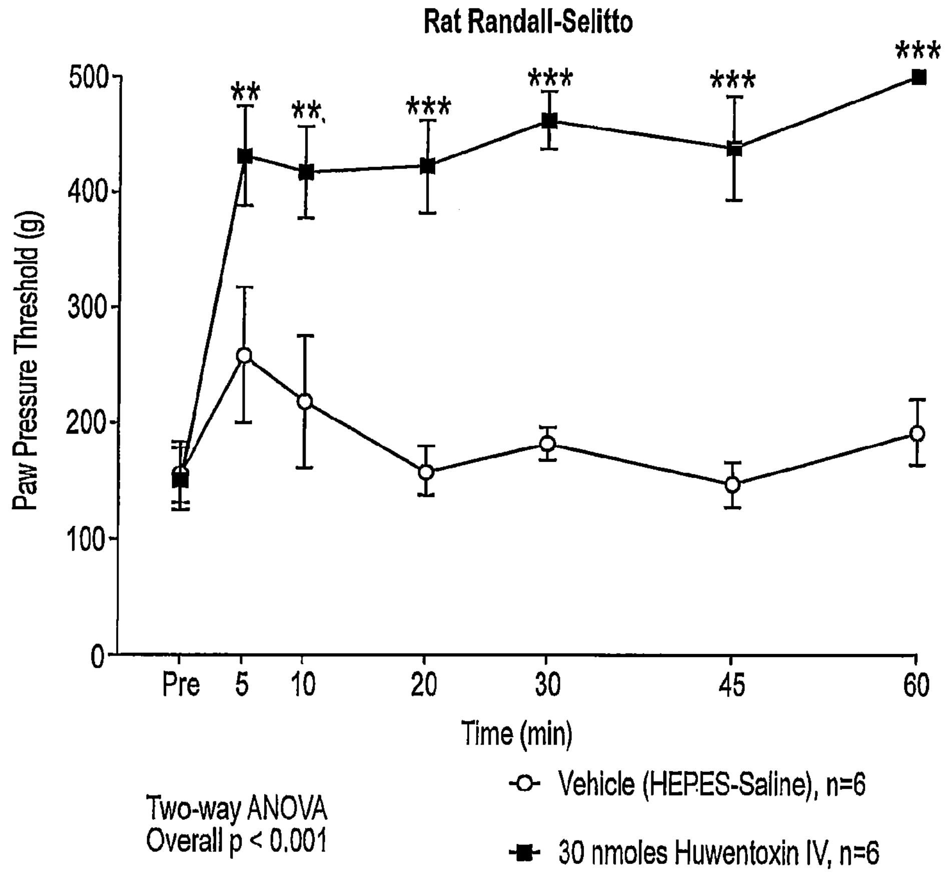
Figure 15C:
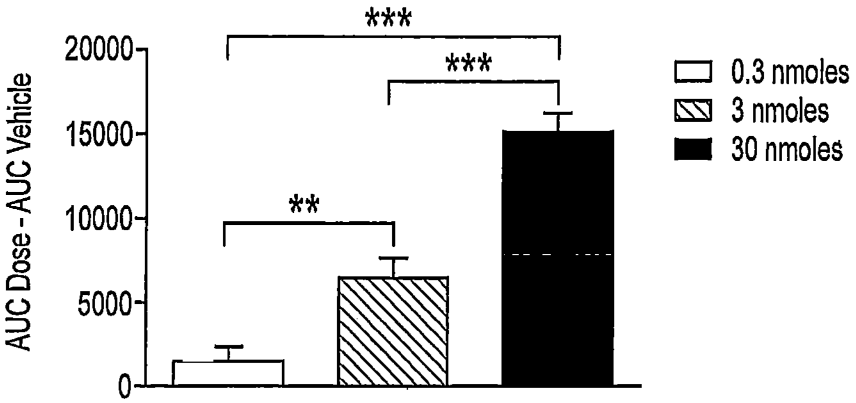

Results. Huwentoxin IV administered locally into the dorsal aspect of the paw produced a dose-dependent increase in paw pressure threshold in the Randall-Selitto test. 3 nmoles (FIG. 15A) and 30 nmoles (FIG. 15B) of Huwentoxin IV, but not 0.3 nmoles (not shown), increased thresholds significantly above those observed for vehicle-treated animals. Areas under the curve (AUC) (FIG. 15C) were significantly different between all 3 peptide treated groups (with mean vehicle AUC subtracted from the AUC for each animal).

Figure 16A:
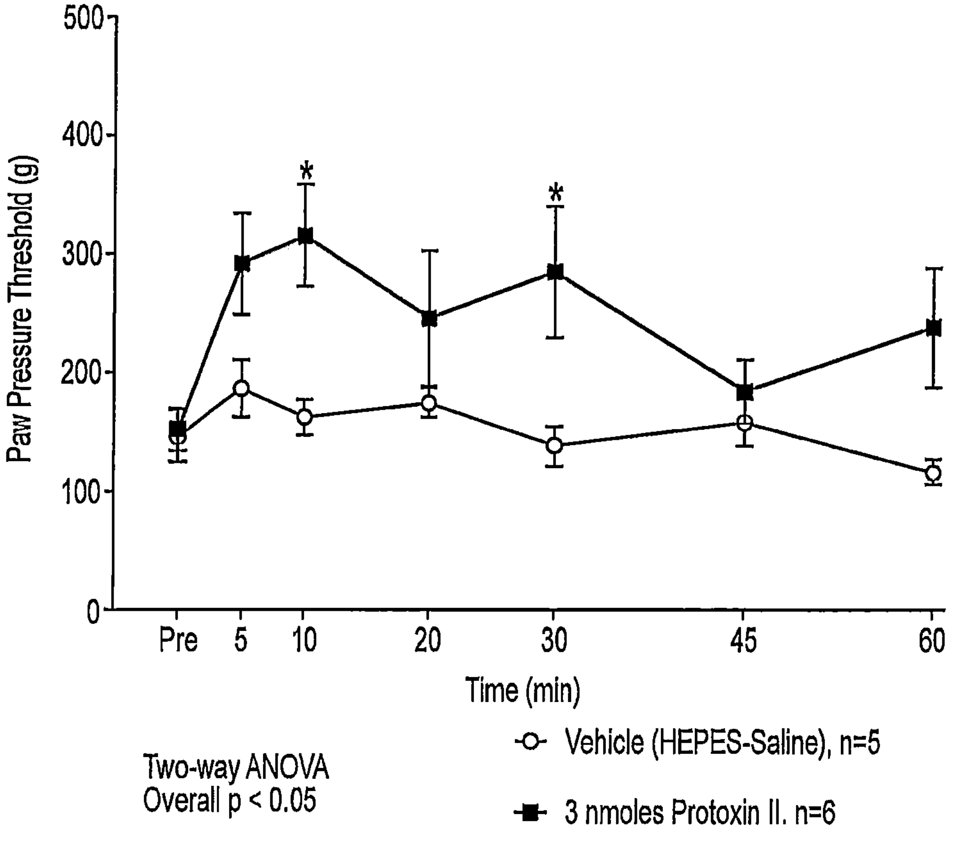
FIG. 16 shows local administration of A) 0.3 nmoles; B) 3 nmoles; C) 30 nmoles Protoxin-II (ProTx-II) provides analgesic effect in a rat model of nociceptive pain as measured by an increase in paw pressure threshold after ProTx-II administration. D) Mean area under the curve (AUC) of paw pressure response for HwTx-IV at indicated concentrations. In C), *$p<0.05$; **$p<0.01$.
Figure 16B:
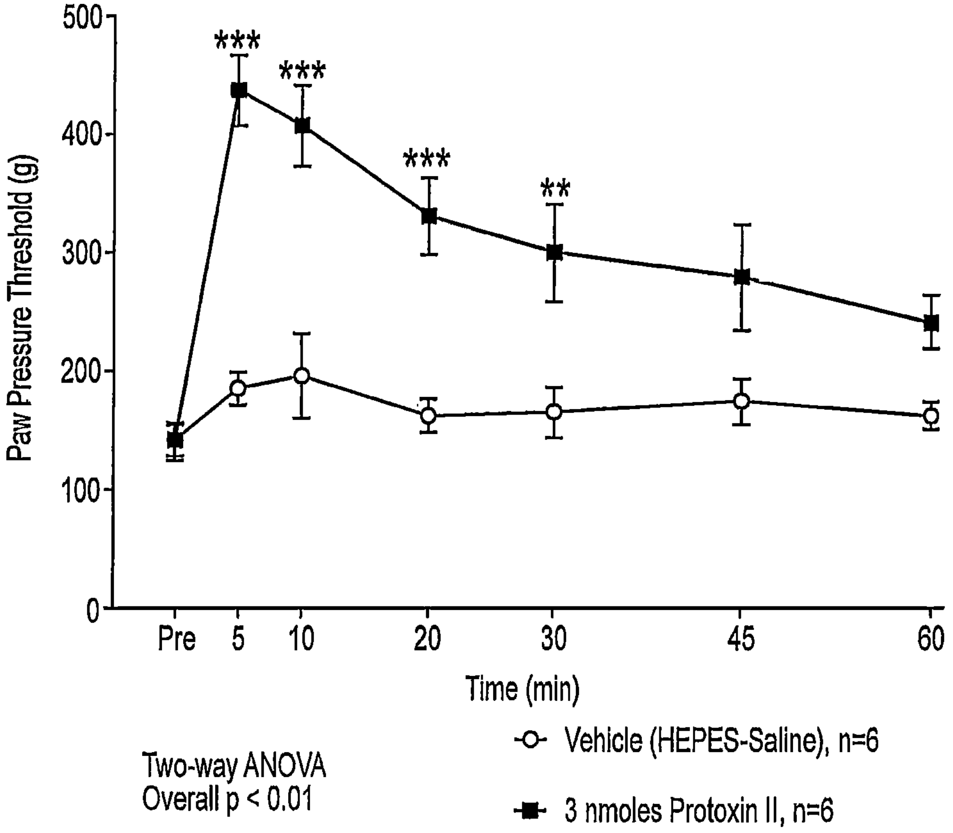
Figure 16C:
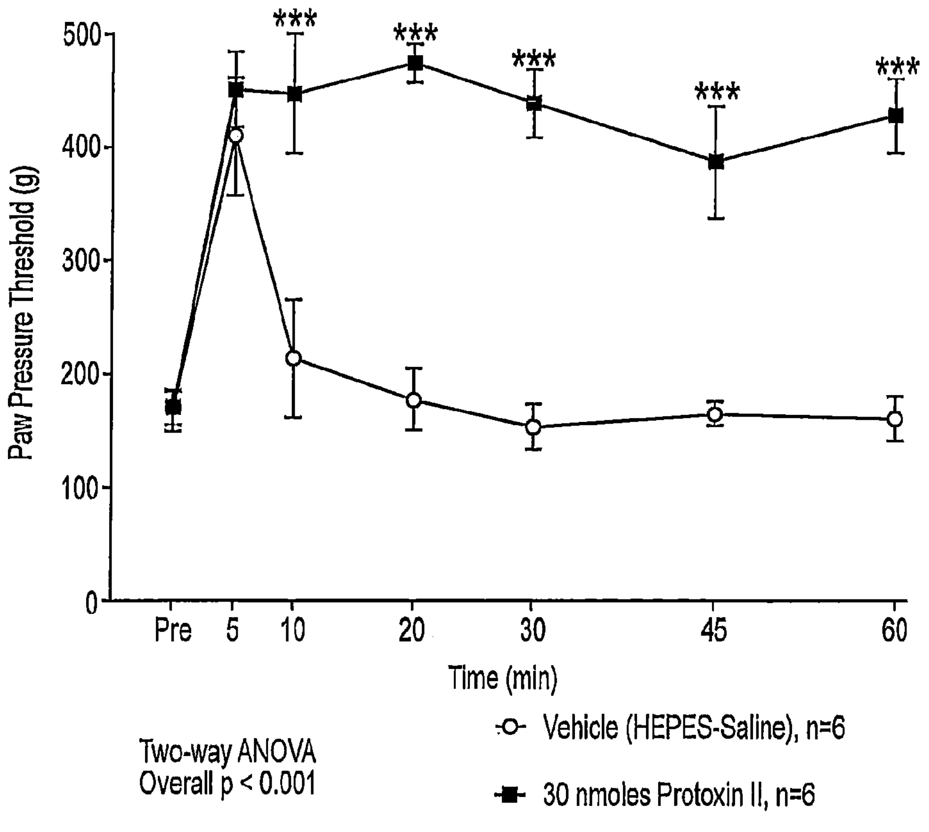
Figure 16D:
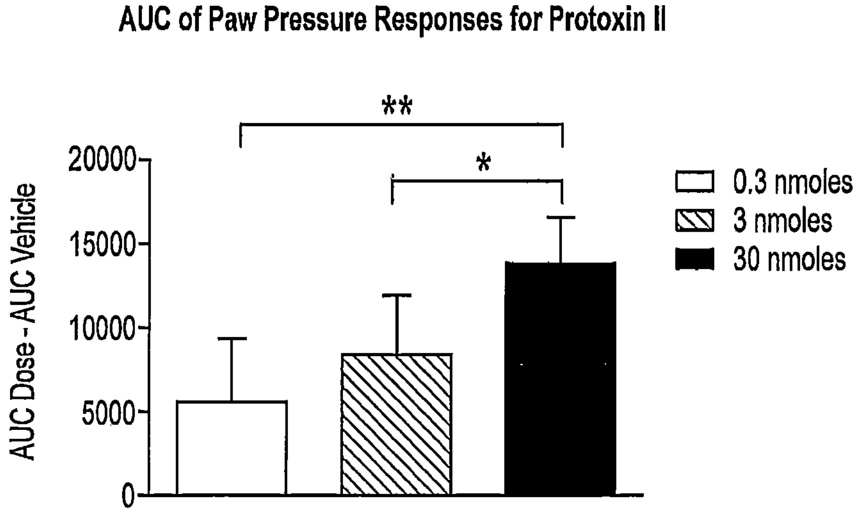

Protoxin II administered locally into the dorsal aspect of the paw produced a dose-dependent increase in paw pressure threshold in the Randall-Selitto test. Each dose of peptide, 0.3 nmoles (FIG. 16A), 3 nmoles (FIG. 16B) and 30 nmoles (FIG. 16C) increased thresholds significantly above those observed for vehicle-treated animals. AUCs were significantly different except between the 0.3 and 3 nmole doses (with mean vehicle AUC subtracted from the AUC for each animal) (FIG. 2D).

KIIIA administered locally into the dorsal aspect of the paw at both doses (3 and 30 nmoles) demonstrated a tendency towards increased paw pressure threshold in the Randall-Selitto test which did not reach statistical significance. There was no significant difference between the AUCs from the two doses (not shown).

The findings of this study demonstrate that ProTX-II and HwTX-IV exhibited significant analgesic effects in a rat model of acute nociceptive pain following local administration. Although KIIIA produced a trend toward analgesic activity, this did not reach the level of statistical significance. The rank order of activity (ProTX-II>HwTX-IV>KIIIA) in the pain assay matched that for Nav1.7 block in-vitro, suggesting that Nav1.7 block may have contributed to the analgesic activity.

EXAMPLE 7

Local Administration of ProTx-II Provides Anti-hyperalgesic Effects in a Model of Inflammatory Pain in Rats Animals. Male Sprague-Dawley rats weighing 240-295 grams (Mean/s.e.m.: 280.2±3.3) at the start of the study.

Behavioral Tests

Tactile Allodynia Testing

Mechanical (tactile) allodynia was assessed by determining the median threshold at which the affected paw was withdrawn from 8 graded stimuli (von Frey filaments: 0.4, 0.6, 1.0, 2.0, 4.0, 6.0, 8.0, and 15.0 g; Stoelting, Wood Dale, Ill.) applied perpendicularly with sufficient force to bend slightly and held for 5-7 seconds against the plantar hindpaw through custom-made wire-mesh observation cages. Paw withdrawal during or immediately following the removal of the stimulus was considered a positive response. A 50% paw withdrawal threshold (PWT) was determined by sequentially increasing and decreasing the stimulus strength and analyzing withdrawal data using an adaptation of the Dixon up-down method (Dixon, 1980), as described in (Chaplan et al., 1994). Rats were acclimated to the wire mesh for 10 minutes prior to testing. Tactile thresholds before and on several different days following injection of Complete Freund's Adjuvant (CFA) were evaluated.

Thermal Allodynia Testing

Paw threshold responses to radiant heat were evaluated using a Thermal Paw Stimulator (Hargreave's Device; UCSD Anesthesiology, San Diego, Calif.) before and following CFA administration. Naive rats were used to set the gain and intensity of the radiant heat such that their responses were in the range of ~8-12 s latency until paw withdrawal (mean ~10 s). Cut-off is set by the device at 20 s. For each time point, 3 separate measurements on the same paw were obtained about 5 minutes apart for each animal and were averaged together.

Monoarthritis Model Induction

An emulsion of Complete Freund's Adjuvant (CFA; Sigma-Aldrich; Saint Louis, Mo.) was prepared in a 1:1 ratio with CFA and 0.9% saline. Animals were anesthetized with isoflurane 5% induction; 2-5% maintenance and 100 μL of the emulsion was injected subcutaneously into the left hind paw. On day 12 following CFA injection, the ipsilateral paw was injected with either 30 nmoles of Protoxin II (Peptides International; Louisville, Ky.) in 100 μL HEPES-buffered saline or vehicle (100 μL HEPES-buffered saline).

Data Analysis. Data are represented as mean±s.e.m. Gram thresholds (tactile) and latencies to thermal paw withdrawal were recorded on paper and entered into Prism 5.01 (Graphpad Software Inc., LaJolla, Calif.) for graphing and statistical analysis. For comparison of threshold values over time, a two-way ANOVA with Bonferroni post hoc test was used with a significance level of $p<0.05$.

Results

Figure 17A:
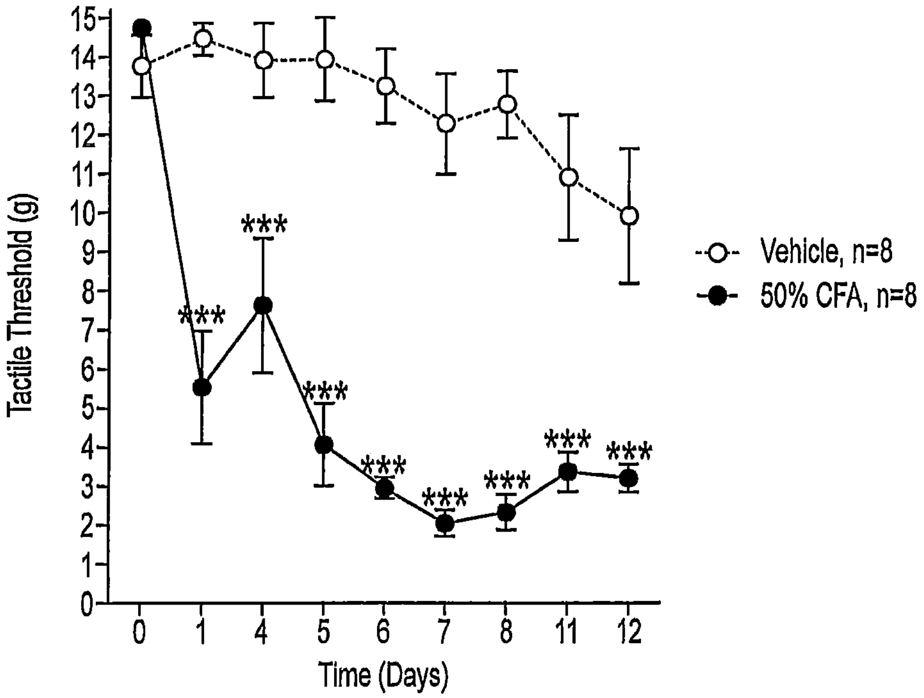
FIG. 17 shows reduced A) tactile allodynia and B) thermal allodynia in rat model of monoarthritis induced by 50% intraplantar CFA in rats. C) Intraplantar ProTx-II administration significantly reduced Complete Freund's Adjuvant (CFA)-induced tactile allodynia.
Figure 17B:
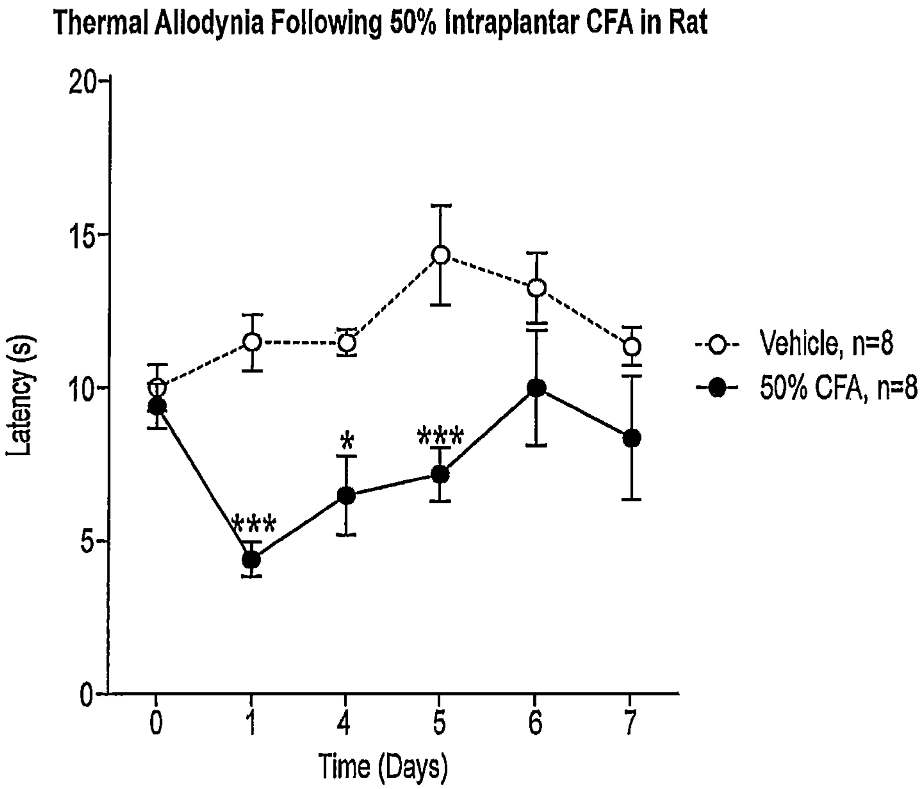
Figure 17C:
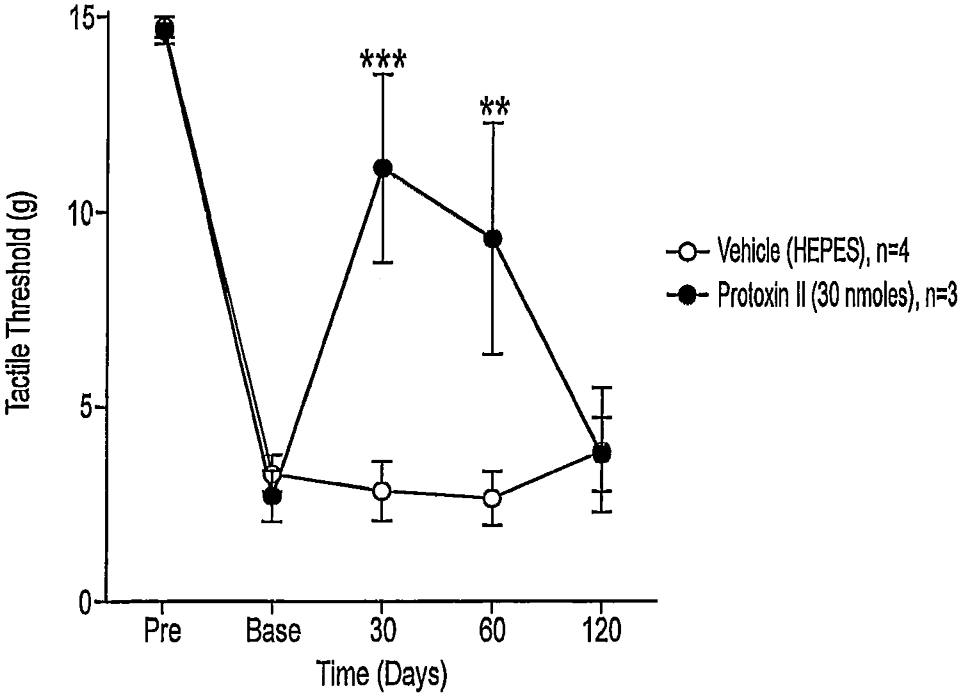

Threshold for tactile allodynia (FIG. 17A) and latency for thermal allodynia (FIG. 17B) were significantly reduced in the animal model of monoarthritis induced by 50% intraplantar CFA in rats. Intraplantar Protoxin II significantly increased the tactile threshold when compared to vehicle injected animals at 30 and 60 minutes after injection.

EXAMPLE 8

Local Administration of ProTx-II Provides Anti-hyperalgesic Effects in a Mouse Model of Inflammatory Pain Animals. Male C57/b16 mice were used weighing, at the start of the study, 24-31 grams (Mean/s.e.m.: 27.5±0.3).

Behavioral Tests

Tactile Allodynia Testing

Mechanical (tactile) allodynia was assessed by determining the median threshold at which the affected paw was withdrawn from 7 graded stimuli (von Frey filaments: 0.07, 0.16, 0.4, 0.6, 1.0, 2.0 & 4.0 g; Stoelting, Wood Dale, Ill.) applied perpendicularly with sufficient force to bend slightly and held for ~3 seconds against the center plantar hindpaw through custom-made wire-mesh observation cages. Paw withdrawal during or immediately following the removal of the stimulus was considered a positive response. A 50% paw withdrawal threshold (PWT) was determined by sequentially increasing and decreasing the stimulus strength and analyzing withdrawal data using an adaptation of the Dixon up-down method (Dixon, 1980), as described in (Chaplan et al., 1994). Mice were acclimated to the wire mesh test conditions for ~1 hour per day for 2 days prior to testing and for 30 minutes prior to testing on each day of testing. Tactile thresholds before and on several different days following injection of Complete Freund's Adjuvant (CFA) were evaluated.

Monoarthritis Model Induction

For 50% Complete Freund's Adjuvant (CFA; Sigma-Aldrich; Saint Louis, Mo.), an emulsion was prepared in a 1:1 ratio with CFA and 0.9% saline (vehicle treated controls received only 0.9% saline). For 100% CFA, animals were injected with neat CFA as it arrives from the vendor and control animals were injected with 0.9% saline. Animals were anesthetized with isoflurane 5% induction; 2-5% maintenance and 20 μL was injected subcutaneously into the left hind paw using a 50 μL Hamilton syringe and a 25 gauge needle.

Treatments

All studies were conducted blinded to treatment. On day 3 following CFA injection, either gabapentin (150 mg/kg, n=6) or vehicle (sterile water; n=6) was administered orally (4 mL/kg) as a positive control with known anti-allodynic efficacy in this model and evaluated for changes in tactile threshold. Following a 6-day washout period (on day 9 following CFA) the same animals were tested with 3 nmoles Protoxin II (Peptides International, Louisville, Ky.) or vehicle (HEPES-buffered saline) administered intraplantar into the left, CFA-treated paw.

Data Analysis

Figure 18A:
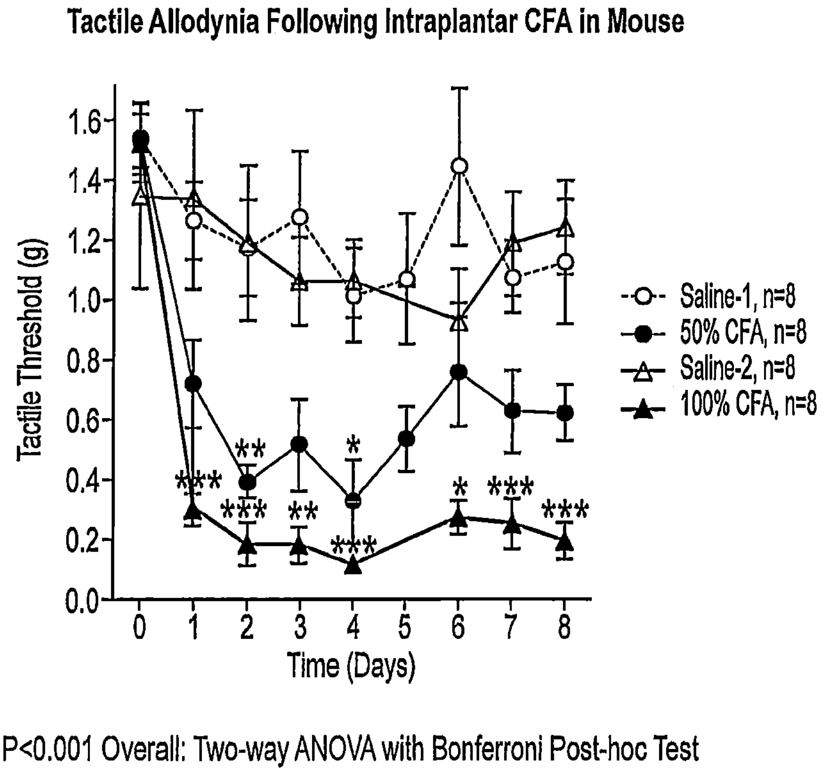
FIG. 18 A) Tactile allodynia is induced by 100% intraplantar CFA but not with 50% CFA in mice. B) Intraplantar ProTx-II administration significantly reduced tactile allodynia in the 100% CFA-treated animals; C) gabapentin also reduced tactile allodynia albeit to a lesser extent than ProTx-II.

Data are represented as mean±s.e.m. Gram thresholds (tactile) and latencies to thermal paw withdrawal were recorded on paper and entered into Prism 5.01 (Graphpad Software Inc., LaJolla, Calif.) for graphing and statistical analysis. For comparison of threshold values over time, a two-way ANOVA with Bonferroni post hoc test was used with a significance level of $p<0.05$. 100% CFA produced a long-lasting, robust tactile allodynia together with local paw edema from days 1-8 post-CFA (FIG. 18A). 50% CFA produced a transient allodynia peaking at 2-4 days day following CFA administration.

Results

Figure 18B:
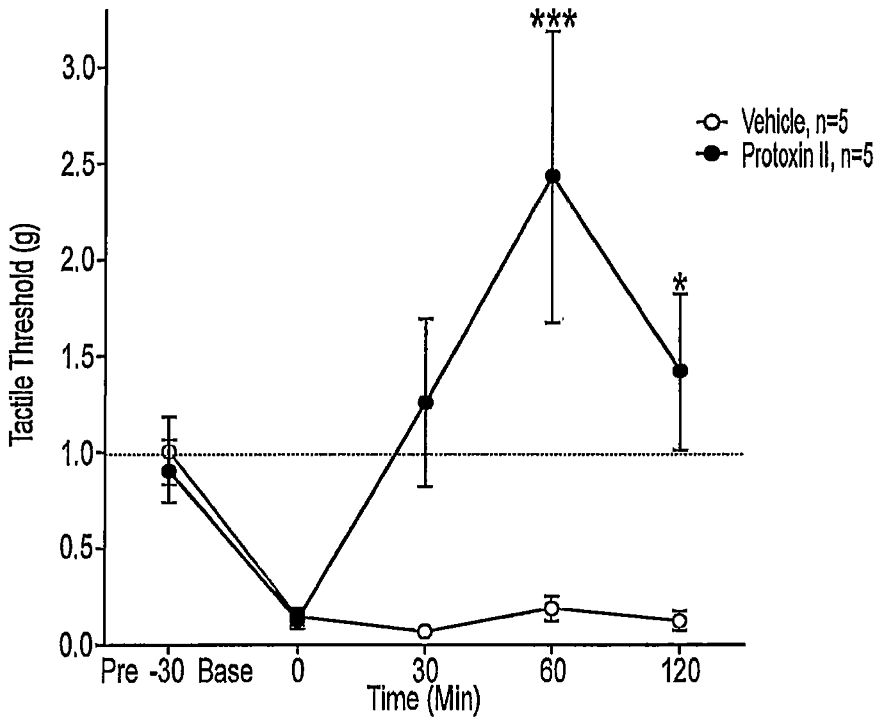
Figure 18C:
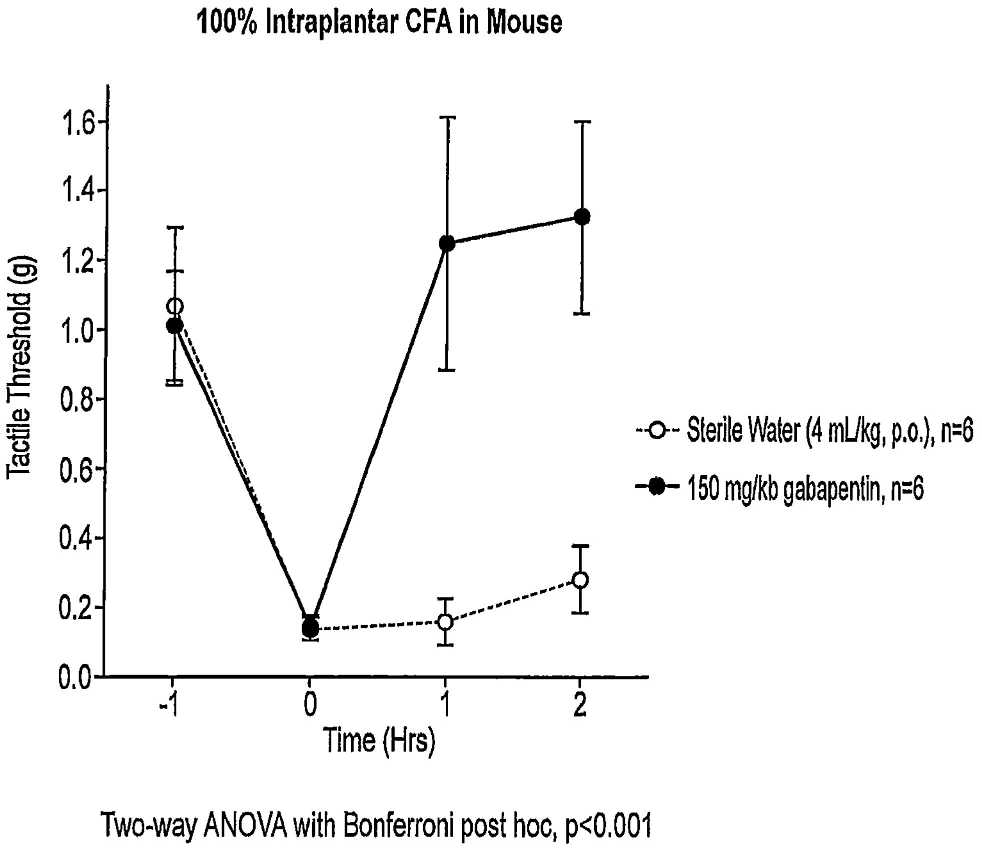

ProTX-II produced a profound anti-allodynic effect following local administration to the inflamed mouse paw. Tactile thresholds were increased above baseline, indicating ProTX-II had additional analgesic effects at the administered dose. The effect of ProTX-II was more pronounced than that achieved with a positive control agent, Gabapentin in increasing CFA-induced tactile allodynia (FIGS. 18B and 18C).

Collectively, the findings demonstrate that local administration of ProTX-II exerted analgesic and anti-allodynic effects in models of acute and inflammatory pain in rats and mice. These results suggest that local administration of Nav1.7 blocking peptides may be beneficial in a variety of human pain states that are Nav1.7 dependent. These results also suggest that suitably selective peptides will be efficacious following systemic administration

EXAMPLE 9

Tolerability of Sustained Systemic Administration of ProTx2

Exposure and tolerability of ProTX-II following delivery via osmotic mini-pumps for up to seven days in mice was assessed in order to select a dose(s) for subsequent evaluation animal models of pain.

Test Compound

Protoxin-II (Peptides International, Louisville, Ky.) was formulated in DPBS (no Calcium and Magnesium) at stock concentrations of 0.05, 0.5 and 3.8 mg/mL.

Mini Pumps

ProTx-II or vehicle was delivered via Alzet micro-osmotic mini pumps at 0.5 μl per hour for 7 days after implantation into the mouse. A pump and its flow moderator were first weighed and then filled with a 1 mL syringe attached with a 27-gague blunt tipped needle. With the pump in an upright position, pumps were filled, the moderator inserted and re-weighed. Weights were recorded (empty and filled weights) to ensure that the fill volume was over 90% of the Mean Fill volume specified in the Alzet pump directions. The pumps were then placed in a 15 mL conical tube filled with 0.9% saline and placed at 37° C. for 5-6 hours prior to implantation.

Implantation of Mini Pumps

Mice were given 20 μl of 0.3 mg/ml Buprenex prior to being anesthetized (5% induction; 2% maintenance) with isoflurane. Their backs were shaved, wiped down with isopropyl alcohol and povidone iodine, and a small incision was made between the scapulae. Using a hemostat, a small pocket was formed by spreading the subcutaneous connective tissues apart. The pump was inserted into the pocket with the flow moderator pointing away from the incision. The skin incision was then closed using 7 mm staples and the animals were allowed to recover in their home cages.

Determination of Plasma ProTX-II Concentrations Using QPatch.

HEK293 cells stably expressing human Nav1.7 were cultured in DMEM/F-12 media (1:1), supplemented with 10% fetal bovine serum, 400 μg/mL Geneticin and 100 μM NEAAs (all reagents from Life Technologies). The cells were maintained at 37° C. and in 5% CO2 and assayed upon reaching ~70-90% confluency. Before testing in QPatch (Sophion), cells were first dissociated using 0.05% trypsin (5 min at 37° C.), resuspended in CHO-S-SFM media (Life Technologies) and gently triturated to break up cell clumps. Cell density was adjusted to $1\text{-}2\times10^6$/mL with the same media and cells were transferred to a cell "hotel" in QPatch HT and used in experiments for several hours.

The voltage protocol used in the assay was as follows. From a holding potential of −75 mV, cells were first hyperpolarized to −120 mV for 2 sec and then depolarized to 0 mV for 5 ms before returning to the holding potential (−75 mV). This protocol was repeated once every 60 sec during liquid applications (see below). Cells were otherwise held at −75 mV when the above voltage protocol was not executed.

For giga-ohm seal formation, the extracellular solution contained 137 mM NaCl, 5.4 mM KCl, 1 mM $MgCl_2$, 2 mM $CaCl_2$, 5 mM glucose, and 10 mM HEPES, pH=7.4 and osmolarity=315 mOsm. The intracellular solution contained 135 mM CsF, 10 mM CsCl, 5 mM EGTA, 5 mM NaCl and 10 mM HEPES, pH=7.3 and osmolarity=290 mOsm.

For whole-cell patch clamp recording, plasma from control or test (vehicle- or peptide-dosed) rodents were first diluted (10-1000 fold) in the above extracellular solution and these plasma-containing buffers were subsequently used as the extracellular solution. The intracellular solution remained the same as above.

Upon establishment of the whole-cell recording configuration, a total of five applications of a plasma-containing (except for the last application, which was 1 μM TTX in the extracellular solution that contained no plasma) extracellular solution were made onto each cell being recorded. The first application (5 μl) contained only the control plasma (i.e.

plasma-containing buffer). The voltage protocol was executed 10 times (for a total duration of 10 min) five sec after the application. The next three applications (5 μl each) contained either plasma (diluted by the same factor as that in the first application for the control plasma) from a vehicle- or peptide-dosed rodent, or, in the case of control cells, the same control plasma as in the first application. As a positive control, a known concentration (300 nM) of synthetic protoxin-II was spiked into the 10×-diluted control plasma-containing buffer, which was further serial-diluted to obtain lower concentrations (i.e., 3-, 10-, 30- and 100-fold diluted concentrations) of the control peptide in the other plasma-containing buffers (i.e., buffers with plasma diluted by 30, 100, 300 and 1000 fold). Five seconds after each of these three applications, the voltage protocol was again executed 10 times (also once per min). The last application contained 1 μM TTX (composed of three 10 μl sub-applications, each separated by 2 sec), five seconds after which the same voltage protocol was executed twice to obtain the baseline current.

Currents were sampled at 25 kHz and filtered at 5 kHz with an 8-pole Bessle filter. The series resistance compensation level was set at 80%. For each cell, the peak current amplitude at 0 mV for each current trace in the first four liquid applications was first subtracted from that of the last trace in the presence of TTX and then normalized to that of the last trace in the first (control buffer) application as % inhibition. To control for current rundown, this (% inhibition) value for each cell in the presence of a test plasma-containing buffer was further normalized to the average % inhibition value for control (typically 5-6) cells (tested with buffer that contained only control plasma that was diluted by the same factor as that for the test plasma) in the same experiment. The mean value of the last two such values in the last (i.e., 4th overall) plasma application was used in concentration response calculations. The ProTx-II concentrations in the undiluted plasma was calculated by comparing the level of channel inhibition in the presence of serial-diluted plasma (from ProTx-II-dose rodents) buffers with that from (diluted) control plasmas in the presence of spiked (i.e., known) concentrations of ProTx-II. All experiments were performed at room temperature (~22° C.). Data are expressed as mean±se.

Results Summary

Plasma concentrations for each dose group at various time points after pump implantation are shown in Table 3.

Plasma concentrations were below the limit of detection (~5 nM) at all time points for the two lower doses. Plasma concentrations were 50-83 nM for the higher dose and were similar at all time points within the dose group (suggesting steady state was reached within 2 days). All doses were well tolerated with no abnormal behavior noted at any dose or time point.

TABLE 3

| Species | Cpd | Pump Type | Conc in pump (ug/ul) | Flow rate (ul/h) | Total dose (ug/day) | Duration (d) | Est Cp (nM) | Behav Obs |
|---|---|---|---|---|---|---|---|---|
| Mouse | ProTX-II | 7 day | 0.05 | 0.5 | 0.6 | 2 | BLOQ | normal |
| Mouse | ProTX-II | 7 day | 0.05 | 0.5 | 0.6 | 5 | BLOQ | normal |
| Mouse | ProTX-II | 7 day | 0.05 | 0.5 | 0.6 | 7 | BLOQ | normal |
| Mouse | ProTX-II | 7 day | 0.5 | 0.5 | 6 | 2 | BLOQ | normal |
| Mouse | ProTX-II | 7 day | 0.5 | 0.5 | 6 | 5 | BLOQ | normal |
| Mouse | ProTX-II | 7 day | 0.5 | 0.5 | 6 | 7 | BLOQ | normal |
| Mouse | ProTX-II | 7 day | 3.8 | 0.5 | 45.6 | 2 | 50 | normal |
| Mouse | ProTX-II | 7 day | 3.8 | 0.5 | 45.6 | 5 | 55 | normal |
| Mouse | ProTX-II | 7 day | 3.8 | 0.5 | 45.6 | 7 | 83 | normal |

ProTX-II was well tolerated at doses up to 45.6 ug/day for 7 days in mice. Given that a maximally tolerated dose was not identified in this study, we decided to evaluate a 5 fold higher dose (228 ug/d) in a pain study.

EXAMPLE 10

Delivery of ProTx-II Using Mini-pumps Provides Anti-allodynic Effects in a Mouse Model of Inflammatory Pain Animals. Male C57Bl/6 mice, ordered from Charles River and housed individually, were used for this study.

Behavioral Tests

Tactile Allodynia Testing

Mechanical (tactile) allodynia was assessed by determining the median threshold at which the affected paw was withdrawn from 7 graded stimuli (von Frey filaments: 0.07, 0.16, 0.4, 0.6, 1, 2, 4 g; Stoelting, Wood Dale, Ill.) applied perpendicularly with sufficient force to bend slightly and held for 3 seconds against the plantar hindpaw through custom-made wire-mesh observation cages. Paw withdrawal during or immediately following the removal of the stimulus was considered a positive response. A paw withdrawal threshold (PWT), recorded in grams, was determined by sequentially increasing and decreasing the stimulus strength and analyzing withdrawal data using an adaptation of the Dixon up-down method (Dixon, 1980), as described in (Chaplan et al., 1994). Mice were acclimated to the wire mesh for 30 minutes prior to testing. Tactile thresholds before and on several different days following injection of 100% Complete Freund's Adjuvant (CFA) were evaluated. Behavioral testing was done completely blinded. A separate investigator, than the one doing the testing, organized the Pre-Threshold values to homogenize them prior to Baseline testing.

Thermal (Hargreaves) Allodynia Testing

A modified Hargreaves box was used to measure thermal allodynia (Hargreaves et al., 1988, Pain, 32:77-88; Dirig et al., 1997, J Neurosci. Methods, 76:183-191). This box consists of Plexiglas chambers with a raised glass floor maintained at a constant temperature (28° C.). The thermal nociceptive stimulus originates from a projection bulb below the glass surface, and the stimulus is delivered separately to one hind paw at a time with a 20 second cutoff time. A constant amperage was used throughout the study, which resulted in Pre-test paw withdrawal latencies between ~8-12 seconds when averaged over 3 read-outs taken 5 minutes apart. The animals were allowed to habituate on the glass surface for 10 minutes before paw withdrawal latencies (PWL) in seconds, were recorded.

CFA

Animals were anesthetized with isoflurane 5% induction and a 2% maintenance and 20 μL of 100% Complete Freund's Adjuvant (CFA; Sigma-Aldrich; Saint Louis, Mo. was injected subcutaneously into the left hind paw using a 25 gauge needle attached to a 1 mL syringe.

Test Compound

Protoxin-II (Peptides International) was formulated in DPBS (no Calcium and Magnesium) at a stock concentration of 9.5 mg/mL.

Mini Pumps

Alzet micro-osmotic mini pumps (Durect Corporation Model 1003D) were used. These pumps delivered the test compound and vehicle at 1.0 μl per hour for 3 days after implantation into the mouse. A pump and its flow moderator were first weighed and then filled with a 1 mL syringe attached with a 27-gague blunt tipped needle. With the pump in an upright position the pump was filled, the flow moderator inserted and re-weighed. Weights were recorded (empty and filled weights) to ensure that the fill volume was over 90% of the Mean Fill volume specified in the Alzet pump directions (92 μL per instruction sheet). The pumps were then placed in a 15 mL conical tube filled with 0.9% saline and placed in 37° C. for 5-6 hours prior to implantation.

Implantation of Mini Pumps Mice were given 20 μl of 0.3 mg/ml Buprenex prior to being anesthetized (5% induction; 2% maintenance) with isoflurane. Their backs were shaved, wiped down with isopropyl alcohol and povidone iodine, and a small incision was made between the scapulae. Using a hemostat, a small pocket was formed by spreading the subcutaneous connective tissues apart. The contents of each pump was not known to the surgeon or experimental operator. The skin incision was then closed using 7 mm staples and the animals were allowed to recover in their home cages.

Data Analysis

Data are represented as mean±s.e.m. Gram thresholds (tactile) and mean latencies (thermal) were recorded on paper and entered into Prism (Graphpad Software Inc., LaJolla, Calif.) for graphing and statistical analysis. For comparison of threshold values over time, a two-way ANOVA with Bonferroni post hoc test was used with a significance level of $p<0.05$.

Procedure

Animals were trained on the Von Frey Stand and the Hargreaves box Tuesday, Wednesday and Thursday of the previous week before testing. They were allowed to sit on the stand/box for ~30 min to get used to being on the apparatus. On Friday, their Pre-Thresholds were tested in both tactile (Von Frey stand) and thermal (Hargreaves). Once Pre-Thresholds were tested the animals were briefly anesthetized and 20 μL of 100% CFA was injected into their left hind paw. The animals were allowed to recover and returned to their home cages. On Monday of the next week, mice were tested for Baseline measurements in both tactile and thermal to confirm that the CFA caused sufficient inflammation to lower their thresholds. The mice were then anesthetized and a mini pump was implanted and the animals were allowed to recover. On Tuesday, Wednesday and Thursday, they had their "Day 1", "Day 2" and "Day 3" tactile and thermal thresholds measured. At the end of Day 3, the animals were sacrificed and terminal blood samples obtained.

Plasma ProTx-II concentrations were determined as described in Example 9. The average concentration of ProTx-II was 224 nM.

Results

Figure 19A:
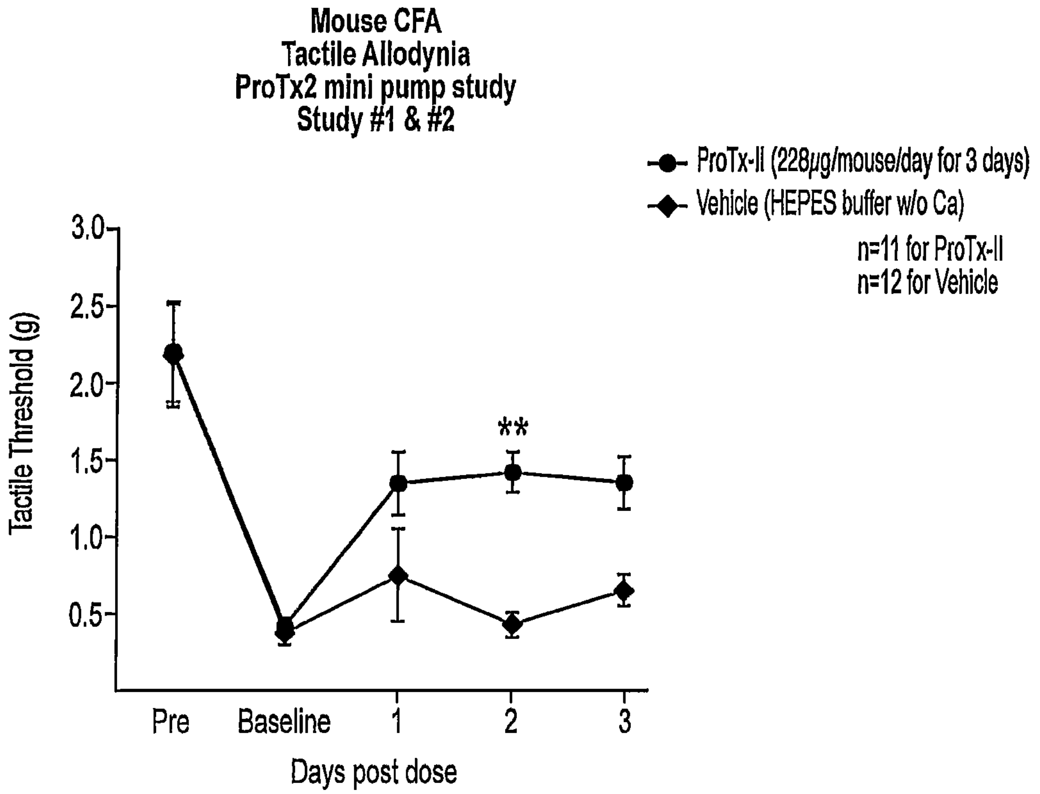
FIG. 19 shows reduced A) tactile allodynia and B) thermal allodynia in a mouse model of CFA-induced inflammatory pain in animals treated with ProTx-II administered via mini-pump at 228 μg/mouse/day for 3 days.
Figure 19B:
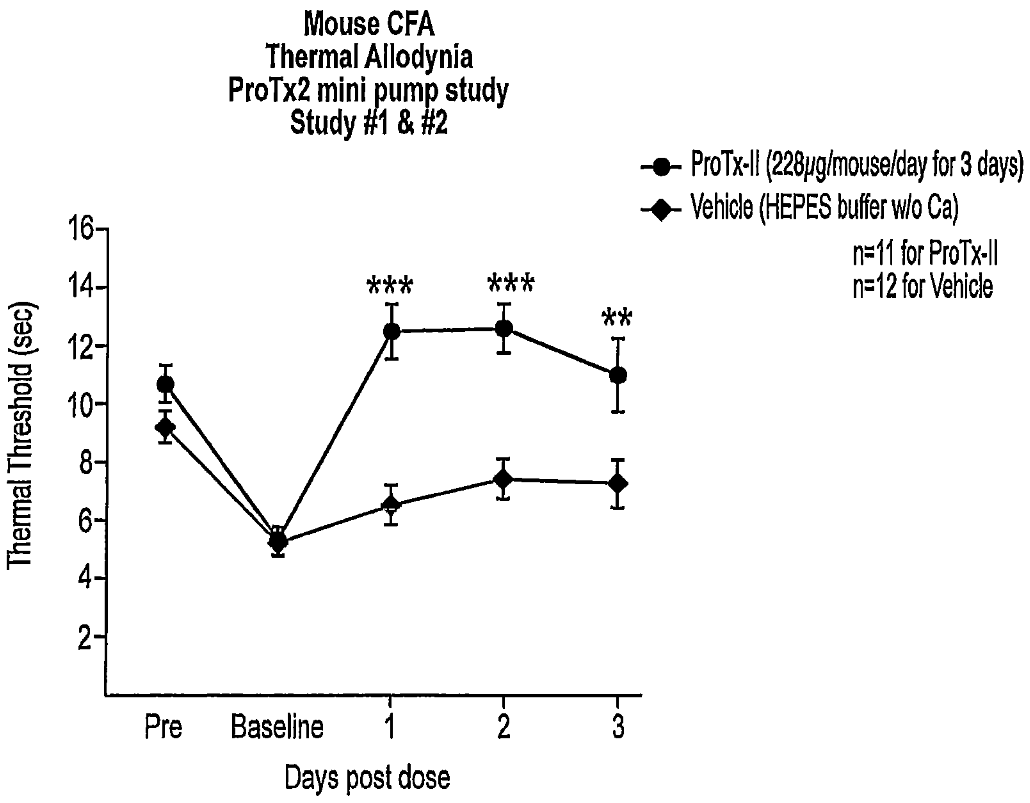

ProTX-II exhibited statistically significant efficacy in a mouse model of inflammatory pain following sustained delivery of 228 μg/day via osmotic mini-pump. Tactile threshold (FIG. 19A) and thermal threshold (FIG. 19B) were significantly increased in ProTx-II treated animals. These observations were reproducible across two independent and fully blinded studies. ProTx-II did not did not produce any obvious motor impairment at this efficacious dose. In contrary to published reports (Schmalhofer et al., Mol Pharm 74:1476-1484, 2008; Hacker et al., Proc Natl Acad Sci USA 109:E2018-27), these data demonstrate that systemic administration with sustained exposure to a Nav1.7 selective peptide can provide robust efficacy in inflammatory pain.

Effects of ProTx-II delivered via a mini pump was assessed in mice with spared nerve injury, a model of neuropathic pain, in the tactile (Von Frey) pain assay. ProTx-II was not efficacious in this mouse spared nerve injury model of neuropathic pain following sustained delivery of 228 μg/day of ProTx-II via osmotic mini-pump.

We claim:

1. A vector comprising a polynucleotide encoding a Huwentoxin-IV variant of SEQ ID NOs: 3, 4, 5, 6, 7, 8, 9, 10, 11, 12, 13, 14, 15, 16, 17, 18, 19, 20, 21, 22, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 102, 103, 104, 105, 106, 107, 108, 109, 110, 112, 113, 114, 115, 116, 117, 118, 119, 120, 121, 123, 124, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 163, 164, 165, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 199, 200, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 233, 234, 235, 236, 237, 238, 239, 240, 241, 245, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354 or 355.

2. A host cell comprising a vector of claim 1.

3. A method of producing an isolated Huwentoxin-IV variant comprising culturing the host cell of claim 2 and recovering the Huwentoxin-IV variant produced by the host cell.

* * * * *